(12) United States Patent
Wachli et al.

(10) Patent No.: US 11,547,444 B2
(45) Date of Patent: Jan. 10, 2023

(54) SYSTEMS AND METHODS FOR TISSUE REMOVAL

(71) Applicant: Applied Medical Resources Corporation, Rancho Santa Margarita, CA (US)

(72) Inventors: Serene Wachli, Rancho Santa Margarita, CA (US); Tracy Breslin, Trabuco Canyon, CA (US); Steven C. Kessler, Rancho Santa Margarita, CA (US); Nikolai Poulsen, Irvine, CA (US); Nathan Collins, Rancho Santa Margarita, CA (US); Alexandra Do, San Clemente, CA (US); Eduardo Bolanos, Rancho Santa Margarita, CA (US); Boun Pravong, Rancho Santa Margarita, CA (US); Patrick Elliott, Rancho Santa Margarita, CA (US); Matthew A. Wixey, San Jose, CA (US); Wayne Young, Brewster, NY (US); Jacob J. Filek, Rancho Santa Margarita, CA (US); Kevin B. Castelo, Mission Viejo, CA (US); Adam Hoke, Shelbyville, MI (US); Gregory K. Hofstetter, Rancho Santa Margarita, CA (US); Jacqueline DeMarchi, Rancho Santa Margarita, CA (US); Amy Garces, Rancho Santa Margarita, CA (US); Heidi Holmes, Rancho Santa Margarita, CA (US); Alexander Sheehan, Shoreline, WA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 227 days.

(21) Appl. No.: 17/101,201

(22) Filed: Nov. 23, 2020

(65) Prior Publication Data

US 2021/0085364 A1    Mar. 25, 2021

Related U.S. Application Data

(63) Continuation of application No. 16/249,123, filed on Jan. 16, 2019, now Pat. No. 10,842,530, which is a
(Continued)

(51) Int. Cl.
*A61B 17/34* (2006.01)
*A61B 17/02* (2006.01)
(Continued)

(52) U.S. Cl.
CPC .... *A61B 17/3462* (2013.01); *A61B 17/00234* (2013.01); *A61B 17/0293* (2013.01);
(Continued)

(58) Field of Classification Search
CPC .............. A61B 1/32; A61B 2017/3425; A61B 2017/3427; A61B 2017/3429;
(Continued)

(56) References Cited

U.S. PATENT DOCUMENTS

| 1,550,403 A | 8/1925 | Turkus |
| 2,013,892 A | 9/1935 | Lucas |

(Continued)

FOREIGN PATENT DOCUMENTS

| DE | 4405831 A1 | 8/1995 |
| DE | 102013217513 A1 | 3/2015 |

(Continued)

OTHER PUBLICATIONS

European Patent Office, Extended European Search Report for European Patent Application No. EP 20165706.1, titled "Systems and Methods for Tissue Removal," dated Jul. 9, 2020, 8 pgs.
(Continued)

*Primary Examiner* — Eric S Gibson
(74) *Attorney, Agent, or Firm* — Shirin Bozorgui; Patrick Ikehara

(57) ABSTRACT

Systems and methods for preventing the seeding of cancerous cells during morcellation of a tissue specimen inside a patient's body and removal of the tissue specimen from inside the patient through a minimally-invasive body open-
(Continued)

ing to outside the patient are provided. One system includes a cut-resistant tissue guard removably insertable into a containment bag. The tissue specimen is isolated and contained within the containment bag and the guard is configured to protect the containment bag and surrounding tissue from incidental contact with sharp instrumentation used during morcellation and extraction of the tissue specimen. The guard is adjustable for easy insertion and removal and configured to securely anchor to the body opening. Protection-focused and containment-based systems for tissue removal are provided that enable minimally invasive procedures to be performed safely and efficiently.

20 Claims, 96 Drawing Sheets

Related U.S. Application Data continuation of application No. 15/068,366, filed on Mar. 11, 2016, now Pat. No. 10,219,831, which is a continuation of application No. PCT/US2015/056978, filed on Oct. 22, 2015.

(60) Provisional application No. 62/107,107, filed on Jan. 23, 2015, provisional application No. 62/081,297, filed on Nov. 18, 2014, provisional application No. 62/079,171, filed on Nov. 13, 2014.

(51) Int. Cl.
*A61B 17/32* (2006.01)
*A61B 17/00* (2006.01)
*A61B 17/3211* (2006.01)
*A61B 90/50* (2016.01)
*A61B 90/00* (2016.01)
*A61B 17/42* (2006.01)

(52) U.S. Cl.
CPC ........... *A61B 17/320016* (2013.01); *A61B 17/3423* (2013.01); *A61B 17/3496* (2013.01); *A61B 17/3211* (2013.01); *A61B 17/3431* (2013.01); *A61B 17/3494* (2013.01); *A61B 90/50* (2016.02); *A61B 2017/00287* (2013.01); *A61B 2017/00557* (2013.01); *A61B 2017/320024* (2013.01); *A61B 2017/347* (2013.01); *A61B 2017/349* (2013.01); *A61B 2017/3466* (2013.01); *A61B 2017/4216* (2013.01); *A61B 2090/08021* (2016.02)

(58) Field of Classification Search
CPC .... A61B 2017/3433; A61B 2017/3435; A61B 2017/3441; A61B 2017/3443
See application file for complete search history.

(56) References Cited

U.S. PATENT DOCUMENTS

| | | | |
|---|---|---|---|
| 2,406,600 A * | 8/1946 | Forestiere | A61B 17/42 600/184 |
| 2,812,758 A * | 11/1957 | Blumenschein | A61B 17/0293 600/215 |
| 3,244,169 A | 4/1966 | Baxter | |
| 3,762,417 A | 10/1973 | Textor | |
| 3,807,393 A * | 4/1974 | McDonald | A61B 1/32 600/245 |
| 4,120,301 A | 10/1978 | Lovick | |
| 4,553,537 A | 11/1985 | Rosenberg | |
| 4,573,452 A | 3/1986 | Greenberg | |
| 4,921,479 A * | 5/1990 | Grayzel | A61M 25/0668 604/509 |
| 4,984,564 A * | 1/1991 | Yuen | A61B 17/0293 600/207 |
| 5,007,926 A * | 4/1991 | Derbyshire | A61F 2/92 606/191 |
| 5,037,379 A | 8/1991 | Clayman et al. | |
| 5,078,726 A * | 1/1992 | Kreamer | A61F 2/07 623/1.13 |
| 5,139,511 A * | 8/1992 | Gill | A61M 25/065 606/198 |
| 5,143,082 A | 9/1992 | Kindberg et al. | |
| 5,159,921 A * | 11/1992 | Hoover | A61B 17/0293 600/245 |
| 5,171,262 A * | 12/1992 | MacGregor | A61F 2/90 623/1.15 |
| 5,176,659 A * | 1/1993 | Mancini | A61M 25/0023 604/523 |
| 5,213,114 A | 5/1993 | Bailey, Jr. | |
| 5,215,101 A | 6/1993 | Jacobs et al. | |
| 5,215,521 A | 6/1993 | Cochran et al. | |
| RE34,327 E * | 7/1993 | Kreamer | A61F 2/92 623/1.15 |
| 5,224,930 A * | 7/1993 | Spaeth | A61B 17/34 606/128 |
| 5,231,974 A | 8/1993 | Giglio et al. | |
| 5,308,327 A | 5/1994 | Heaven et al. | |
| 5,312,416 A | 5/1994 | Spaeth et al. | |
| 5,320,627 A | 6/1994 | Sorensen et al. | |
| 5,330,483 A | 7/1994 | Heaven et al. | |
| 5,337,754 A | 8/1994 | Heaven et al. | |
| 5,354,303 A | 10/1994 | Spaeth et al. | |
| 5,368,545 A * | 11/1994 | Schaller | A61B 17/00234 128/850 |
| 5,374,272 A * | 12/1994 | Arpa | A61B 17/0231 606/107 |
| 5,380,304 A * | 1/1995 | Parker | A61M 25/0012 138/144 |
| 5,411,549 A * | 5/1995 | Peters | A61F 2/93 606/195 |
| 5,441,515 A * | 8/1995 | Khosravi | A61F 2/93 623/1.42 |
| 5,449,382 A * | 9/1995 | Dayton | A61F 2/93 623/1.42 |
| 5,465,731 A | 11/1995 | Bell et al. | |
| 5,486,183 A | 1/1996 | Middleman et al. | |
| 5,520,610 A | 5/1996 | Giglio et al. | |
| 5,578,075 A * | 11/1996 | Dayton | A61F 2/92 623/1.21 |
| 5,611,803 A * | 3/1997 | Heaven | A61B 17/00234 606/113 |
| 5,618,296 A | 4/1997 | Sorensen et al. | |
| 5,636,639 A | 6/1997 | Turturro et al. | |
| 5,647,372 A | 7/1997 | Tovey et al. | |
| 5,649,550 A | 7/1997 | Crook | |
| 5,669,927 A | 9/1997 | Boebel et al. | |
| 5,707,385 A * | 1/1998 | Williams | A61M 31/00 606/198 |
| 5,769,794 A * | 6/1998 | Conlan | A61B 17/00234 600/562 |
| 5,785,677 A | 7/1998 | Auweiler | |
| 5,788,709 A * | 8/1998 | Riek | A61B 17/00234 606/127 |
| 5,810,721 A | 9/1998 | Mueller et al. | |
| 5,836,936 A | 11/1998 | Cuschieri | |
| 5,895,392 A | 4/1999 | Riek et al. | |
| 5,957,884 A | 9/1999 | Hooven | |
| 5,957,888 A * | 9/1999 | Hinchliffe | A61B 17/3421 606/174 |
| 5,971,995 A | 10/1999 | Rousseau | |
| 5,993,427 A * | 11/1999 | Rolland | A61M 25/0119 604/271 |
| 6,027,779 A * | 2/2000 | Campbell | A61L 29/041 428/36.1 |
| 6,036,681 A | 3/2000 | Hooven | |
| 6,039,748 A | 3/2000 | Savage et al. | |
| 6,045,566 A | 4/2000 | Pagedas | |
| 6,048,309 A | 4/2000 | Flom et al. | |
| 6,059,793 A | 5/2000 | Pagedas | |

(56) References Cited

U.S. PATENT DOCUMENTS

| | | | |
|---|---|---|---|
| 6,090,136 A * | 7/2000 | McDonald | A61F 2/92 623/1.23 |
| 6,142,935 A | 11/2000 | Flom et al. | |
| 6,162,172 A * | 12/2000 | Cosgrove | A61B 17/0293 600/245 |
| 6,187,000 B1 * | 2/2001 | Davison | A61B 17/0218 606/1 |
| 6,206,889 B1 | 3/2001 | Bernardo | |
| 6,228,095 B1 | 5/2001 | Dennis | |
| 6,254,534 B1 * | 7/2001 | Butler | A61B 17/0218 600/206 |
| 6,258,102 B1 | 7/2001 | Pagedas | |
| 6,270,505 B1 | 8/2001 | Yoshida et al. | |
| 6,312,443 B1 * | 11/2001 | Stone | A61F 2/4455 623/1.1 |
| 6,350,267 B1 | 2/2002 | Stefanchik | |
| 6,361,528 B1 * | 3/2002 | Wilson | A61M 25/0023 604/500 |
| 6,382,211 B1 * | 5/2002 | Crook | A61B 17/0293 128/853 |
| 6,387,102 B2 | 5/2002 | Pagedas | |
| 6,406,440 B1 | 6/2002 | Stefanchik | |
| 6,524,320 B2 * | 2/2003 | DiPoto | A61B 17/3439 606/108 |
| 6,569,105 B1 | 5/2003 | Kortenbach et al. | |
| 6,616,678 B2 * | 9/2003 | Nishtala | A61M 29/02 606/198 |
| 6,652,553 B2 * | 11/2003 | Davison | A61B 17/3439 606/190 |
| 6,685,628 B2 | 2/2004 | Vu | |
| 6,706,017 B1 * | 3/2004 | Dulguerov | A61M 16/085 128/207.29 |
| 6,814,700 B1 * | 11/2004 | Mueller | A61B 17/0293 600/206 |
| 6,958,037 B2 * | 10/2005 | Ewers | A61B 1/32 600/208 |
| 7,041,055 B2 | 5/2006 | Young et al. | |
| 7,052,454 B2 * | 5/2006 | Taylor | A61B 17/3423 600/114 |
| 7,144,393 B2 * | 12/2006 | DiPoto | A61B 17/3439 606/1 |
| 7,238,154 B2 | 7/2007 | Ewers et al. | |
| 7,297,106 B2 * | 11/2007 | Yamada | A61B 17/3423 600/208 |
| 7,377,898 B2 | 5/2008 | Ewers et al. | |
| 7,491,168 B2 | 2/2009 | Raymond et al. | |
| 7,510,524 B2 * | 3/2009 | Vayser | G02B 23/2469 606/14 |
| 7,537,564 B2 | 5/2009 | Bonadio et al. | |
| 7,547,310 B2 | 6/2009 | Whitfield | |
| 7,670,346 B2 * | 3/2010 | Whitfield | A61B 17/00234 606/114 |
| 7,699,864 B2 * | 4/2010 | Kick | A61B 17/3439 600/184 |
| 7,704,207 B2 * | 4/2010 | Albrecht | A61B 90/40 600/233 |
| 7,758,500 B2 | 7/2010 | Boyd et al. | |
| 7,758,501 B2 | 7/2010 | Fraiser et al. | |
| 7,762,969 B2 | 7/2010 | Bilsbury | |
| 7,766,820 B2 * | 8/2010 | Core | A61M 25/0023 600/140 |
| 7,785,341 B2 * | 8/2010 | Forster | A61F 2/2433 606/194 |
| 7,892,273 B2 * | 2/2011 | George | A61F 2/915 623/1.11 |
| 7,896,877 B2 | 3/2011 | Hall et al. | |
| 7,955,292 B2 | 6/2011 | Leroy et al. | |
| 7,981,130 B2 | 7/2011 | Seeh | |
| 7,998,068 B2 | 8/2011 | Bonadio et al. | |
| 8,016,771 B2 | 9/2011 | Orban, III | |
| 8,016,839 B2 | 9/2011 | Wilk | |
| 8,038,611 B2 | 10/2011 | Raymond et al. | |
| 8,075,567 B2 | 12/2011 | Taylor et al. | |
| 8,100,928 B2 | 1/2012 | Nohilly et al. | |
| 8,114,119 B2 | 2/2012 | Spivey et al. | |
| 8,152,820 B2 | 4/2012 | Mohamed et al. | |
| 8,157,834 B2 | 4/2012 | Conlon | |
| 8,337,510 B2 | 12/2012 | Rieber et al. | |
| 8,366,754 B2 | 2/2013 | Teague et al. | |
| 8,409,112 B2 | 4/2013 | Wynne et al. | |
| 8,409,216 B2 | 4/2013 | Parihar et al. | |
| 8,414,596 B2 | 4/2013 | Parihar et al. | |
| 8,425,533 B2 | 4/2013 | Parihar et al. | |
| 8,500,799 B2 * | 8/2013 | Forster | A61F 2/243 623/2.11 |
| 8,517,935 B2 | 8/2013 | Marchek et al. | |
| 8,579,914 B2 | 11/2013 | Menn et al. | |
| 8,597,180 B2 | 12/2013 | Copeland et al. | |
| 8,622,897 B2 | 1/2014 | Raymond et al. | |
| 8,690,936 B2 * | 4/2014 | Nguyen | A61M 25/0023 606/191 |
| 8,721,538 B2 | 5/2014 | Bucholz | |
| 8,721,658 B2 | 5/2014 | Kahle et al. | |
| 8,734,336 B2 | 5/2014 | Bonadio et al. | |
| 8,758,236 B2 * | 6/2014 | Albrecht | A61B 17/0293 600/206 |
| 8,777,849 B2 | 7/2014 | Haig et al. | |
| 8,790,387 B2 * | 7/2014 | Nguyen | A61F 2/2427 604/525 |
| 8,821,377 B2 | 9/2014 | Collins | |
| 8,857,440 B2 | 10/2014 | Gundlapalli et al. | |
| 8,864,658 B2 | 10/2014 | Wilkins et al. | |
| 8,920,431 B2 | 12/2014 | Shibley et al. | |
| 8,956,286 B2 | 2/2015 | Shibley et al. | |
| 8,961,408 B2 | 2/2015 | Wilkins et al. | |
| 8,961,409 B2 | 2/2015 | O'Prey et al. | |
| 9,005,115 B2 * | 4/2015 | Vayser | G02B 23/2469 606/17 |
| 9,017,253 B2 * | 4/2015 | Guralnik | A61B 17/0218 600/206 |
| 9,039,610 B2 * | 5/2015 | Wilkins | A61B 17/0218 600/206 |
| 9,044,210 B1 | 6/2015 | Hoyte et al. | |
| 9,168,031 B2 | 10/2015 | Copeland et al. | |
| 9,192,751 B2 * | 11/2015 | Macaulay | A61M 39/0247 |
| 9,211,140 B2 * | 12/2015 | Lauryssen | A61B 17/3462 |
| 10,219,831 B2 * | 3/2019 | Wachli | A61B 17/3462 |
| 10,842,530 B2 * | 11/2020 | Wachli | A61B 17/0293 |
| 2001/0012950 A1 * | 8/2001 | Nishtala | A61M 25/0662 606/198 |
| 2002/0013542 A1 * | 1/2002 | Bonadio | A61M 25/0119 601/134 |
| 2002/0123765 A1 * | 9/2002 | Sepetka | A61B 17/221 606/198 |
| 2003/0078478 A1 | 4/2003 | Bonadio et al. | |
| 2004/0097960 A1 | 5/2004 | Terachi et al. | |
| 2004/0158261 A1 | 8/2004 | Vu | |
| 2004/0171405 A1 | 9/2004 | Amano et al. | |
| 2005/0080443 A1 * | 4/2005 | Fallin | A61B 17/3417 606/191 |
| 2005/0197537 A1 | 9/2005 | Bonadio et al. | |
| 2005/0222576 A1 * | 10/2005 | Kick | A61B 17/3439 606/104 |
| 2005/0267492 A1 | 12/2005 | Poncet et al. | |
| 2006/0069404 A1 * | 3/2006 | Shluzas | A61B 17/3439 606/198 |
| 2006/0200169 A1 * | 9/2006 | Sniffin | A61B 17/00234 606/113 |
| 2006/0200170 A1 * | 9/2006 | Aranyi | A61B 17/00234 606/113 |
| 2006/0235458 A1 * | 10/2006 | Belson | A61B 1/00135 606/191 |
| 2006/0247498 A1 | 11/2006 | Bonadio et al. | |
| 2007/0051375 A1 * | 3/2007 | Milliman | A61B 17/3439 128/856 |
| 2007/0135780 A1 | 6/2007 | Pagedas | |
| 2007/0016187 A1 | 7/2007 | Fowler, Jr. et al. | |
| 2007/0161866 A1 | 7/2007 | Fowler et al. | |
| 2007/0288026 A1 * | 12/2007 | Shluzas | A61B 17/7083 606/86 A |

(56) References Cited

U.S. PATENT DOCUMENTS

| | | | |
|---|---|---|---|
| 2008/0058604 A1* | 3/2008 | Sorensen | A61B 1/32 600/208 |
| 2008/0200943 A1* | 8/2008 | Barker | A61B 17/3431 606/191 |
| 2008/0319261 A1* | 12/2008 | Lucini | A61B 17/3421 600/114 |
| 2009/0036744 A1* | 2/2009 | Vayser | A61B 1/32 600/245 |
| 2009/0138024 A1 | 5/2009 | Ichihara et al. | |
| 2009/0026471 A1 | 10/2009 | Chana et al. | |
| 2010/0081871 A1* | 4/2010 | Widenhouse | A61B 17/3462 600/104 |
| 2010/0219091 A1 | 9/2010 | Turner | |
| 2010/0312189 A1* | 12/2010 | Shelton, IV | A61B 17/3431 604/164.03 |
| 2011/0021879 A1* | 1/2011 | Hart | A61B 17/0293 600/207 |
| 2011/0021882 A1* | 1/2011 | Selover | A61B 17/3423 600/245 |
| 2011/0054260 A1* | 3/2011 | Albrecht | A61B 17/0293 600/208 |
| 2011/0092909 A1* | 4/2011 | Andersson | A61B 17/02 604/164.04 |
| 2011/0124969 A1* | 5/2011 | Stopek | A61B 17/3423 600/206 |
| 2011/0184311 A1 | 7/2011 | Parihar et al. | |
| 2011/0184435 A1 | 7/2011 | Parihar et al. | |
| 2011/0190779 A1 | 8/2011 | Gell et al. | |
| 2011/0196206 A1* | 8/2011 | Hammond | A61B 17/3421 600/204 |
| 2011/0306843 A1* | 12/2011 | Lenker | A61B 17/3439 600/207 |
| 2011/0319719 A1* | 12/2011 | O'Prey | A61B 17/3423 600/206 |
| 2012/0078264 A1 | 3/2012 | Taylor et al. | |
| 2012/0083795 A1 | 4/2012 | Fleming et al. | |
| 2012/0095296 A1* | 4/2012 | Trieu | A61M 29/02 606/86 R |
| 2012/0109144 A1 | 5/2012 | Chin et al. | |
| 2012/0130161 A1* | 5/2012 | Lauryssen | A61F 2/4611 600/104 |
| 2012/0130184 A1* | 5/2012 | Richard | A61B 17/3423 600/208 |
| 2012/0130191 A1* | 5/2012 | Pribanic | A61B 17/3423 600/208 |
| 2012/0157777 A1 | 6/2012 | Okoniewski | |
| 2012/0203069 A1* | 8/2012 | Hannaford | A61B 90/00 600/201 |
| 2012/0238823 A1 | 9/2012 | Hagerty et al. | |
| 2012/0245426 A1* | 9/2012 | Salvas | A61B 17/3421 606/108 |
| 2012/0245428 A1* | 9/2012 | Smith | A61B 17/3423 600/208 |
| 2012/0316572 A1 | 12/2012 | Rosenblatt et al. | |
| 2013/0066157 A1* | 3/2013 | Guralnik | A61B 17/3439 600/204 |
| 2013/0103042 A1 | 4/2013 | Davis | |
| 2013/0103043 A1 | 4/2013 | Cabrera | |
| 2013/0131457 A1 | 5/2013 | Seckin | |
| 2013/0138115 A1 | 5/2013 | Seckin | |
| 2013/0178711 A1* | 7/2013 | Avneri | A61M 25/0023 604/164.13 |
| 2013/0184536 A1 | 7/2013 | Shibley et al. | |
| 2013/0204092 A1* | 8/2013 | Hannaford | A61B 1/06 600/236 |
| 2013/0226029 A1* | 8/2013 | Kleyman | A61B 10/0266 600/564 |
| 2013/0253267 A1* | 9/2013 | Collins | A61B 17/3421 600/104 |
| 2013/0284186 A1 | 10/2013 | Touati | |
| 2014/0052018 A1* | 2/2014 | Hawkins | A61B 17/42 600/562 |
| 2014/0058210 A1 | 2/2014 | Raymond et al. | |
| 2014/0058403 A1 | 2/2014 | Menn et al. | |
| 2014/0135788 A1* | 5/2014 | Collins | A61B 17/3423 606/114 |
| 2014/0142509 A1* | 5/2014 | Bonutti | A61M 25/0662 604/164.03 |
| 2014/0194681 A1* | 7/2014 | Scott | A61B 17/0643 600/37 |
| 2014/0235952 A1 | 8/2014 | Haig et al. | |
| 2014/0236110 A1 | 8/2014 | Taylor et al. | |
| 2014/0275795 A1* | 9/2014 | Little | A61B 17/3423 600/208 |
| 2014/0275801 A1* | 9/2014 | Menchaca | A61B 17/3439 600/212 |
| 2014/0296649 A1 | 10/2014 | Fehling et al. | |
| 2014/0316210 A1* | 10/2014 | Koehler | A61M 1/85 600/208 |
| 2014/0330285 A1 | 11/2014 | Rosenblatt et al. | |
| 2014/0379074 A1* | 12/2014 | Spence | A61F 2/2409 623/2.11 |
| 2015/0005584 A1 | 1/2015 | Wilkins et al. | |
| 2015/0018625 A1 | 1/2015 | Miraki et al. | |
| 2015/0094541 A1 | 4/2015 | Wilkins et al. | |
| 2015/0119647 A1 | 4/2015 | Vaillancourt et al. | |
| 2015/0164552 A1* | 6/2015 | Chen | A61B 1/00154 600/204 |
| 2015/0209074 A1* | 7/2015 | Payne | A61B 17/24 600/114 |
| 2016/0100857 A1* | 4/2016 | Wachli | A61B 17/00234 600/204 |
| 2016/0262794 A1* | 9/2016 | Wachli | A61B 17/320016 |
| 2019/0150979 A1* | 5/2019 | Wachli | A61B 17/00234 |

FOREIGN PATENT DOCUMENTS

| | | |
|---|---|---|
| EP | 1 312 318 A1 | 5/2003 |
| EP | 1 935 356 A1 | 10/2004 |
| EP | 2 138 113 A2 | 12/2009 |
| EP | 2 359 758 A2 | 8/2011 |
| EP | 2 668 907 A2 | 12/2013 |
| WO | WO 00/32116 A1 | 6/2000 |
| WO | WO 03/061480 A1 | 7/2003 |
| WO | WO 03/071926 A2 | 9/2003 |
| WO | WO 2004/075730 A2 | 9/2004 |
| WO | WO 2008/083222 A2 | 7/2008 |
| WO | WO 2011/143410 A1 | 11/2011 |
| WO | WO 2013/093030 A2 | 6/2013 |
| WO | WO 2013/150391 A1 | 10/2013 |
| WO | WO 2015/164591 A1 | 10/2015 |

OTHER PUBLICATIONS

European Patent Office, Extended European Search Report for European Patent Application No. EP 21178022.6, titled "Systems and Methods for Tissue Removal," dated Sep. 16, 2021, 8 pgs.

European Patent Office, Extended European Search Report for European Patent Application No. EP 21163226.0, titled "Systems and Methods for Tissue Removal," dated Jul. 8, 2021, 9 pgs.

European Patent Office, The International Search Report and Written Opinion for International Application No. PCT/US2015/027274, titled "Suture Clinch with Traction Enhanced," dated Jul. 10, 2015 (14 pgs.).

European Patent Office, The International Search Report and Written Opinion of the International Searching Authority for International Application No. PCT/US2015/056978 titled "Systems and Methods for Tissue Removal", dated Jan. 15, 2016.

European Patent Office, The International Search Report and Written Opinion for International Application No. PCT/US2015/045705, entitled "Systems and Methods for Tissue Containment and Retrieval," dated Apr. 18, 2016, 18 pgs.

European Patent Office, The International Search Report and Written Opinion for International Application No. PCT/US2016/029154, entitled "Systems and Methods for Tissue Removal," dated Aug. 19, 2016, 17 pgs.

(56) References Cited

OTHER PUBLICATIONS

The International Bureau of WIPO, International Preliminary Report on Patentability for International Application No. PCT/US2015/027274, entitled "Systems and Methods for Tissue Removal," dated Nov. 3, 2016, 9 pgs.

The International Bureau of WIPO, International Preliminary Report on Patentability for International Application No. PCT/US2015/045705, entitled "Systems and Methods for Tissue Containment and Retrieval," dated Mar. 2, 2017, 10 pgs.

European Patent Office, Invitation to Pay Additional Fees for International Application No. PCT/US2017/014402, titled "Systems and Methods for Tissue Removal", dated Apr. 6, 2017, 10 pgs.

The International Bureau of WIPO, International Preliminary Report on Patentability for International Application No. PCT/US2015/056978, entitled "Systems and Methods for Tissue Removal," dated May 26, 2017, 10 pgs.

European Patent Office, The International Search Report and Written Opinion for International Application No. PCT/US2017/014402, entitled "Systems and Methods for Tissue Removal," dated Jun. 6, 2017, 20 pgs.

The International Bureau of WIPO, International Preliminary Report on Patentability for International Application No. PCT/US2016/029154, entitled "Systems and Methods for Tissue Removal," dated Nov. 2, 2017, 11pgs.

The International Bureau of WIPO, International Preliminary Report on Patentability for International Application No. PCT/US2017/014402, entitled "Systems and Methods for Tissue Removal," dated Aug. 2, 2018, 11pgs.

* cited by examiner

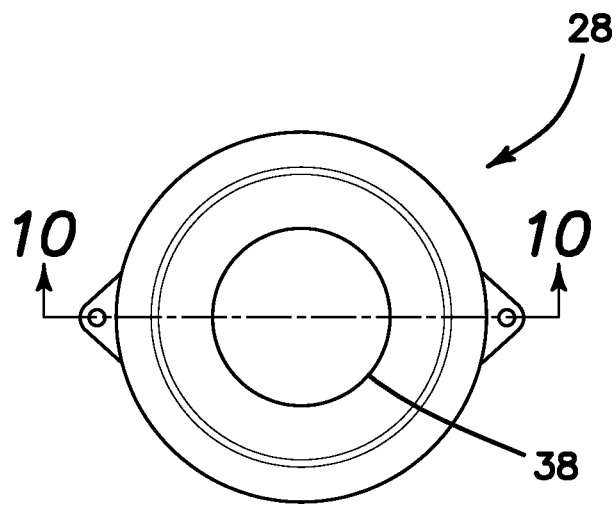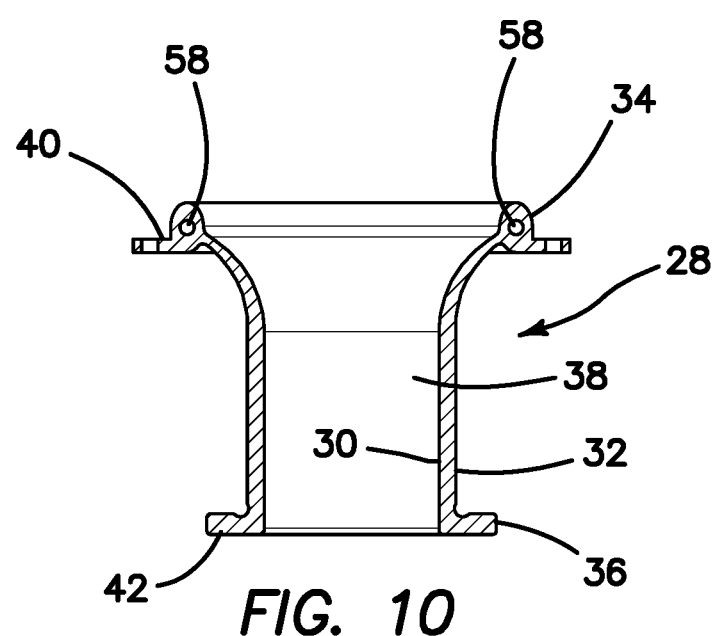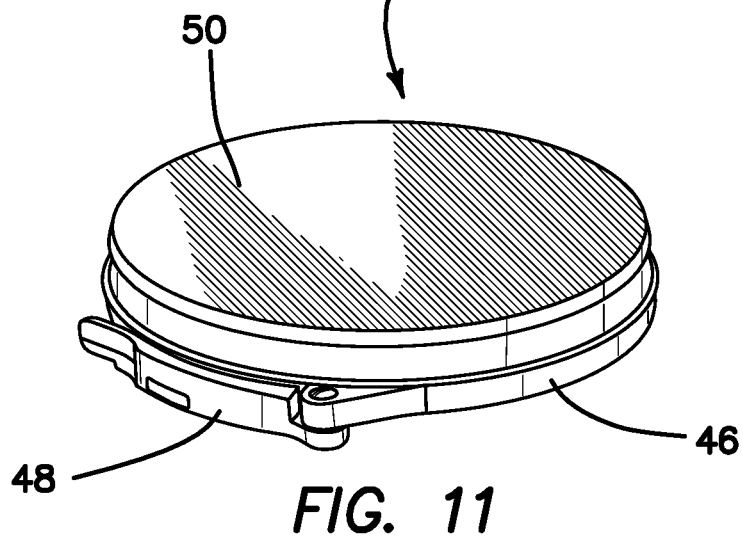

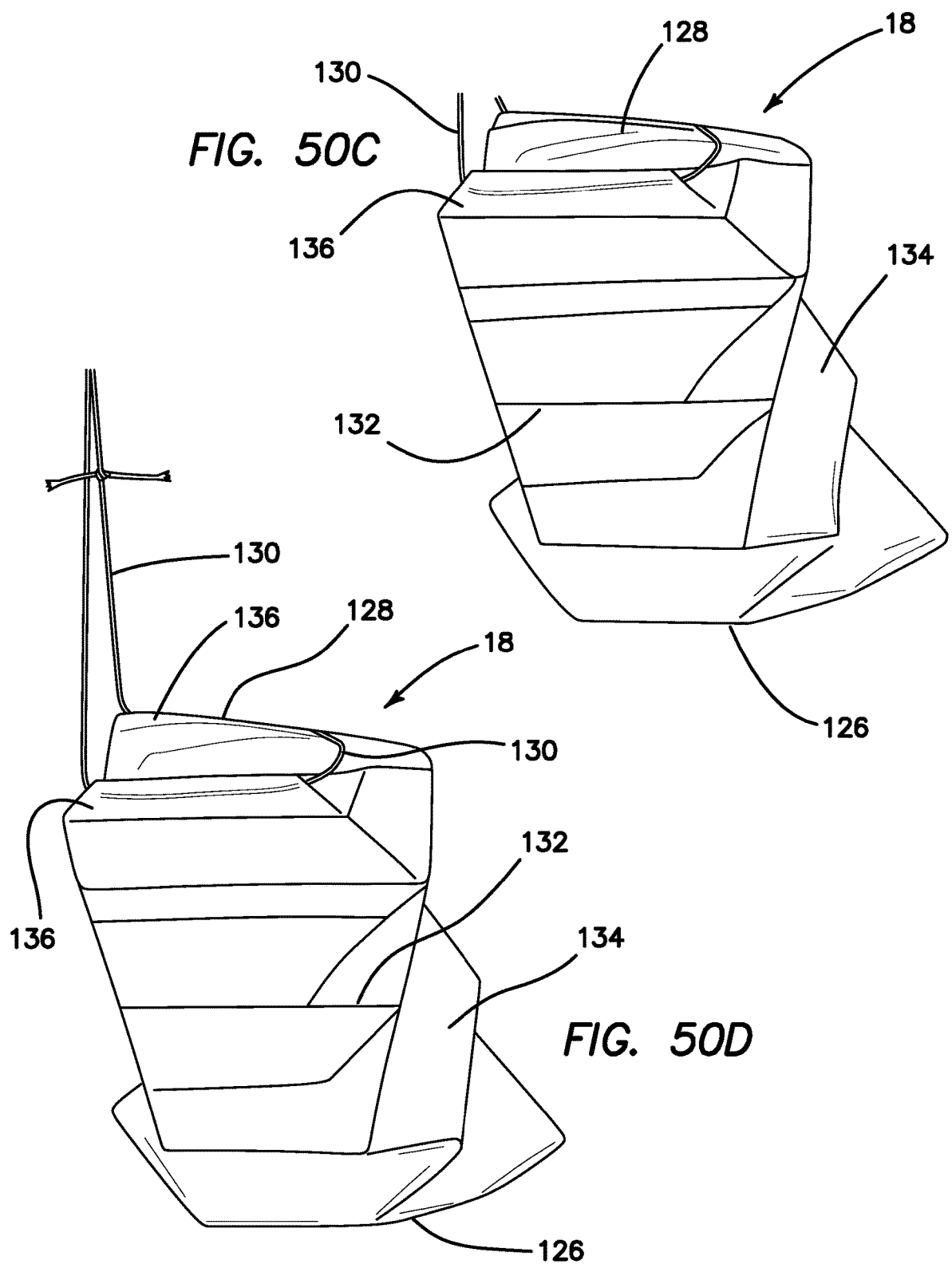

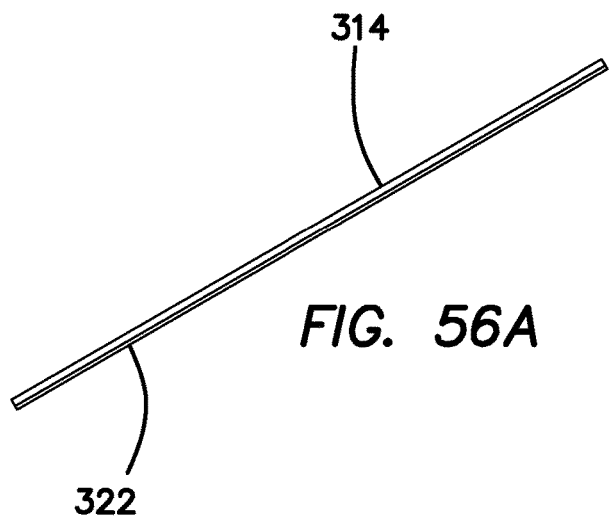
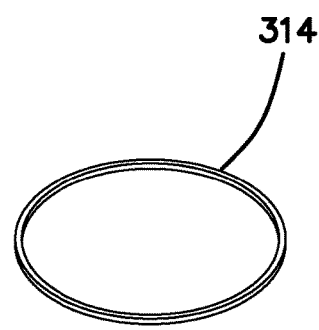
FIG. 56A
FIG. 56B
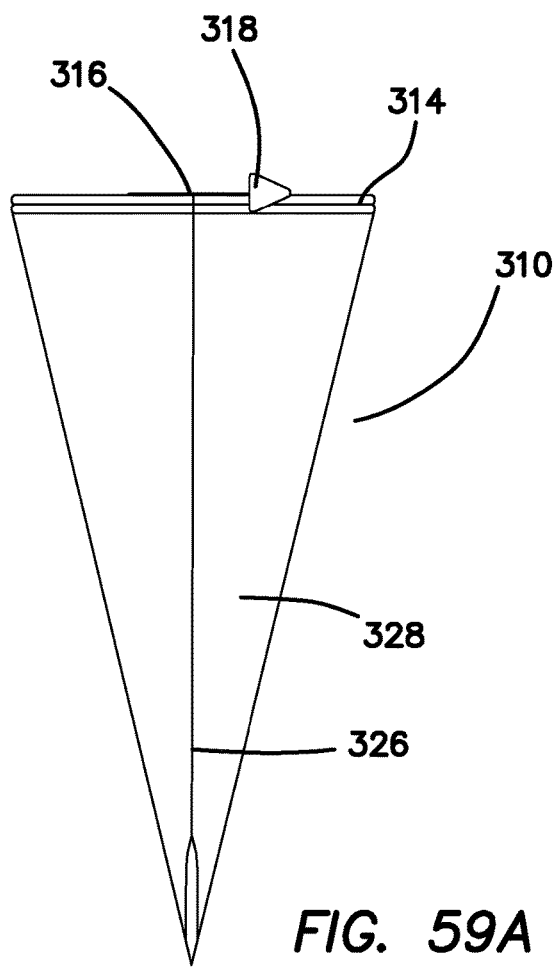
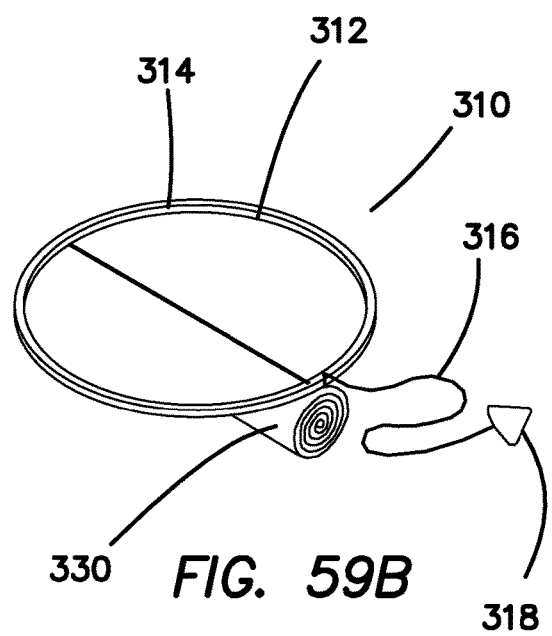
FIG. 59A
FIG. 59B

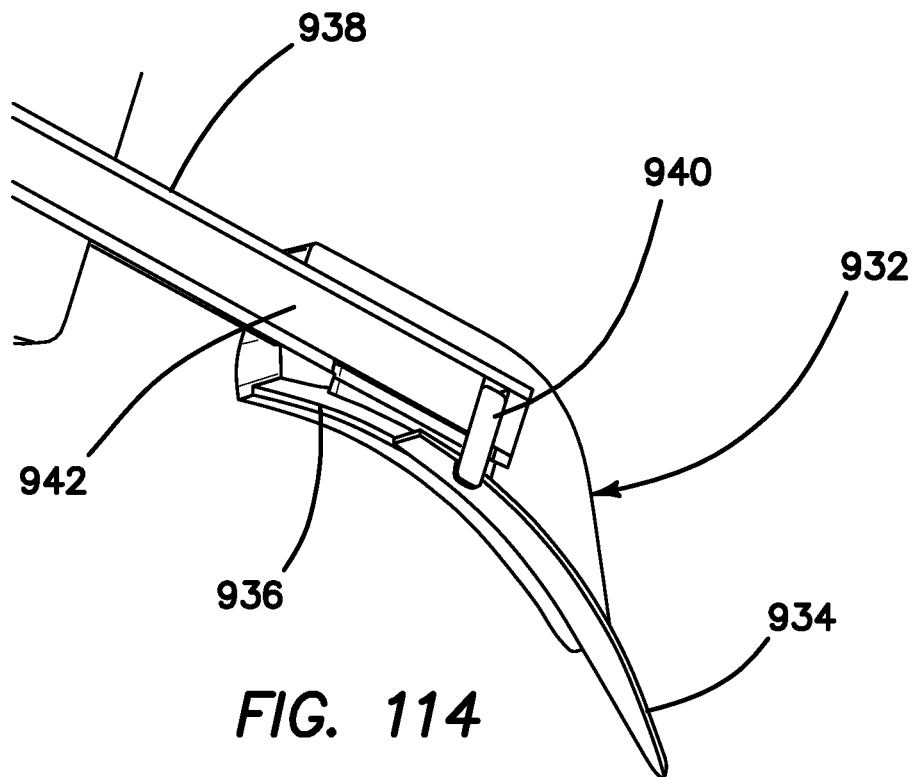
FIG. 114
FIG. 115
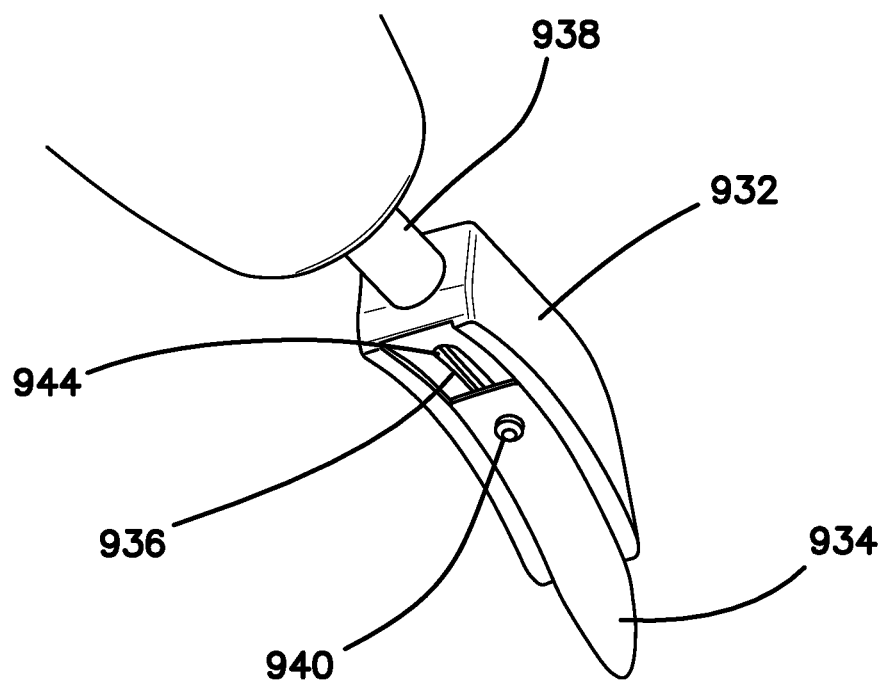

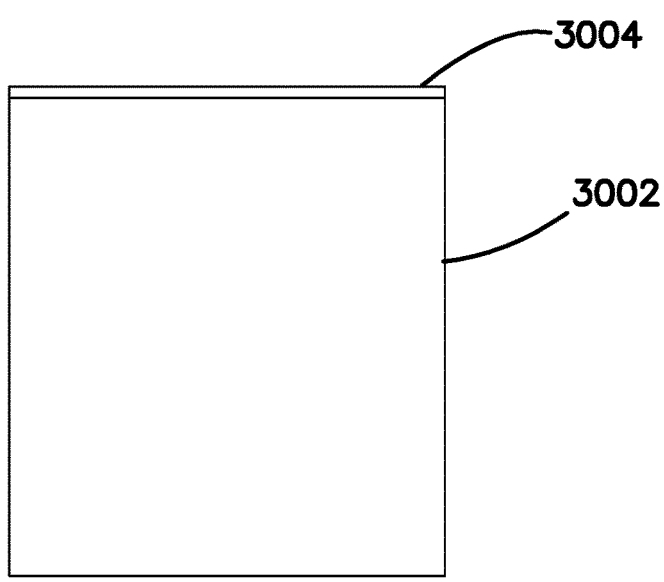
FIG. 135A
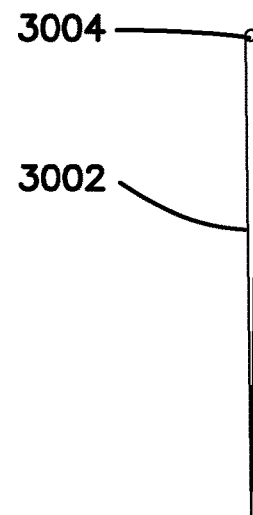
FIG. 135D
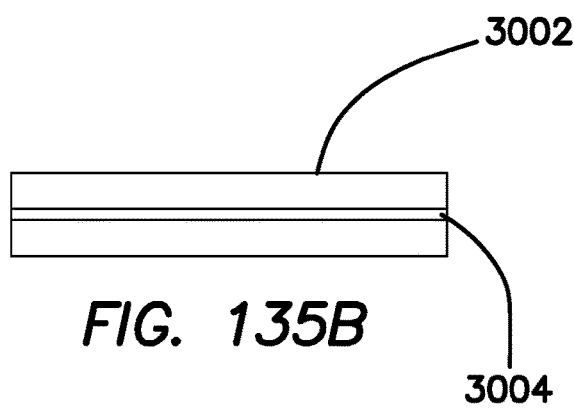
FIG. 135B
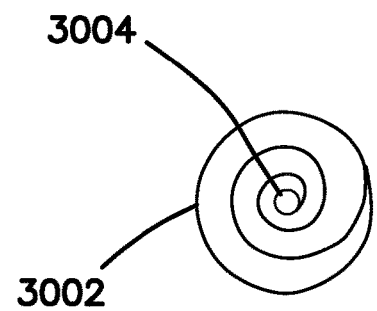
FIG. 135C
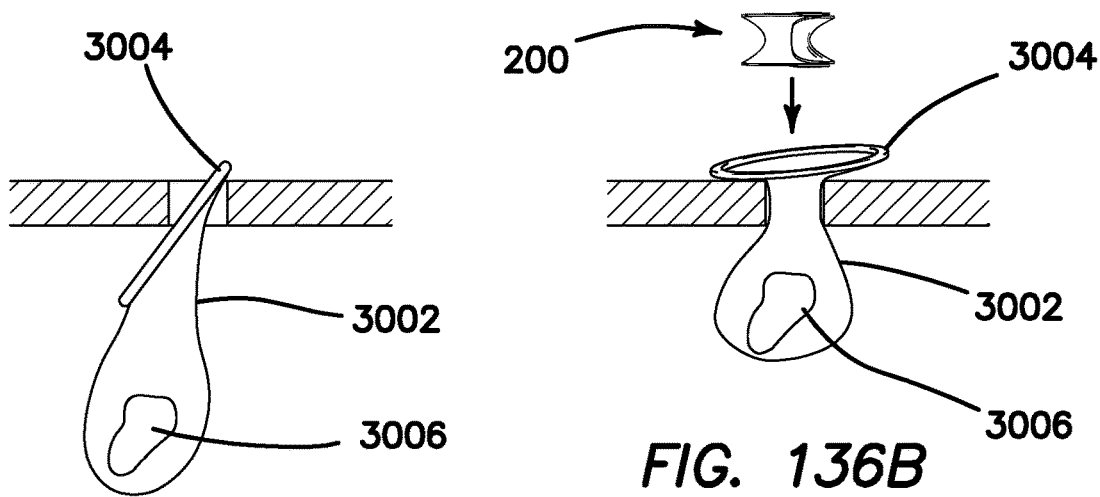
FIG. 136A
FIG. 136B

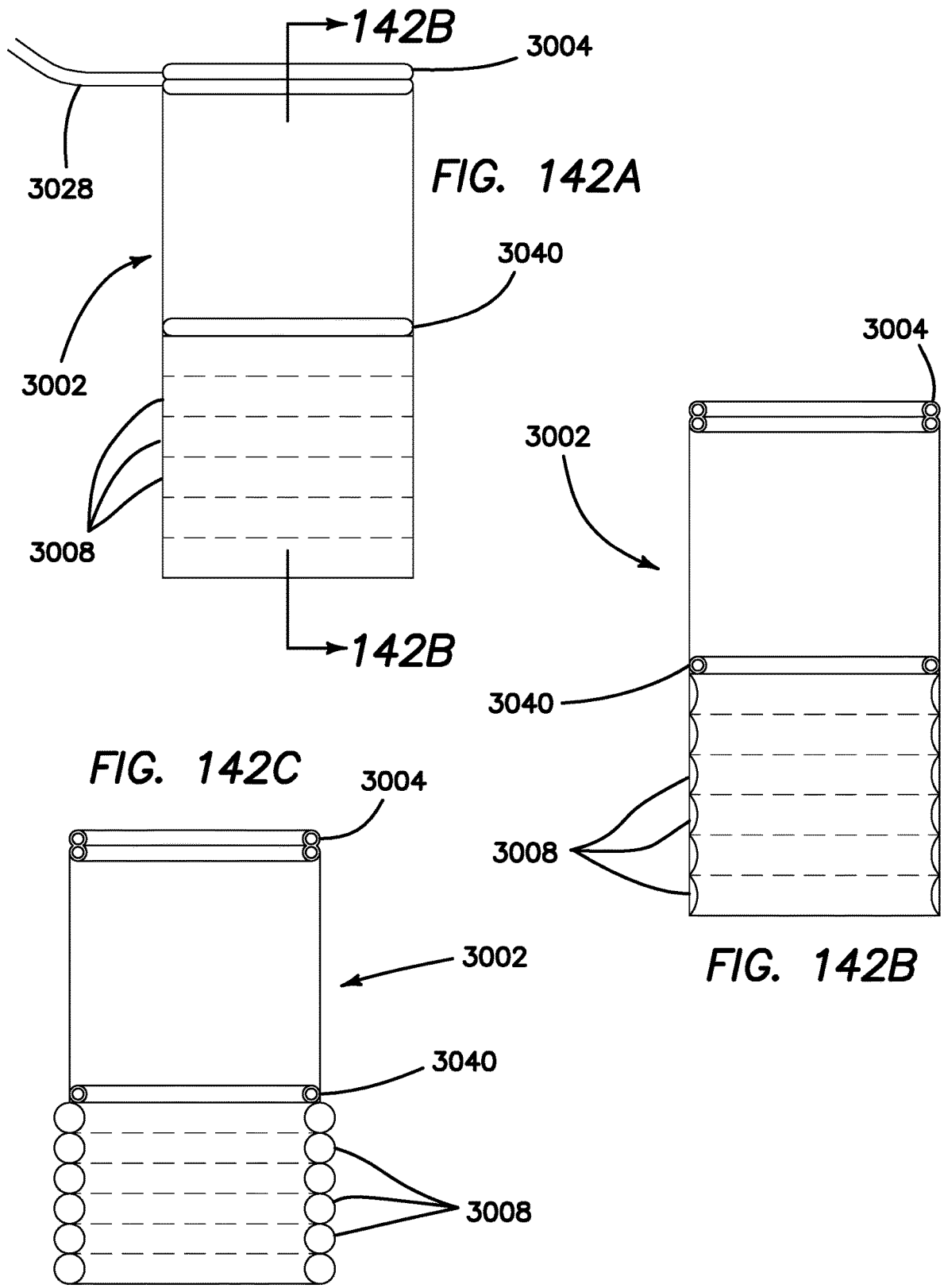

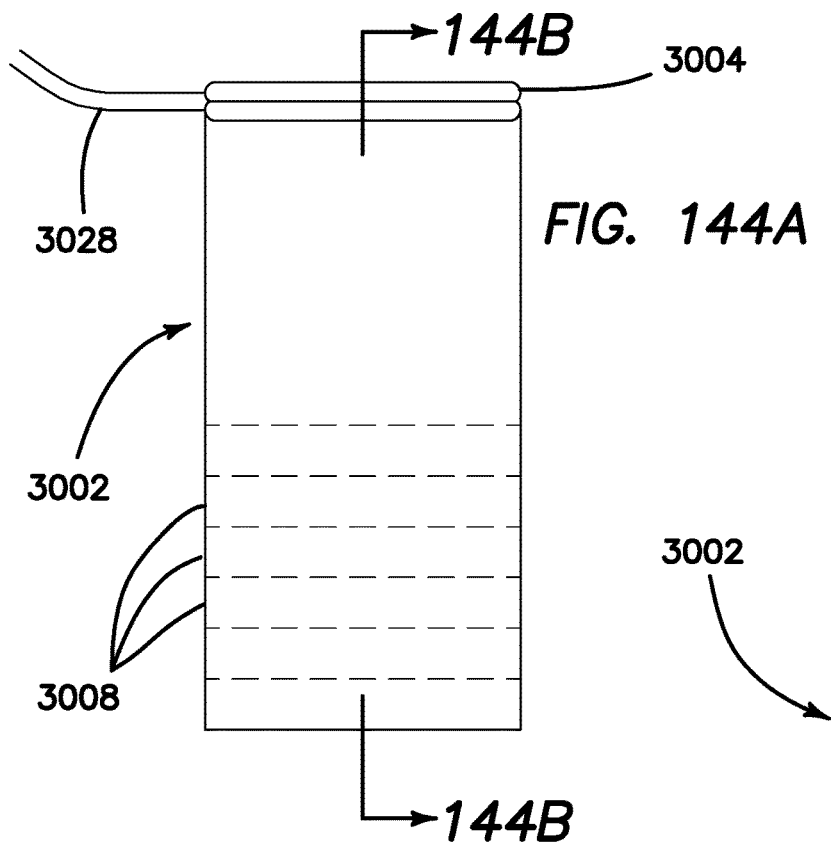
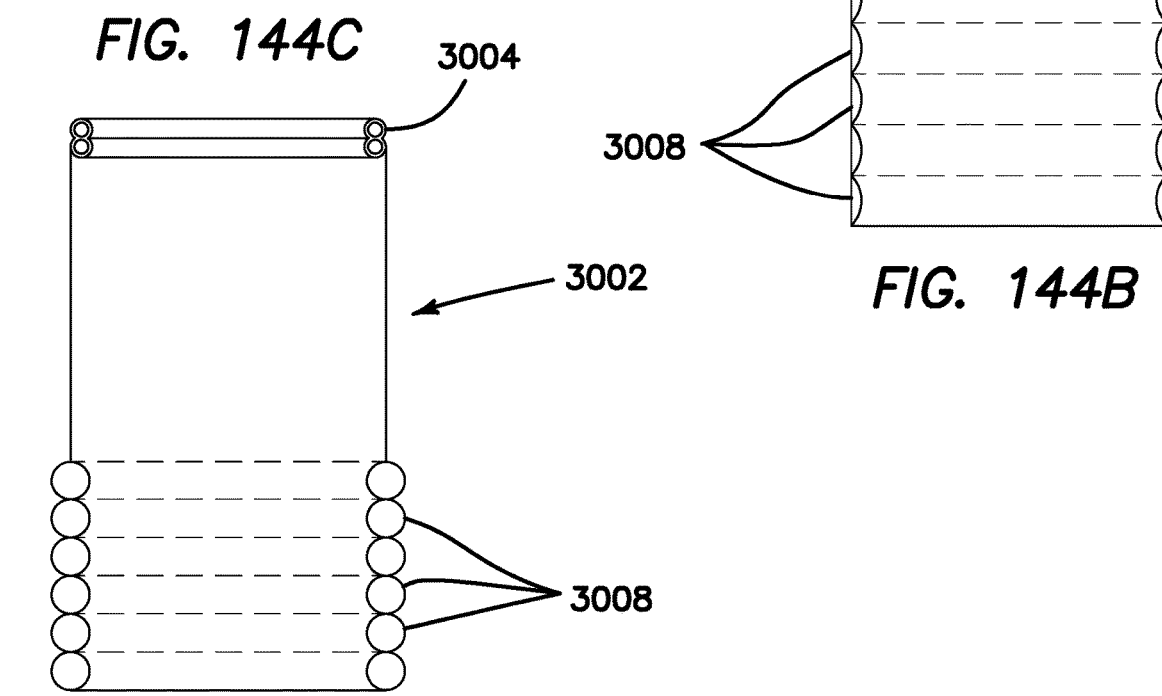
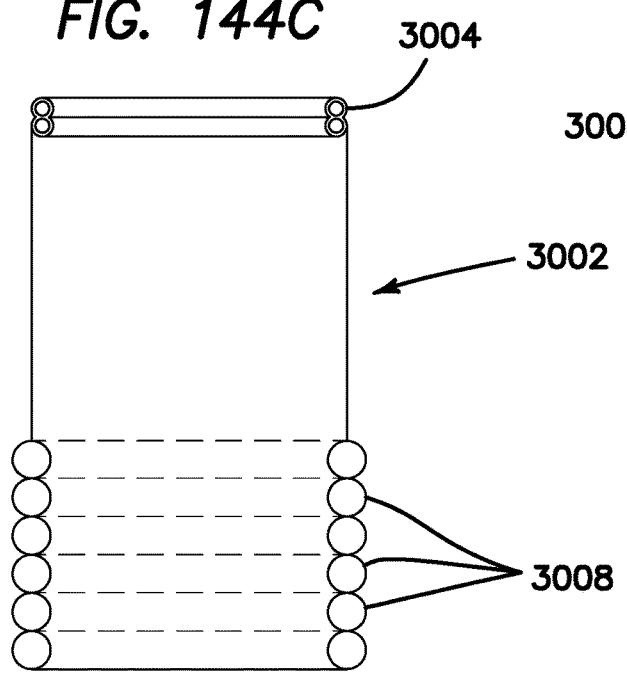

SYSTEMS AND METHODS FOR TISSUE REMOVAL

CROSS-REFERENCE TO RELATED APPLICATIONS

This application is a continuation of U.S. patent application Ser. No. 16/249,123 entitled "Systems and methods for tissue removal" filed Jan. 16, 2019, which is a continuation of U.S. patent application Ser. No. 15/068,366 entitled "Systems and methods for tissue removal" filed Mar. 11, 2016, now U.S. Pat. No. 10,219,831, issued Mar. 5, 2019, which is a continuation of International Application No. PCT/US2015/056978 entitled "Systems and methods for tissue removal" filed on Oct. 22, 2015, which claims priority to and benefit of U.S. Provisional Patent Application Ser. No. 62/079,171 entitled "Systems and methods for tissue removal" filed on Nov. 13, 2014, U.S. Provisional Patent Application Ser. No. 62/081,297 entitled "Systems and methods for tissue removal" filed on Nov. 18, 2014, and U.S. Provisional Patent Application Ser. No. 62/107,107 entitled "Cut-resistant retracting tissue bag" filed on Jan. 23, 2015, all of which are hereby incorporated herein by reference in their entireties.

FIELD OF THE INVENTION

This invention relates to medical devices, and in particular, to systems and methods for the removal of tissue through a body opening.

BACKGROUND OF THE INVENTION

Systems and methods for the surgical removal of tissue through body openings including small incision sites and/or body orifices are described. Where needed, a small incision is made in a patient to access surgically targeted tissue located inside a body cavity. Surgically targeted tissue may also be approached through a body orifice without an initial incision. Sometimes the targeted tissue is approached directly through the incision or body orifice. Other times, an access device system is placed and/or positioned into, across, at, and/or within the incision and/or body orifice to retract tissue, enlarge, reshape, and/or isolate the incision or body orifice. The access device system serves as a portal for accessing targeted tissue that is located in or adjacent to the body cavity or body orifice. The targeted tissue is detached from adjacent and surrounding tissue employing known surgical techniques and procedures. Once freed, the targeted tissue is ready for removal through the small incision or body orifice. If the targeted tissue is too large to be removed in whole, then it is reduced in size and removed in parts through the small incision. Ideally, the surgeon will "core" or "peel" the targeted tissue to keep it in one piece as much as possible. However, more likely than not, the targeted tissue will be reduced into multiple pieces.

Reducing the size of the targeted tissue is called morcellation. A morcellation procedure includes cutting the targeted tissue into smaller pieces manually with a scalpel or knife, for example, or employing a power morcellator to cut the targeted tissue so that it is removable through the small incision. Pieces of the targeted tissue are removed from the patient through the small incision. As the targeted tissue is being reduced in size in order to fit through the small incision, small pieces of tissue may be cut off and left behind in the patient. As such, morcellation is contraindicated in cases of malignancy or endometriosis. If cancer is morcellated, it can spread malignant tissue and upstage cancer and increase patient mortality.

A hysterectomy is an example of a surgical procedure that may involve morcellation. More than 500,000 hysterectomies are performed annually on women in the United States. Common reasons that a woman may have a hysterectomy are the presence of fibroids, cancer, endometriosis or prolapse. Of these hysterectomies, about 200,000 are performed laparoscopically. When the uterus is too large (>300 g) to be removed through the vagina or if the cervix is still in place, the specimen must be reduced in size to be removed through an abdominal incision or through the vagina. During myomectomy (fibroid removal), large fibroids may also need to be extracted using a morcellation procedure. During morcellation, the targeted tissue (usually a uterus and sometimes adnexal structures) is brought to the abdominal wall surface such as with a tissue grasper and is reduced in size using a blade and removed through the incision from the pelvic cavity. In another variation, the targeted tissue is removed through a body orifice such as through the vagina. Fibroids, or uterine leiomyoma, account for about 30-40% of hysterectomies. These are benign tumors of the uterus that can lead to heavy and painful bleeding. In the past there has been a mild concern that these tumors could be undetected cancer, or Leiomyosarcoma, and it was believed to affect about 1 in 10,000 women. More recent data has come out to support a much higher risk of undetected malignancy in these tumors, putting the range at 1:1000 to 1:400. Because of this elevated risk, many surgeons have begun changing their technique to try to enclose the specimen to do a closed morcellation process by morcellating in a bag to contain errant pieces and prevent dispersion and seeding of tumor cells, rather than morcellating without a bag in a process called open morcellation. Many GYN societies, including AAGL, ACOG, and SGO, have released statements warning of the potential danger of open morcellation. On Apr. 17 2014, the FDA issued a statement discouraging the use of open power morcellation for hysterectomies and myomectomies for women undergoing these procedures for fibroids. The FDA also increased their estimated of malignant likelihood to 1 in 350. For these reasons, systems and methods are needed to safely and effectively reduce tissue specimens. The present invention sets forth such safe systems and methods for both manual morcellation and power morcellation performed in a closed system.

SUMMARY OF THE INVENTION

According to one aspect of the invention, a system for removing a tissue specimen through a body opening defining a tissue margin is provided. The system includes a shield. The shield includes a band made of flexible cut-resistant material. The band has an inner surface and an outer surface interconnected by a top end and a bottom end and by a first end and a second end. The band is configured to define a central lumen having a longitudinal axis. The central lumen has a lumen diameter that is perpendicular to the longitudinal axis. The band is split such that the band is movable into a reduced configuration wherein at least a portion of the outer surface at the first end overlaps and is in juxtaposition with the inner surface at the second end to form a spiral and define an overlapping portion. The shield is configured to have a variable lumen diameter by varying the overlapping portion. The shield includes a locking mechanism configured to fix the lumen diameter. The locking mechanism includes at least one inner abutment formed on the inner surface. The inner abutment extends along the longitudinal axis along at least a portion of the band between the top end and the bottom end. The first end of the band is configured to contact the inner abutment to prevent reduction of the inner diameter in a locked configuration.

According to another aspect of the invention, a system for removing a tissue specimen through a body opening defining a tissue margin is provided. The system includes a shield. The shield includes a band made of flexible cut-resistant material. The band has an inner surface and an outer surface interconnected by a top end and a bottom end and by a first end and a second end. The band is configured to define a central lumen having a longitudinal axis. The central lumen has a lumen diameter that is perpendicular to the longitudinal axis. The band is split such that the band is movable into a reduced configuration wherein at least a portion of the outer surface at the first end overlaps and is in juxtaposition with the inner surface at the second end to form a spiral and define an overlapping portion. The shield is configured to have a variable lumen diameter by varying the overlapping portion. The shield includes a locking mechanism configured to fix the lumen diameter. The locking mechanism includes at least one inner abutment formed on the inner surface and at least one outer abutment formed on the outer surface. The inner abutment and the outer abutment extend along the longitudinal axis along at least a portion of the band between the top end and the bottom end. The at least one inner abutment is configured to contact the at least outer abutment inner abutment to prevent reduction of the inner diameter in a locked configuration.

According to another aspect of the invention, a system for removing a tissue specimen through a body opening defining a tissue margin is provided. The system includes a shield. The shield includes a band made of flexible cut-resistant material. The band has an inner surface and an outer surface interconnected by a top end and a bottom end and by a first end and a second end. The band is configured to define a central lumen having a longitudinal axis. The central lumen has a lumen diameter that is perpendicular to the longitudinal axis. The band is split such that the band is movable into a reduced configuration wherein at least a portion of the outer surface at the first end overlaps and is in juxtaposition with the inner surface at the second end to form a spiral and define an overlapping portion. The shield is configured to have a variable lumen diameter by varying the overlapping portion. The shield includes a locking mechanism configured to fix the lumen diameter. The locking mechanism including at least one inner abutment formed in the inner surface. The at least one inner abutment is configured to contact one of the first end or at least one outer abutment formed in the outer surface to define a locked configuration having a locked lumen diameter.

BRIEF DESCRIPTION OF THE DRAWINGS

FIG. 9 is an end view of a guard according to the present invention.

FIG. 10 is a cross-sectional view taken along line 10-10 of FIG. 9 of a guard according to the present invention.

FIG. 11 is a top perspective view of a cap according to the present invention.

FIG. 50C is a top perspective view of a containment bag according to the present invention.

FIG. 50D is a top perspective view of a containment bag according to the present invention.

FIG. 56A is a top perspective view of a semi-rigid rod prior to being formed into a ring for a containment bag according to the present invention.

FIG. 56B is a top perspective view of a ring of a containment bag according to the present invention.

FIG. 59A is a side view of a containment bag according to the present invention.

FIG. 59B is a top perspective view of a containment bag according to the present invention.

FIG. 101 is a cross-sectional, top perspective view of a retractor and guard according to the present invention.

FIG. 102 is a sectional, top perspective view of a retractor and guard according to the present invention.

FIG. 103 is a semi-transparent, top perspective view of a retractor and guard according to the present invention.

FIG. 104 is a side view of a guard according to the present invention.

FIG. 105 is a top view of a guard according to the present invention.

FIG. 106 is a top perspective view of a retractor and a guard according to the present invention.

FIG. 107 is a top view of a retractor and guard according to the present invention.

FIG. 108 is a bottom perspective view of a guard according to the present invention.

FIG. 109A is a top perspective view of a guard according to the present invention.

FIG. 109B is a top perspective view of guard according to the present invention.

FIG. 109C is a bottom perspective view of a guard according to the present invention.

FIG. 109D is a top view of a guard according to the present invention.

Figure 109A:
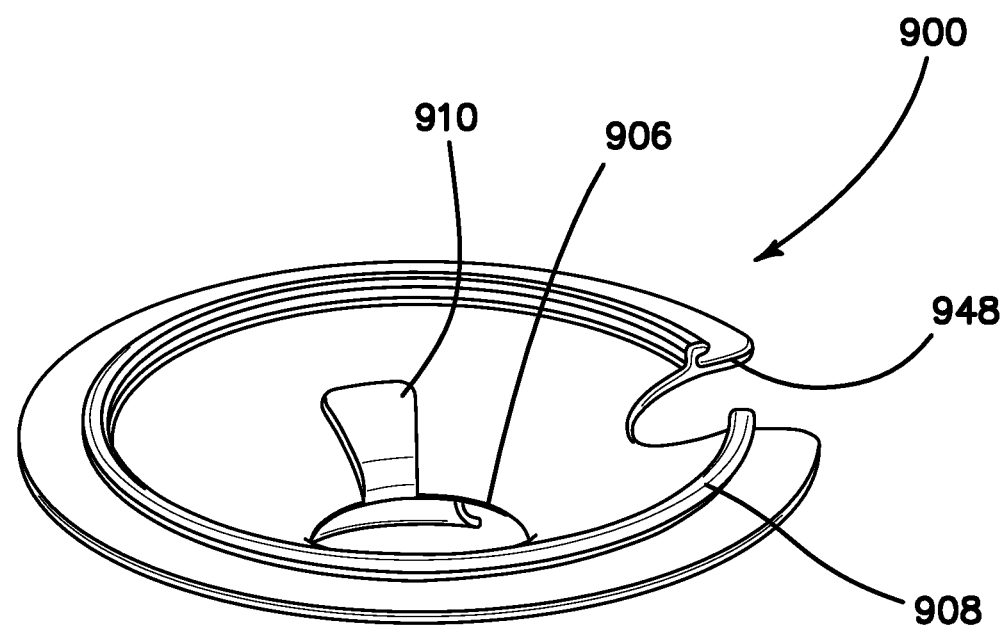
Figure 109B:
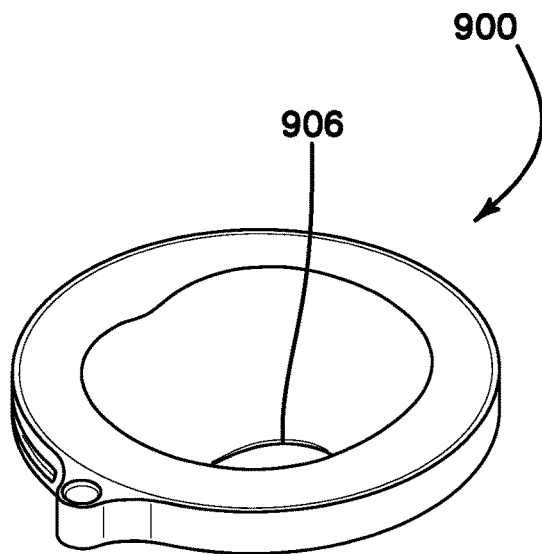
Figure 109C:
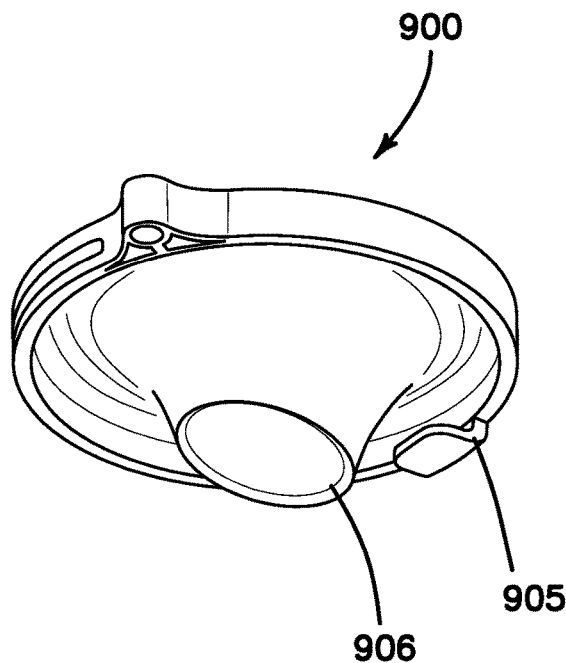
Figure 109D:
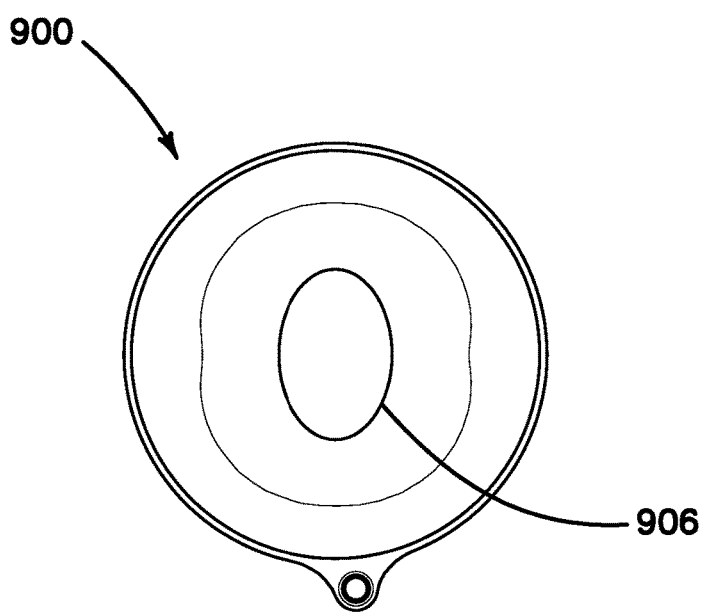
Figure 109E:
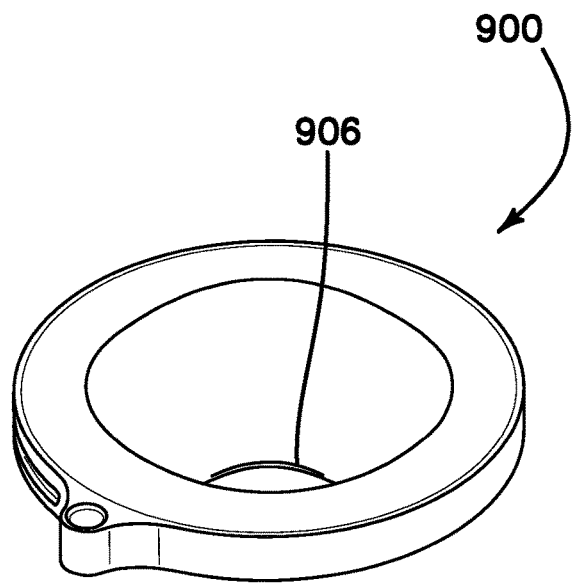

FIG. 109E is a top perspective view of a guard according to the present invention.

Figure 109F:
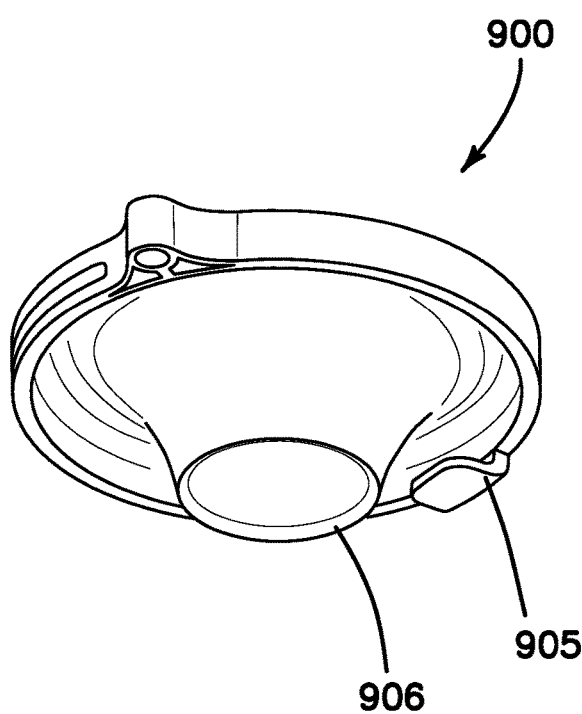

FIG. 109F is a bottom perspective view of a guard according to the present invention.

Figure 109G:
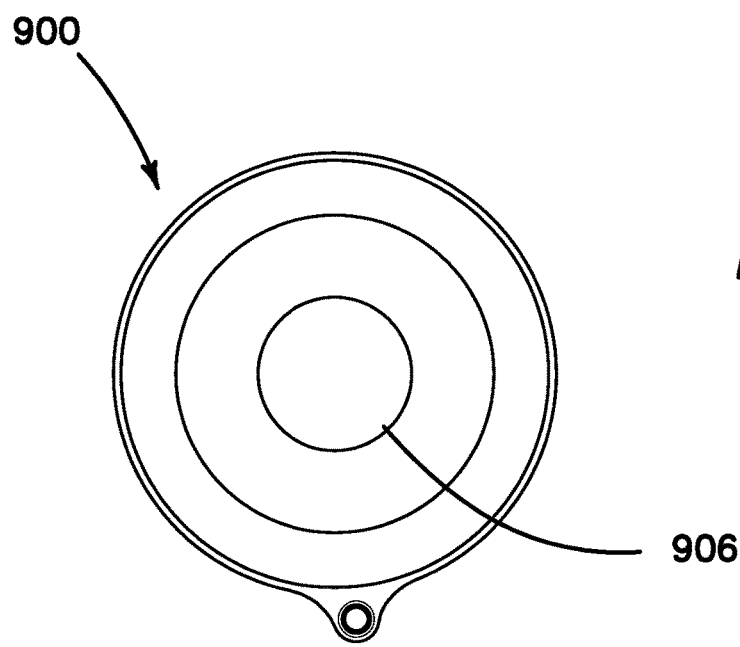

FIG. 109G is a top view of a guard according to the present invention.

Figure 110:
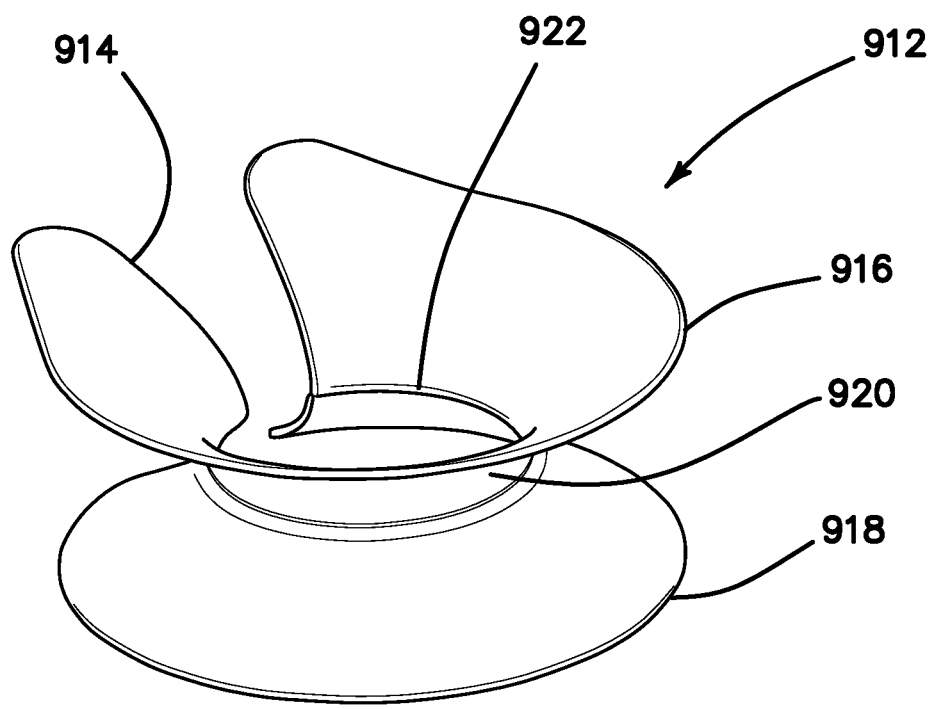

FIG. 110 is a top perspective view of a guard according to the present invention.

Figure 111:
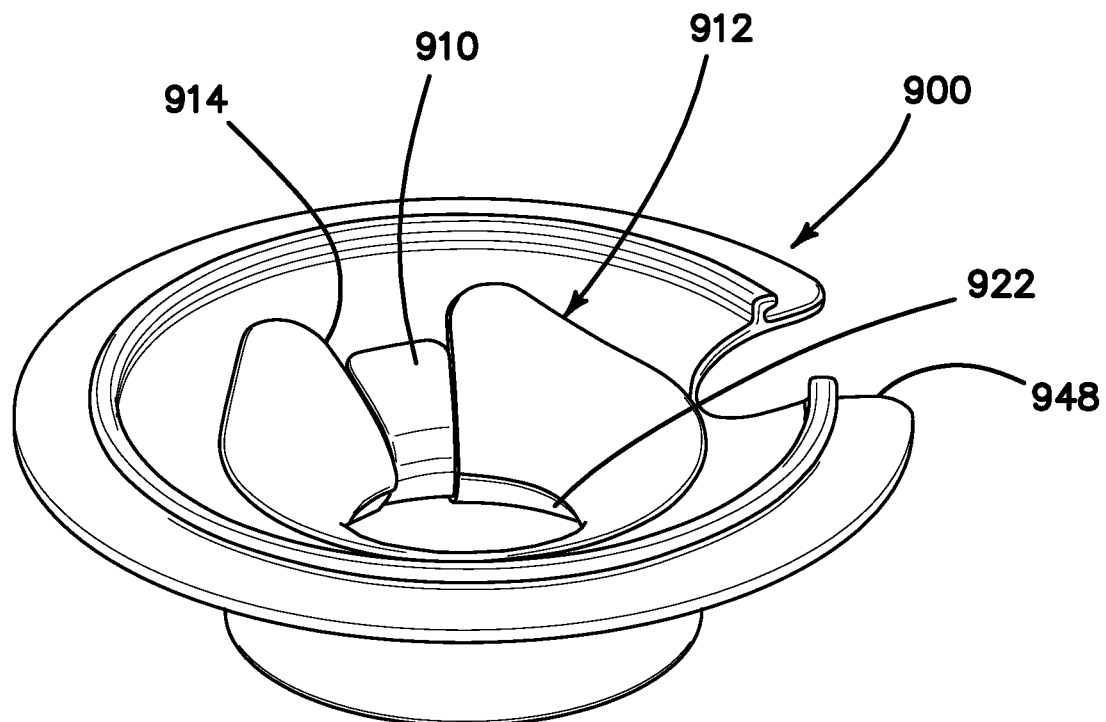

FIG. 111 is a top perspective of a two-piece guard according to the present invention.

Figure 112:
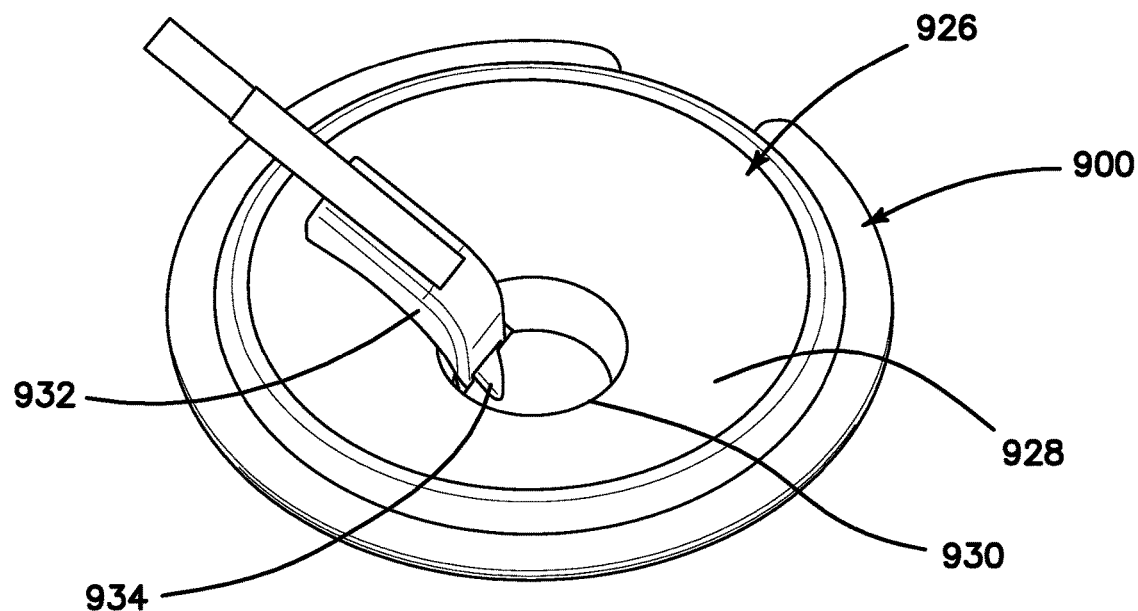

FIG. 112 is a top perspective view of a blade guard according to the present invention.

Figure 113:
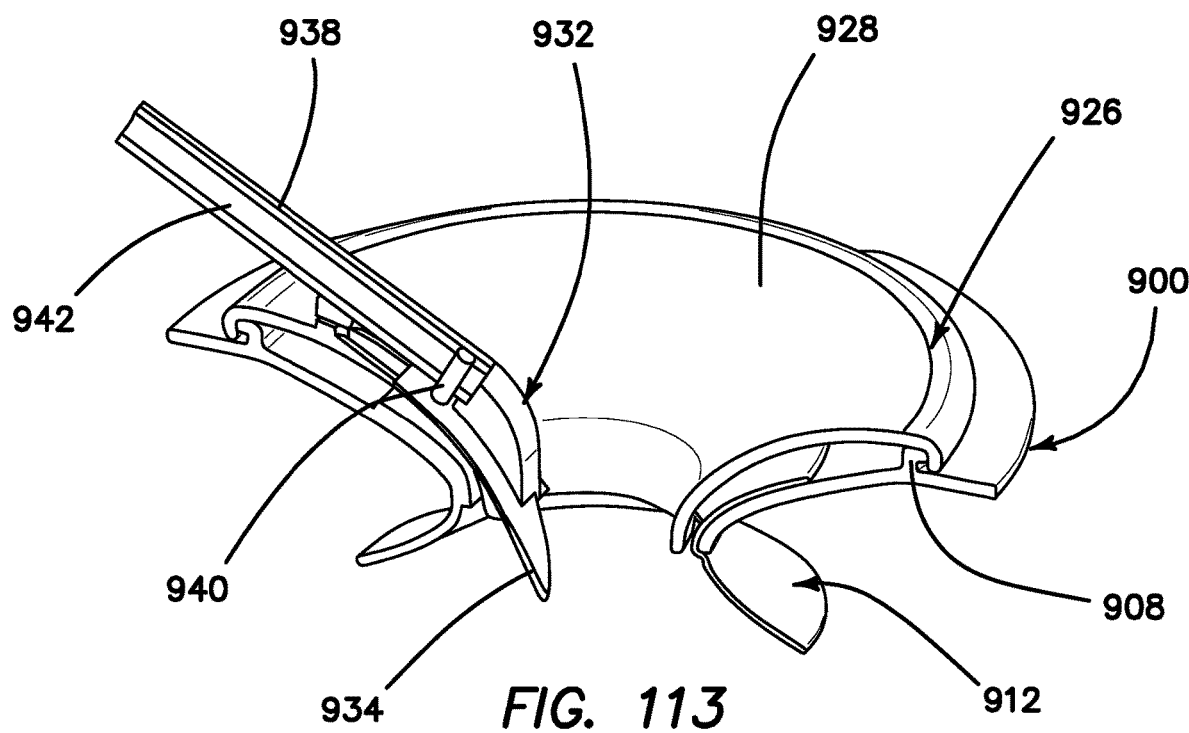

FIG. 113 is a cross-sectional, top perspective view of a blade guard according to the present invention.

FIG. 114 is a cross-sectional view of a blade receiver of a blade guard according to the present invention.

FIG. 115 is a bottom perspective view of a blade according to the present invention.

Figure 116:
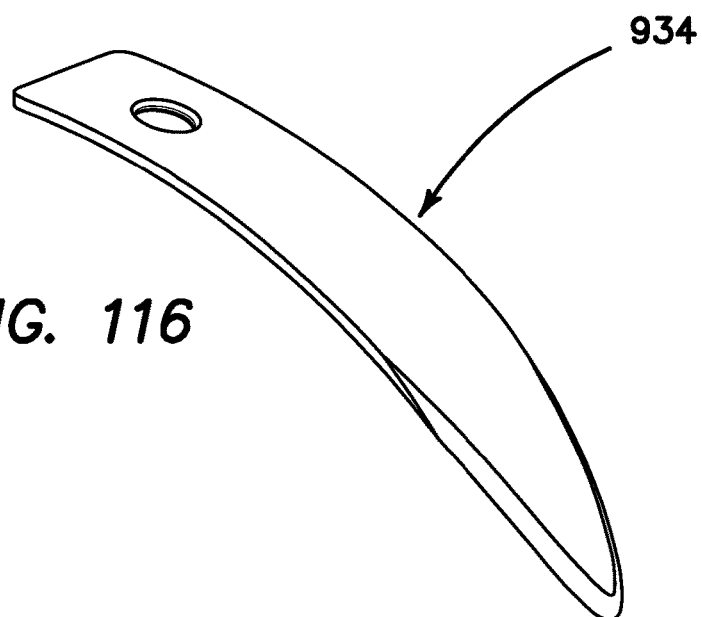

FIG. 116 is a top perspective view of a blade according to the present invention.

Figure 117:
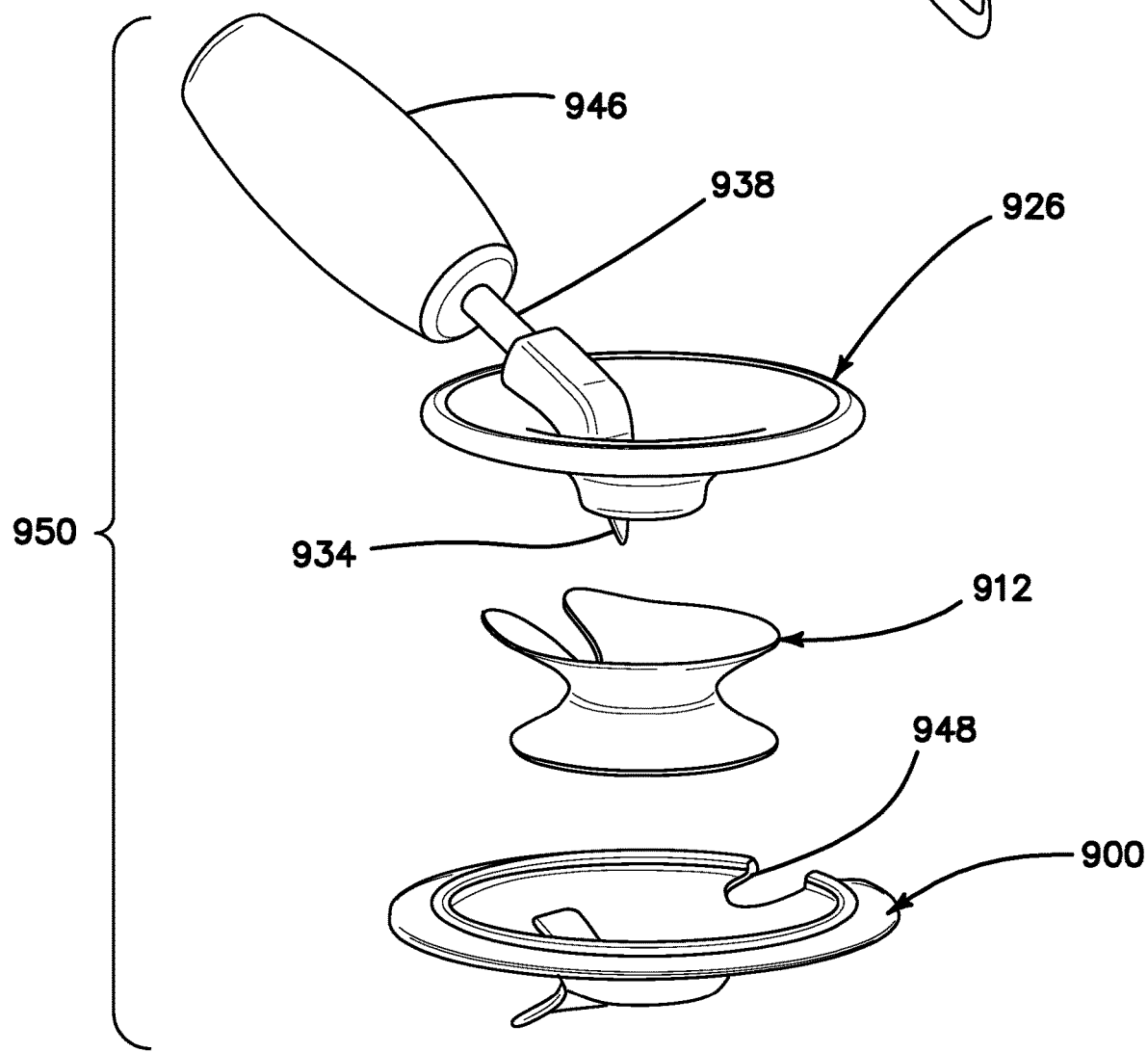

FIG. 117 is an exploded, top perspective view of a blade guard assembly according to the present invention.

Figure 118:
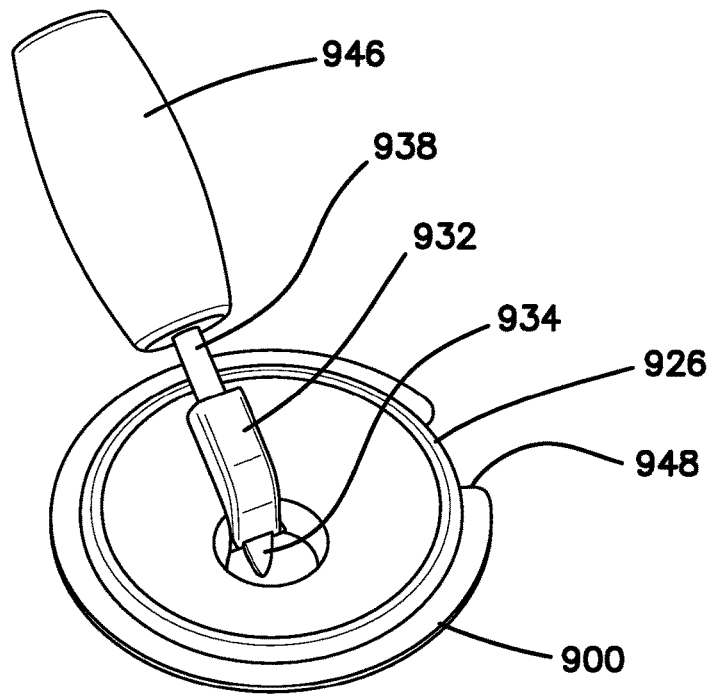

FIG. 118 is a top perspective is a top perspective view of a blade guard assembly according to the present invention.

Figure 119:
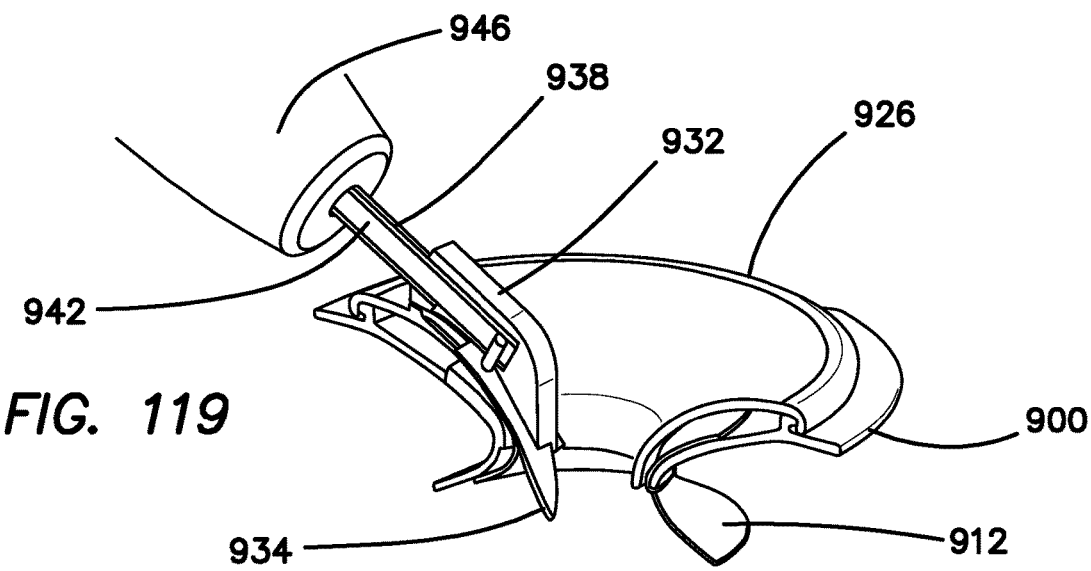

FIG. 119 is a cross-sectional, top perspective view of a blade guard assembly according to the present invention.

Figure 120:
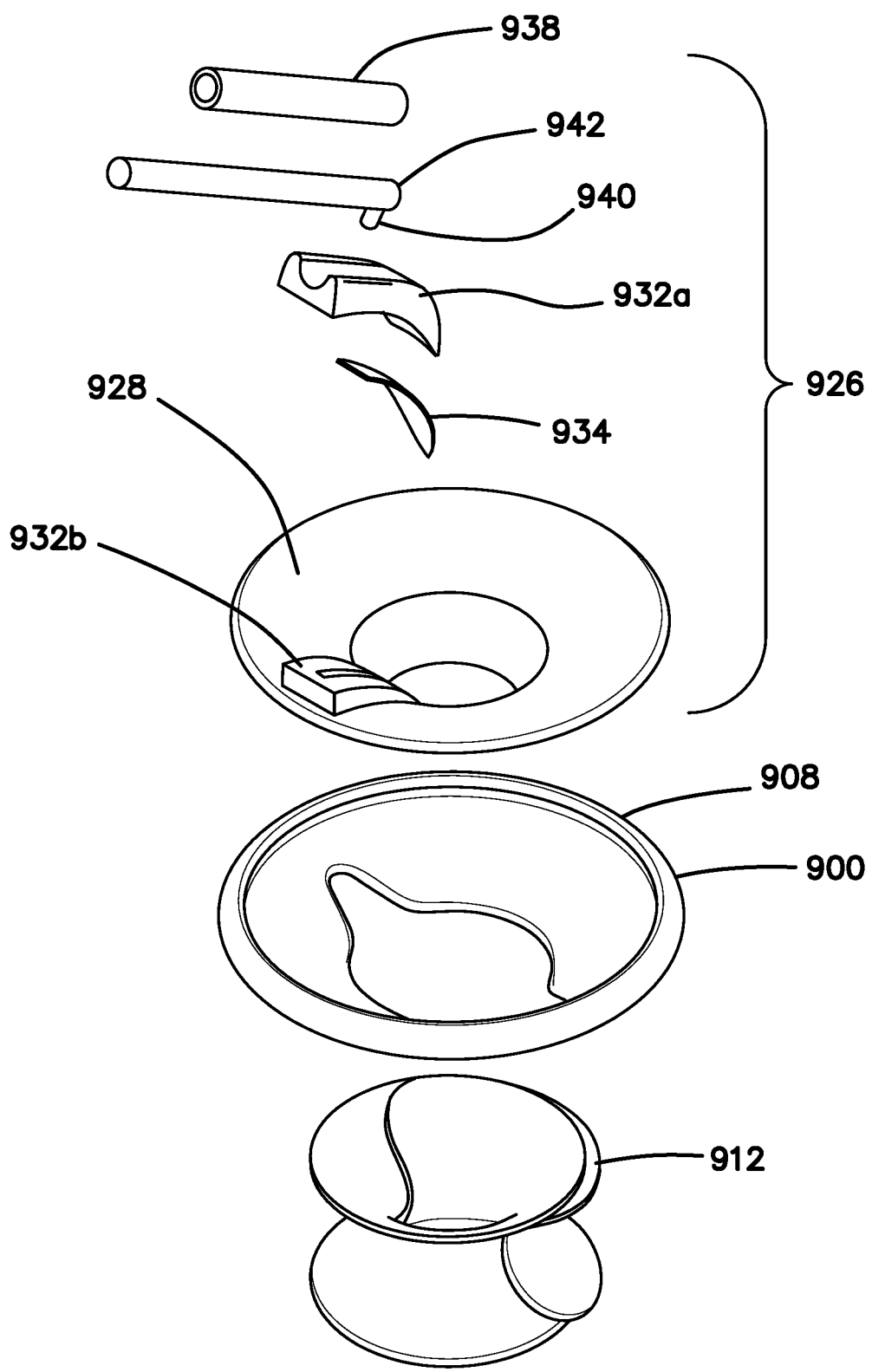

FIG. 120 is an exploded, top perspective view of a blade guard assembly according to the present invention.

Figure 121:
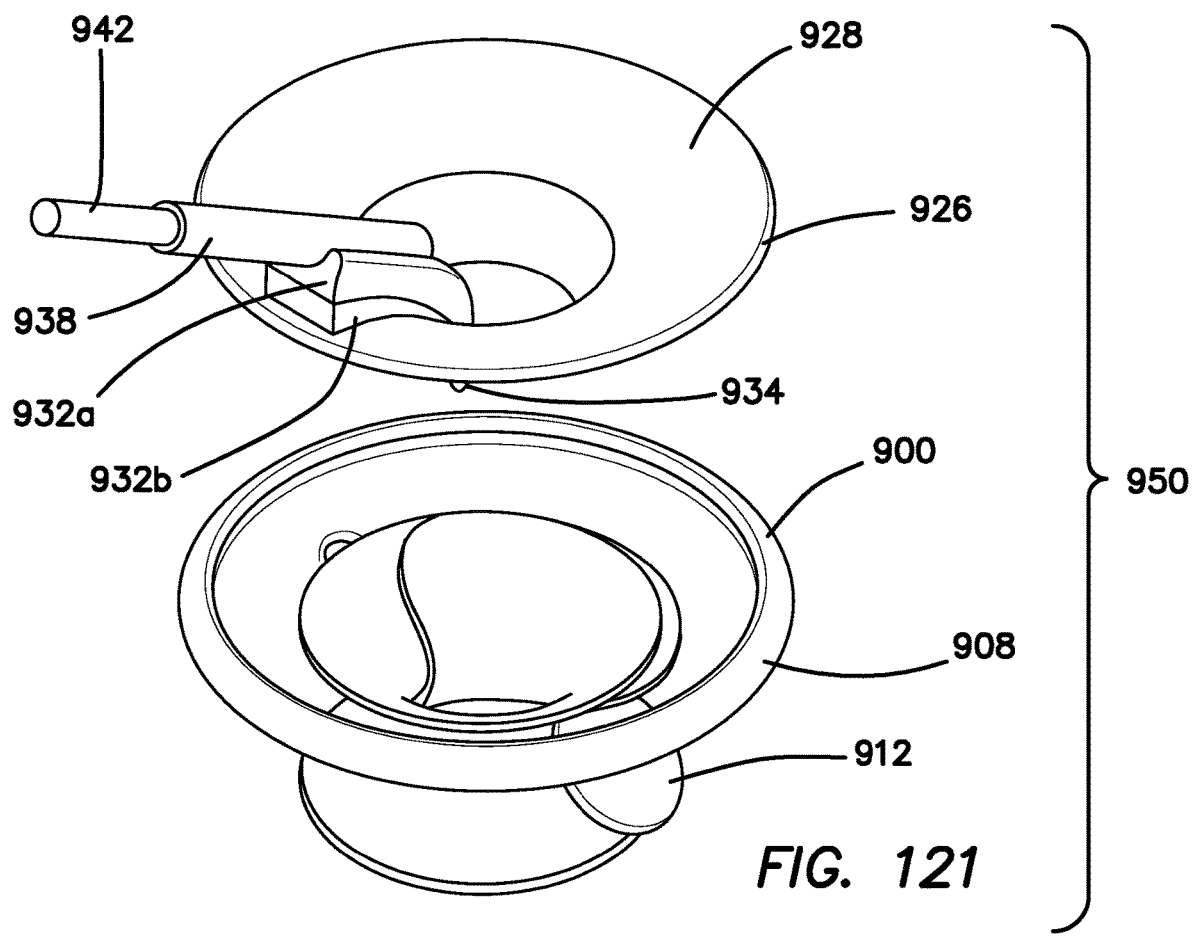

FIG. 121 is an exploded, top perspective view of a blade guard assembly according to the present invention.

Figure 122:
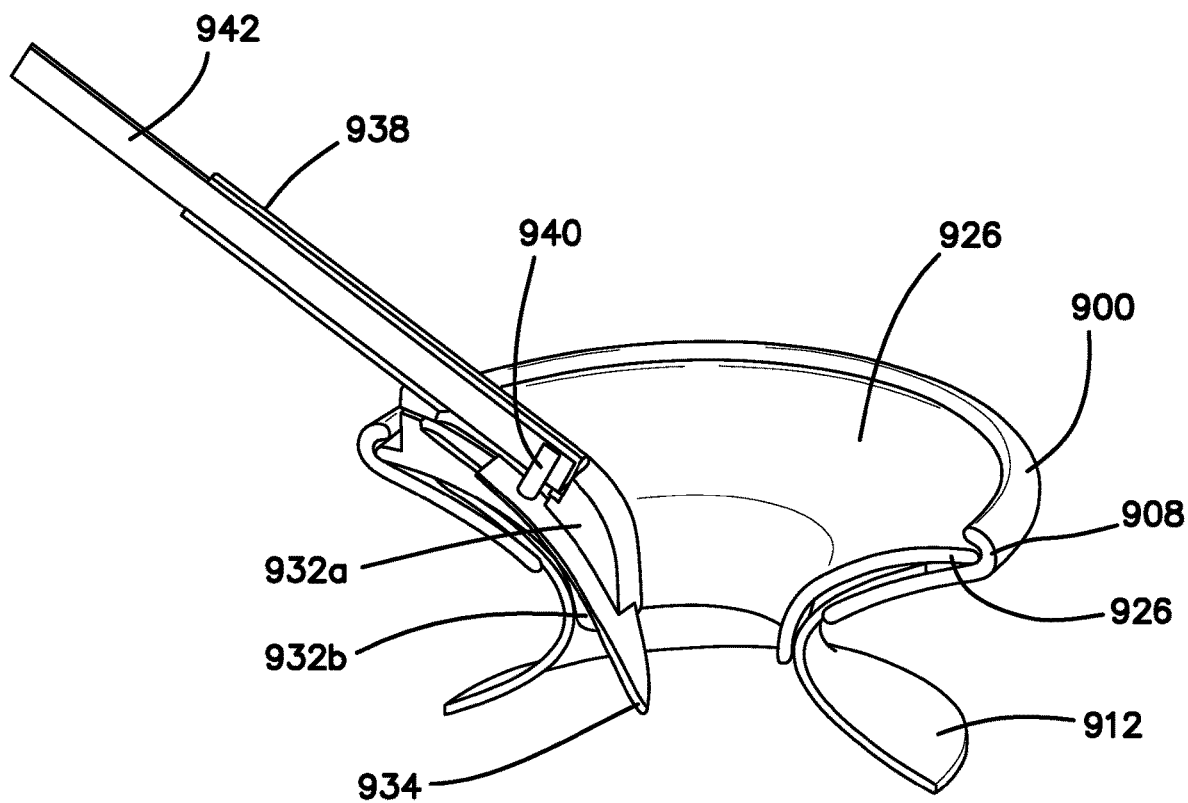

FIG. 122 is a cross-sectional, top perspective view of a blade guard assembly according to the present invention.

Figure 123:
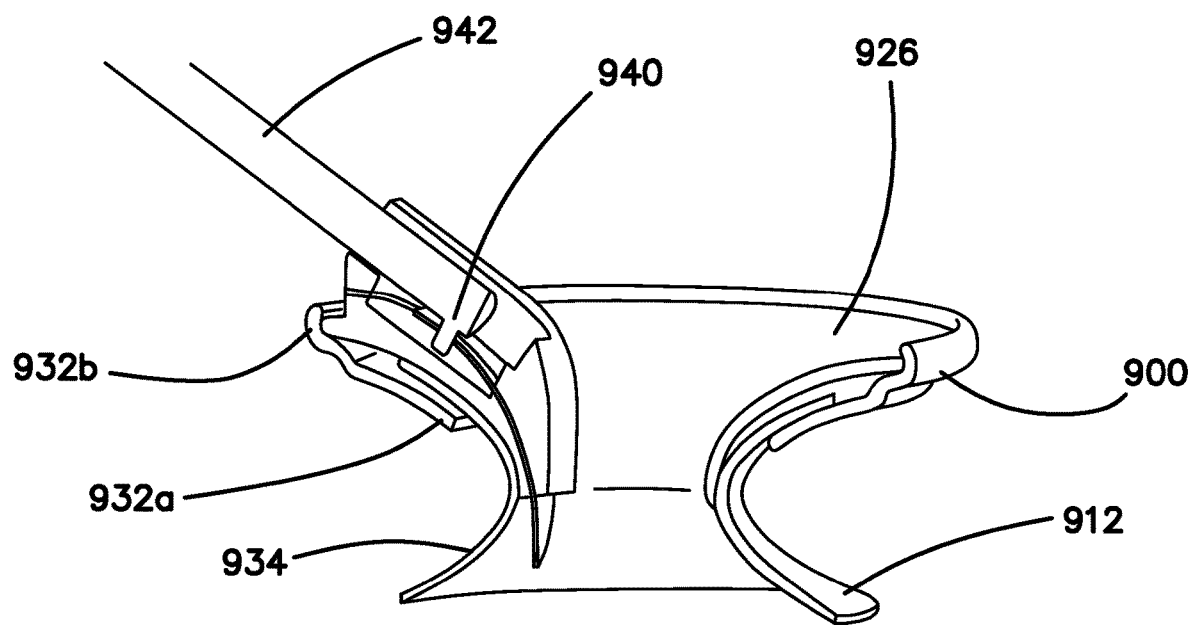

FIG. 123 is a cross-sectional, top perspective view of a blade guard assembly according to the present invention.

Figure 124:
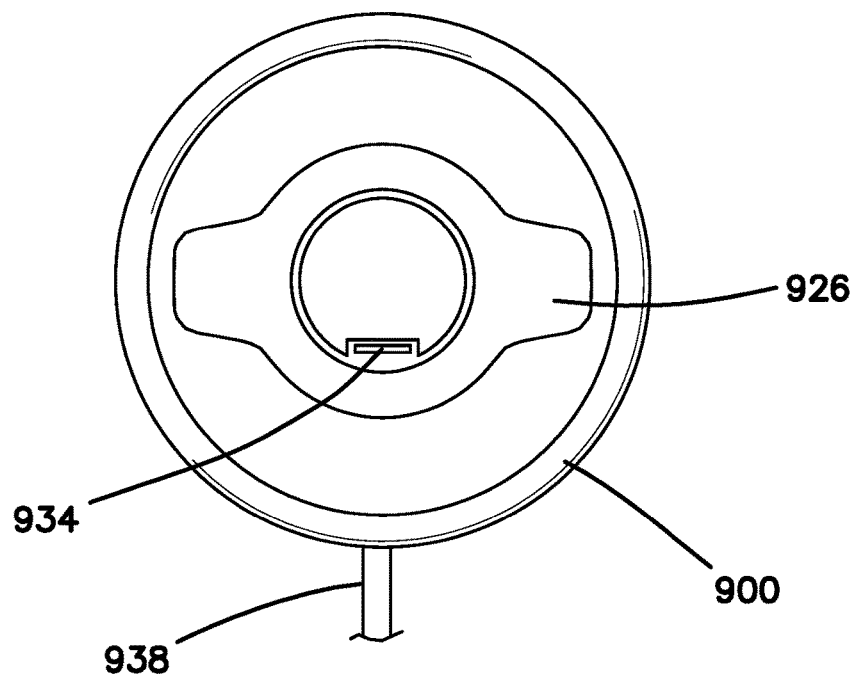

FIG. 124 is a bottom view of a blade guard assembly according to the present invention.

Figure 125:
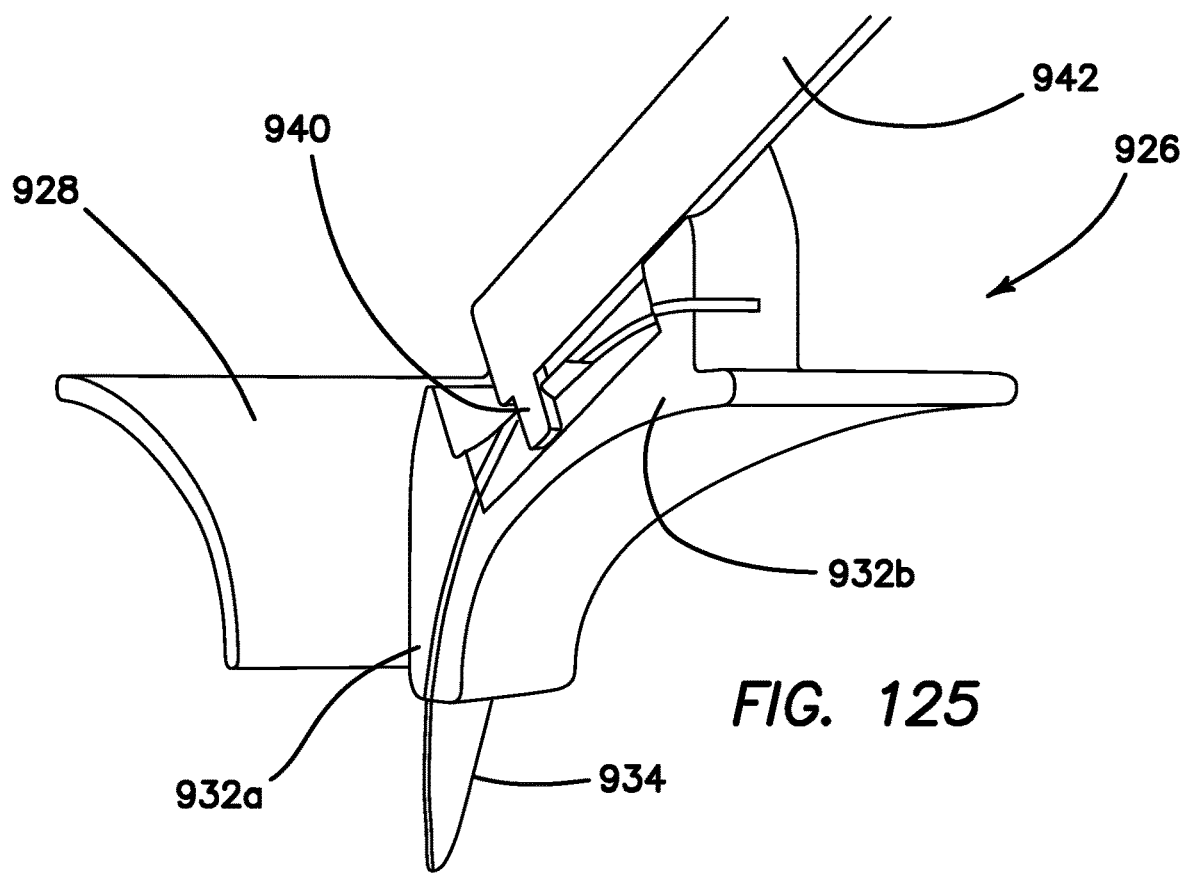

FIG. 125 is a sectional, top perspective view of a blade guard assembly according to the present invention.

Figure 126:
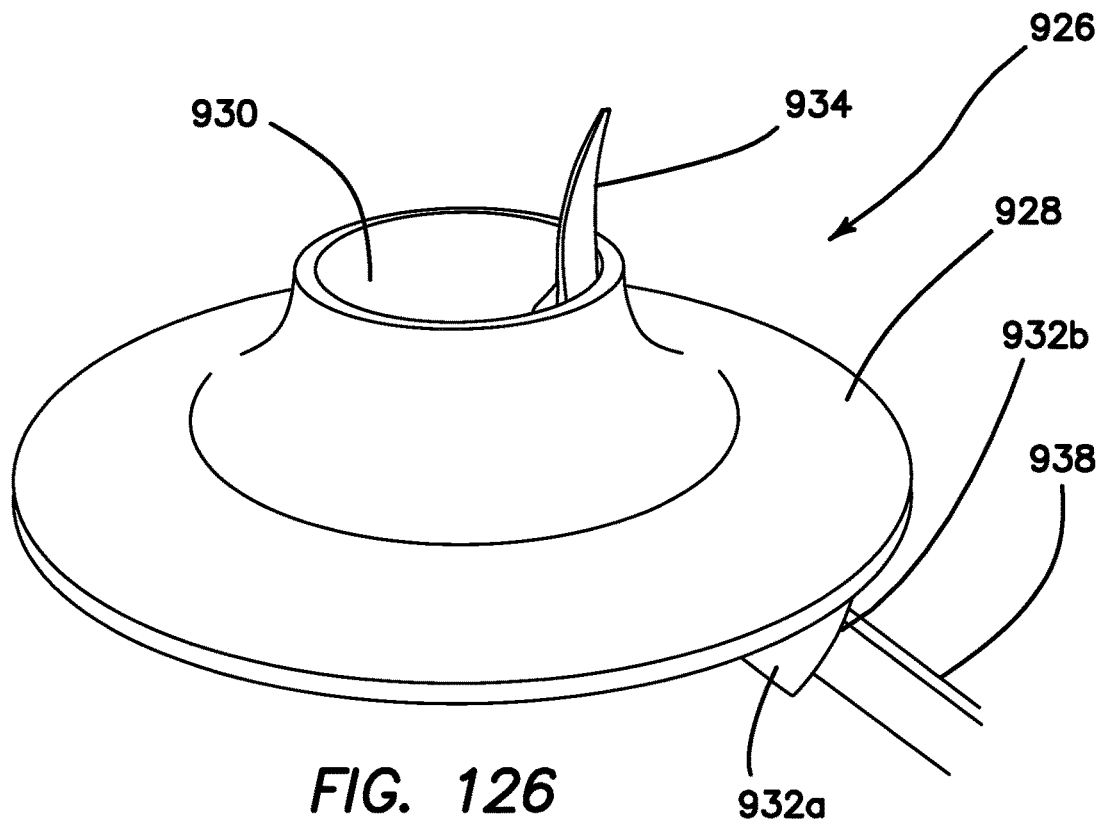

FIG. 126 is a bottom perspective view of a blade guard assembly according to the present invention.

Figure 127:
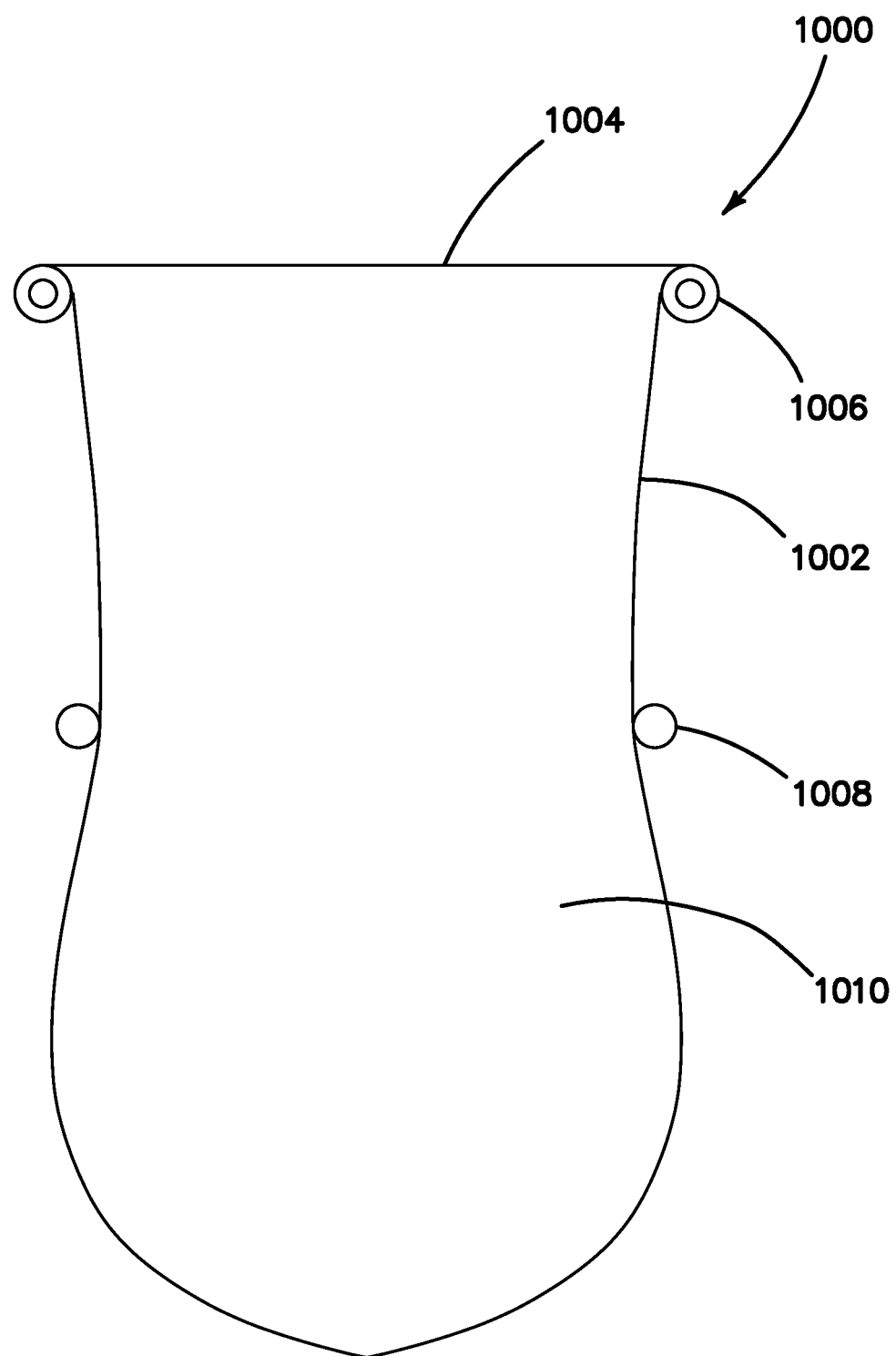

FIG. 127 is a side view of a containment bag according to the present invention.

Figure 128:
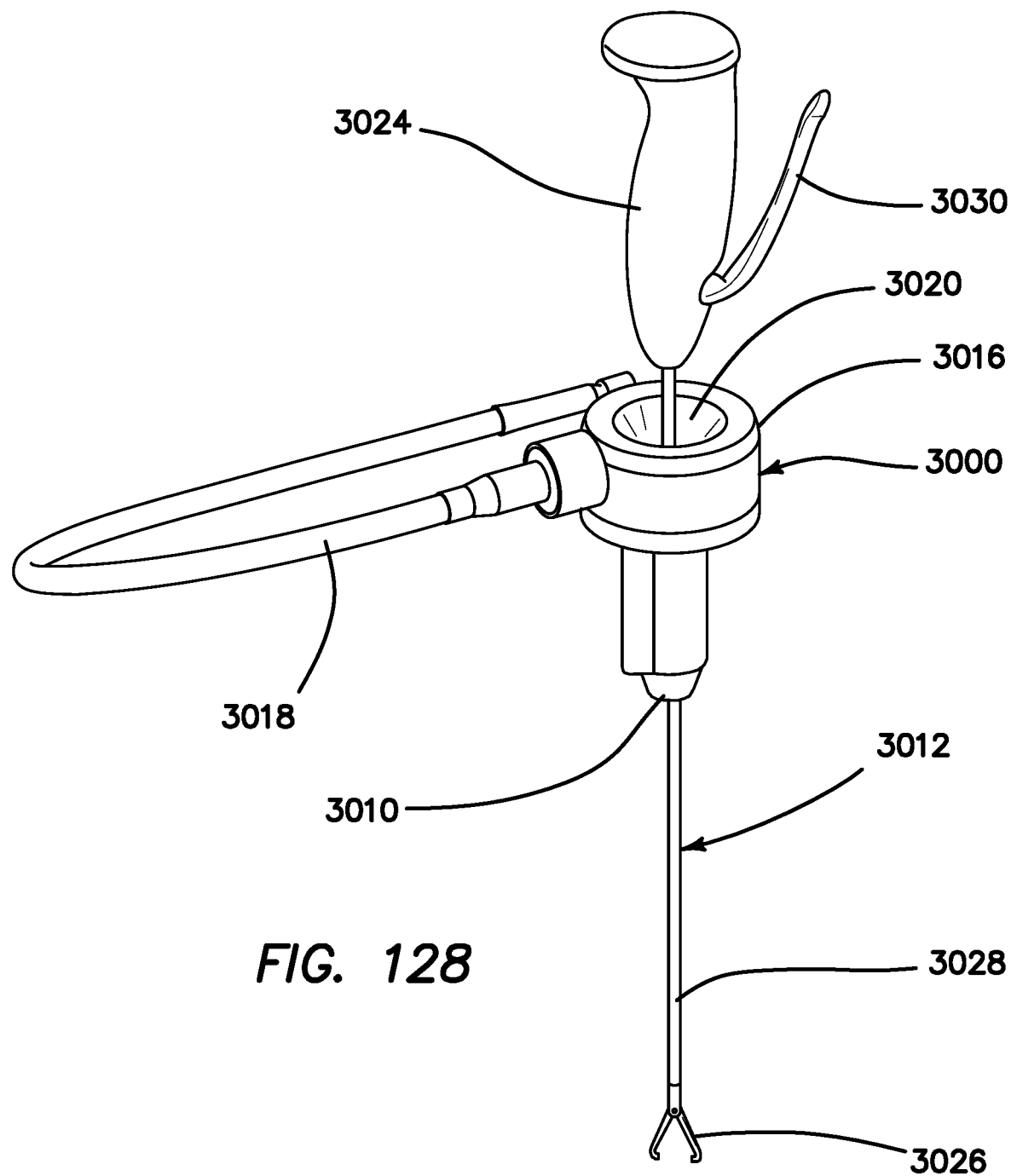

FIG. 128 is a top perspective view of a tissue grasper and morcellator according to the present invention.

Figures 129, 130:
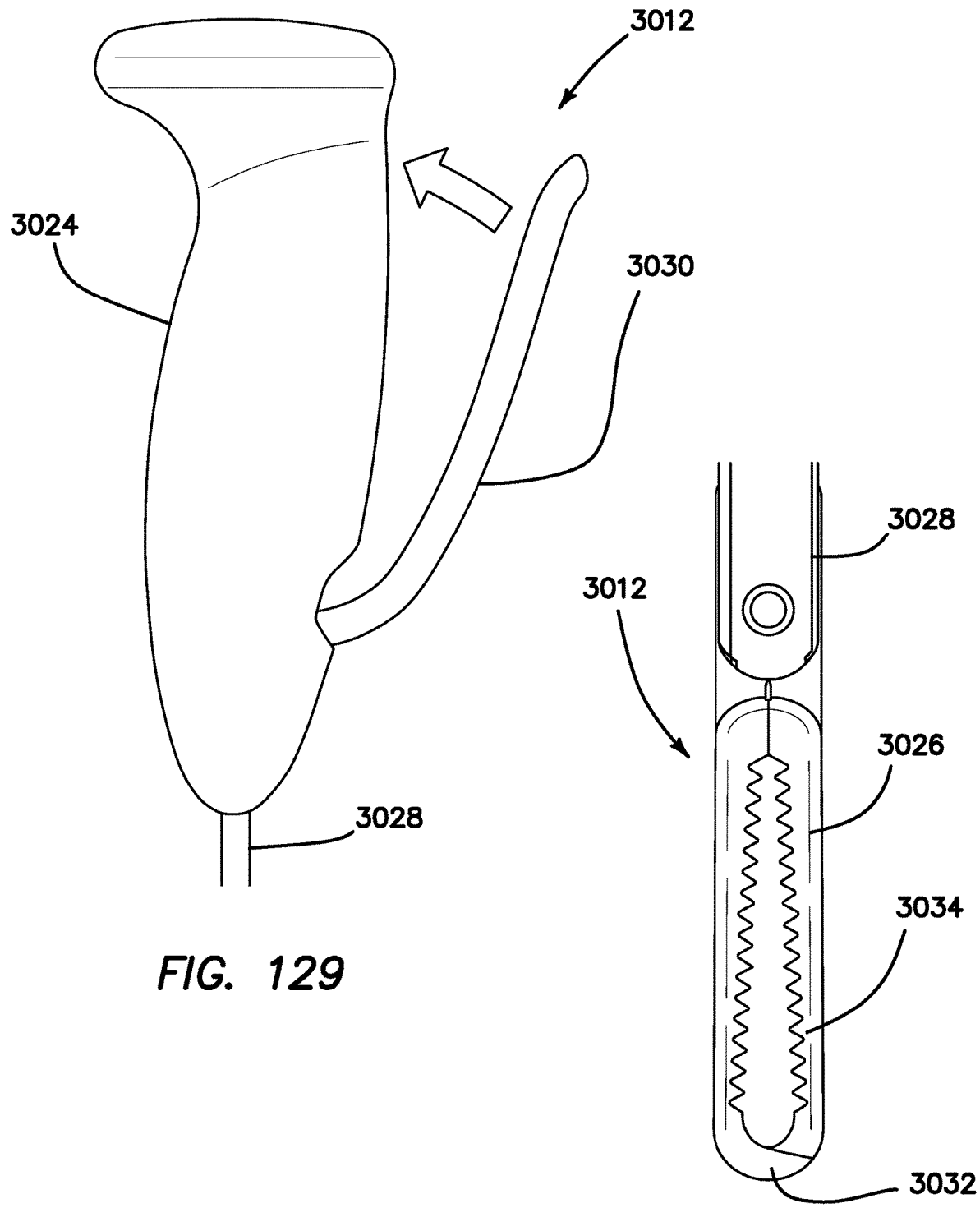

FIG. 129 is a sectional side view of a handle of a tissue grasper according to the present invention.

FIG. 130 is a sectional side view of the distal end of the tissue grasper according to the present invention.

Figure 131:
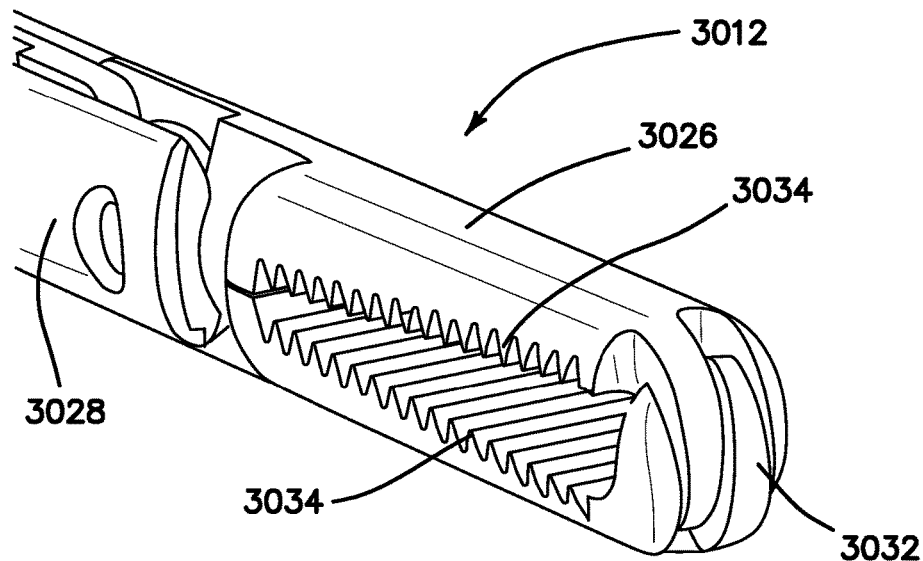

FIG. 131 is a sectional, top perspective view of the distal end of the tissue grasper according to the present invention.

Figure 132:
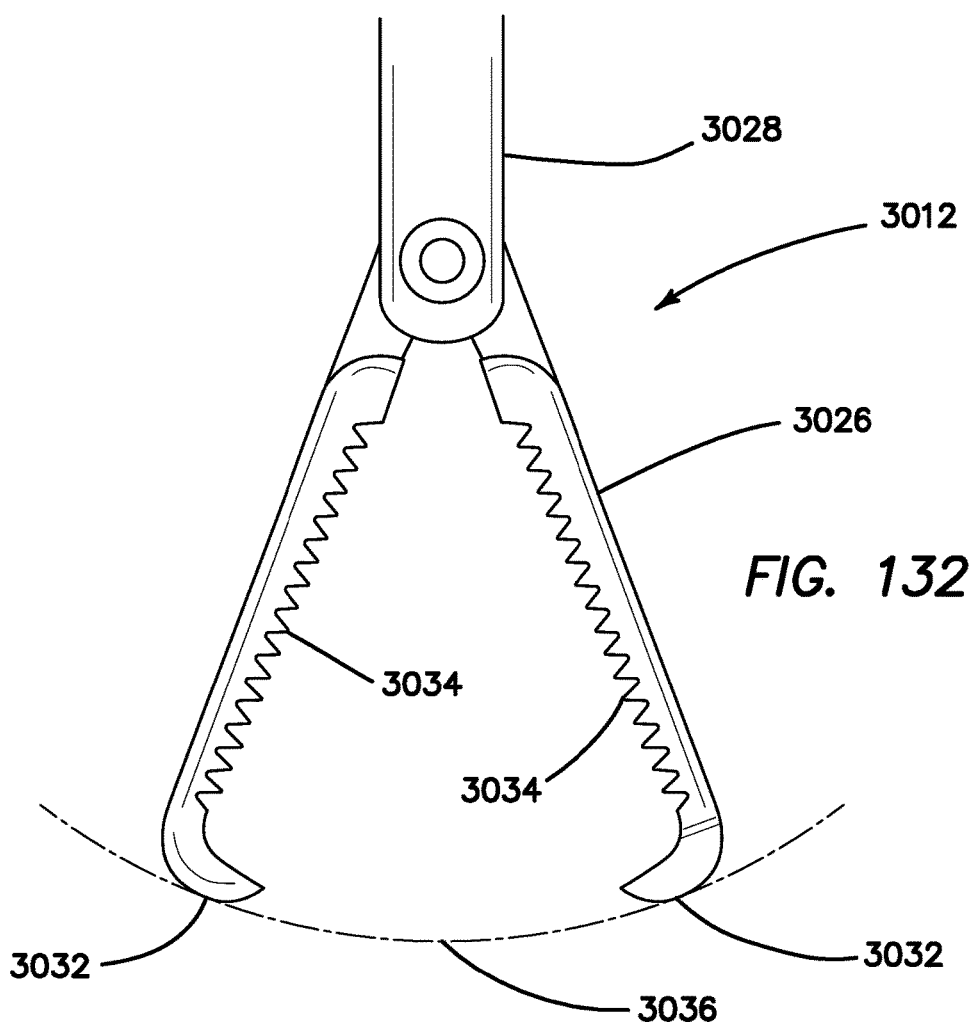

FIG. 132 is a sectional, side view of the distal end of the tissue grasper according to the present invention.

Figure 133:
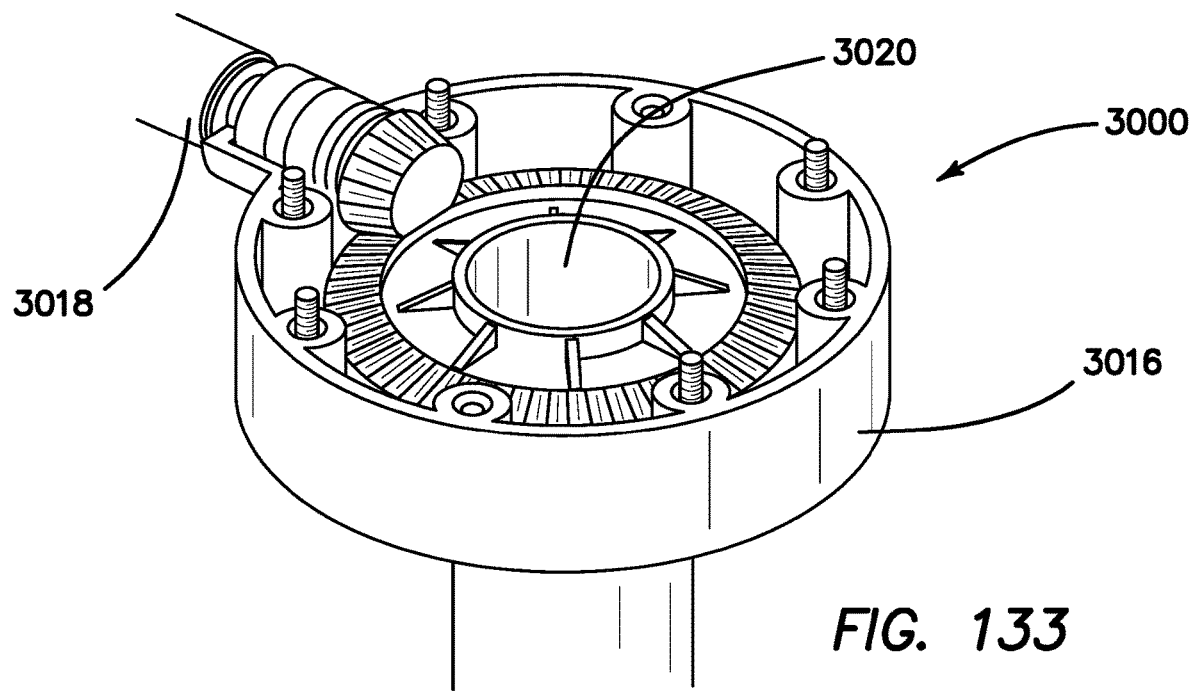

FIG. 133 is a top perspective view of a morcellator according to the present invention.

Figure 134:
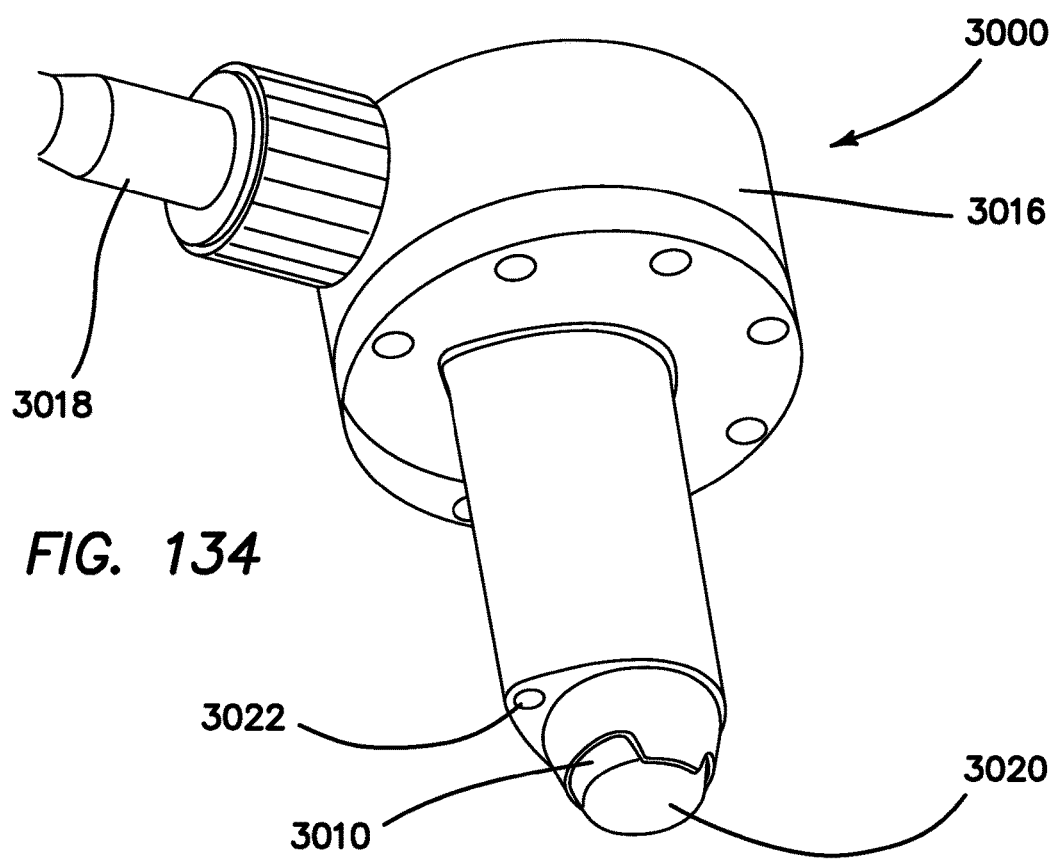

FIG. 134 is a bottom perspective of a morcellator according to the present invention.

FIG. 135A is a side view of a containment bag according to the present invention.

FIG. 135B is a top view of a containment bag in a rolled-up configuration according to the present invention.

FIG. 135C is an end view of a containment bag in a rolled-up configuration according to the present invention.

FIG. 135D is an end view of a containment bag according to the present invention.

FIG. 136A is a side sectional view of a body wall and a tissue specimen inside a containment bag according to the present invention.

FIG. 136B is a side sectional view of a body wall and a tissue specimen inside a containment bag and a tissue guard according to the present invention.

Figure 137A:
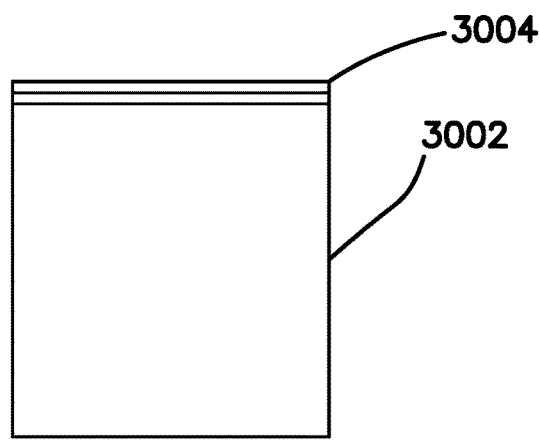

FIG. 137A is a side view of a containment bag according to the present invention.

Figure 137B:
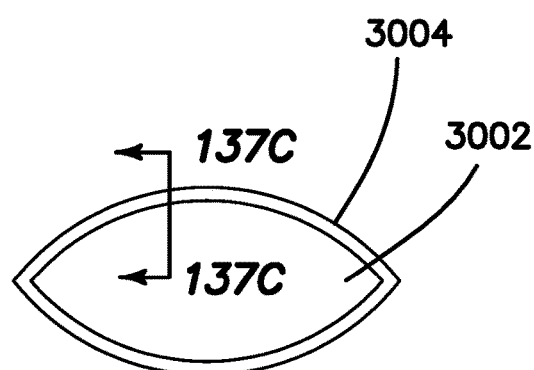

FIG. 137B is a top view of an open containment bag according to the present invention.

Figure 137C:
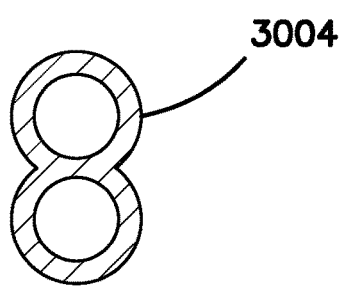

FIG. 137C is a cross-sectional view of a ring of a containment bag according to the present invention.

Figure 138A:
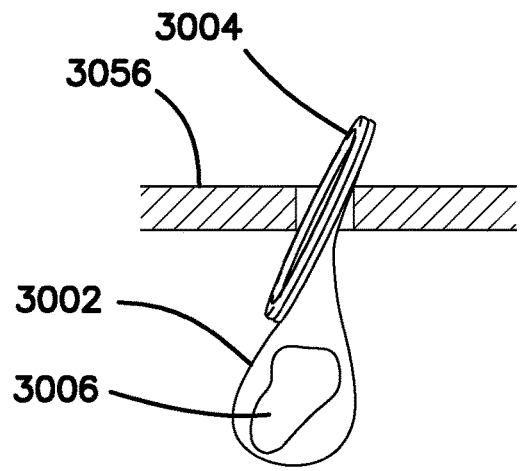

FIG. 138A is a side sectional view of a body wall and a tissue specimen inside a containment bag according to the present invention.

Figure 138B:
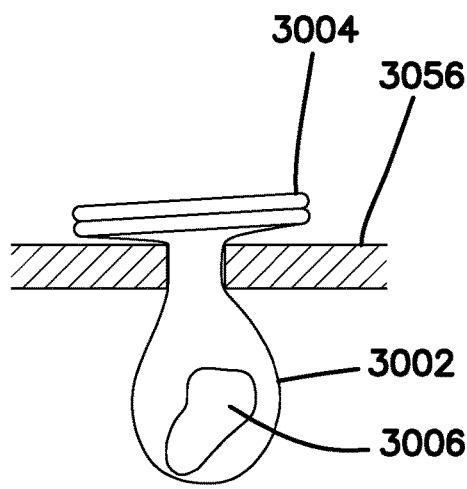

FIG. 138B is a side sectional view of a body wall and a tissue specimen inside a containment bag and a tissue guard according to the present invention.

Figure 138C:
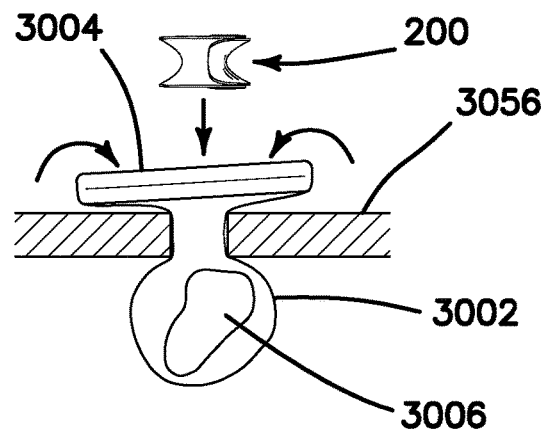

FIG. 138C is a side sectional view of a body wall and a tissue specimen inside a containment bag rolled-up around the bag ring and a tissue guard according to the present invention.

Figure 139A:
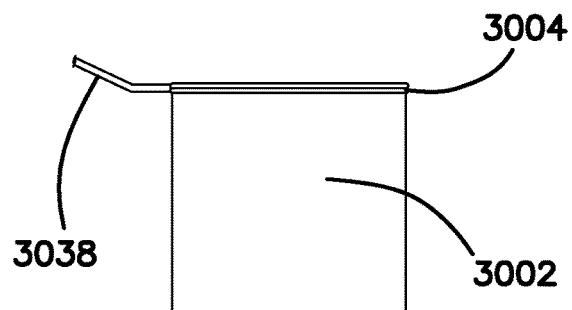

FIG. 139A is a side view of a containment bag according to the present invention.

Figure 139B:
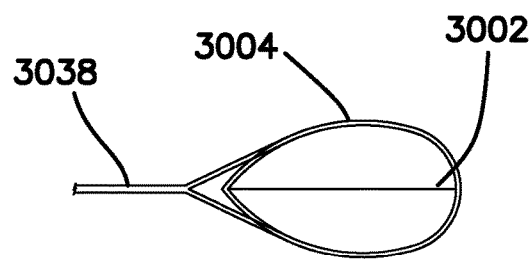

FIG. 139B is a top view of an open containment bag according to the present invention.

Figure 139C:
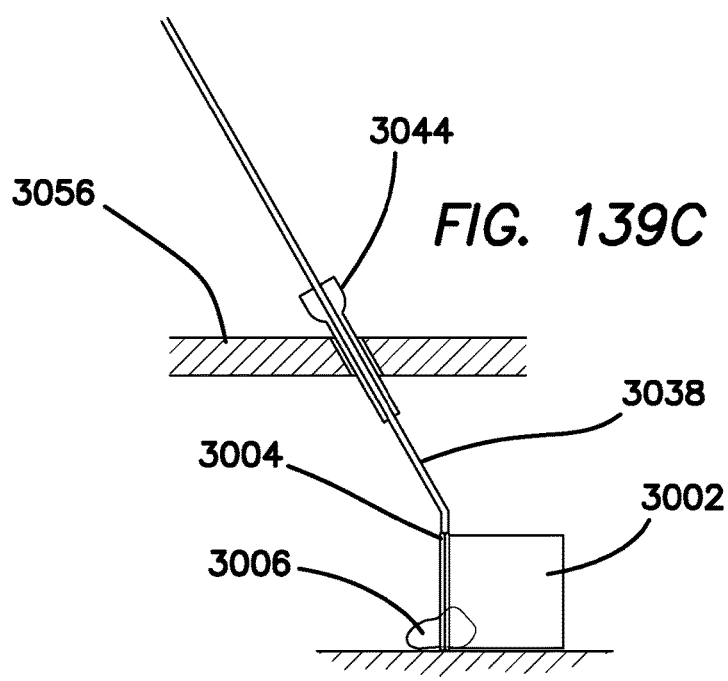

FIG. 139C is a side sectional view of a body wall and a tissue specimen inside a containment bag according to the present invention.

Figure 140A:
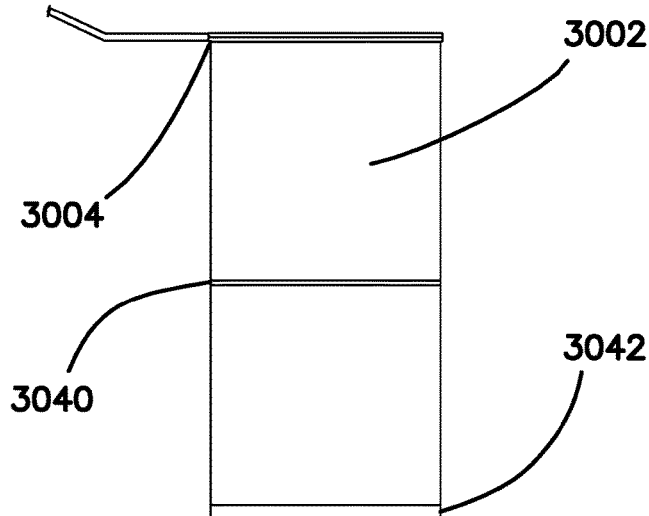

FIG. 140A is a side view of a containment bag according to the present invention.

Figure 140B:
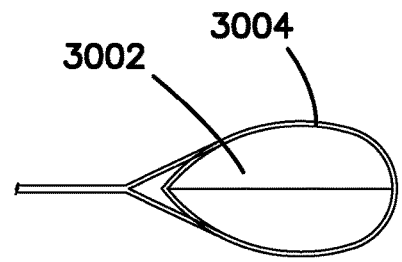

FIG. 140B is a top view of a containment bag according to the present invention.

Figure 141C:
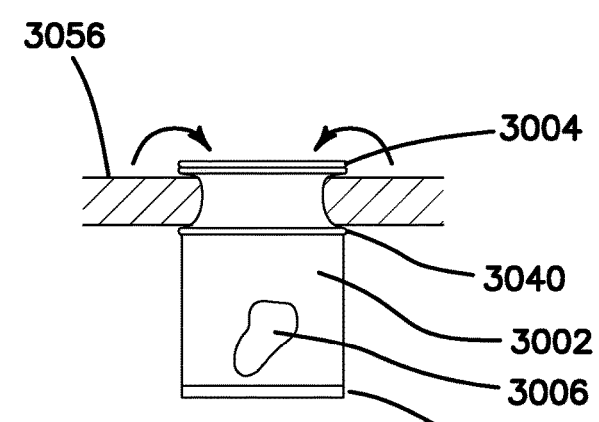
Figure 141A:
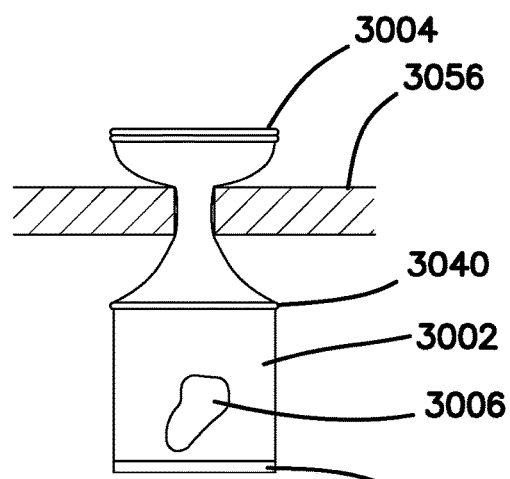

FIG. 141A is a side sectional view of a body wall and a tissue specimen inside a containment bag according to the present invention.

Figure 141D:
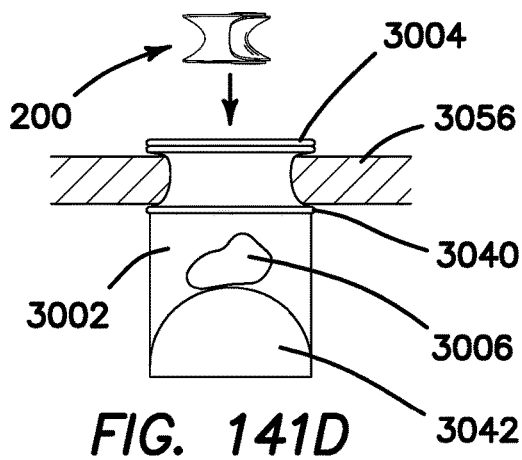
Figure 141B:
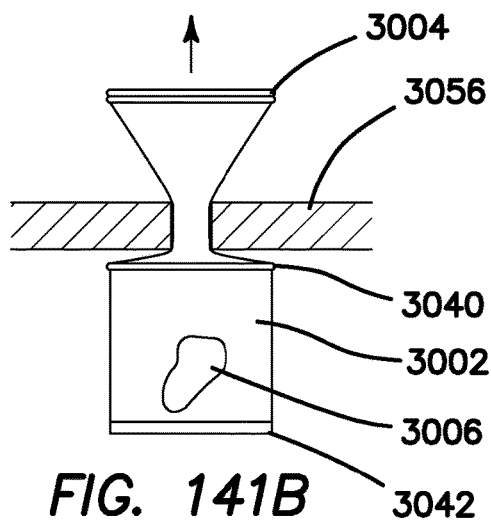

FIG. 141B is a side sectional view of a body wall and a tissue specimen inside a containment bag according to the present invention.

FIG. 141C is a side sectional view of a body wall and a tissue specimen inside a containment bag according to the present invention.

FIG. 141D is a side sectional view of a body wall and a tissue specimen inside a containment bag and a tissue guard according to the present invention.

FIG. 142A is a side view of a containment bag according to the present invention.

FIG. 142B is a cross-sectional view taken along line 142B-142B of FIG. 142A of a containment bag according to the present invention.

FIG. 142C is a cross-sectional view of an inflated containment bag according to the present invention.

Figure 143A:
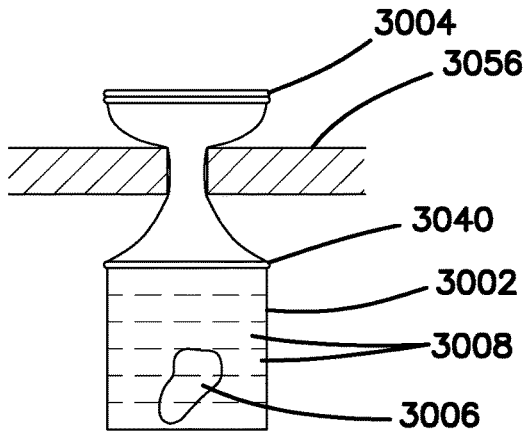

FIG. 143A is a side sectional view of a body wall and a tissue specimen inside a containment bag according to the present invention.

Figure 143B:
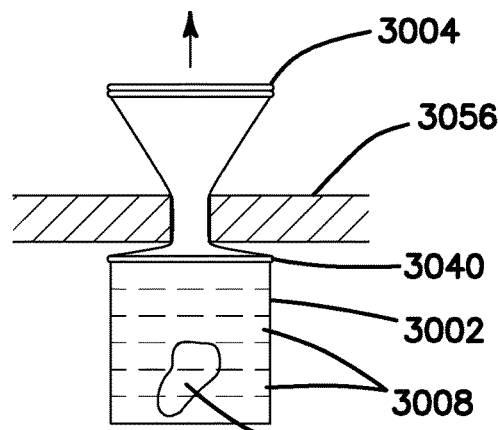

FIG. 143B is a side sectional view of a body wall and a tissue specimen inside a containment bag according to the present invention.

Figure 143C:
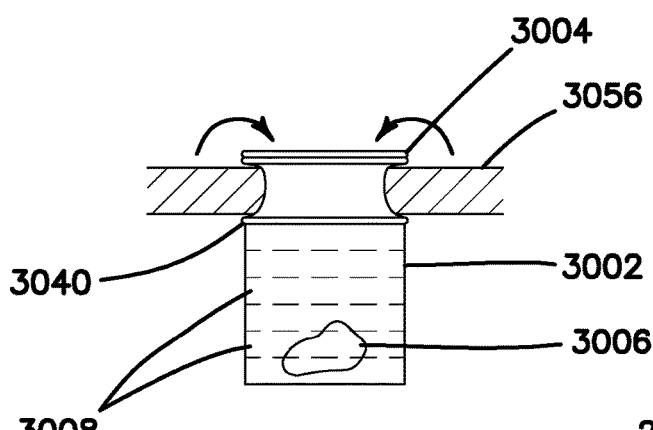

FIG. 143C is a side sectional view of a body wall and a tissue specimen inside a containment bag according to the present invention.

Figure 143D:
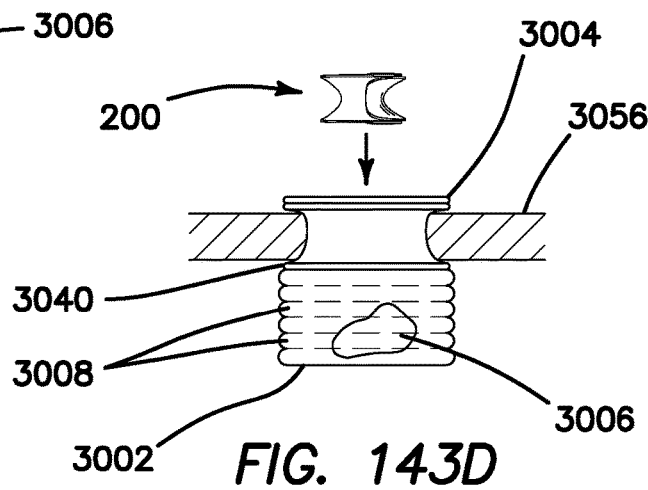

FIG. 143D is a side sectional view of a body wall and a tissue specimen inside an inflated containment bag and a tissue guard according to the present invention.

FIG. 144A is a side view of a containment bag according to the present invention.

FIG. 144B is a cross-sectional view taken along line 144A-144A of FIG. 144A of a containment bag according to the present invention.

FIG. 144C is a cross-sectional view of an inflated containment bag according to the present invention.

Figure 145A:
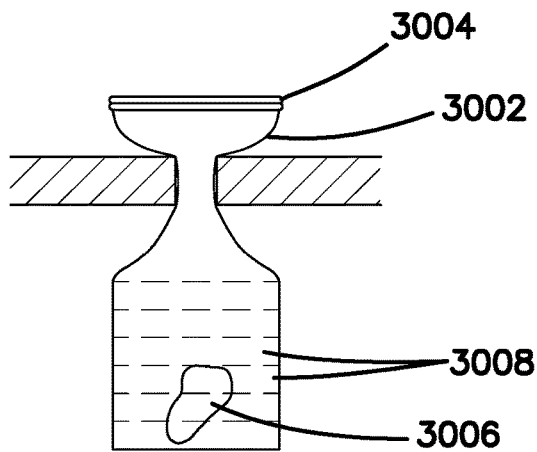

FIG. 145A is a side sectional view of a body wall and a tissue specimen inside a containment bag according to the present invention.

Figure 145B:
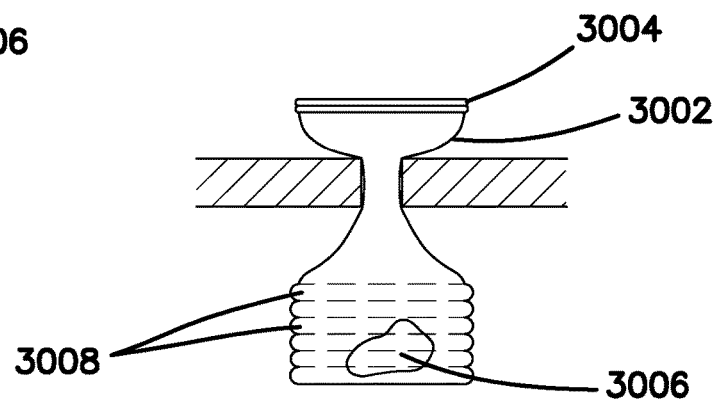

FIG. 145B is a side sectional view of a body wall and a tissue specimen inside an inflated containment bag according to the present invention.

Figure 145C:
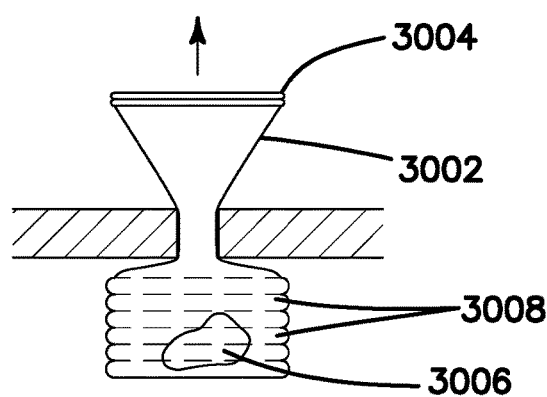

FIG. 145C is a side sectional view of a body wall and a tissue specimen inside an inflated containment bag pulled upwardly according to the present invention.

Figure 145D:
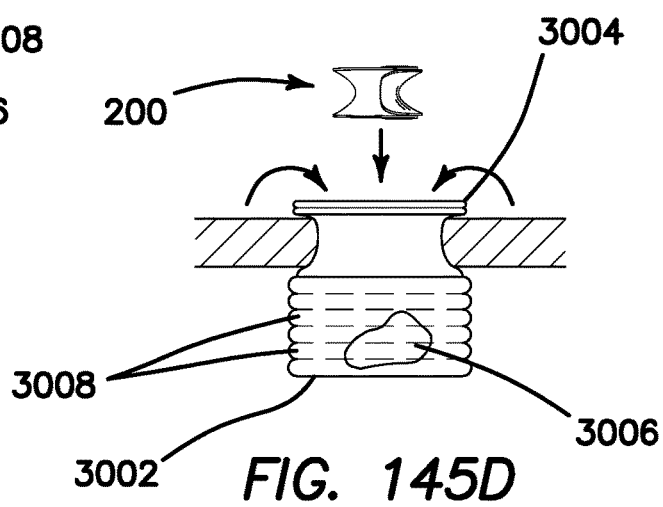

FIG. 145D is a side sectional view of a body wall and a tissue specimen inside an inflated containment bag and a tissue guard according to the present invention.

Figure 146A:
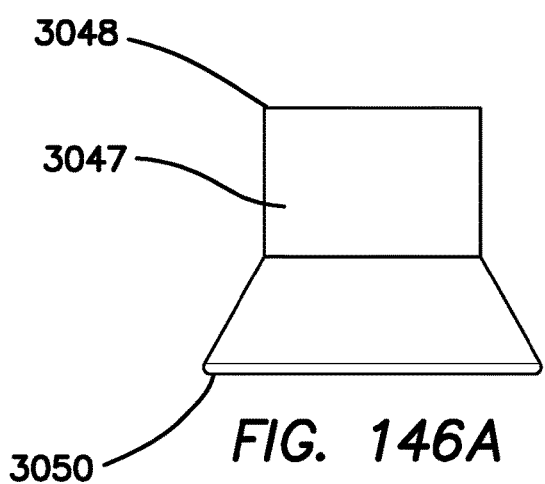

FIG. 146A is a side view of a guard according to the present invention.

Figure 146B:
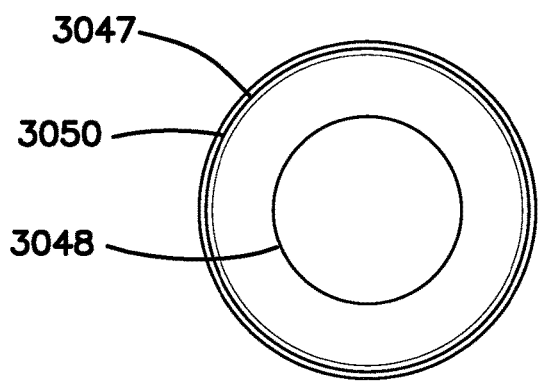

FIG. 146B is a top view of a bottom view of a guard according to the present invention.

Figure 147A:
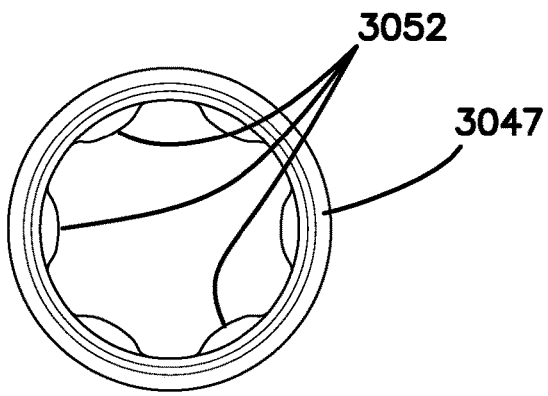

FIG. 147A is a top view of a guard according to the present invention.

Figure 147B:
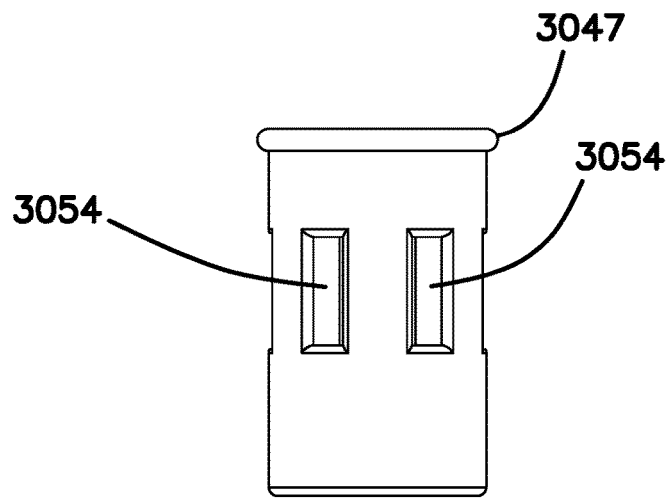

FIG. 147B is a side view of a guard according to the present invention.

Figure 148A:
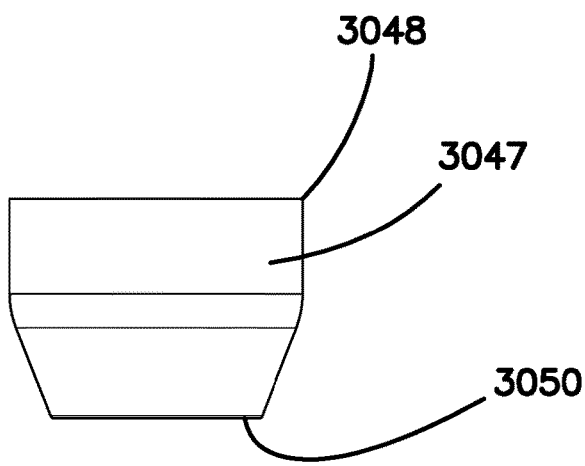

FIG. 148A is a side view of a guard according to the present invention.

Figure 148B:
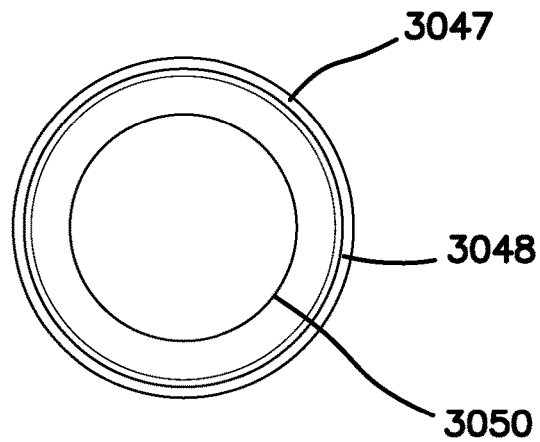

FIG. 148B is a top view of a guard according to the present invention.

Figure 149:
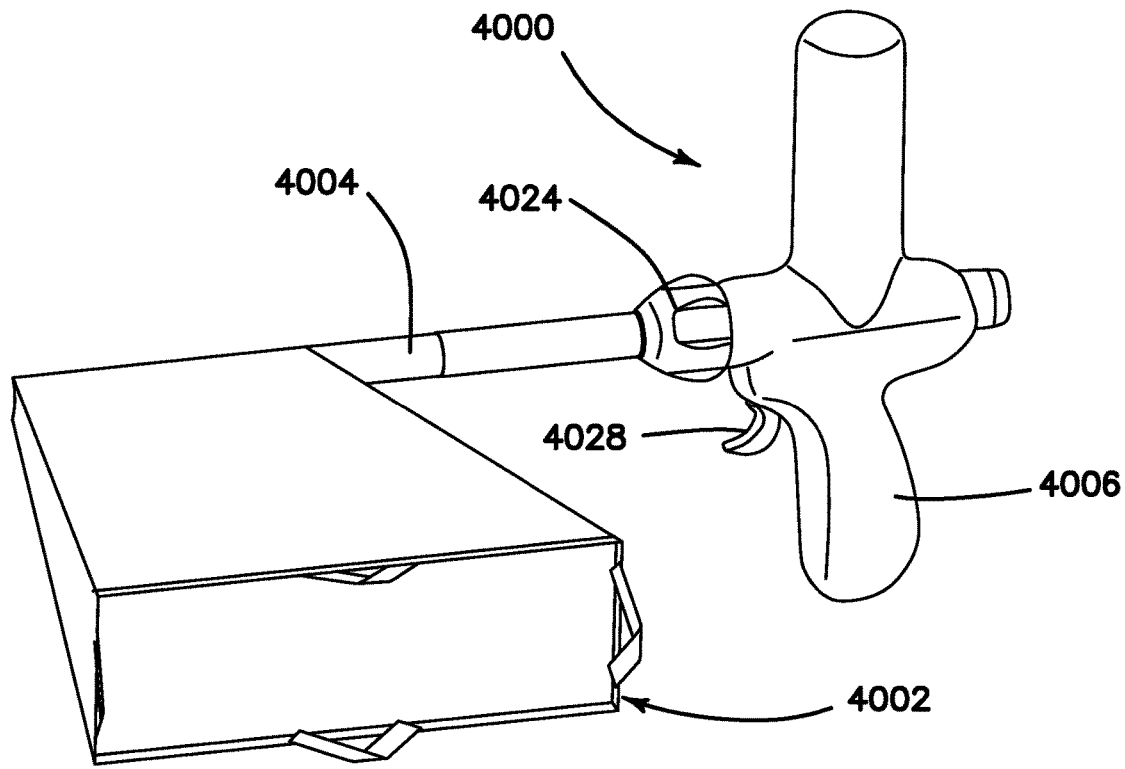

FIG. 149 is a top perspective view of a morcellation and bag system according to the present invention.

Figure 150A:
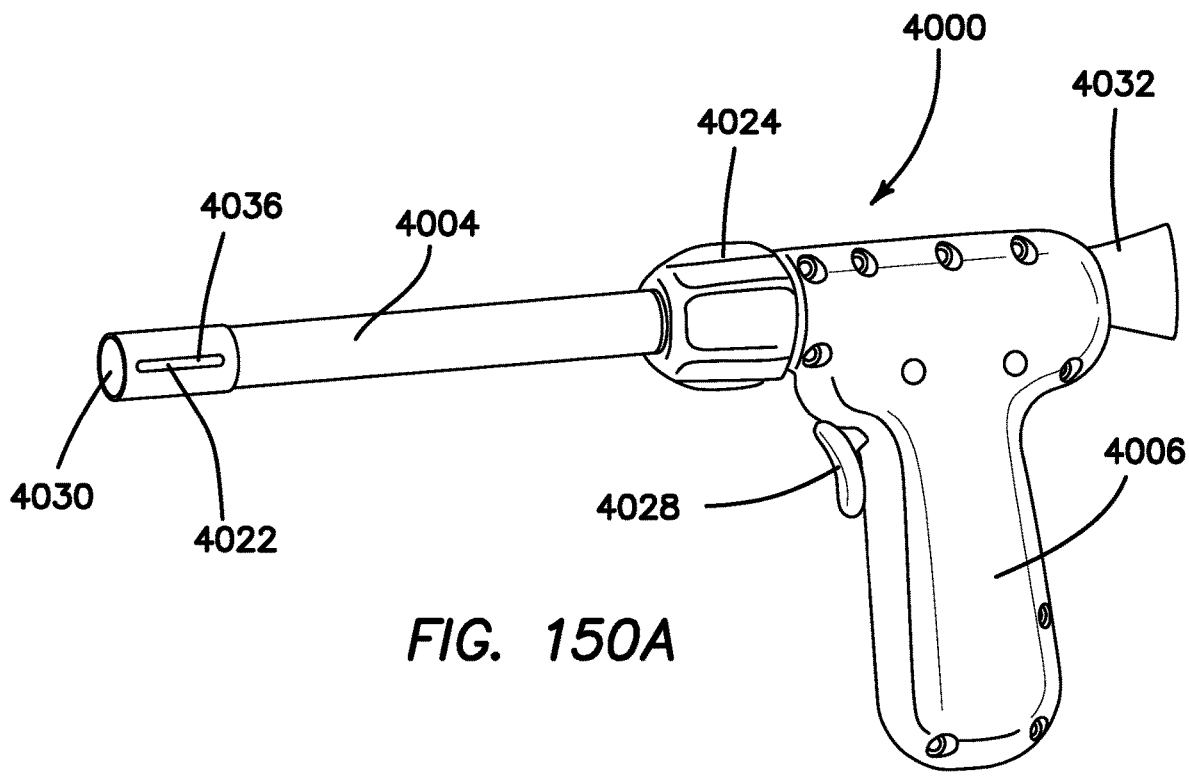

FIG. 150A is a top perspective view of a power morcellator according to the present invention.

Figure 150B:
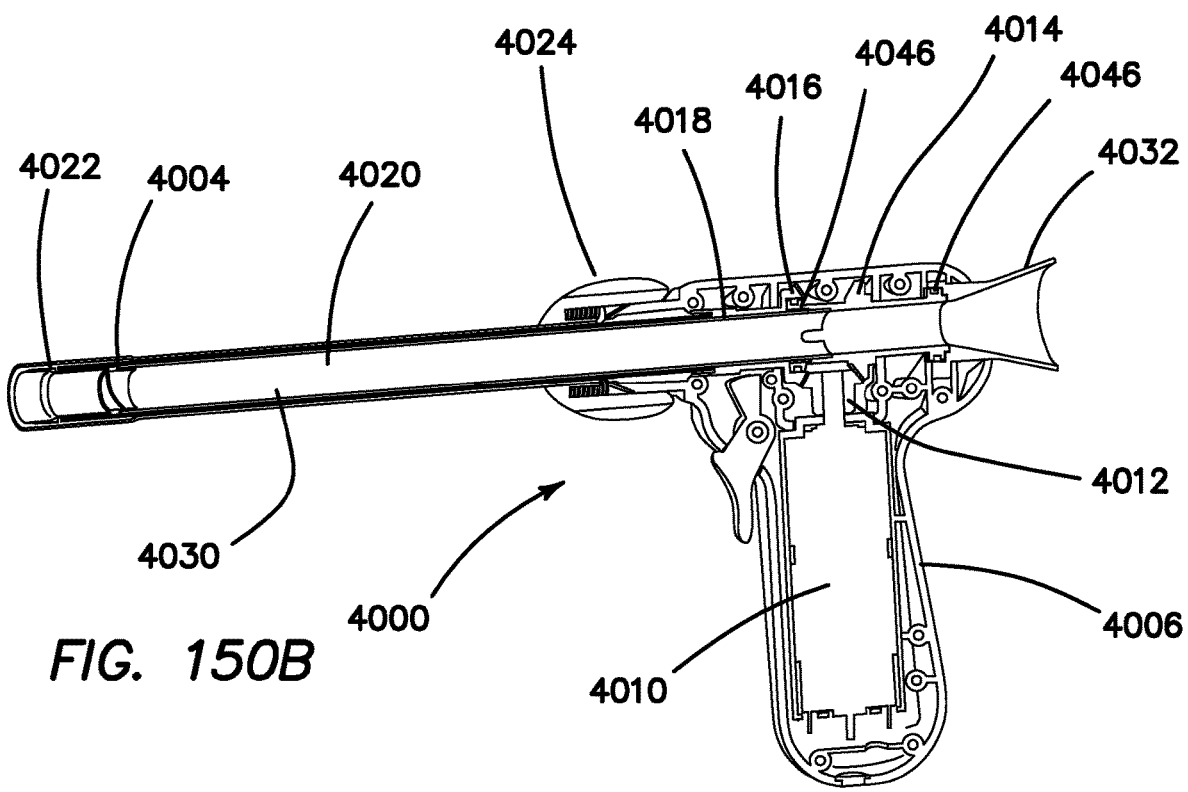

FIG. 150B is a top perspective cross-sectional view of a power morcellator according to the present invention.

Figure 150C:
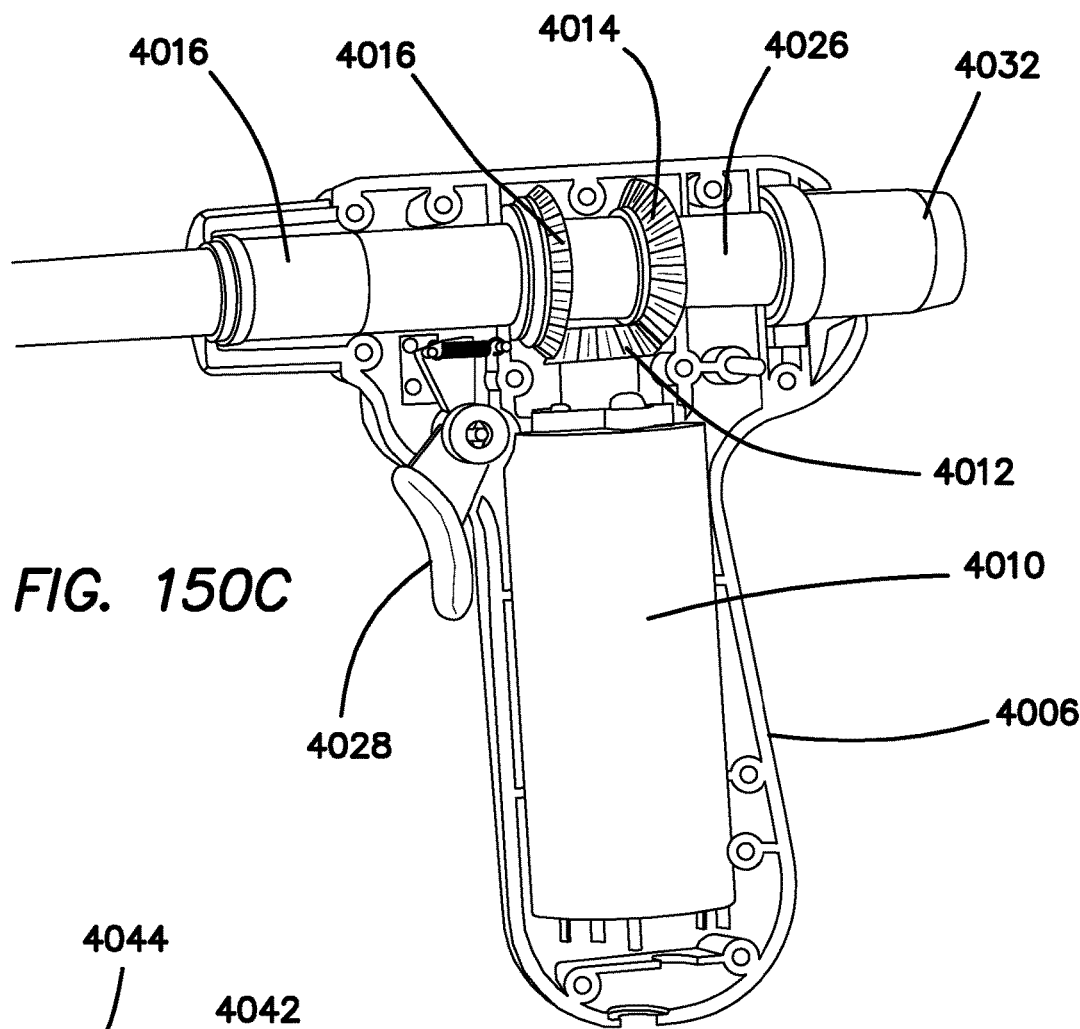

FIG. 150C is a sectional view of a power morcellator according to the present invention.

Figure 150D:
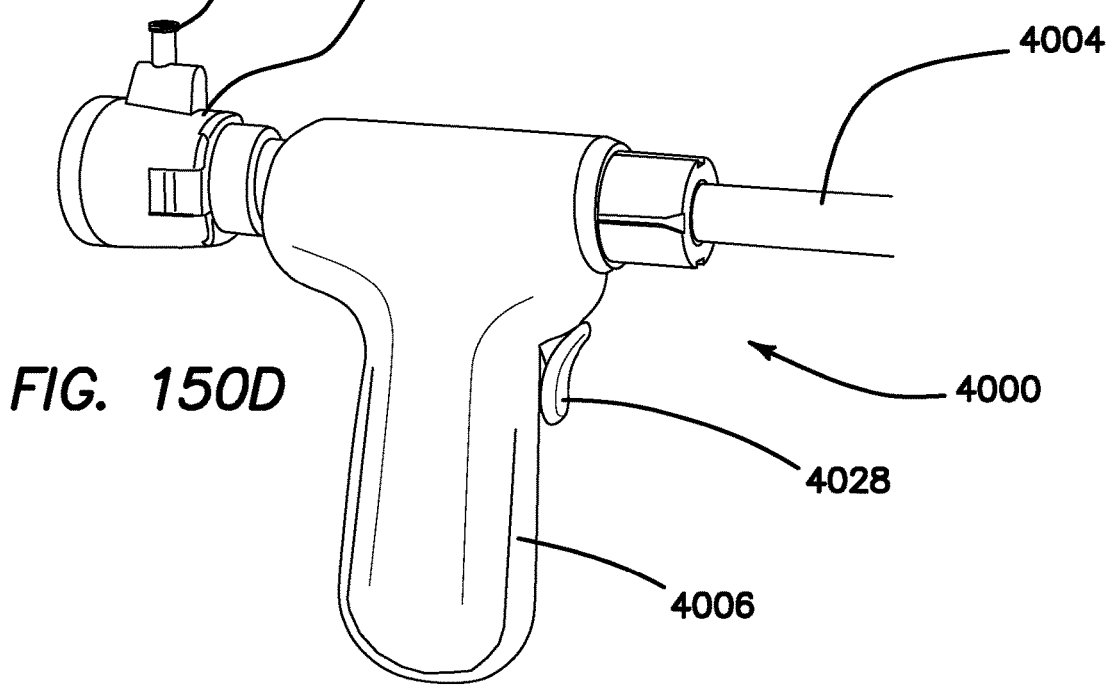

FIG. 150D is a sectional view of a power morcellator according to the present invention.

Figure 151:
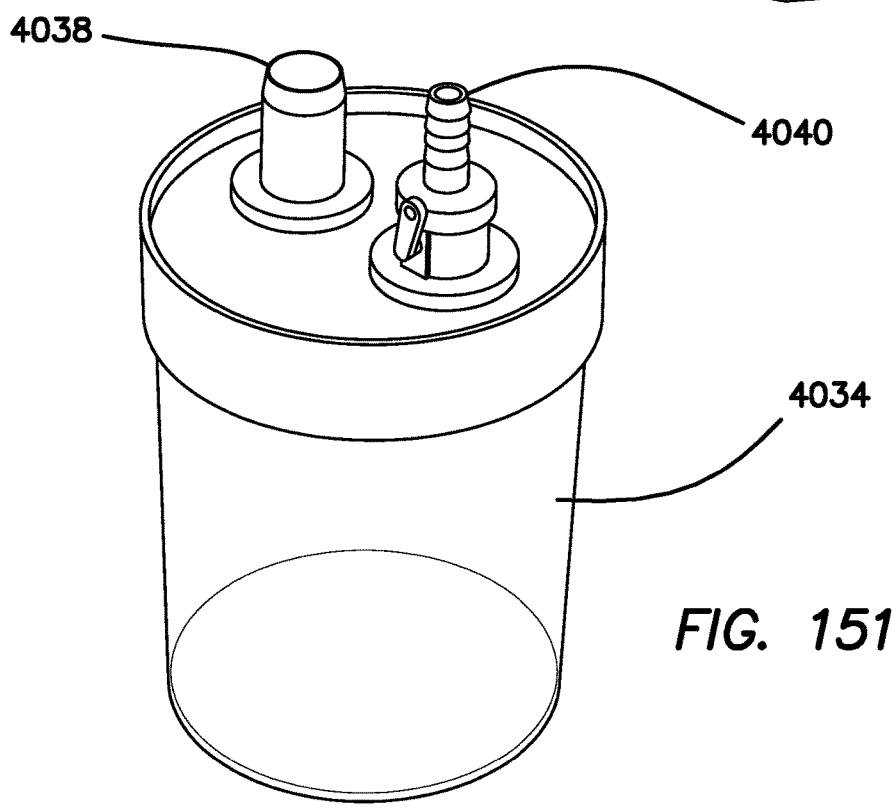

FIG. 151 is a top perspective view of a specimen receptacle according to the present invention.

Figure 152:
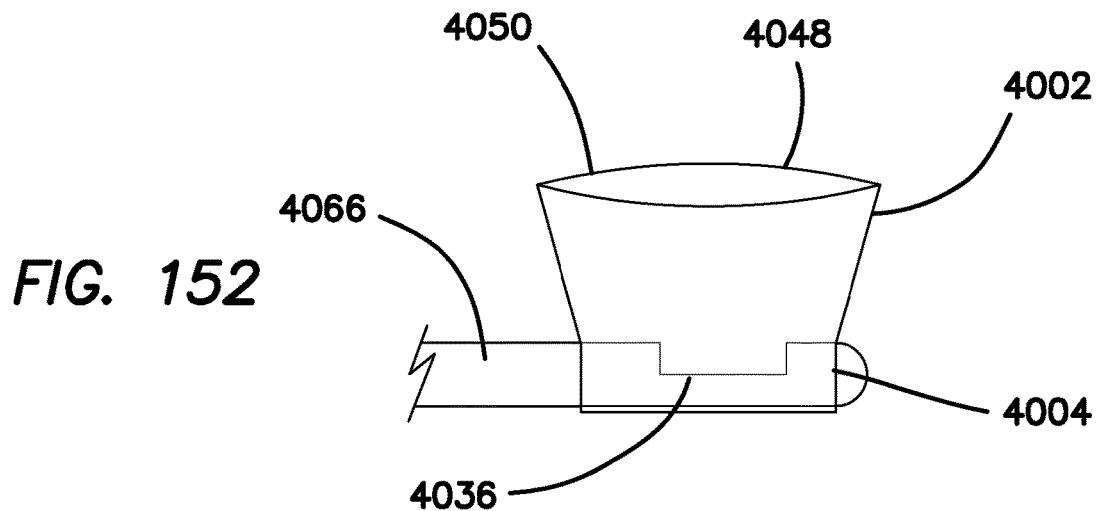

FIG. 152 is a top perspective, sectional view of a bag tube and bag according to the present invention.

Figures 153A, 153B:
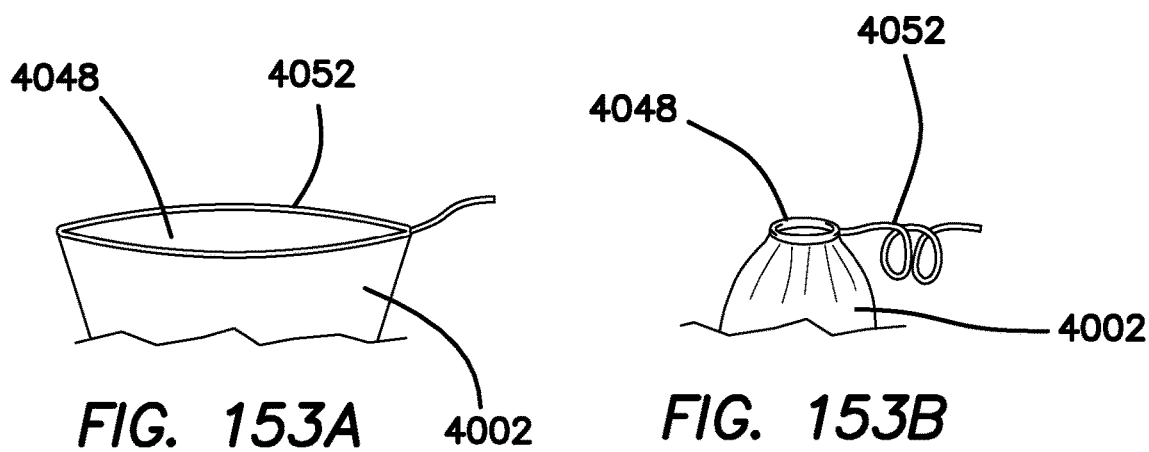

FIG. 153A is a top perspective, sectional view of a containment bag in an open configuration according to the present invention.

FIG. 153B is a top perspective, sectional view of a containment bag in a closed configuration according to the present invention.

Figures 154A, 154B:
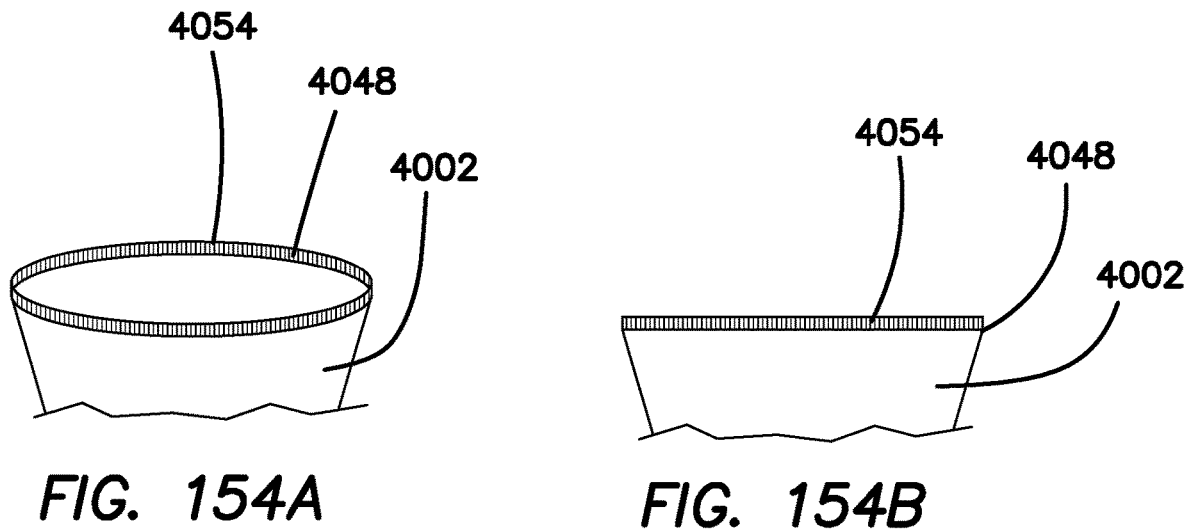

FIG. 154A is a top perspective, sectional view of a containment bag in an open configuration according to the present invention.

FIG. 154B is a top perspective, sectional view of a containment bag in a closed configuration according to the present invention.

Figure 155A:
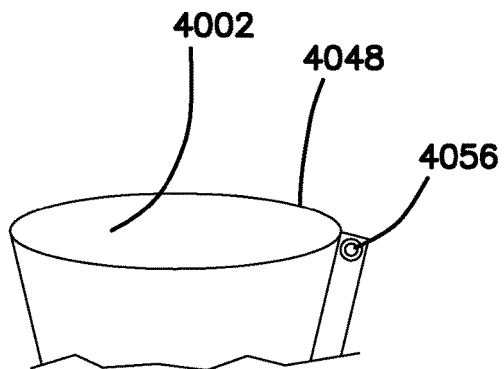

FIG. 155A is a top perspective, sectional view of a containment bag in an open configuration according to the present invention.

Figure 155B:
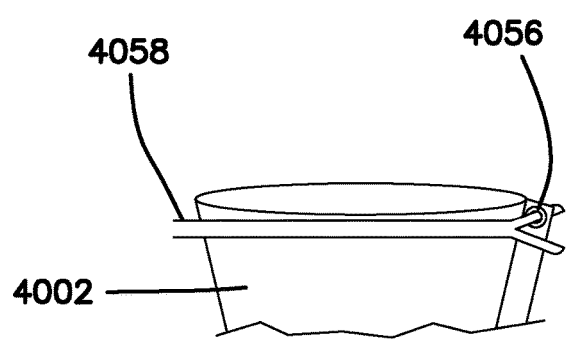

FIG. 155B is a top perspective, sectional view of a grasper and containment bag in an open configuration according to the present invention.

Figure 155C:
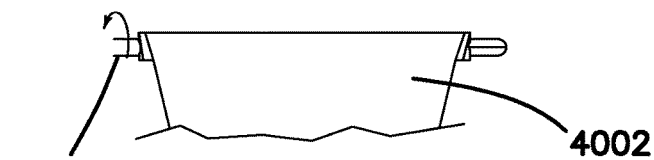

FIG. 155C is a top perspective, sectional view of a containment bag rolled about a grasper according to the present invention.

Figure 156A:
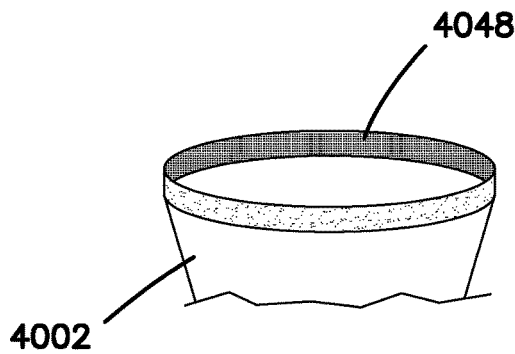

FIG. 156A is a top perspective, sectional view of a containment bag in an open configuration according to the present invention.

Figure 156B:
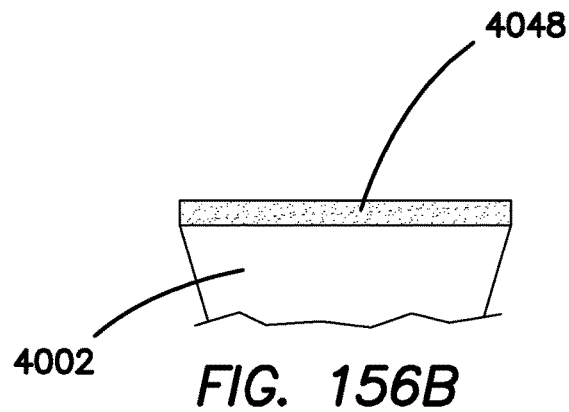

FIG. 156B is a top perspective, sectional view of a containment bag in a closed configuration according to the present invention.

Figure 157A:
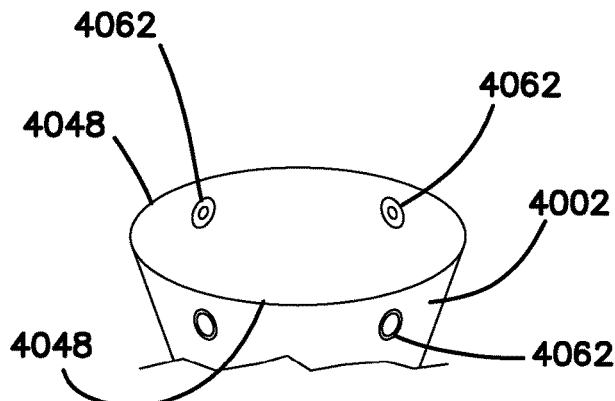

FIG. 157A is a top perspective, sectional view of a containment bag in an open configuration according to the present invention.

Figure 157B:
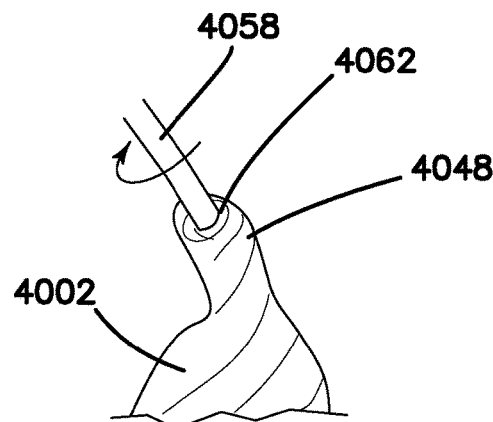

FIG. 157B is a top perspective, sectional view of a containment bag and an instrument twisting the containment bag into a closed configuration according to the present invention.

Figure 158A:
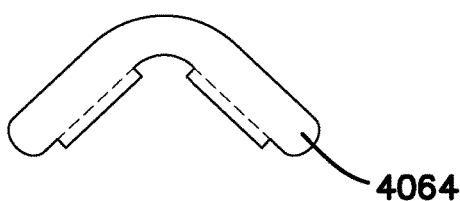

FIG. 158A is a top view of a guard according to the present invention.

Figure 158B:
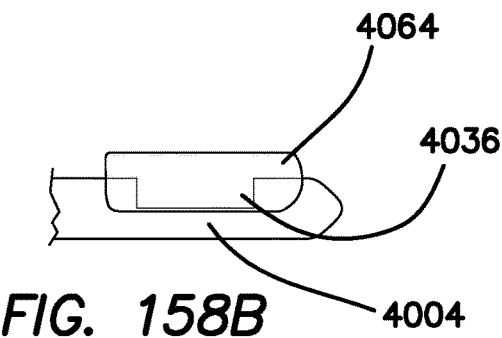

FIG. 158B is a side view of a guard attached to a morcellator shaft according to the present invention.

Figure 158C:
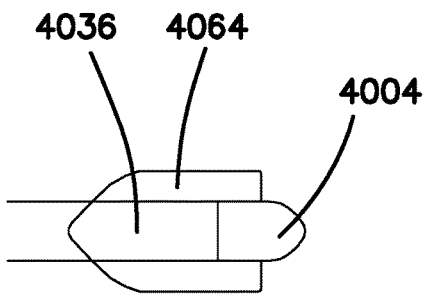

FIG. 158C is a top view of a guard attached to a morcellator shaft according to the present invention.

Figure 158D:
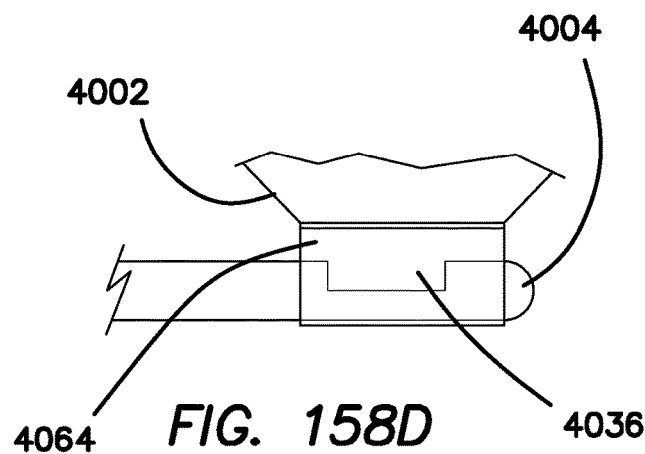

FIG. 158D is a side, sectional view of a guard and containment bag attached to a morcellator shaft according to the present invention.

Figure 158E:
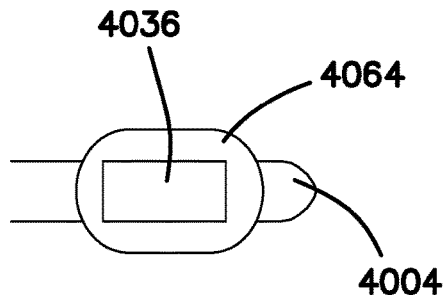

FIG. 158E is a top, sectional view of a guard attached to a morcellator shaft according to the present invention.

Figure 158F:
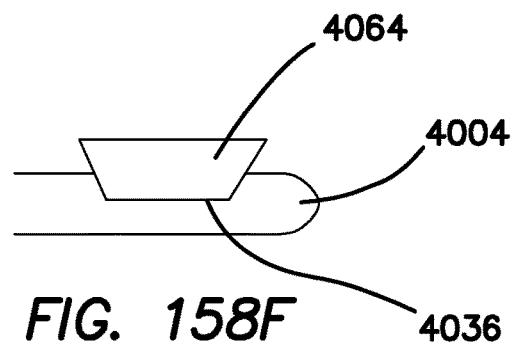

FIG. 158F is a side, sectional view of a guard attached to a morcellator shaft according to the present invention.

Figure 159:
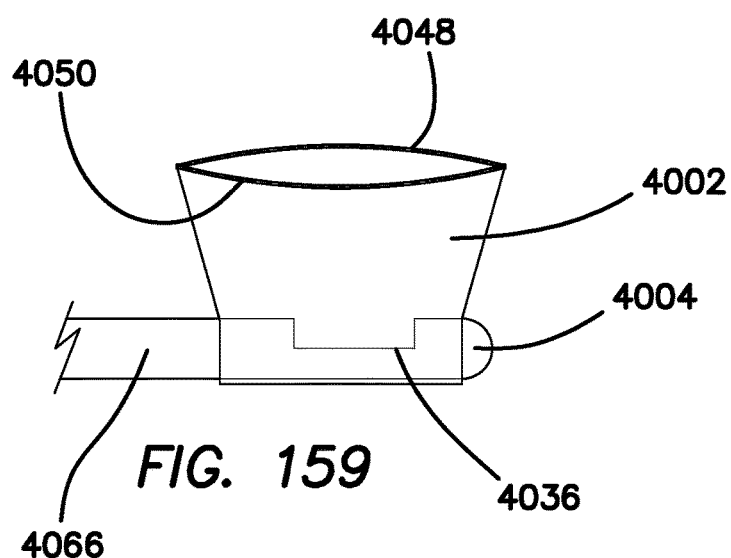

FIG. 159 is a top perspective, sectional view of a bag tube and containment bag with a top opening according to the present invention.

Figure 160:
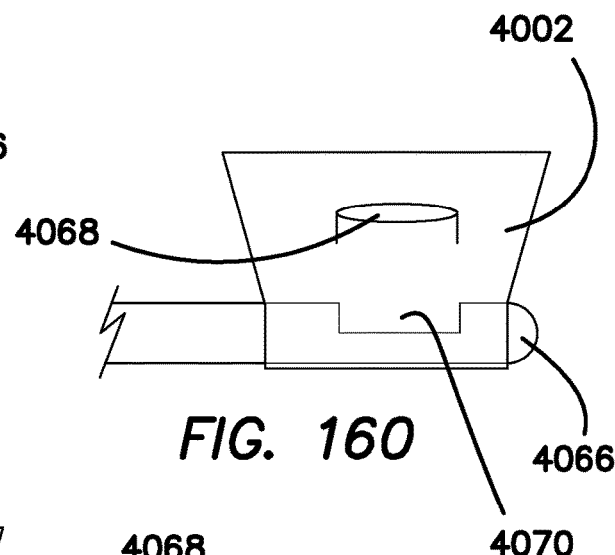

FIG. 160 is a side, sectional view of a bag tube and containment bag with a side opening according to the present invention.

Figure 161:
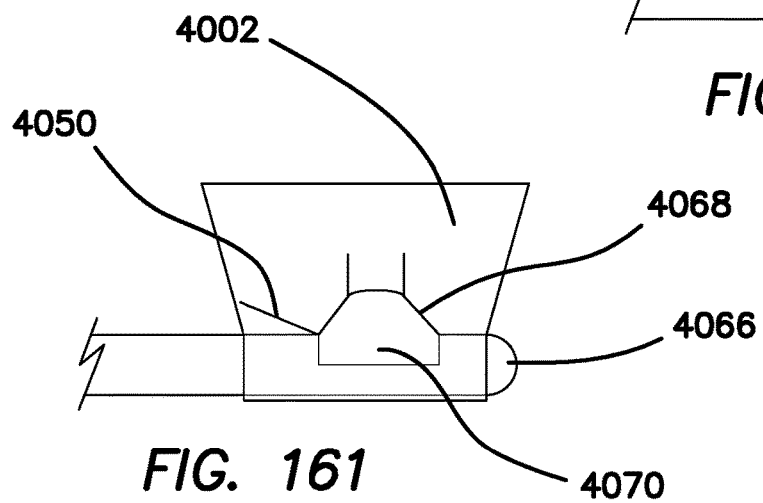

FIG. 161 is a side, sectional view of a bag tube and containment bag with a side opening according to the present invention.

Figure 162A:
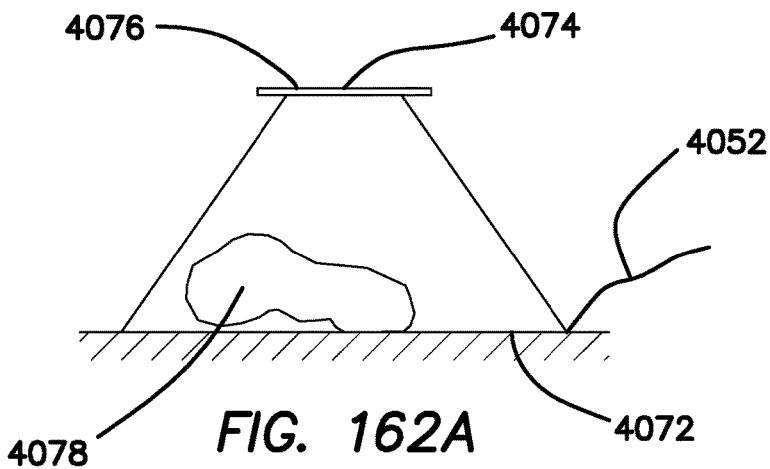

FIG. 162A is a side view of a tissue specimen inside a containment bag according to the present invention.

Figure 162B:
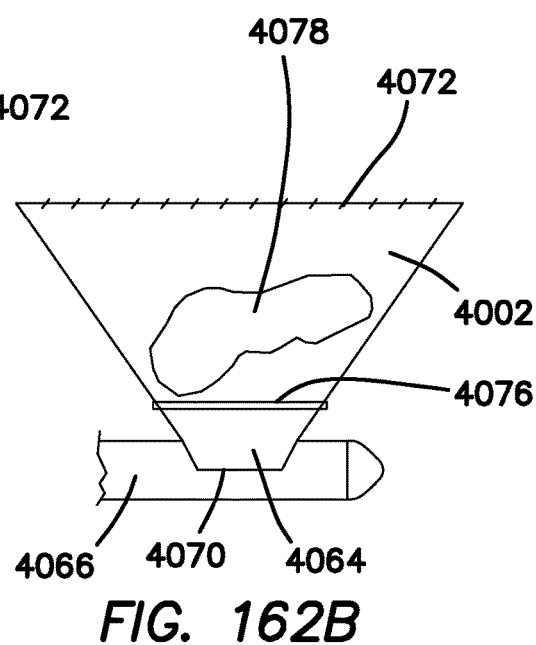

FIG. 162B is a side, sectional view of a tissue specimen inside a containment bag attached to a morcellator according to the present invention.

Figure 162C:
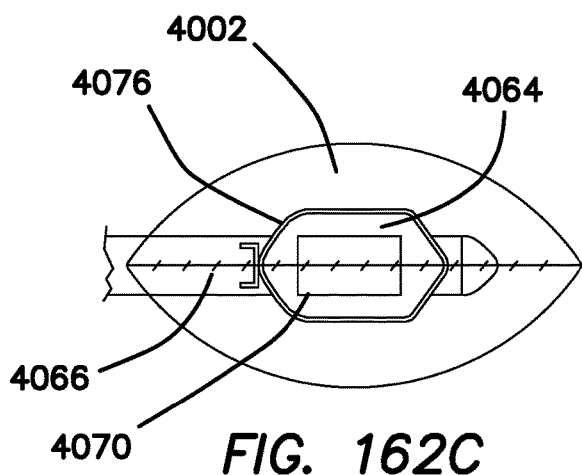

FIG. 162C is top view of a containment bag attached to a morcellator according to the present invention.

Figure 163A:
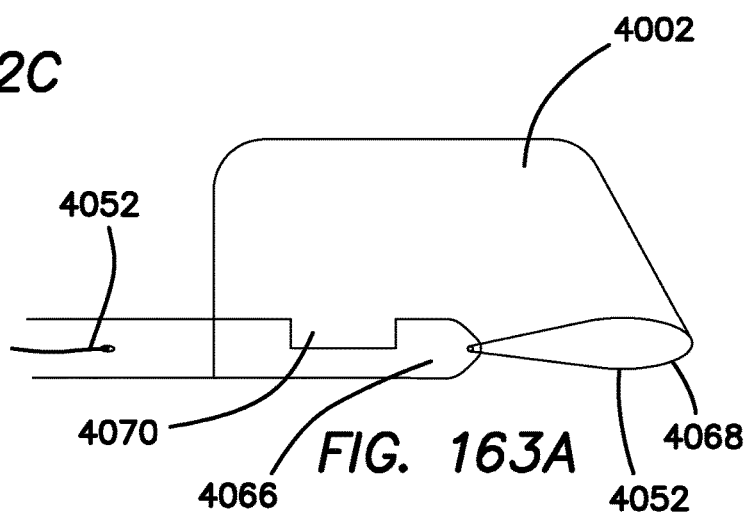

FIG. 163A is side, sectional view of a containment bag and morcellator system according to the present invention.

Figure 163B:
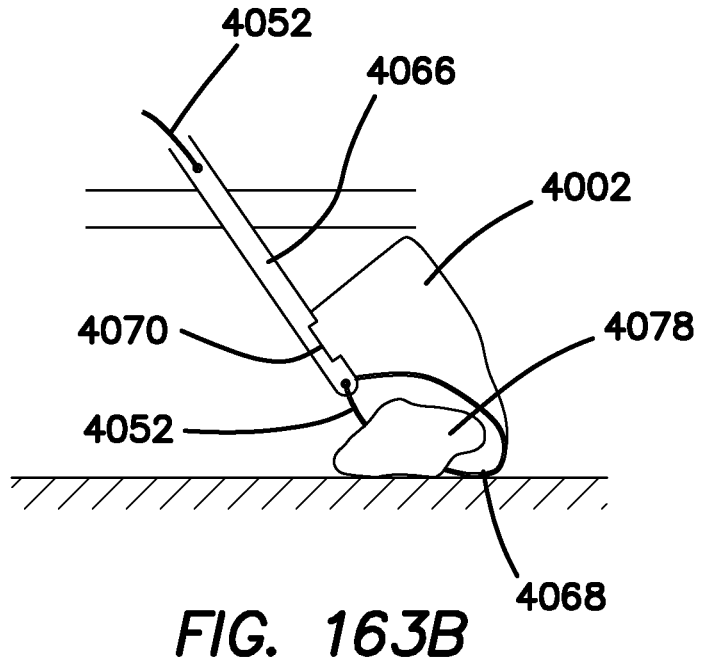

FIG. 163B is a side, sectional view of a body wall, a tissue specimen and a containment bag and morcellator system according to the present invention.

Figure 163C:
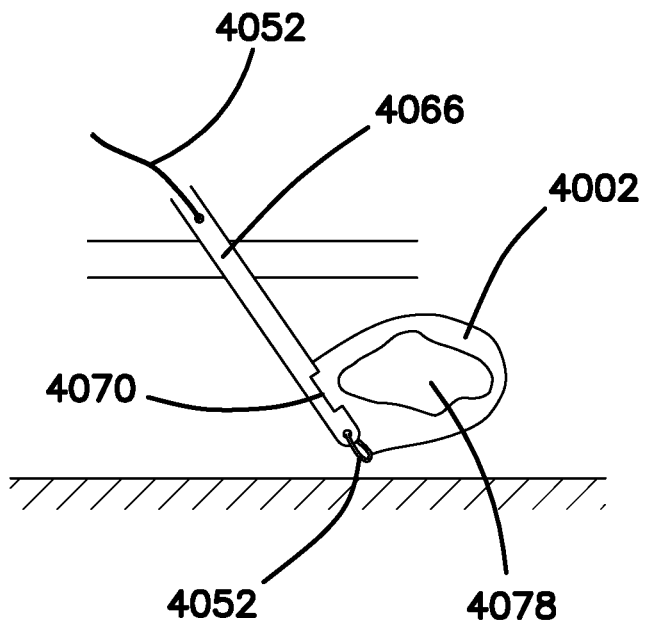

FIG. 163C is a side, sectional view of a body wall, tissue specimen inside a containment bag and morcellator system according to the present invention.

Figure 164:
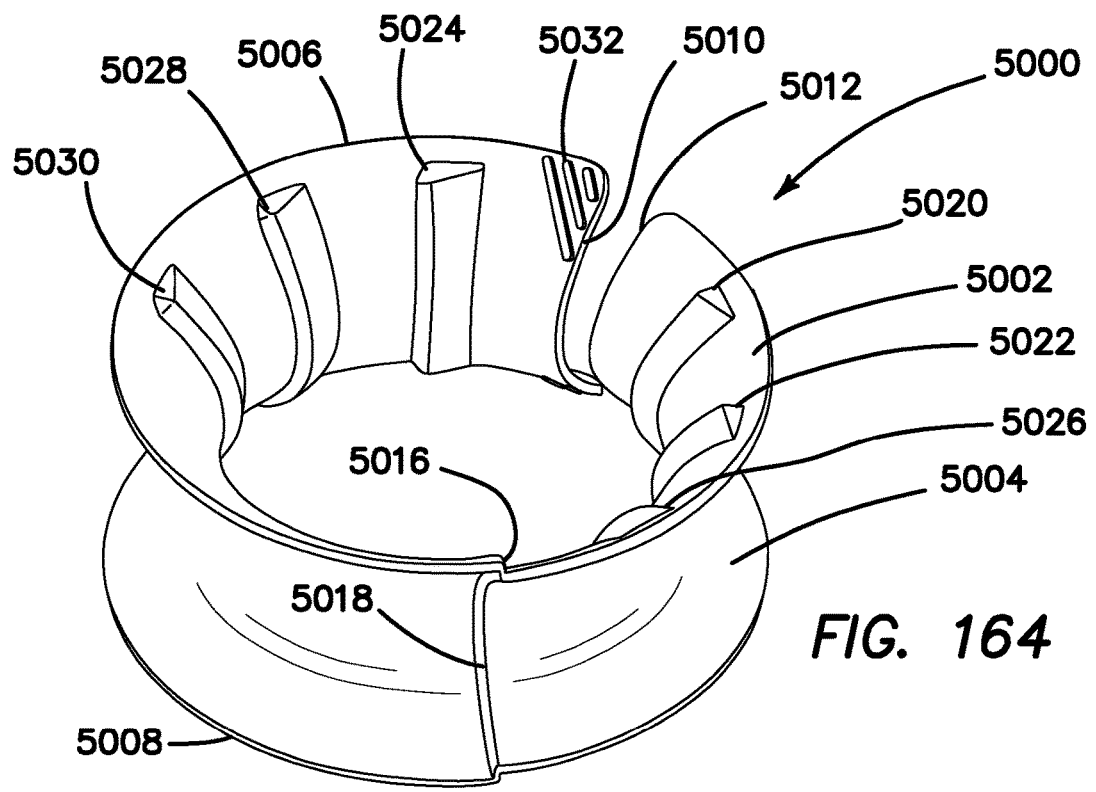

FIG. 164 is a top perspective view of a shield according to the present invention.

Figure 165:
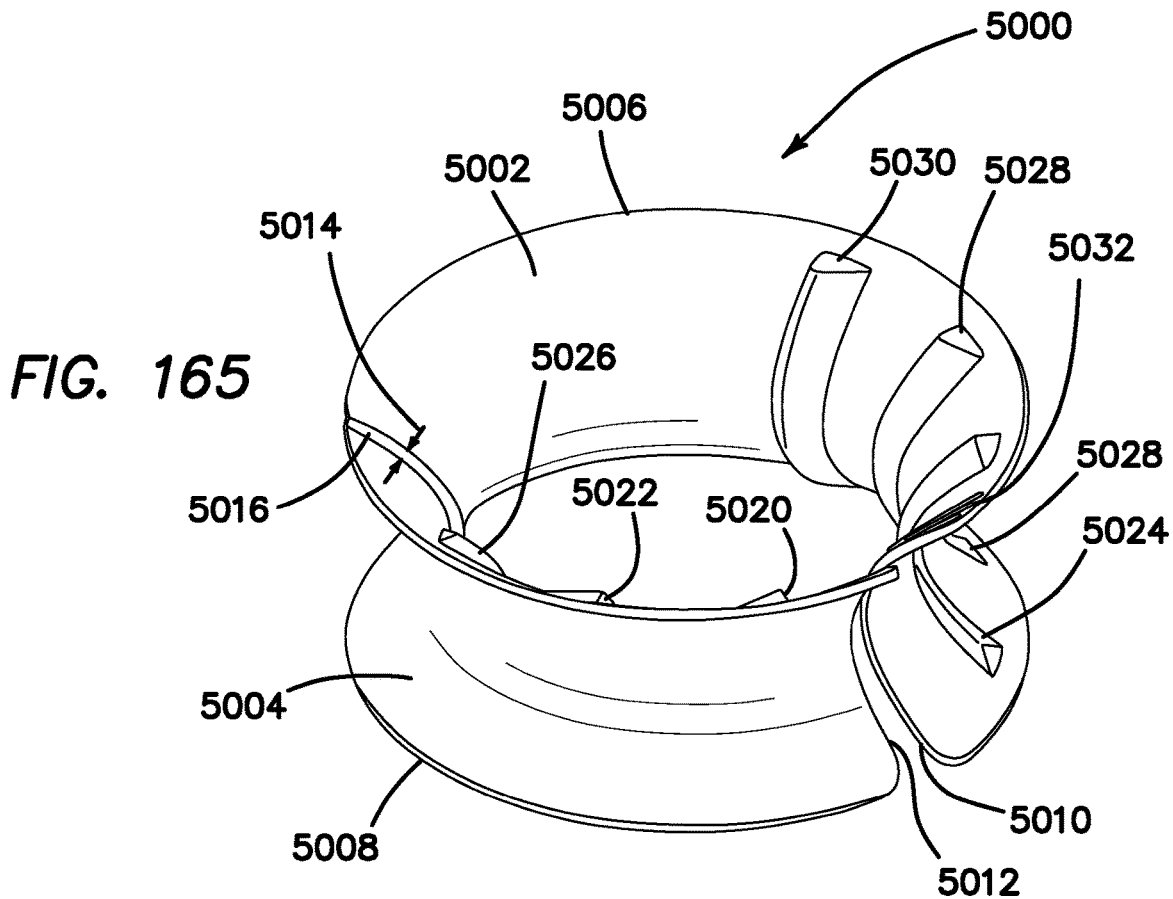

FIG. 165 is a top perspective view of a shield according to the present invention.

Figure 166:
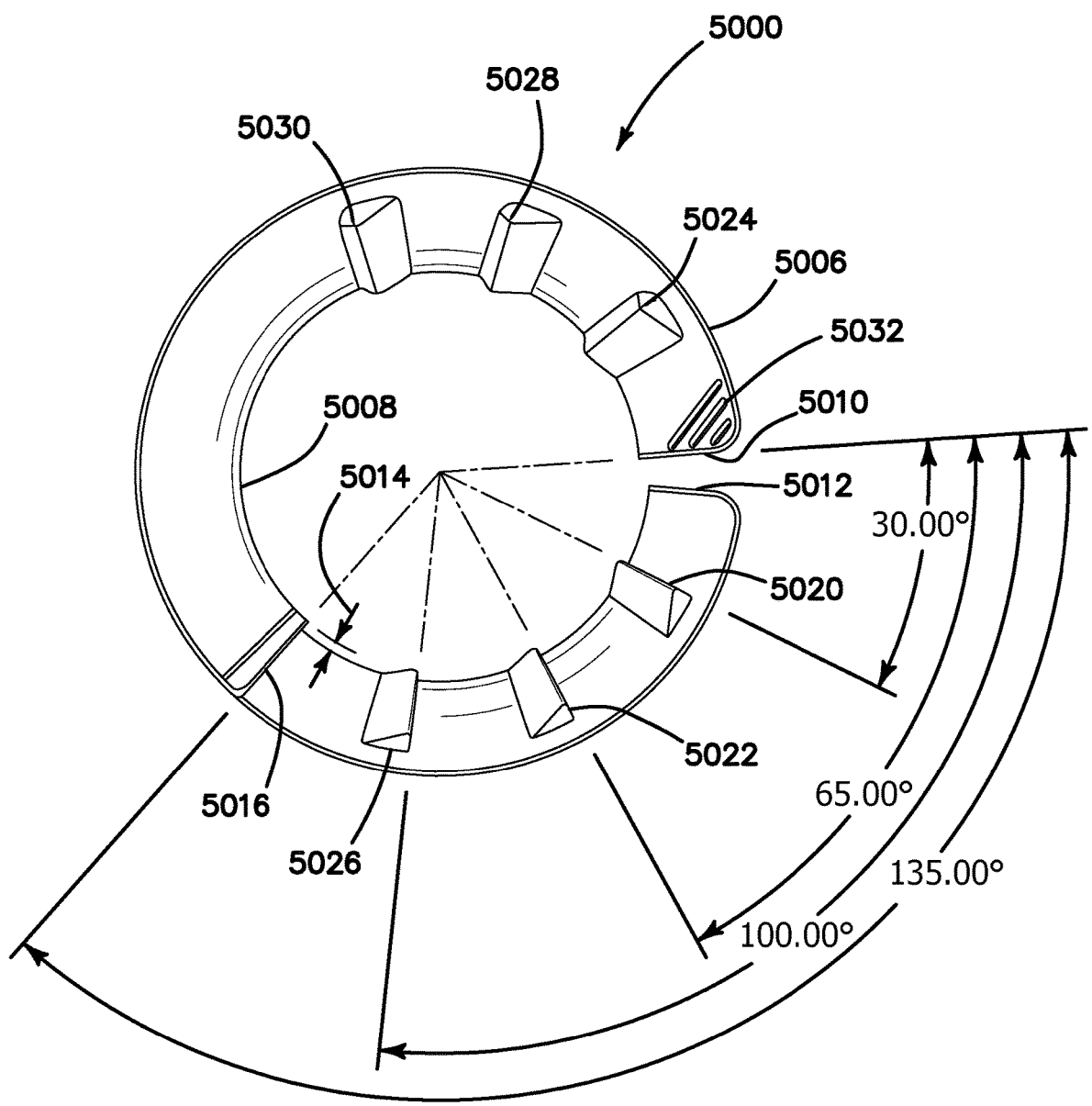

FIG. 166 is a top view of a shield according to the present invention.

Figure 167:
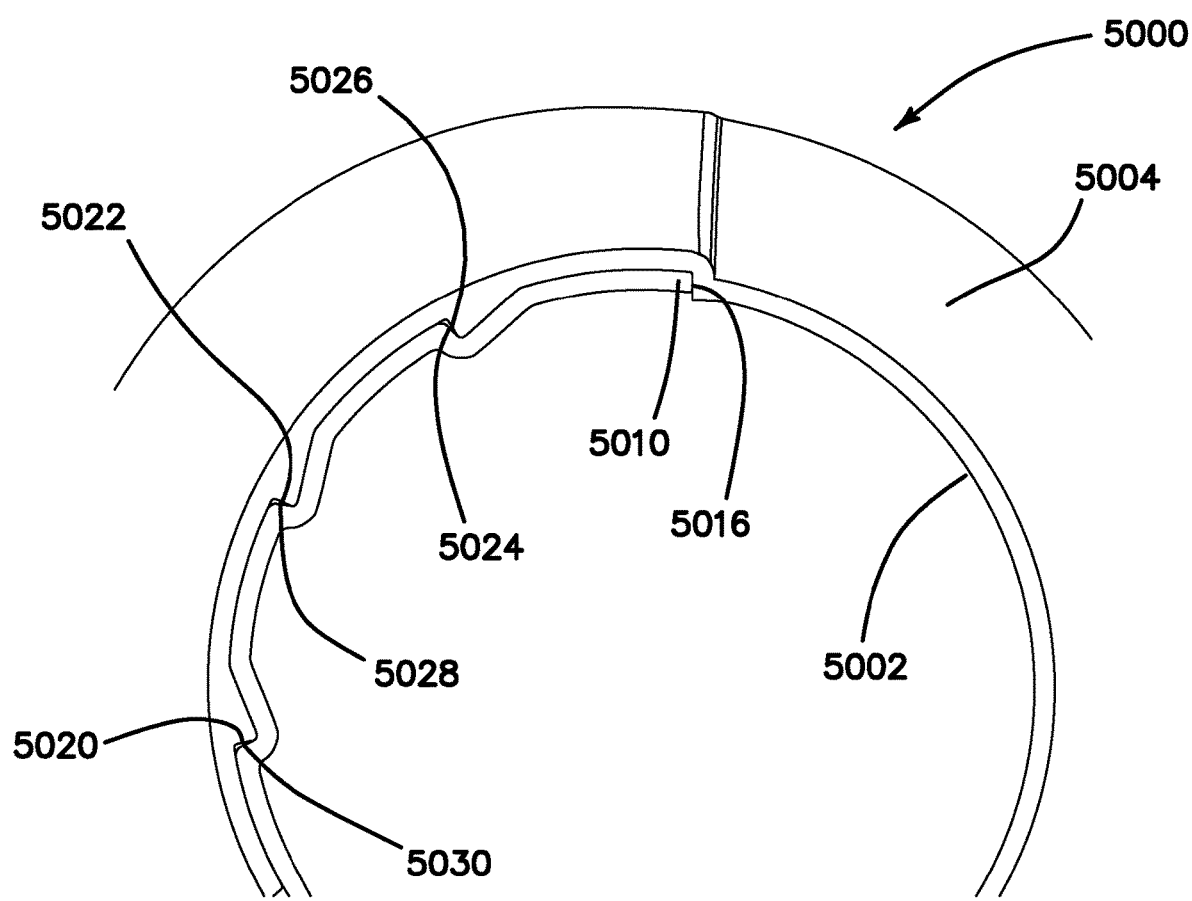

FIG. 167 is a top partial cross-sectional view of a shield in a locked configuration according to the present invention.

Figure 168:
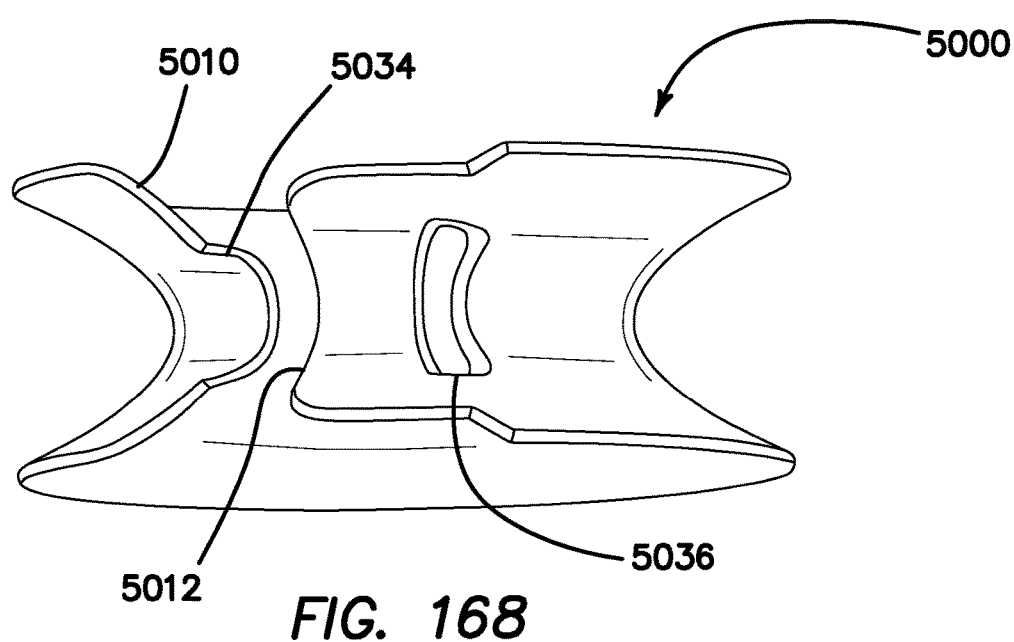

FIG. 168 is a bottom perspective view of a shield according to the present invention.

Figure 169:
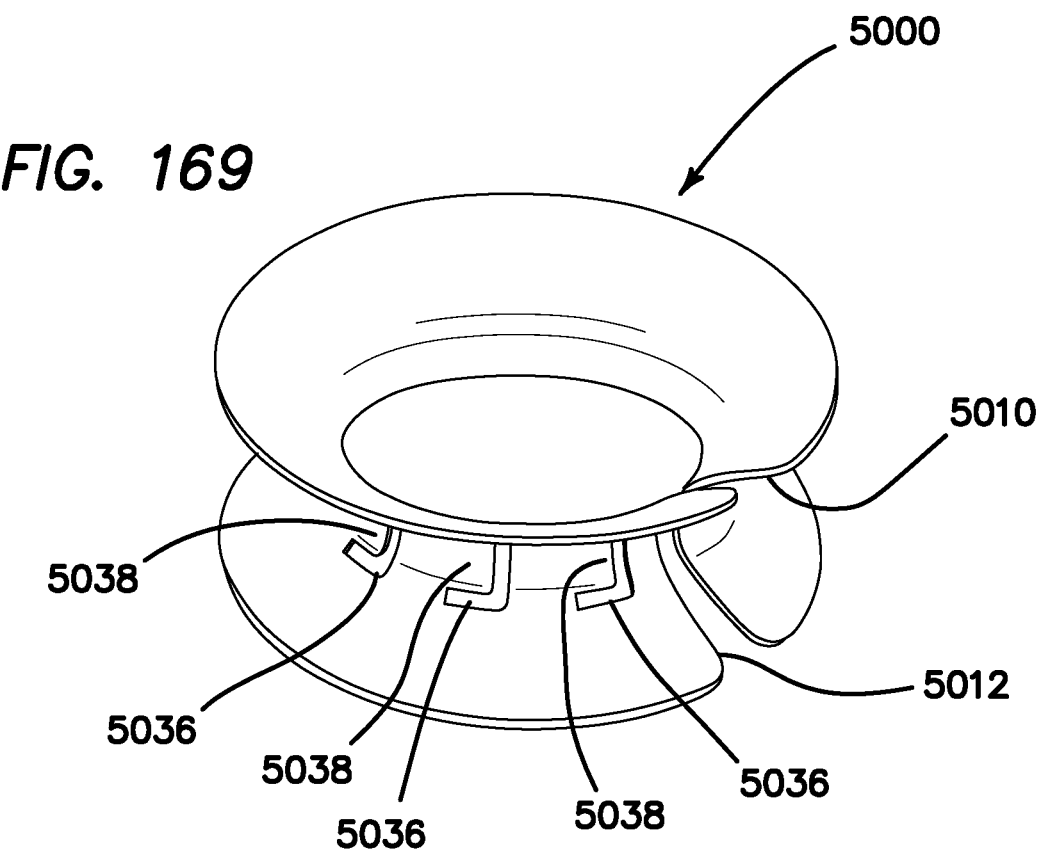

FIG. 169 is a top perspective view of a shield according to the present invention.

Figure 170:
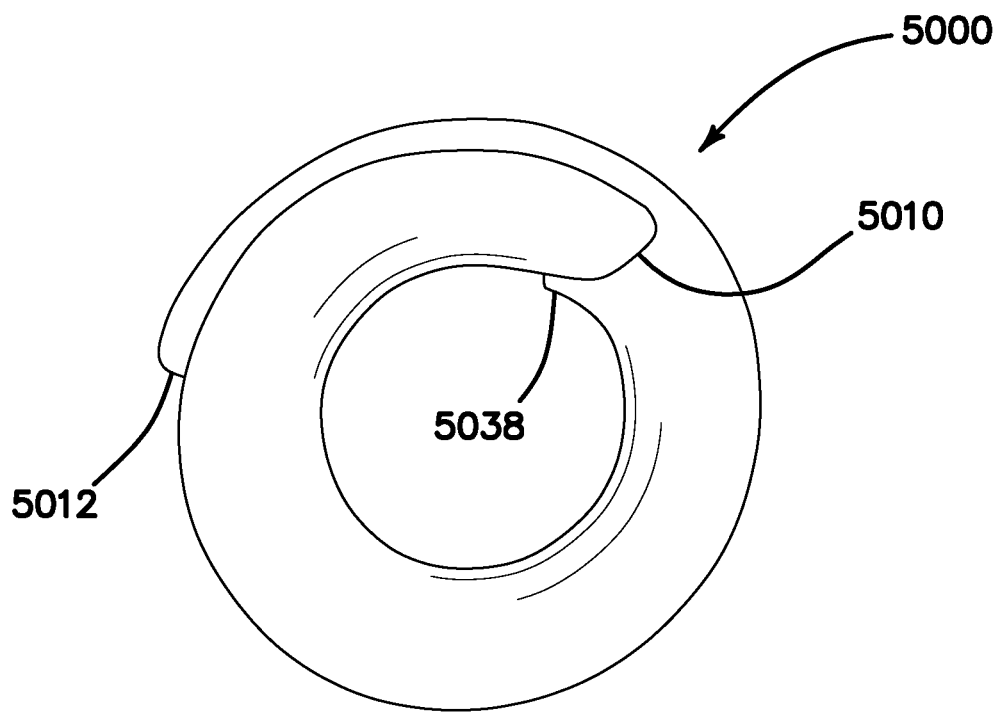

FIG. 170 is a top view of a shield according to the present invention.

Figure 171:
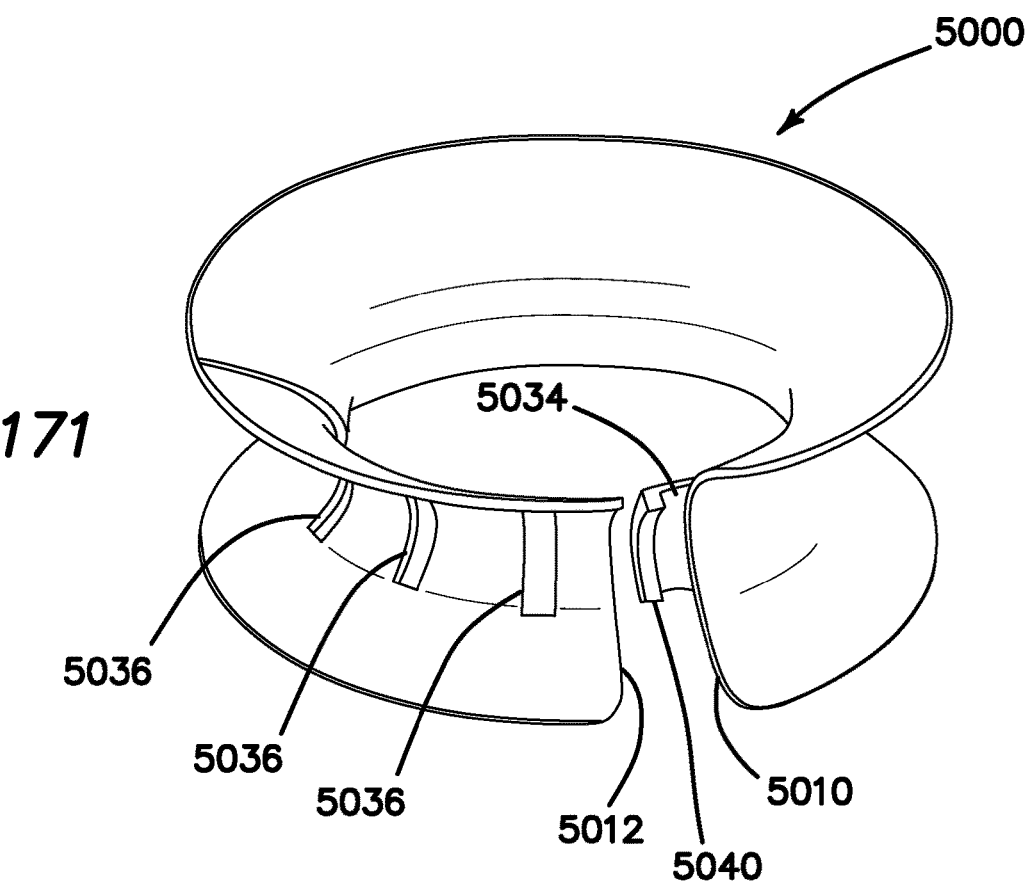

FIG. 171 is a top perspective view of a shield according to the present invention.

Figure 172:
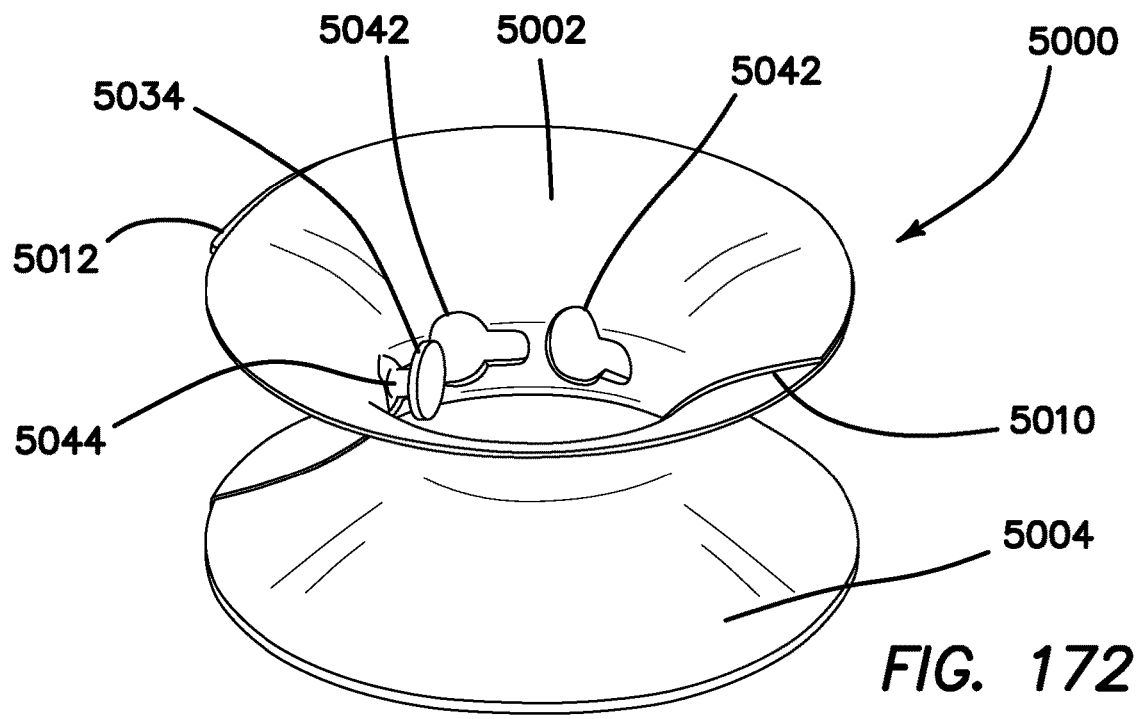

FIG. 172 is a top perspective view of a shield according to the present invention.

Figure 173:
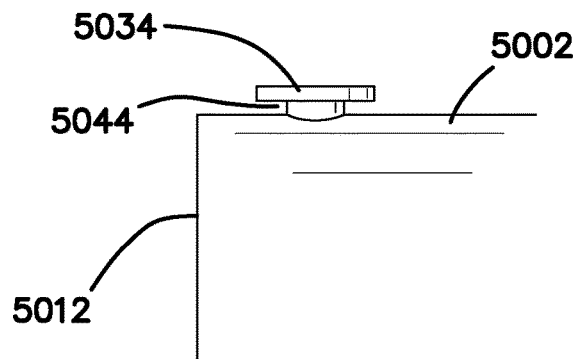

FIG. 173 is a top partial view of a shield according to the present invention.

Figure 174:
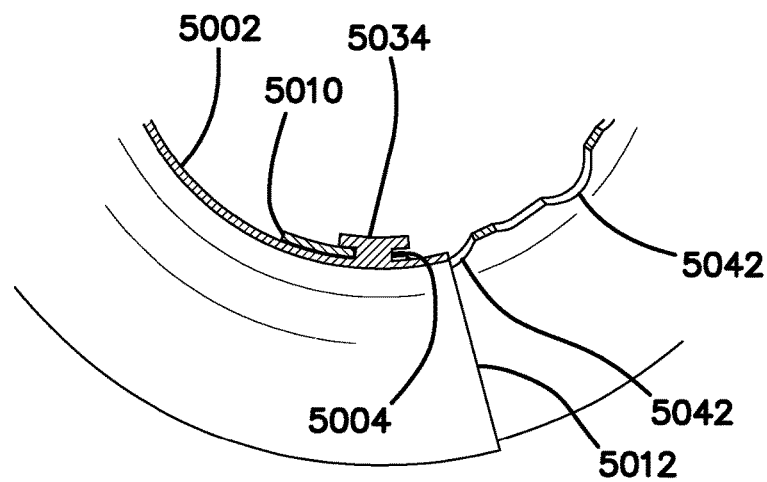

FIG. 174 is a top partial cross-sectional view of a shield according to the present invention.

Figure 175:
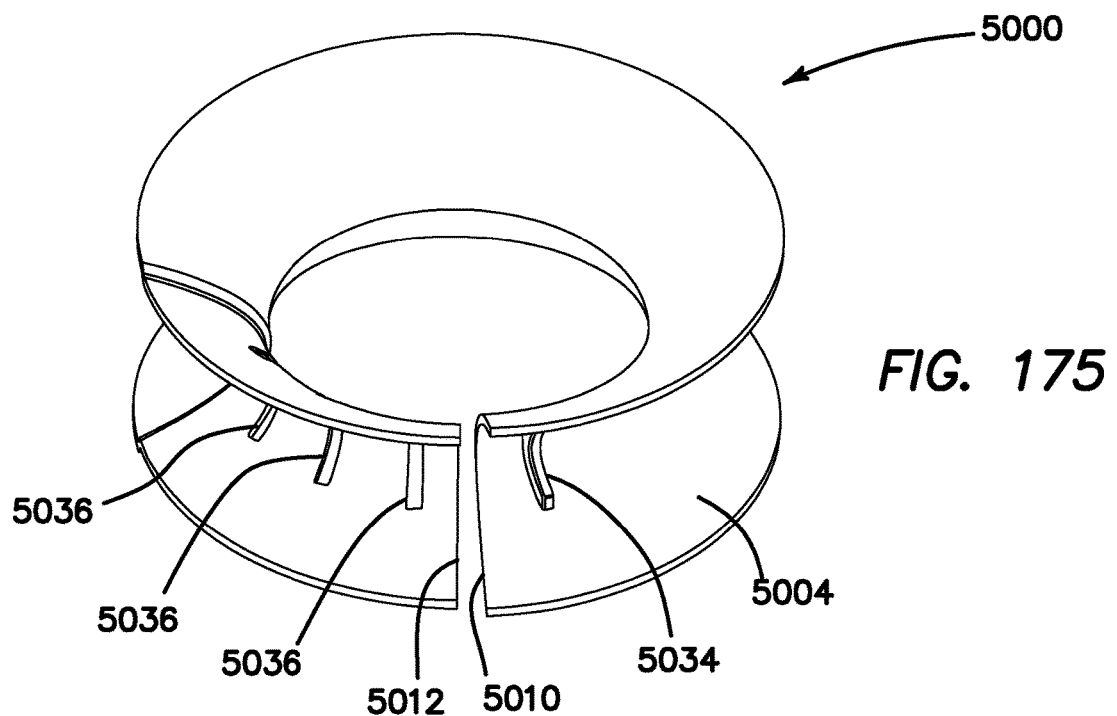

FIG. 175 is a top perspective view of a shield according to the present invention.

Figure 176:
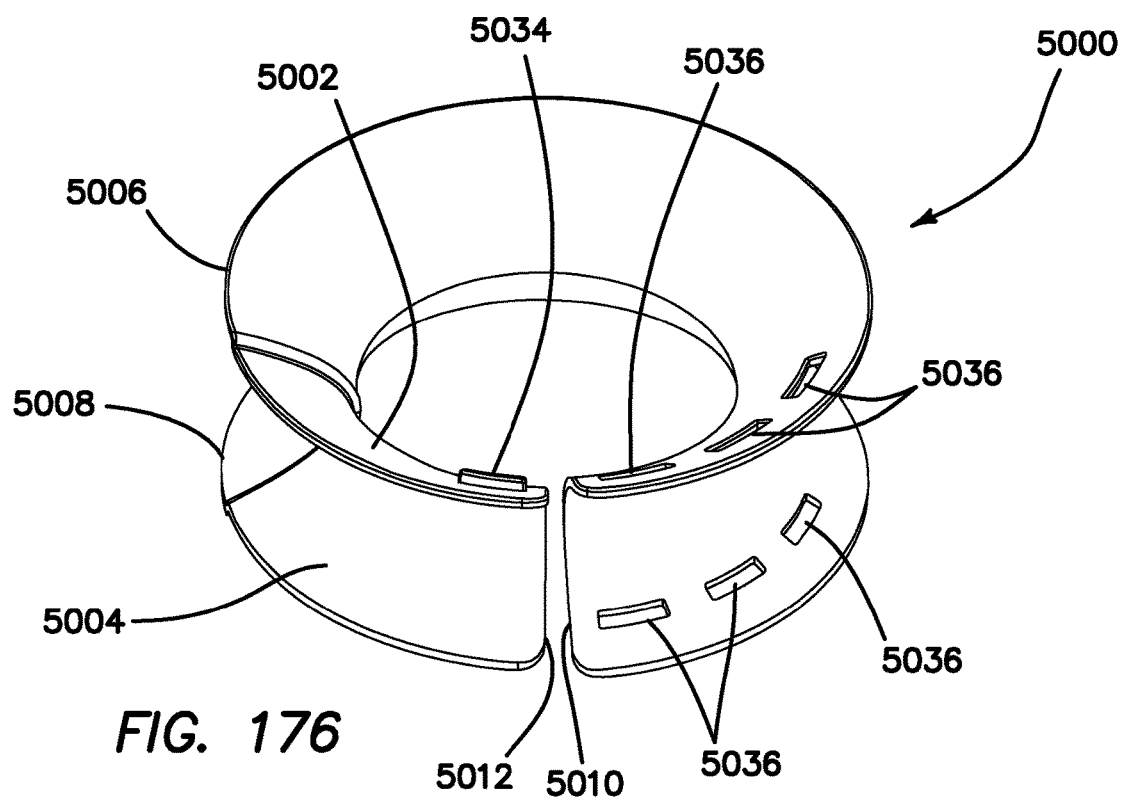

FIG. 176 is a top perspective view of a shield according to the present invention.

Figure 177:
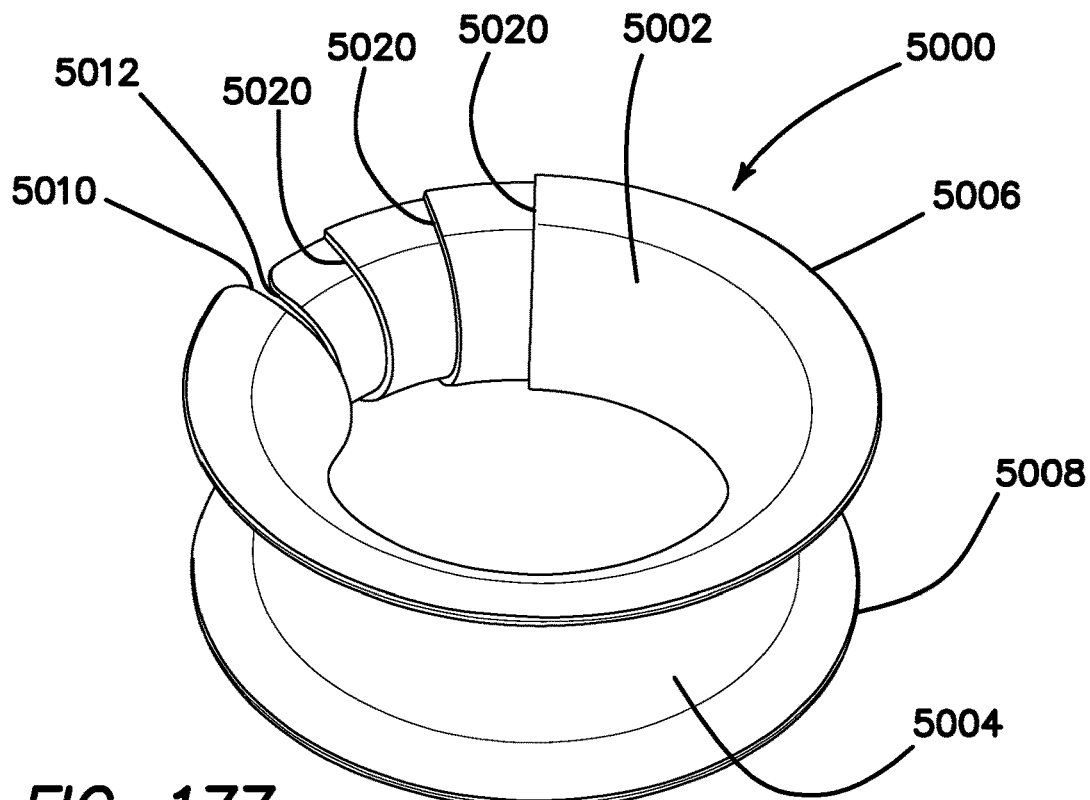

FIG. 177 is a top perspective view of a shield according to the present invention.

Figure 178:
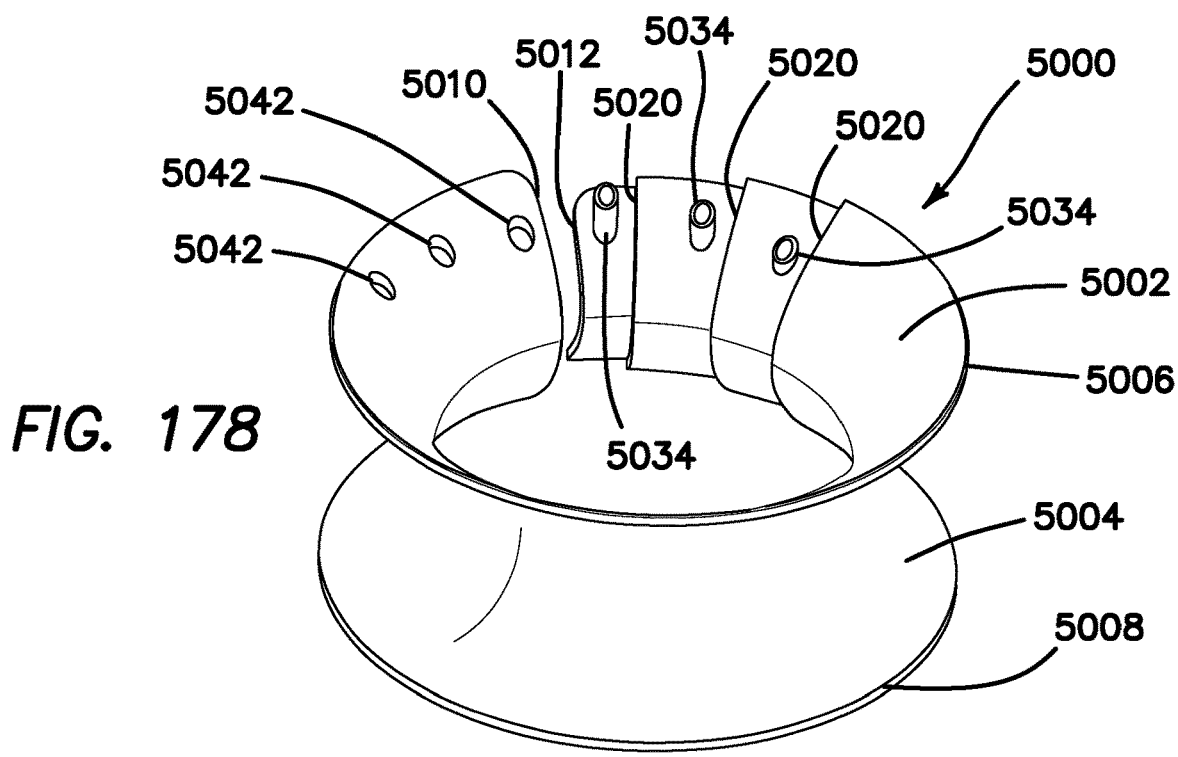

FIG. 178 is a top perspective view of a shield according to the present invention.

Figure 179:
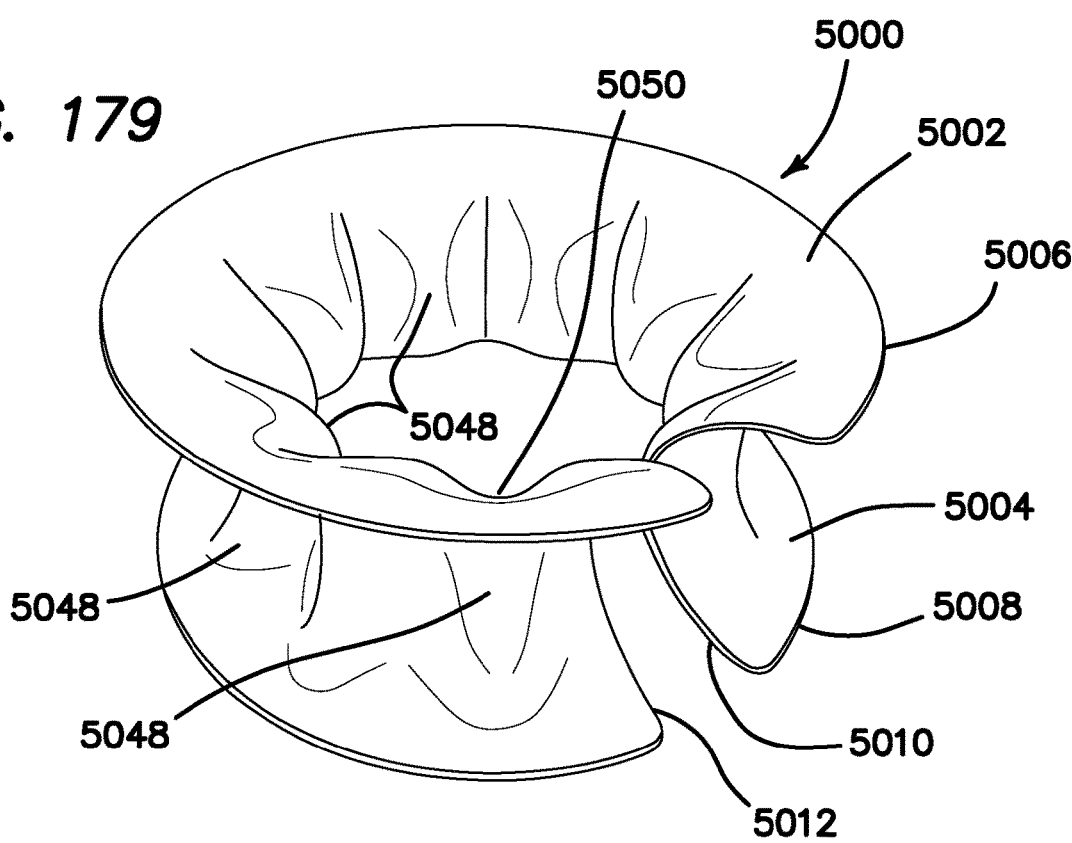

FIG. 179 is a top perspective view of a shield according to the present invention.

Figure 180:
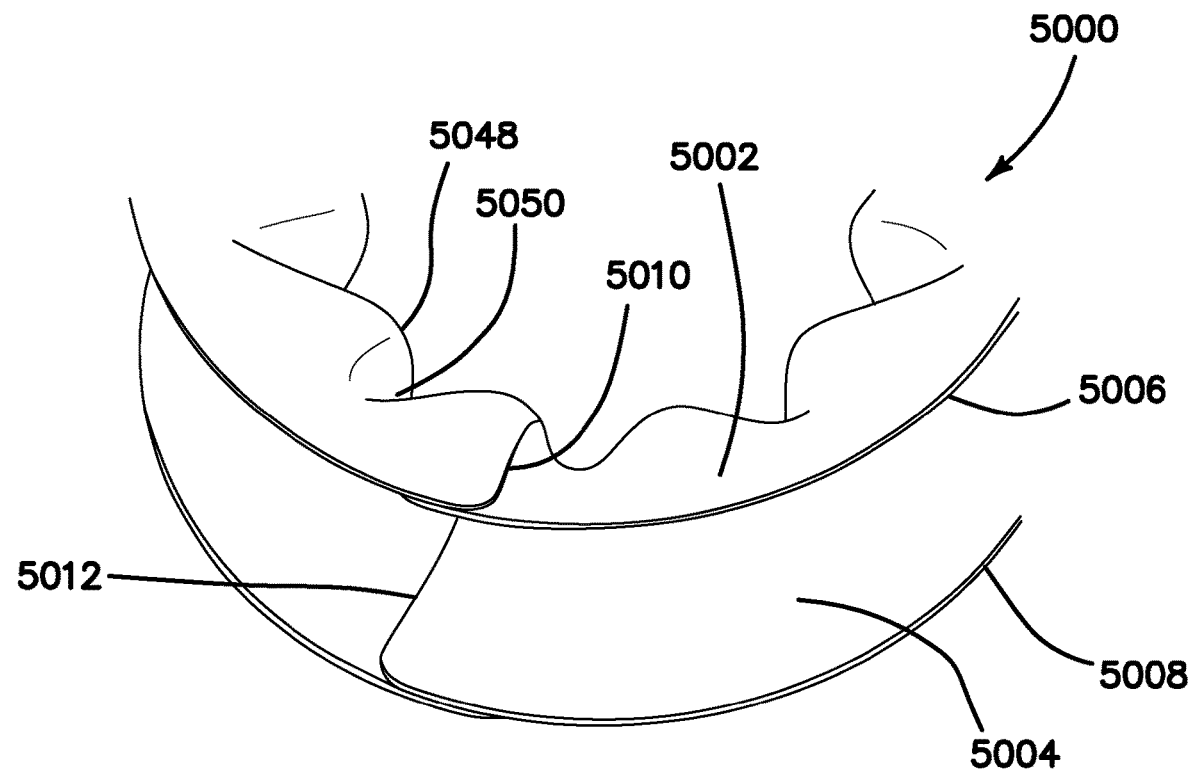

FIG. 180 is a partial top perspective view of a shield according to the present invention.

Figure 181:
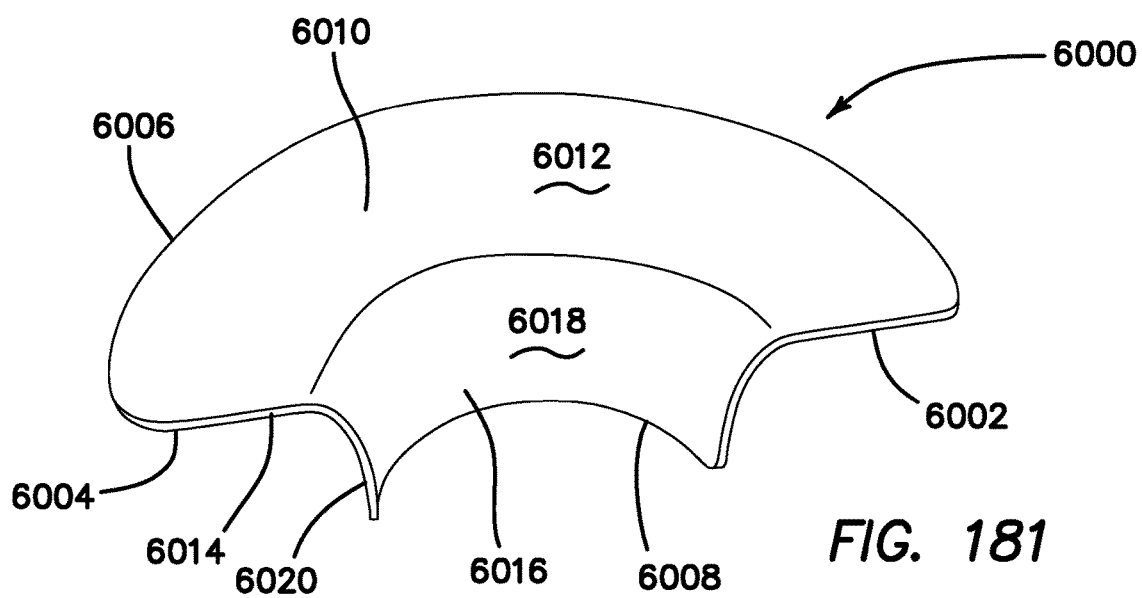

FIG. 181 is a top perspective view of a shield according to the present invention.

DETAILED DESCRIPTION OF THE INVENTION

The following description is provided to enable any person skilled in the art to make and use the surgical tools and perform the methods described herein and sets forth the best modes contemplated by the inventors of carrying out their inventions. Various modifications, however, will remain apparent to those skilled in the art. It is contemplated that these modifications are within the scope of the present disclosure. Different embodiments or aspects of such embodiments may be shown in various figures and described throughout the specification. However, it should be noted that although shown or described separately each embodiment and aspects thereof may be combined with one or more of the other embodiments and aspects thereof unless expressly stated otherwise. It is merely for easing readability of the specification that each combination is not expressly set forth.

Figure 1:
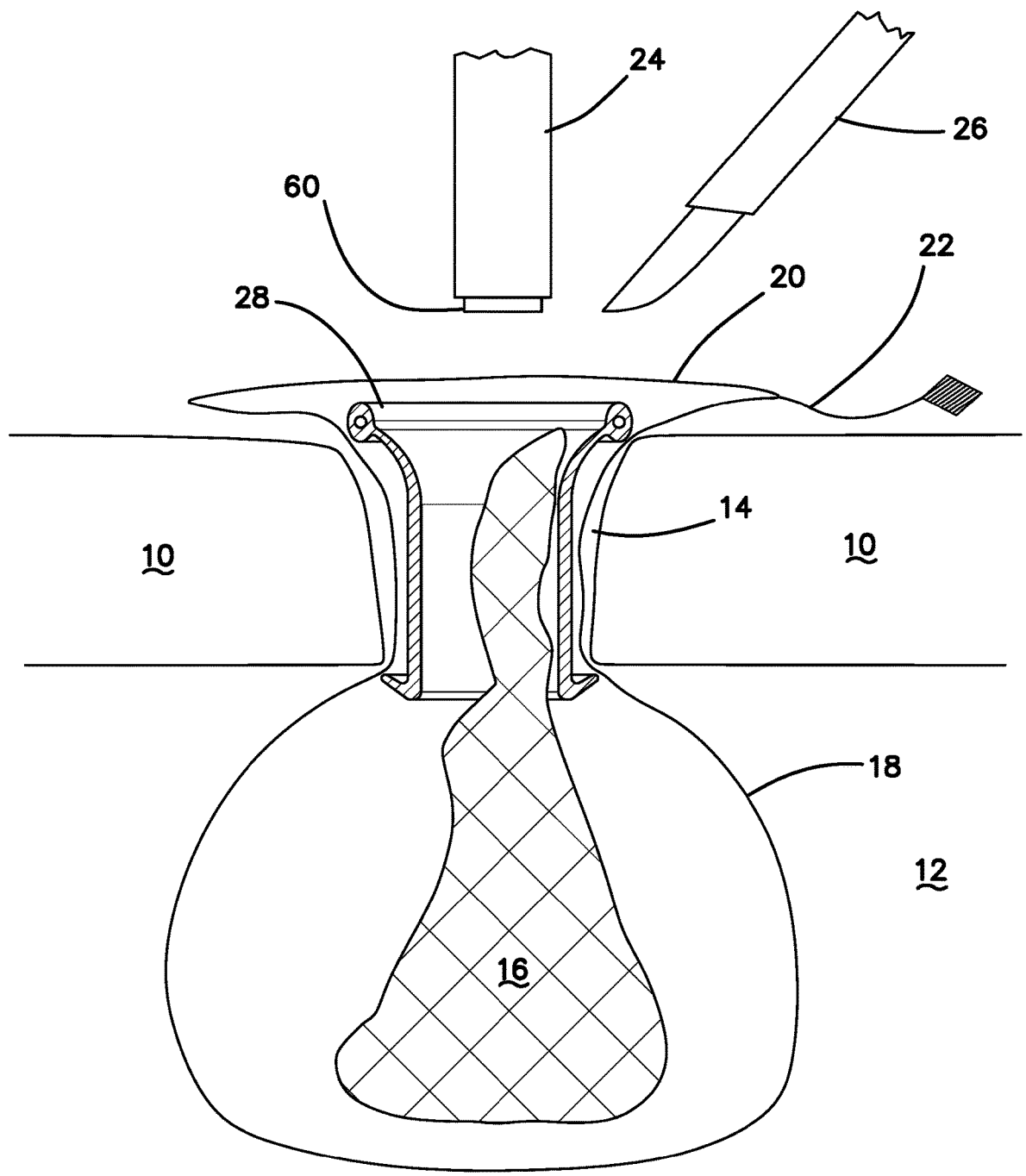
FIG. 1 is a cross-sectional view of a containment bag and guard placed in an opening in a body wall according to the present invention.
Figure 2:
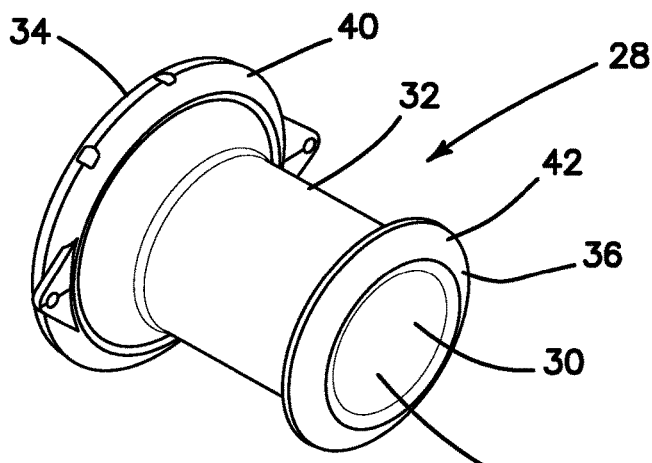
FIG. 2 is a top perspective view of a guard according to the present invention.
Figure 3:
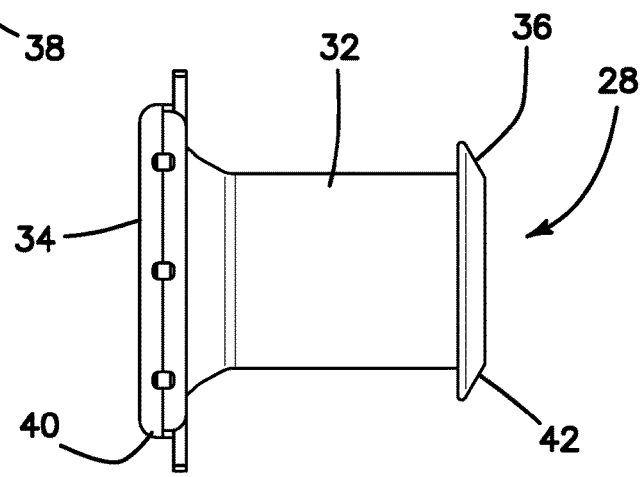
FIG. 3 is a side view of a guard according to the present invention.
Figure 7:
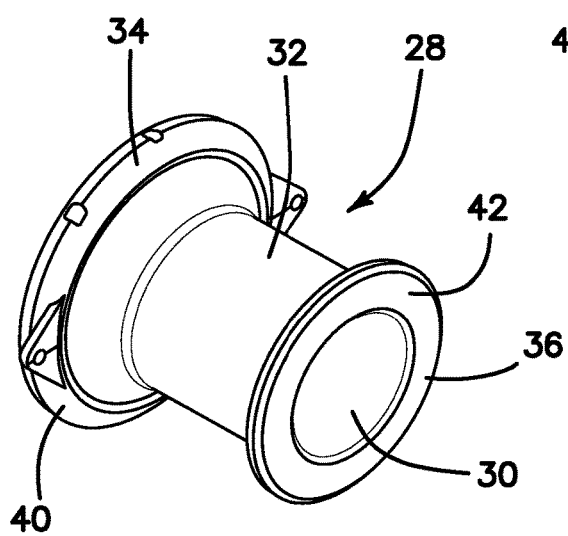
FIG. 7 is a top perspective view of a guard according to the present invention.
Figure 8:
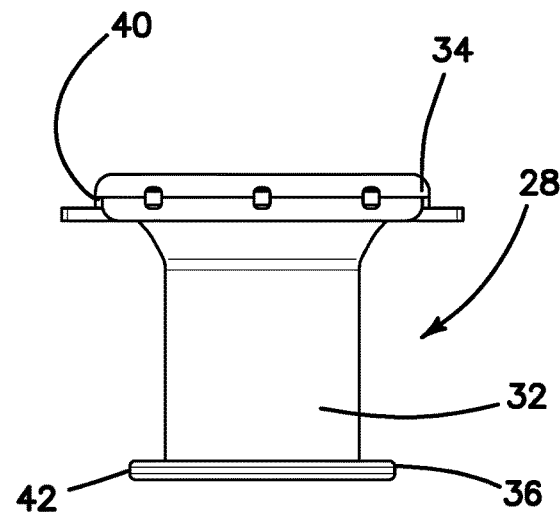
FIG. 8 is a side view of a guard according to the present invention.
Figure 4:
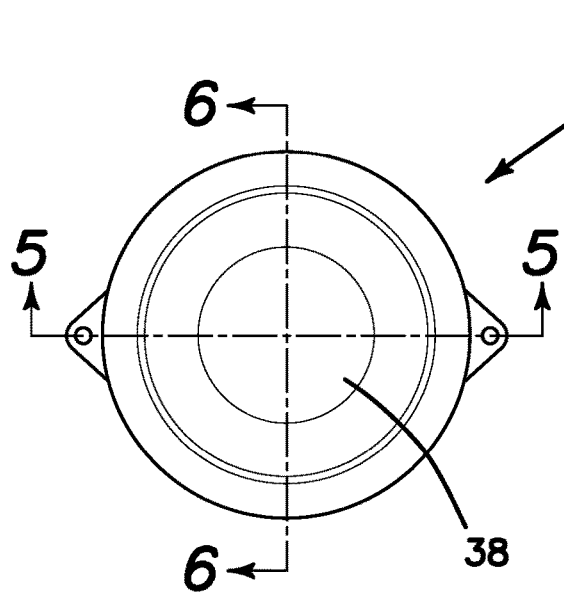
FIG. 4 is an end view of a guard according to the present invention.
Figure 5:
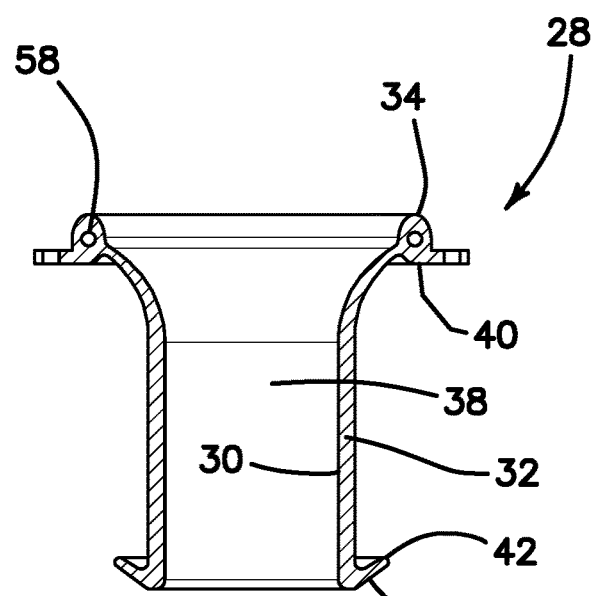
FIG. 5 is a cross-sectional view taken along line 5-5 of FIG. 4 of a guard according to the present invention.
Figure 6:
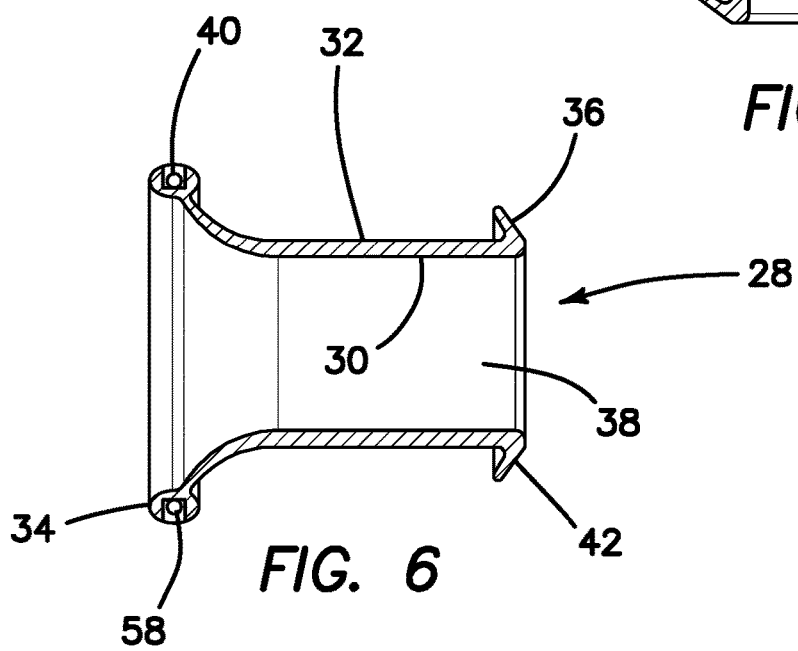
FIG. 6 is a cross-sectional view taken along 6-6 of FIG. 4 of a guard according to the present invention.

Turning now to FIG. 1, there is shown a closed morcellation procedure according to the present invention. A small incision is made in a patient in the location of an abdominal wall 10 and a body cavity 12 is accessed through an opening 14 across the abdominal wall 10. Laparoscopic techniques and instruments such as trocars, laparoscopes, graspers and scalpels may be employed to create the single site opening, spy the targeted tissue and detach the targeted tissue from surrounding tissue structures. Additional incisions or access sites may be employed to insert instruments and scopes to facilitate the procedure. After the targeted tissue 16 such as at least a part of the uterus in a hysterectomy procedure is completely detached, a specimen retrieval bag 18 is inserted through the opening 14 in the abdominal wall 10 and placed inside the body cavity 12. The bag 18 may be delivered through a trocar or cannula that is placed across the abdominal wall 10. The bag 18 is unfurled and oriented inside the body cavity 12. The targeted tissue 16 is placed into the bag 18 through an opening 20 in the bag 18. Various types of bags 18 may be employed. The bag 18 may be transparent such that the contents may be observable from outside the bag 18 via a scope placed into the body cavity 12 through a secondary incision site across the abdominal wall 10. The contents of the bag 18 may be illuminated from outside the bag 18. The location of the targeted tissue 16 may also be observed through a transparent bag 18 to ascertain the progress of morcellation as well as the position and proximity of the targeted tissue 16 relative to the opening 14. Also, the bag 18 is observed via a secondary site insertion to ascertain the state of the bag 18 making sure that it is not tangled and twisted and that the specimen is moved toward the opening without pulling the bag 18 along with it which may result in the bag being accidentally coming into contact with a blade and being severed. An opaque bag 18 may also be employed. The material of the bag 18 is also important. Generally, made of plastic, the bag is strong enough to withstand pulls and tugs, has sufficient stretch properties and is relatively thin, flexible and resilient to puncture and tears. The bag is folded and reduced in size such that it can be inserted through the small incision/trocar of approximately at least 5 mm in diameter. Also, when opened, the bag is large enough to receive a large piece of tissue, extend through the opening 14 to the surface of the abdominal wall 10 and create a sufficiently large working space inside the bag 18 for instruments, scopes, morcellators 24, and scalpels 26 as shown in FIG. 1. The bag 18 includes a tether or drawing string 22 configured to cinch the opening closed and to open the bag 18. The bag 18 withstands insufflation pressures and does not leak. Various examples of bags and devices for inserting, deploying and/or retrieving bags to be included or integrated into the morcellation system in which the entire systems, portions of the systems or combinations of the systems and/or components thereof arranged to provide a containment of object to be morcellated in accordance with various embodiments of the present invention are described in U.S. patent application Ser. No. 08/540,795, filed Oct. 11, 1995; Ser. No. 11/549,701, filed Oct. 16, 2006; Ser. No. 11/549,971, filed Oct. 16, 2006; Ser. No. 12/902,055, filed Oct. 11, 2010; and Ser. No. 13/252,110, filed Oct. 3, 2011; the entire disclosures of which are hereby incorporated by reference as if set forth in full herein. Additional bag variations will be described in greater detail hereinbelow.

After the targeted tissue 16 is placed inside the bag 18, the tether 22 is grasped by hand or with a laparoscopic grasper and at least a portion of the bag 18 is pulled through the abdominal wall opening 14. Pulling the tether 22 closes the bag opening 20. The initial incision may be increased to approximately 15-40 mm prior to pulling the bag 18 through the opening 14. If the targeted tissue 16 is too large to fit through the opening 14, the targeted tissue 16 will sit inside the body cavity 12 below the abdominal wall 10. The remainder of the bag 18 including the opening 20 of the bag 18 will be pulled through the abdominal wall opening 14 and extend through the opening 14 to outside the patient and along the upper surface of the abdominal wall 10 as shown in FIG. 1. The bag 18 may be rolled down and/or pulled taut across the surface of the abdominal wall 10 to maintain its position and provide some tissue retraction at the opening 14.

A guard 28 is inserted in through the opening 20 of the bag 18. The guard 28 has a diameter in the incision/opening 14 such that when it is placed inside the opening 14 the guard 28 is retained in position. The guard 28 may also retract tissue at the incision/opening and, as such, be called a retractor. One variation of a guard 28 is shown in FIGS. 2-6 and another variation is shown in FIGS. 7-10. The guard 28 includes an inner surface 30 and an outer surface 32 defining a sidewall interconnected between a top 34 and a bottom 36. The inner surface 30 defines a central lumen 38 that extend between the top 34 and the bottom 36. The inner surface 30 includes a curved, funnel portion near the top 34 that may be convex or frusto-conical. The guard 28 includes a top circumferential flange 40 and a bottom circumferential flange 42 that extend radially outwardly to create surfaces for seating against the upper and lower surfaces, respectively, of the abdominal wall 10. The top flange 40 may include features such as apertures for passing the tether 22 and securing the guard 28 to the bag 18. The guard 28 has an overall length of approximately 2.5 inches; however, guards 28 of various lengths may be employing depending on the thickness of the tissue wall 10 to be penetrated. A guard 28 that has a variable length, such as a telescoping guard 28, is within the scope of the present invention. The inner diameter of the guard 28 at mid-length is approximately 1.3 inches and can be as small as approximately 0.6 inches. The outer diameter of the guard 28 at mid-length is approximately 1.6 inches and conforms to the incision/opening such that the top circumferential flange 40 is retained in position due to its larger overall diameter relative to the diameter of the guard 28 at mid-length. The wall thickness at mid-length is approximately 0.16 inches and may be as thick as approximately 0.3 inches. The guard 28 is made of any polymer such as KRATON® or polyethylene; however, the guard may be made of any suitable material including metal. A guard 28 can be flexible such that it can be slightly compressed for ease of insertion through the opening 14 in the abdominal wall 10. The thickness of the guard 28 and/or choice of material for the guard 28 are selected such that the guard 28 is capable of withstanding cutting and puncture forces from blades, knives, scalpels, morcellators and the like. The guard 28 serves as a cutting board or surface against which targeted tissue is placed for cutting prior to removal. The targeted tissue 16 is grasped with a laparoscopic grasper and pulled upwardly toward the opening 14. At least a portion of the targeted tissue 16 that is to be cut is then held in position in the location of the guard 28 anywhere along its length. A blade such as a scalpel or morcellator is then moved into contact with that portion of the targeted tissue to be cut in the location of the guard 28 and that portion of the targeted tissue is cut. The cut portion of targeted tissue is pulled up through the opening 14 to the surface outside the patient and a new section of targeted tissue is brought into position along the guard 28 to be cut and removed. This process is repeated until the entirety of the specimen is removed in whole or in part from the bag 18. The guard 28 serves as protection for the bag 18. The practitioner is free to cut the targeted tissue in the location of the guard 28 and even against the guard's inner surface 30 mitigating the consequences of severing the bag 18 with the scalpel or morcellator. The guard 28 not only protects the specimen retrieval bag 18 from accidental incision, but also, the guard 28 protects surrounding tissue, such as the abdominal wall, from accidental incision. The guard 28 preserves the integrity of the bag 16 and effectively maintains a closed morcellation system. The surgeon is able to quickly and safely reduce the specimen and remove it from the abdominal cavity.

Once the guard 28 is placed, the surgeon will grasp the specimen 16 and pull it up through the incision as far as possible. The surgeon will then begin morcellating the specimen 16 with a scalpel 26, cutting the specimen 16 to reduce its size. Ideally, the surgeon will "core" or "peel" the specimen 16 to keep it in one piece as much as possible. However, more likely than not, the specimen 16 will be reduced in multiple pieces. While morcellating through the incision, the surgeon may maintain pneumoperitoneum in the abdominal cavity 12 so that the progress of the morcellation can be observed laparoscopically through a lateral port placed at a secondary site into the cavity 12. The lateral port lies outside the bag 18 and the surgeon may look through the transparent bag, or at the bag itself to ensure it maintains its integrity. Once the specimen 16 is morcellated, crushed, reduced enough to pull the remaining portion through the incision, the guard 28 is removed, and the bag 18 and its contents, including the pieces created during morcellation, are pulled out of the patient. The bag 18 will prevent the remaining small pieces from being left in the abdominal cavity 12, maintaining the closed system; whereas in a traditional morcellation, the surgeon must go back and painstakingly search and collect the pieces scattered amid the pelvic cavity to prevent potentially seeding new tumor sites. The surgeon may choose to take a final look at the patient laparoscopically and then close the wounds.

While described for an abdominal removal and morcellation, the above-described procedure can be performed via the vagina orifice as well if the cervix has been removed. Following the same process, the bag 18 will be introduced and the specimen 16 placed into the bag 18 laparoscopically. Rather than pull the tether 22 through the abdominal wall opening 14, it would be pulled through the vagina. In the same way, the specimen 16 would sit at the base of the vagina while the bag 18 goes through the vagina and opens up outside the patient. The surgeon may roll the bag 18 down or pull it taut to maintain its position and provide some retraction. The surgeon would place the guard 28 vaginally to protect integrity of bag 18 and to maintain a closed system, grasp the specimen 16 to bring it out, and morcellate to reduce the size of the specimen 16. Morcellation of the specimen is performed in the location of the guard 28 and/or against the guard 28 surface protecting the surrounding tissue and bag from inadvertent incisions. The surgeon may maintain pneumoperitoneum and watch the progress of the morcellation laparoscopically. Once the specimen 16 is morcellated, crushed, reduced enough to pull the remaining portion through the vagina, the guard 28 is removed, and the bag 18 and its contents, including the pieces created during morcellation, are pulled out of the patient. The bag 18 will prevent the remaining small pieces from being left in the abdominal cavity preventing harmful material such as cancerous cells form being disseminated in the abdominal cavity, maintaining the closed system; whereas in a traditional morcellation, the surgeon must go back and painstakingly search and collect the pieces scattered amid the pelvic cavity search for the pieces amid the pelvic cavity. The surgeon may choose to take a final look at the patient laparoscopically and will close the vaginal cuff and abdominal incisions.

Figure 12:
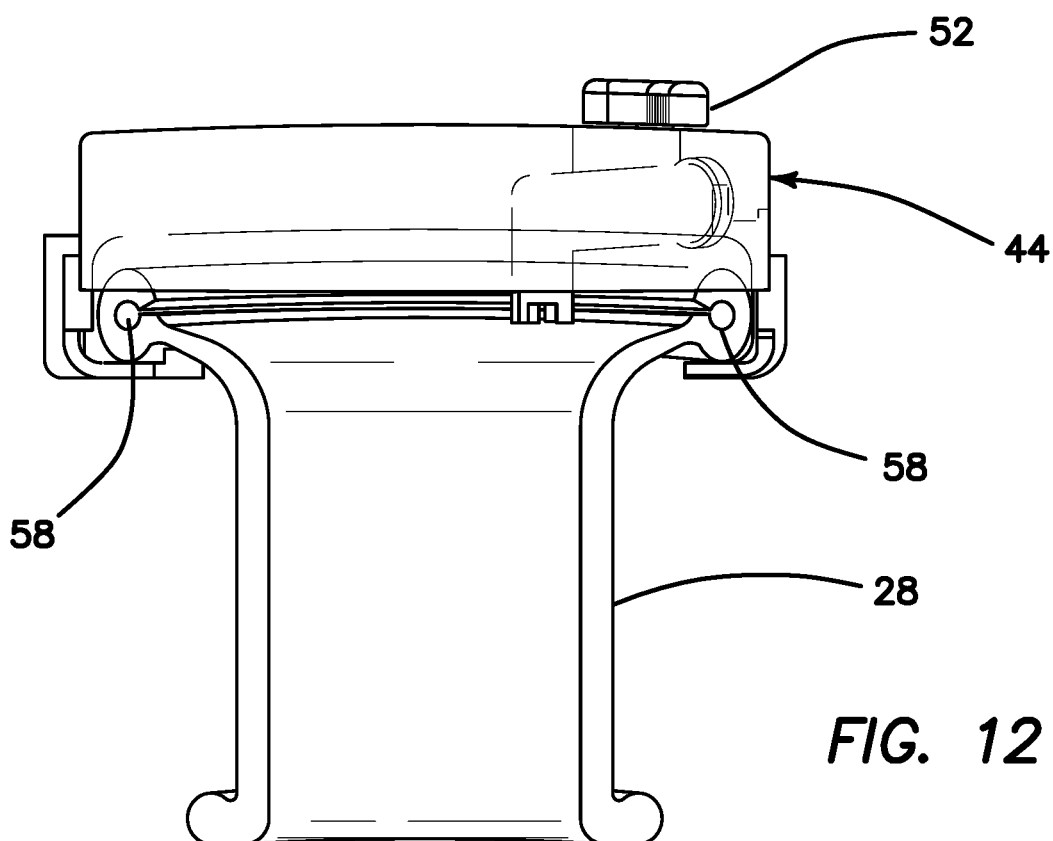
FIG. 12 is a cross-sectional side view of a cap and guard according to the present invention.
Figure 13:
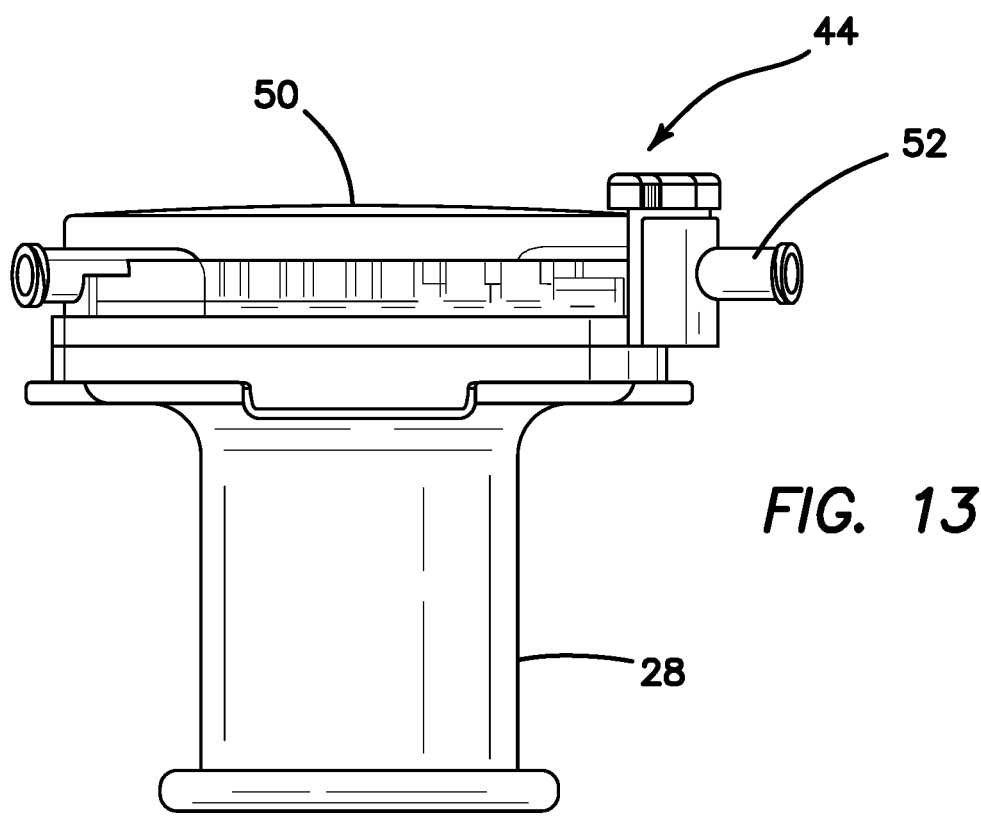
FIG. 13 is a side view of a cap and guard according to the present invention.
Figure 14:
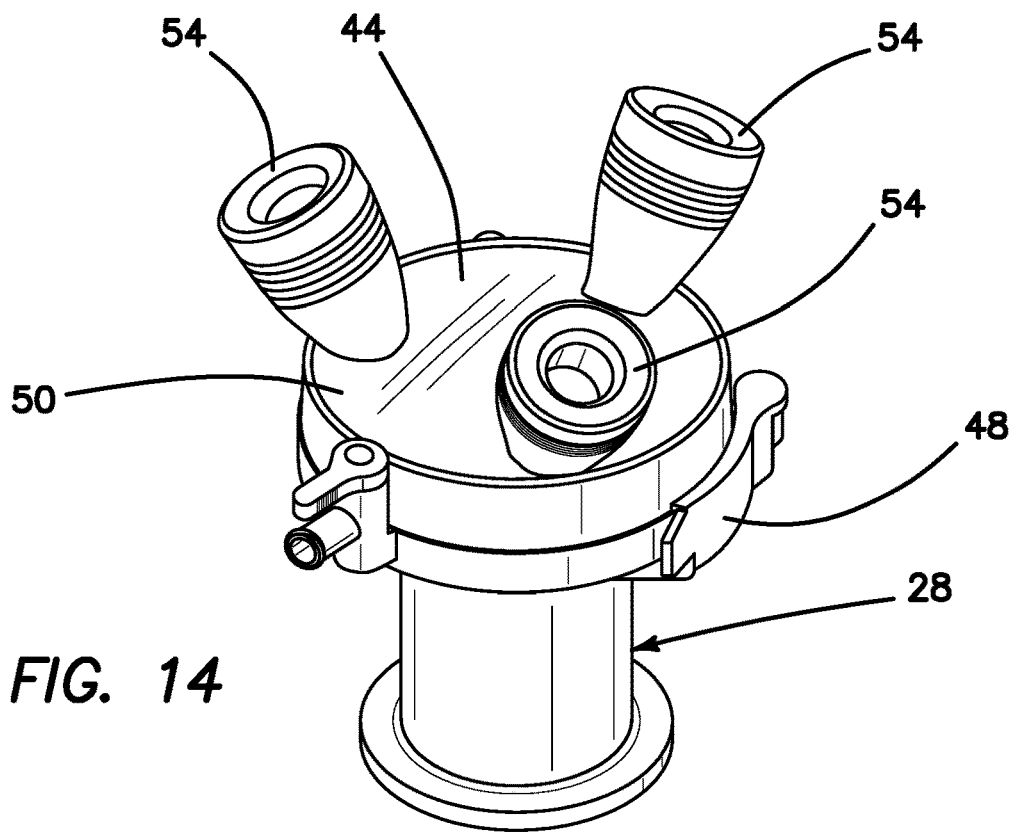
FIG. 14 is a top perspective view of a cap and guard according to the present invention.

In one variation shown in FIG. 11, the guard 28 is configured to attach to a cap 44 such as a GELSEAL® cap manufactured by Applied Medical Resources Corporation in California. The cap 44 includes a rigid ring 46 detachably connectable to the proximal end of the guard 28. The cap 44 includes a lever 48 for locking the cap 44 to the guard 28. The cap 44 includes a penetrable portion 50 that can be made of gel configured to seal against instruments inserted therethrough and maintain pneumoperitoneum inside the abdominal cavity. FIGS. 12-13 illustrate the cap 44 connected to the guard 28. An insufflation port 52 may be provided in the cap 44. The cap 44 snaps onto the guard 28 and may be sealingly locked thereto with the lever lock 48 such that pneumoperitoneum is maintained. FIG. 14 illustrates a cap 44 having multiple ports 54. Each port 54 is configured to receiving laparoscopic instruments and includes one or more internal seals for sealing against inserted instruments. A multi-port cap 44 advantageously permits the insertion of a grasper, laparoscope and/or morcellator through a single site.

Figure 15:
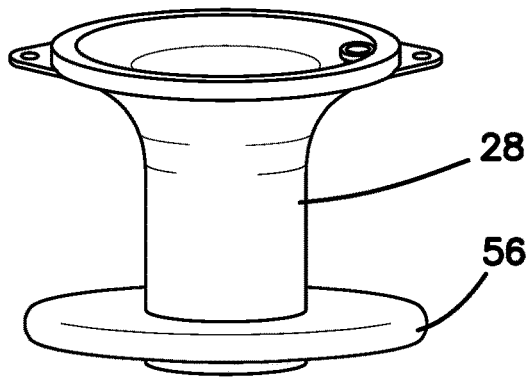
FIG. 15 is a top perspective view of a guard according to the present invention.
Figure 16:
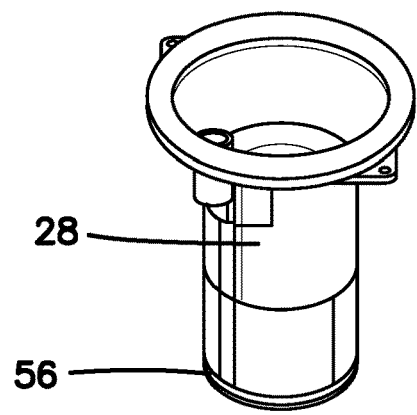
FIG. 16 is a top perspective view of a guard according to the present invention.
Figure 17:
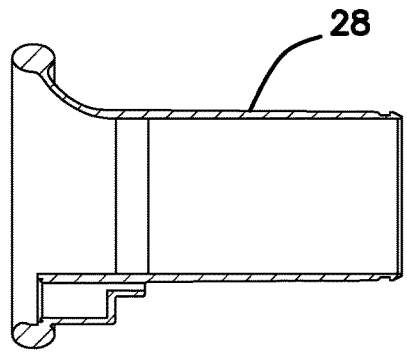
FIG. 17 is a cross-sectional side view of a guard according to the present invention.

FIGS. 15-17 illustrate another variation of the guard 28 that includes a balloon 56 at the distal end of the guard 28. The balloon 56 is shown in an inflated configuration in FIG. 15. In the inflated configuration, the balloon 56 extends radially outwardly to create a wide flange for securing against the abdominal wall 10 inside the abdominal cavity 12 making it difficult for the guard 28 to be inadvertently removed from the opening 14. FIG. 16 illustrates the balloon in a deflated configuration in which the guard 28 is easily inserted into and removed from the opening 14. The guard 28 of FIGS. 15-17 may also connect to a cap 44. The guard 28 can be made of any polymer material including polycarbonate or similar material.

A funnel-shaped entry at the proximal end of the guard 28 has been described above. The funnel-shaped entry may be enlarged radially outwardly in another variation to create a larger surface area against which tissue may be cut. The flared proximal end also assists in retaining the bag in position outside the patient and between the guard 28 and the tissue margin 10. In another variation, the guard 28 includes a flared distal end that is frusto-conical or curved in shape. The flared distal end may include an enlarged radially extending flange that spreads the bag 18 laterally inside the abdominal cavity. The flared distal end assists in keeping the bag in an open position and away from coming into contact with the specimen and away from the distal entry into the guard 28, thereby, further protecting the bag 18 from inadvertent contact with a blade. In the flared distal end variation of the guard 28, the distal diameter of the guard 28 at the distal opening is greater than the diameter of the guard 28 at mid-length. In the flared proximal end variation of the guard 28, the proximal diameter of the guard 28 at the proximal opening is greater than the diameter of the guard 28 at mid-length. In yet another variation, the guard 28 includes a flared proximal end and flared distal end retaining the advantages of both described above.

Methods for removal of tissue that employ the guard 28 with a cap 44 will now be described. After completing the laparoscopic hysterectomy or any other dissection, the specimen 16 described previously is completely detached from surrounding tissue and awaiting removal. The surgeon will insert the specimen bag 18 which may be transparent into the pelvis and place the specimen 16 in the bag 18. The surgeon will then grab the tether 22 on the bag 20 with a laparoscopic grasper and pull the bag 18 up and through the abdominal wall incision 14 where a trocar was previously positioned. If necessary, the surgeon will extend the incision to 15-25 mm prior to pulling the bag all the way through. Because the specimen 16 is too large to fit through the opening 14, the specimen 16 will sit right below the abdominal wall 10, inside the pelvic cavity, while the remainder of the bag 18 is pulled up out of the incision and is opened outside the patient as shown in FIG. 1. The surgeon may roll the bag down or pull it taut to maintain its position and provide some retraction. The surgeon will then insert the guard 28 into the incision to protect the bag 18 and abdominal wall 10 during morcellation, as well as to retract the incision. The integrity of the bag is preserved and the closed system is maintained.

The guard 28 is placed into the opening 20 of the bag 18 and positioned within the incision such that the guard 28 extends across the tissue margin 10. A cap 44 is connected to the guard 28. The cap 44 snaps onto the proximal top flange 40 and the lever 48 of the cap 44 is moved into a locked position sealing the cap 44 onto the guard 28. The guard 28 may include a reinforced wire 58 to maintain the shape and rigidity of the top flange 40. The wire 58 is visible in FIGS. 1, 5-6, 10 and 12. With the cap 44 in position, the bag 18 may be insufflated. In one variation, the bag 18 alone is insufflated relative to the abdominal cavity 12. In another variation, both the bag 18 and the abdominal cavity 12 are insufflated. In another variation, both the bag 18 and the abdominal cavity 12 are insufflated such that the pressure inside the bag 18 is greater than the insufflation pressure of the cavity 12. Insufflation may be provided through a trocar inserted through the cap 44 or via the insufflation port 52 in the cap 44. With the cap 44 in position, a power morcellator 24 is inserted through the penetrable portion 50 of the cap 44 and into the interior of the bag 18. Alternatively, if a multi-port cap 44 is employed, a morcellator 24 may be inserted through one of the ports 54. A surgical grasper is also inserted through the cap 44 either through the penetrable portion 50 or through one of the ports 54 and the targeted tissue is grasped and pulled proximally toward the opening and into the central lumen 38 of the guard 28 where the targeted tissue is morcellated in the zone of protection afforded by the guard 28. As mentioned previously, the guard 28 protects the bag 18 from being punctured and, thereby, assists in maintaining a closed morcellation system. The power morcellator 24 is placed through the gel cap 44 to a depth so as to maintain the bladed distal end 60 of the power morcellator 24 in the central lumen 38 and in the protected region or length of the guard 28. Targeted tissue is pulled by a grasper toward the blade 60 for morcellation and removal. Removed tissue will travel through the central lumen of the power morcellator 24.

Rather than place the morcellator 24 through the penetrable portion 50 of the cap 44, a stabilizer is provided which will work with the bag 18 or guard 28 and serve to hold the morcellator 24 in place at a depth within the protected zone inside central lumen 38 of the guard 28. Maintaining the morcellator within the lumen 38 of the guard 28 prevents the morcellator 24 from coming into contact with the bag 18 wall during the procedure thereby protecting the bag from inadvertent tearing. A variation of the stabilizer will be described further below.

After placing the morcellator 24 and cap 44, the surgeon may choose to insufflate the bag 18 as well as the abdominal cavity 12. The surgeon may observe the position of the morcellator 24 and targeted tissue 16 as well as the integrity of the bag 18 making sure it is not twisted or approaching too closely to the distal end 60 of the morcellator 24. The observation is made via a laparoscope placed through a port 54 at the same incision site or through a secondary incision site providing a lateral port. The specimen 16 is grasped with a tenaculum and pulled through the power morcellator 24 to reduce its size. Ideally, the surgeon will "core" or "peel" the specimen to keep it in one piece as much as possible. However, more likely than not, the specimen 16 will be reduced to multiple pieces. Once the specimen 16 is morcellated enough to pull the remaining tissue through the incision, the morcellator 24, gel cap 44 or stabilizer, and guard 28 retractor are removed, and the bag 18 and its contents, including the pieces created during morcellation, are pulled out of the patient. The bag 18 will prevent the remaining small pieces from being left behind in the abdominal cavity 12, maintaining the closed system; whereas in a traditional morcellation, the surgeon must go back and painstakingly search and collect the pieces scattered amid the pelvic cavity. The surgeon may choose to take a final look at the patient laparoscopically and will close the wounds.

While described for an abdominal removal and morcellation, the above described power morcellation procedure can be performed via a bodily orifice such as a vagina as well. Following the same process, the bag 18 will be introduced and the specimen 16 placed into the bag 18 laparoscopically. Rather than pull the tether 22 through the abdominal wall opening 14, the tether 22 would be pulled through the vagina. In the same way, the specimen 16 would sit at the base of the vagina while the bag 18 goes through the vagina and opens up outside the patient. The surgeon may roll the bag down or pull it taut to maintain its position and provide some retraction. The surgeon would place the guard 28 vaginally into the bag 18 to protect integrity of bag and to maintain a closed morcellation system, place the cap 44 on the guard 28 and place the power morcellator 24 through a gel cap 44 or stabilizing cap. The surgeon would then grasp the specimen 16 with a tenaculum and bring it out through the power morcellator 24 vaginally to reduce the size of the specimen 16. The surgeon would maintain pneumoperitoneum and observe the progress of the morcellation laparoscopically. Once the specimen 16 is morcellated enough to pull the remaining portion through the vagina, the morcellator 24, gel cap 44 or stabilizing cap, guard 28 and/or retractor are removed, and the bag 18 and its contents, including the pieces created during morcellation, are pulled out of the patient. The bag 18 will prevent the remaining small pieces from being left in the abdominal cavity 12, maintaining the closed morcellation system; whereas in a traditional morcellation, the surgeon must go back and painstakingly search and collect the pieces amid the pelvic cavity and vagina. The surgeon may choose to take a final look at the patient laparoscopically and will close the vaginal cuff and abdominal incisions.

Figure 18:
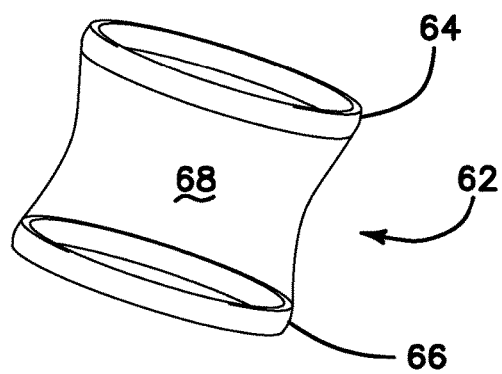
FIG. 18 is a top perspective view of a retractor according to the present invention.
Figure 19:
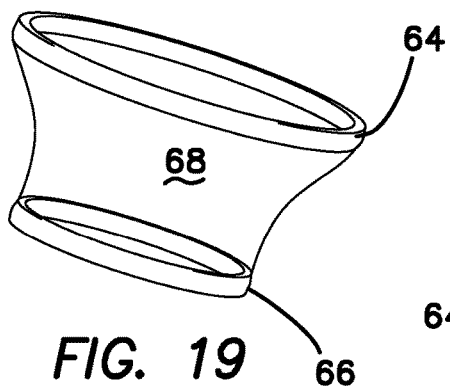
FIG. 19 is a top perspective view of a retractor according to the present invention.

Turning now to FIGS. 18-19, there is shown a retractor 62 comprising a first ring 64 and a second ring 66 interconnected by a flexible sidewall 68. The retractor 62 is described in greater detail in one or more of the references incorporated in this application by reference. The second ring 66 can be compressed and inserted through the small incision where it expands to create a securement against the abdominal wall 10 inside the cavity 12. The first ring 64 resides above the abdominal wall 10 outside the patient where it can be rolled down to retract and enlarge the opening 14 in the abdominal wall. The retractor 62 can be employed with any of the variations described above. In use, the retractor 62 is inserted prior to insertion of the bag 18 into the cavity or orifice. In one variation, the first ring 64 has a larger diameter than the second ring 66 as shown in FIG. 19. The larger first ring 64 relative to the second ring 66 allows for more space to work and cut tissue against. The sidewall 68 is made of a polyurethane laminate or similar material including woven material to resist cutting through the sidewall 68.

Figure 20A:
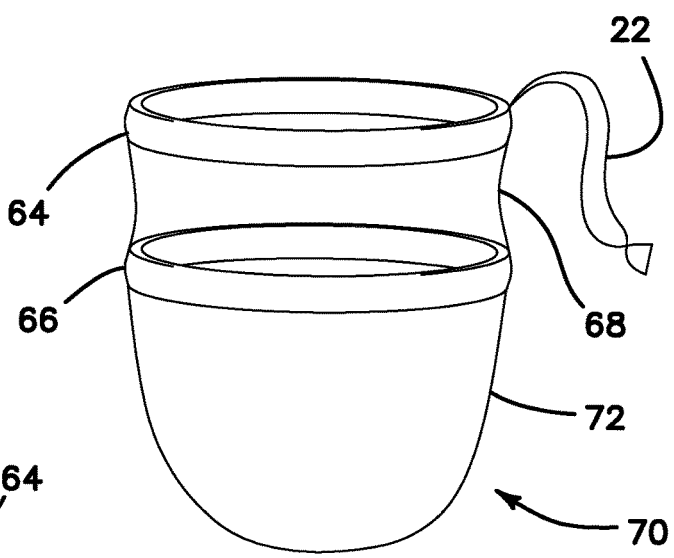
FIG. 20A is a top perspective view of a containment bag and retractor combination according to the present invention.
Figure 20B:
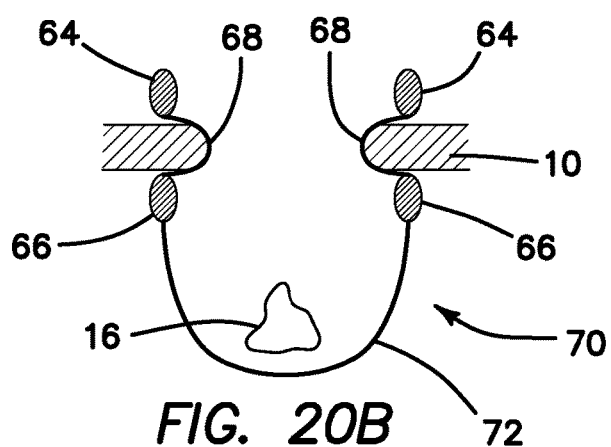
FIG. 20B is a cross-sectional side view of a tissue specimen, body wall and a containment bag with two rings according to the present invention.
Figure 21:
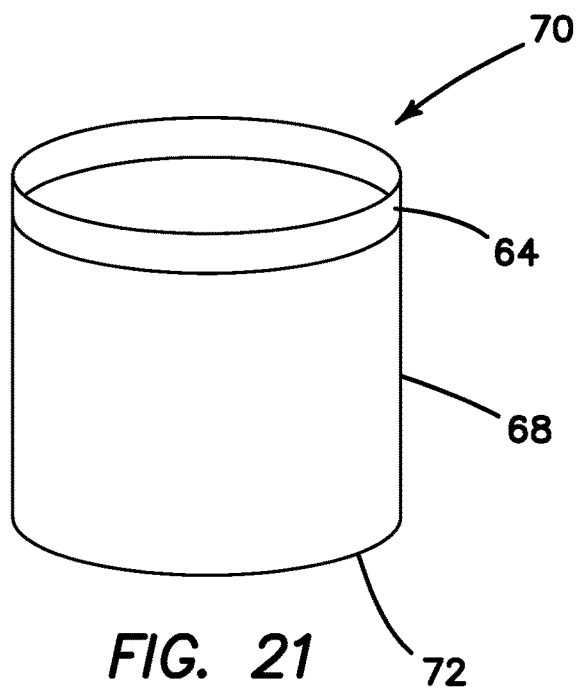
FIG. 21 is a top perspective view of an expanded containment bag according to the present invention.

FIGS. 20A-20B illustrate a modified retractor 62 configured into a bag 70. The bag 70 includes the first ring 64 and second ring 66 interconnected by a flexible substantially cylindrical sidewall 68. The opening at the second ring 66 is closed off by a depending bag portion forming a base 72 for the bag 70. The bag 70 is inserted in the same manner as described above with respect to the bag 18 and used in the same manner. The second ring 66 is compressed and passed through the small incision into the abdominal cavity 12. The sidewall 68 is rolled around the top ring 64 to retract and enlarge the opening 14 and a guard 28 connectable to the first ring 64 may or may not be employed at the opening inside the bag 70. The specimen 16 is removed in the same manner as described above via manual or power morcellation. The first ring 64 is also connectable to the gel cap 44.

Figure 22:
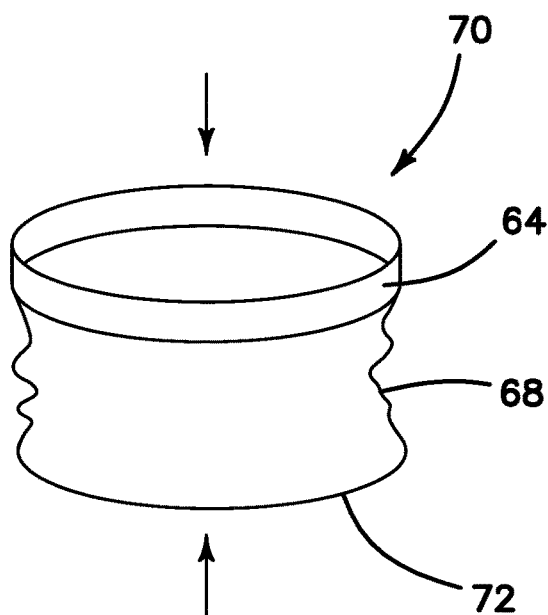
FIG. 22 is a top perspective view of a partially collapsed containment bag according to the present invention.
Figure 23:
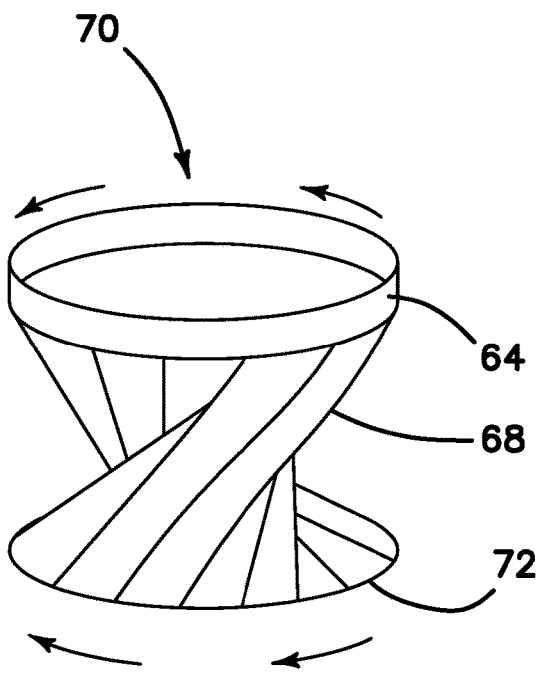
FIG. 23 is a top perspective view of a twisted containment bag according to the present invention.
Figure 24:
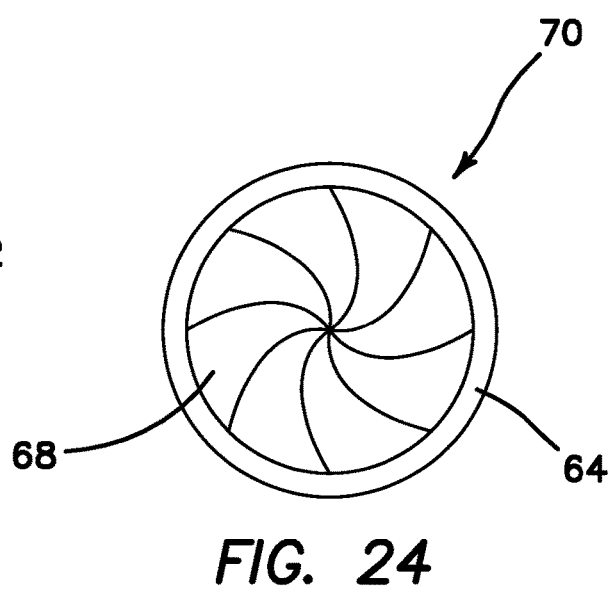
FIG. 24 is a top view of a twisted containment bag according to the present invention.

Turning now to FIGS. 21-24, there is shown a bag 70 having only a first ring 64 forming an opening, a flexible cylindrical sidewall 68 and a base 72. The first ring 64 is resilient and compressible into a collapsed elongate configuration suitable for passing into a small incision or through the lumen of a trocar. The arrow in FIG. 22 illustrates the vertical direction of collapse of the bag 70. The collapsed bag 70 is then subsequently easily compressed in a lateral direction and deployed into the abdominal cavity. The first ring 64 is compressed into an elongated shape. The compressed bag is allowed to form is original shape with the first ring 64 expanding. In the expanded configuration, the bag 70 is easily oriented within the cavity 12. The collapsed bag 70 conveniently lies flat inside the abdominal cavity and includes two sides. The bag 70 in a collapsed configuration does not have a right side up because either side can be used to place the specimen within the boundaries of the first ring 64. The first ring 64 serves as a perimeter guide for specimen placement and may be brightly colored so that it can be easily observed with a laparoscope. After the specimen is placed within the perimeter of the first ring 64, the first ring 64 is grasped and lifted to locate the specimen inside the bag 70. The same may be said of the two-ring bag 70 described above. As shown in FIGS. 23-24, the bag 70 may be twisted to create a spiral form to collapse or to shorten the length of the bag. This feature is advantageous not only for insertion of the bag through a small incision but also to raise the specimen closer to the opening of the bag as it is being morcellated.

Figure 25A:
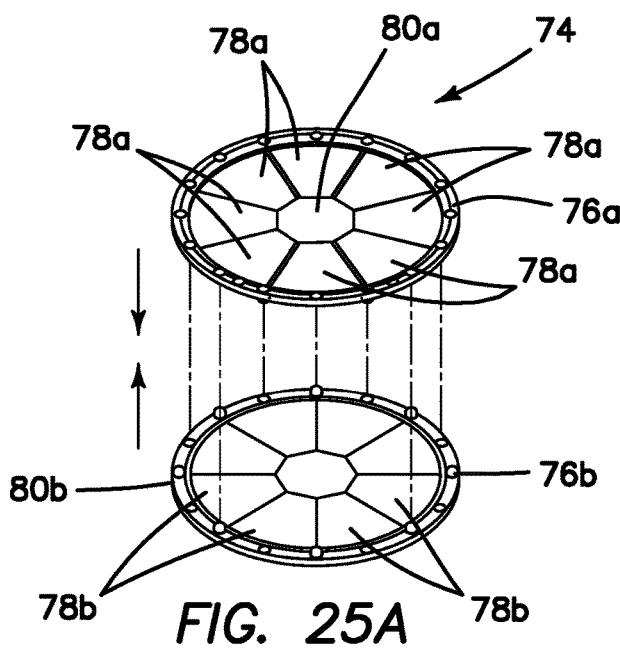
FIG. 25A is a top perspective view of an unassembled two-piece guard according to the present invention.
Figure 25B:
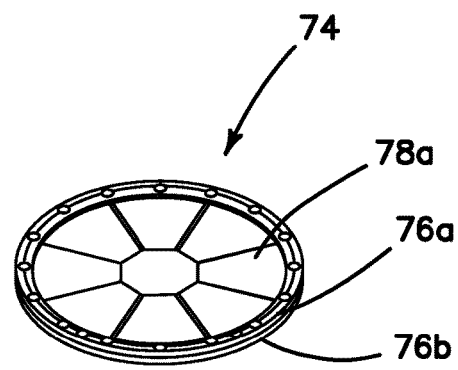
FIG. 25B is a top perspective view of an assembled two-piece guard according to the present invention.

Turning now to FIG. 25, there is shown a guard 74 that is configured for use with a retractor 62 depicted in FIGS. 18-19 or with a bag 70 of FIGS. 20-24. The guard 74 includes a rigid ring 76 with a plurality of inwardly extending flaps 78 meeting in the center or, as shown in FIG. 25, forming an opening 80 in the center. The flaps 78 are attached to the ring 76 such that they flex relative to the ring 76 permitting targeted tissue 16 to be removed out past the flaps 76. The flaps 78 also flex distally permitting instruments to be inserted past the guard. The flaps 78 are made of the same material as the guard 28 such as polycarbonate, LDPE, HDPE or similar material and as such, the flaps 78 are sufficiently resilient, cut-resistant and resist penetration with a blade and, thereby, protect the retractor 62 or bag 70. The guard 74 may comprise a single ring 76 with flaps 78 or be comprised of two similar rings 76a, 76b having flaps 78a, 78b, respectively. The two rings 76a, 76b are connected together such that the flaps 78a are offset from the flaps 78b so as to create a layered flap construct that provides protection between the flaps 78a, 78b. The targeted tissue 16 is pulled up through the openings 80a, 80b wherein when in the region of the guard 76, the targeting tissue 16 is cut. The targeted tissue 16 may also be cut when positioned against the flaps 78a, 78b.

Figure 26:
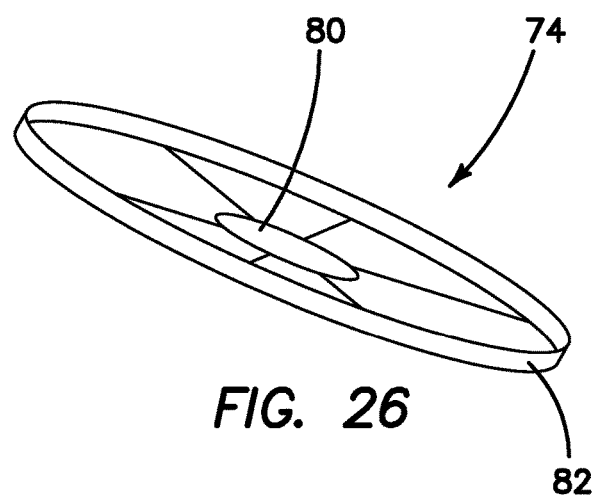
FIG. 26 is a top perspective view of a guard according to the present invention.
Figure 27:
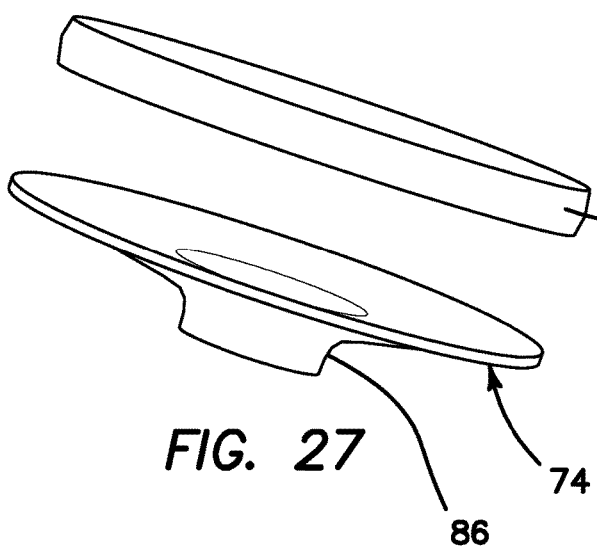
FIG. 27 is a top perspective view of a retractor ring and guard according to the present invention.
Figure 29:
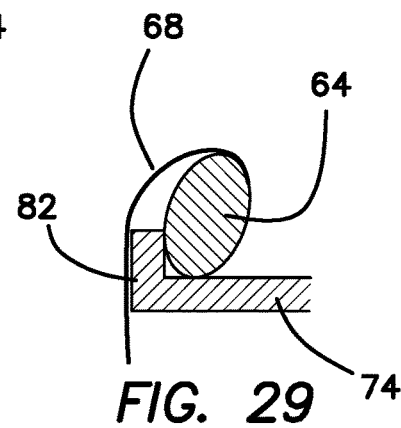
FIG. 29 is a partial cross-sectional view of a retractor ring and guard according to the present invention.
Figure 28:
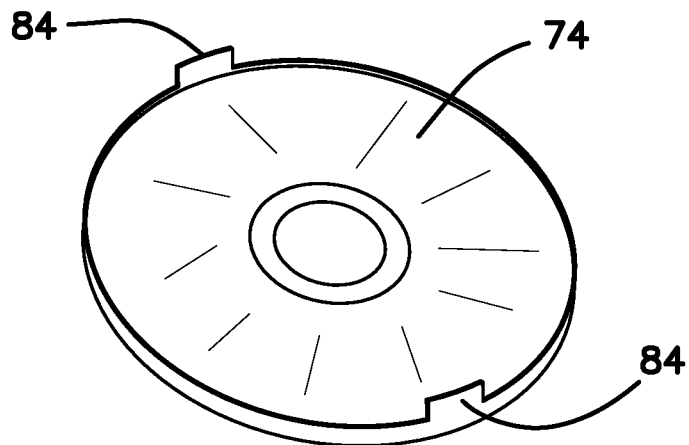
FIG. 28 is a top perspective view of a guard according to the present invention.

Turning now to FIG. 26, the guard 74 includes an upstanding flat perimeter wall 82 configured to snap under the first ring 64 of the retractor 62 or bag 70 as shown in FIG. 29. The guard 74 may also include flanges 84 configured to snap with the first ring 64 of the retractor 62 or bag 70 as shown in FIG. 28. FIG. 27 illustrates a rigid guard 74 without flaps. The rigid guard 74 of FIG. 27 provides a large cutting surface against which targeted tissue may be located and cut without flexing as much as a guard 74 with flexible flaps 78. The guard 74 may also include a depending portion 86 in the shape of a funnel to provide greater protection in the vertical direction for the bag/retractor 70, 62 and/or wound. The guard 74 is placed on top of the retractor 62 or bag 70 and within the perimeter of the first ring 64. The guard 74 is then snapped under the first ring 64 to join the guard 74 to the first ring 64. The guard 74 also assists in keeping the bag 70 or retractor 62 in position while being made of material that resists penetration when being morcellated. In other variations, the guard is configured to snap over the ring.

Figure 30:
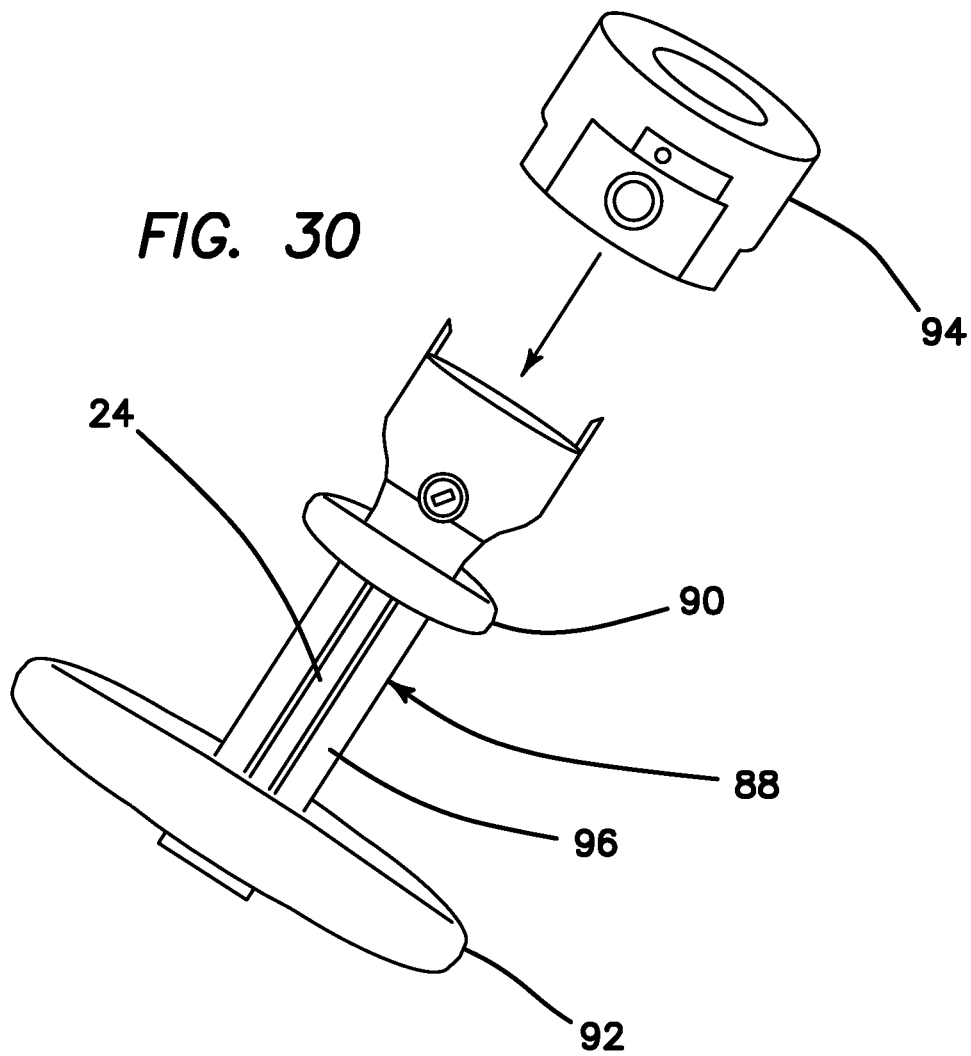
FIG. 30 is a top perspective view of a balloon trocar with a removable seal housing according to the present invention.
Figure 31:
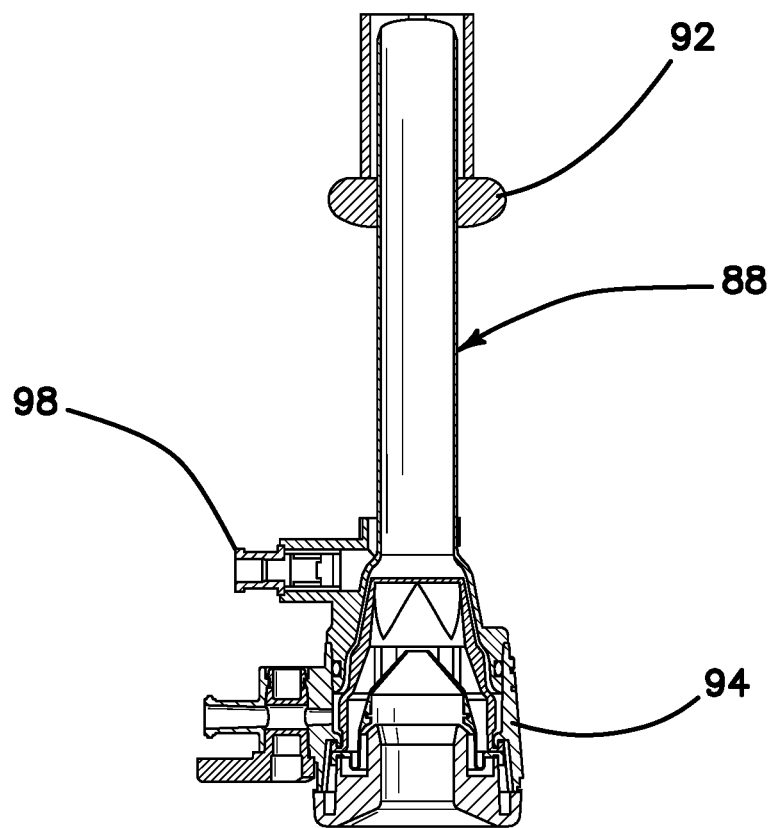
FIG. 31 is cross-sectional side view of a balloon trocar according to the present invention.
Figure 32:
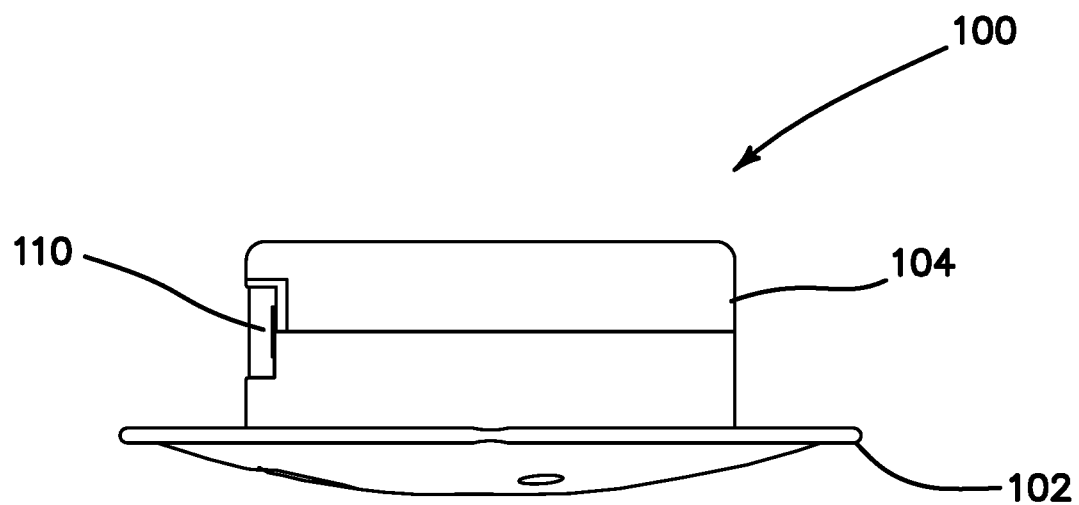
FIG. 32 is a side view of a stabilizer according to the present invention.
Figure 33:
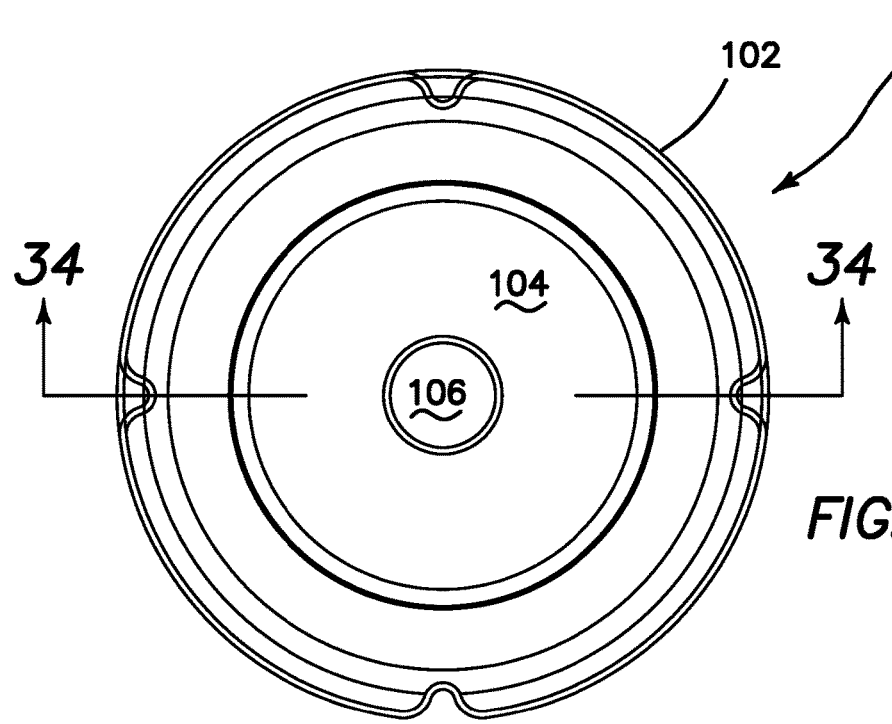
FIG. 33 is a bottom view of a stabilizer according to the present invention.
Figure 34:
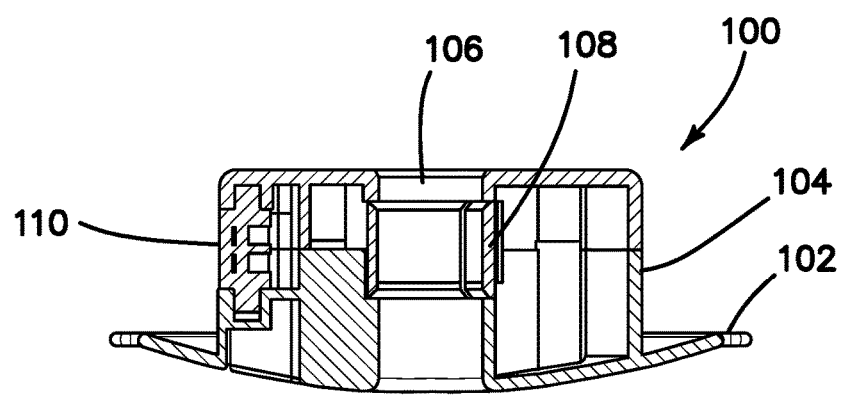
FIG. 34 is a cross-sectional view taken along line 34-34 of FIG. 33 of a stabilizer according to the present invention.
Figure 35:
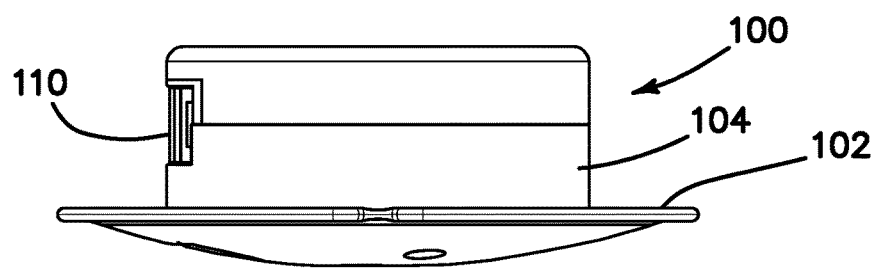
FIG. 35 is a side view of a morcellator stabilizer according to the present invention.
Figure 36:
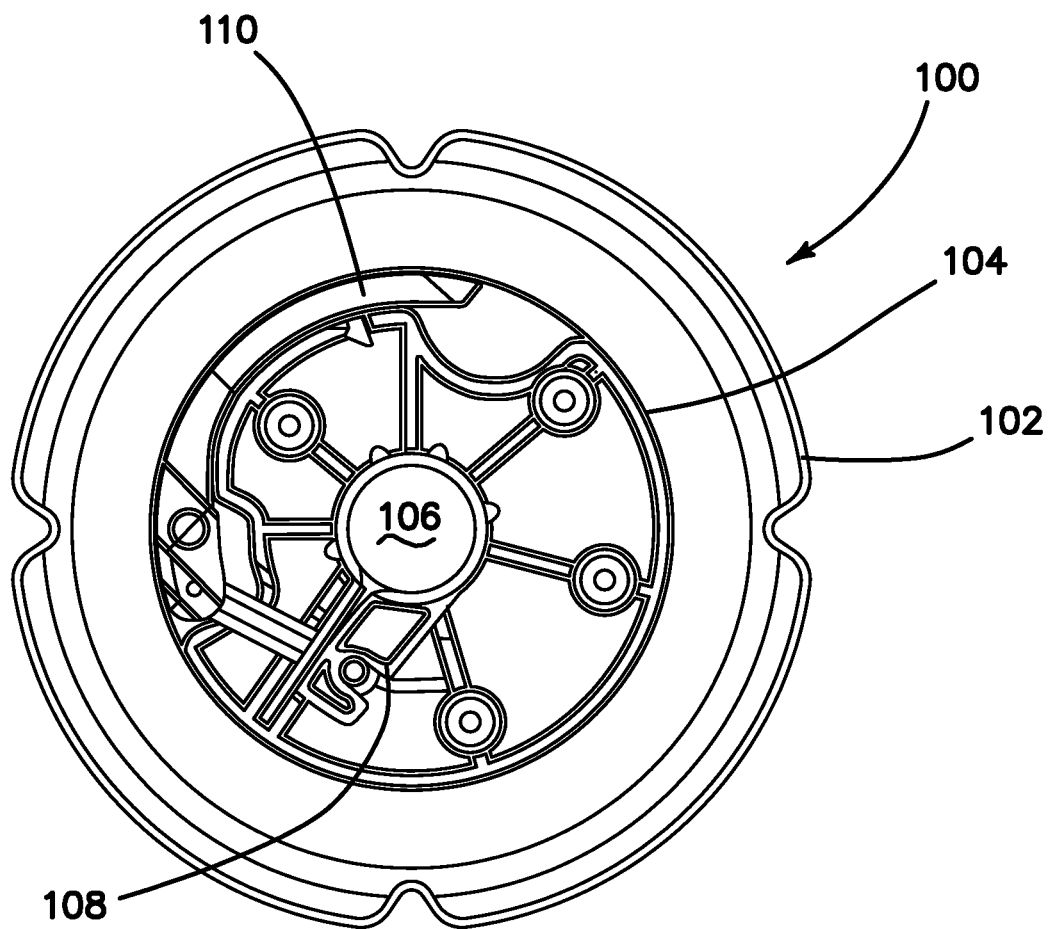
FIG. 36 is a cross-sectional top view of a morcellator stabilizer in a locked configuration according to the present invention.
Figure 38:
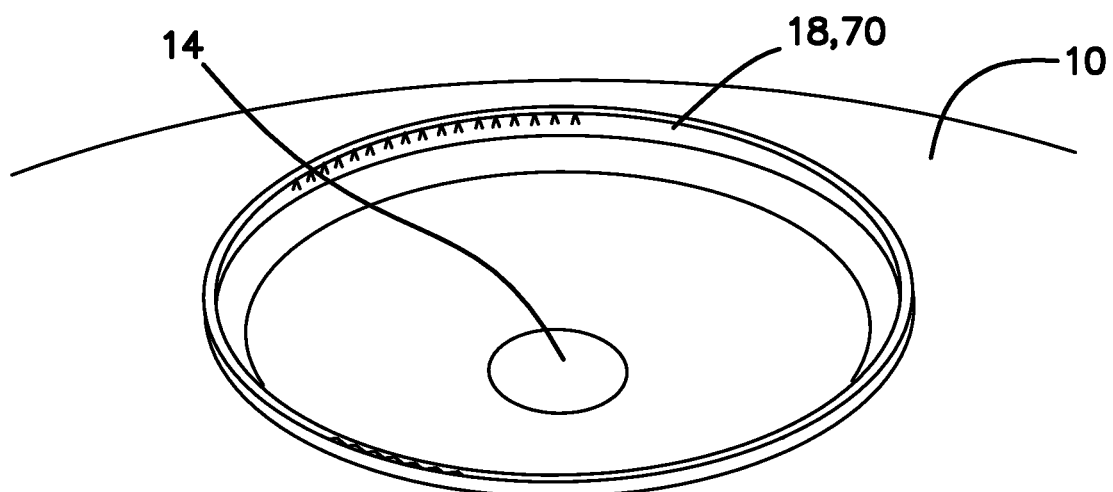
FIG. 38 is a top perspective view of a containment bag located in a body opening according to the present invention.
Figure 37A:
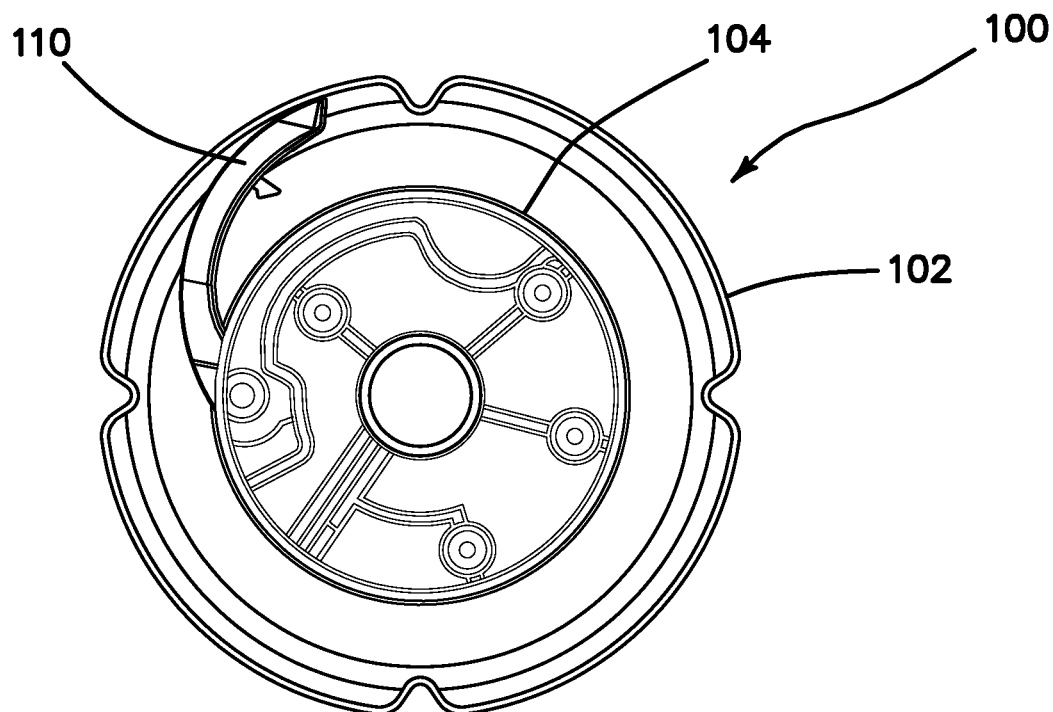
FIG. 37A is a top view of a stabilizer in an unlocked configuration according to the present invention.
Figure 37B:
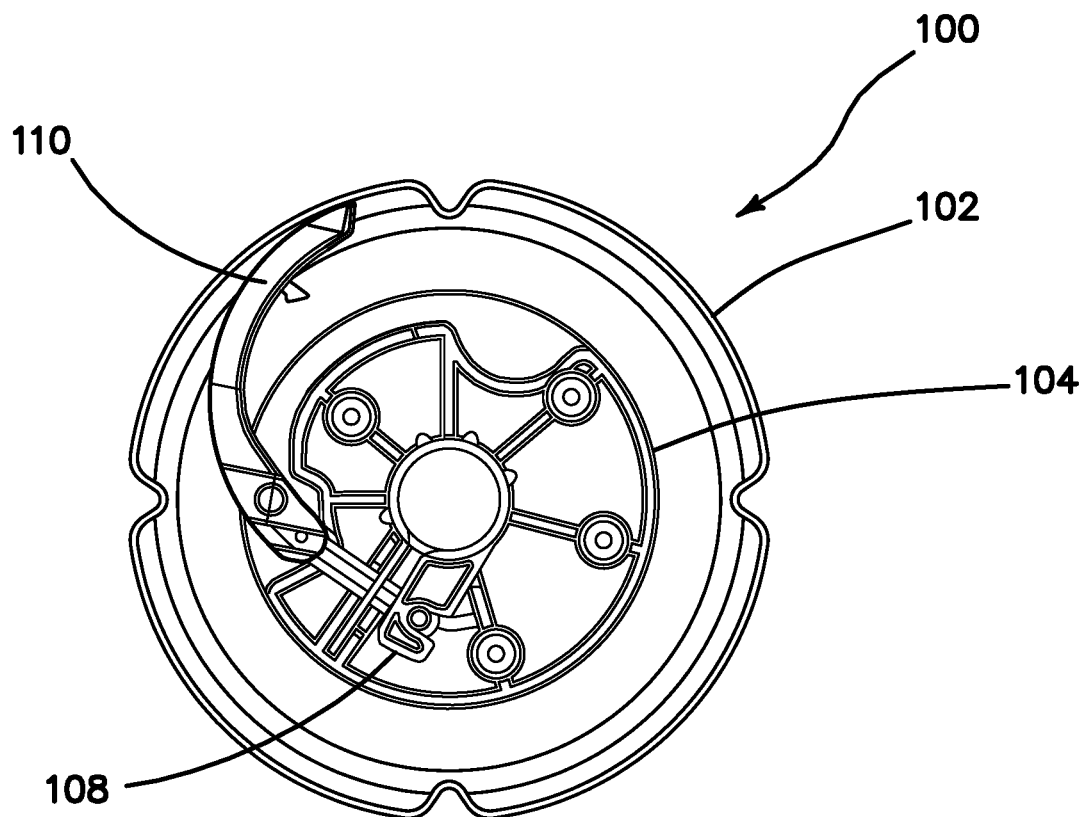
FIG. 37B is a cross-sectional top view of morcellator stabilizer in an unlocked configuration according to the present invention.
Figure 39:
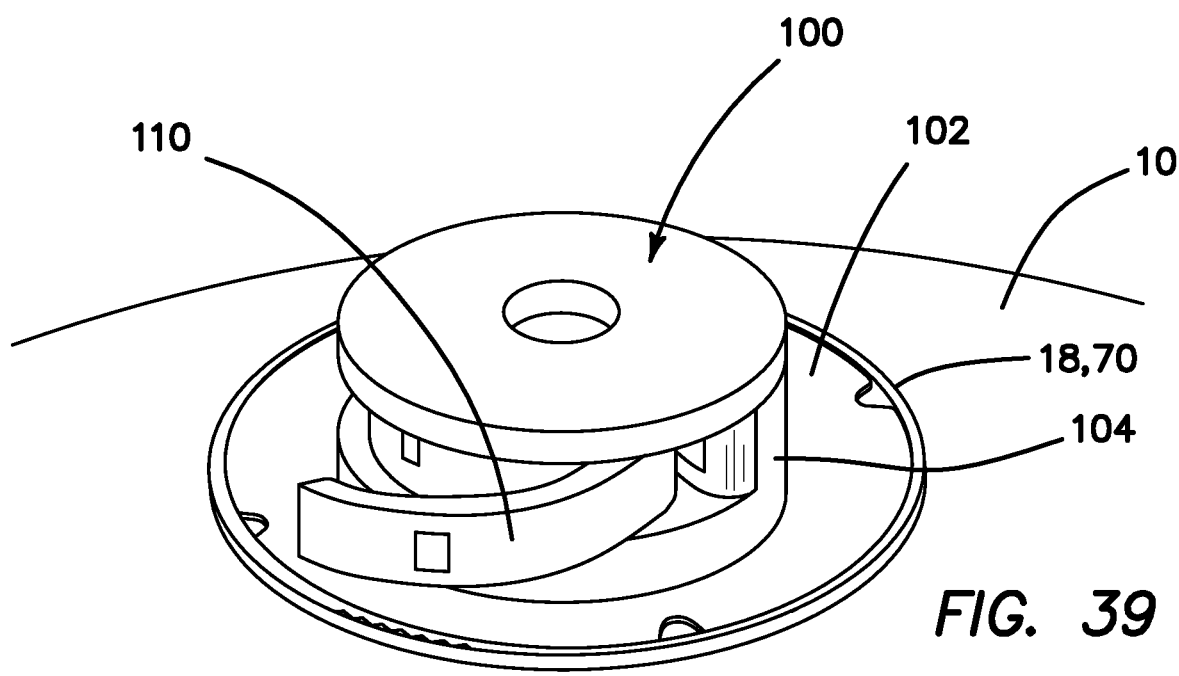
FIG. 39 is a top perspective view of a containment bag located in a body opening and a morcellator stabilizer in an unlocked connected to the containment bag according to the present invention.

Turning now to FIG. 30, there is shown a trocar 88 having a first balloon 90 and a second balloon 92. The trocar 88 includes a removable seal housing 94 containing one or more seals for sealing against inserted instruments. The trocar 88 includes a central lumen 96 that extends through the seal housing 94 and trocar 88. The lumen 86 is sized and configured to receive a power morcellator 24. The trocar 88 may further include an obturator (not shown) configured to penetrate an abdominal wall. The trocar 88 may be inserted through a gel cap 44 described above or directly through an incision in the abdomen. A bag 18, 62 may be deployed through the lumen 86, and a specimen 16 inserted into the bag 18, 62. The tether 22 of the bag 18 or first ring of bag 62 is pulled through the incision and the trocar 88 is reinserted. The second balloon 92 is inflated. In the inflated configuration, the second balloon 92 extends laterally pushing the bag 18, 62 laterally and out of the way of the distal end of the trocar 88 and away from the bladed distal end of a morcellator. A power morcellator 24 is inserted into the lumen 96 of the trocar 88. The morcellator 24 may be prevented from extending beyond the distal end of the trocar 88 by way of a stop formed on the trocar 88 that would abut the morcellator 24 and prevent it from moving distally. A tenaculum is inserted into the lumen of the morcellator 24 and tissue is grasped and pulled toward the morcellator. Tissue is cut and extracted from the specimen bag. The first balloon 90 is inflated and is resident above the abdominal wall. Both the first balloon 90 and the second 92 help retain the trocar 88 in position relative to the abdominal wall 12. FIG. 31 illustrates another trocar 88 having a seal housing 94 and an insufflation port 98 for inflating the at least one balloon 92.

Turning now to FIGS. 32-39, a stabilizer 100 will now be described. The stabilizer 100 includes a flange 102 configured to connect with a bag 18, 70 or guard 28. The stabilizer 100 includes a central portion 104 that defines a lumen 106 and houses a lock 108. The lumen 106 is sized and configured to receive a power morcellator 24. When inserted into the lumen 106, the height of the morcellator 24 relative to the abdominal wall may be adjusted and then locked in position with the lock 108. The lock 108 has an unlocked configuration in which the lever 110 is released permitting the morcellator 24 to translate vertically within the lumen 106. The lock 108 also has a locked configuration in which the lever 110 is depressed locking the translation of the morcellator 24. The lock 108 operates to increase friction onto the morcellator 24 shaft holding it in place.

Figure 43:
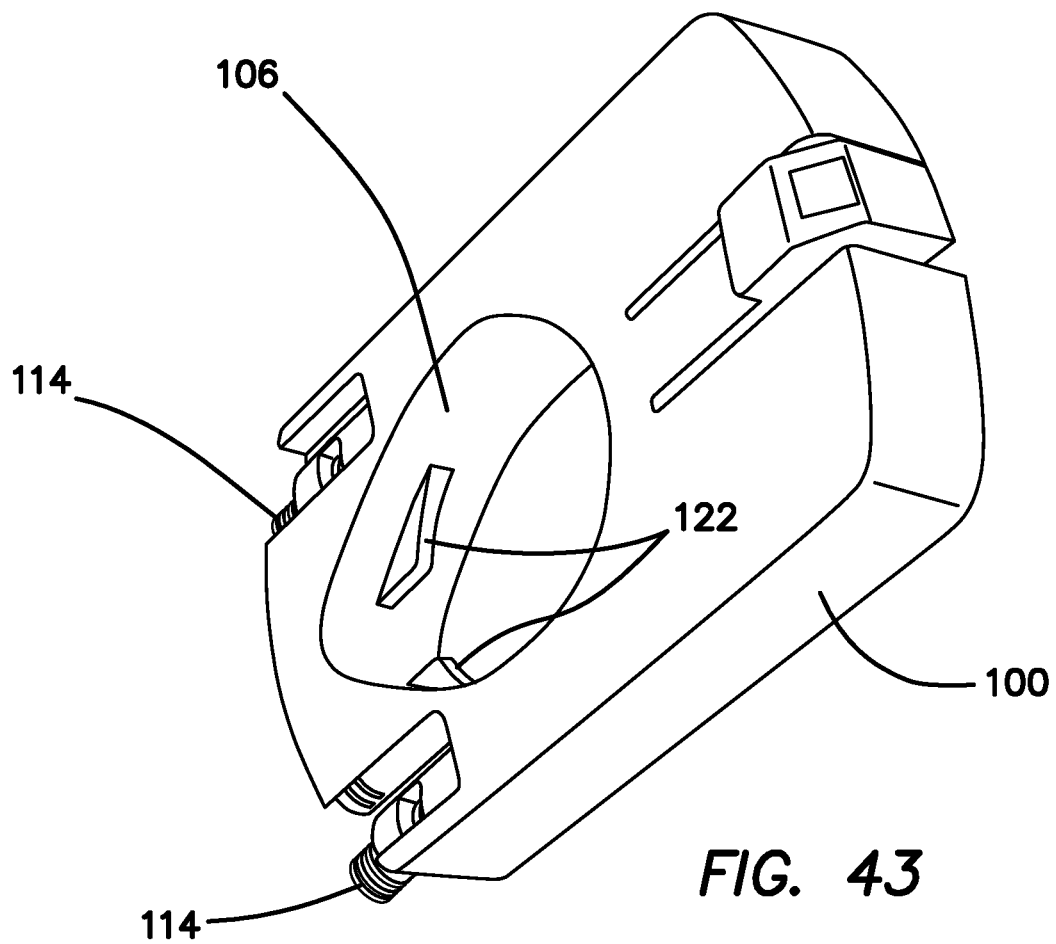
FIG. 43 is a top perspective view of a stability cap according to the present invention.
Figure 40:
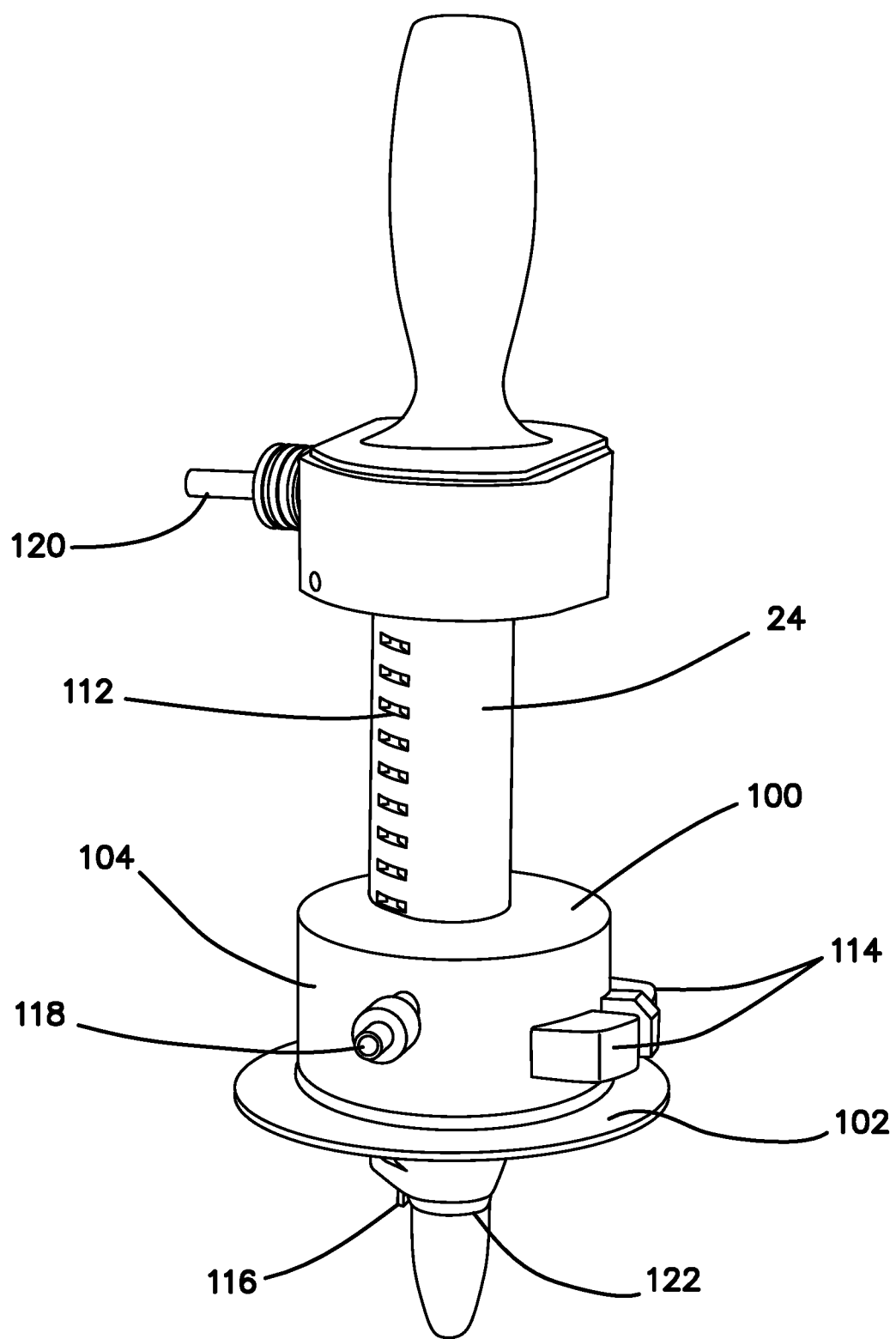
FIG. 40 is a top perspective view of a morcellator with a protective obturator connected to a stability cap according to the present invention.
Figure 41:
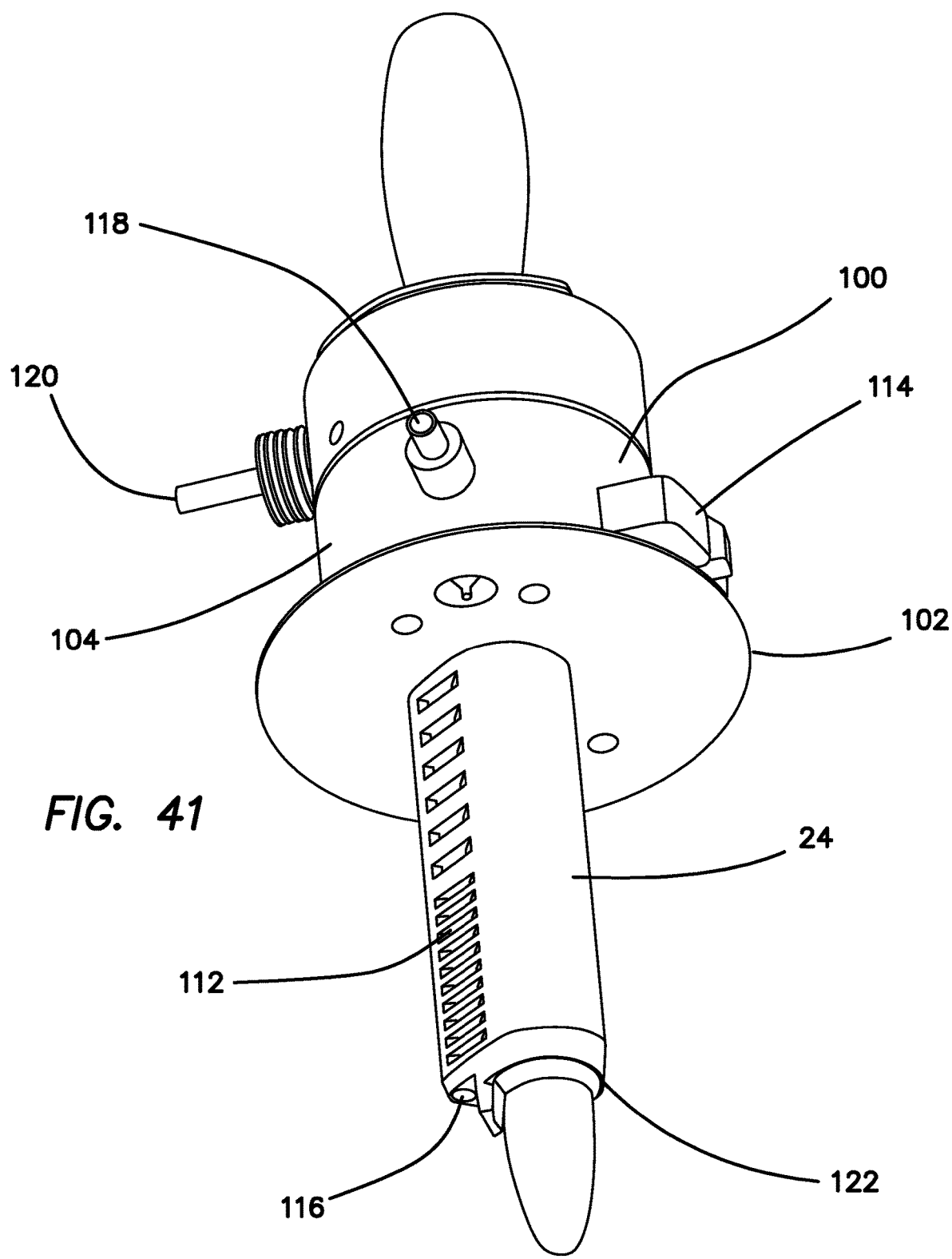
FIG. 41 is a bottom perspective view of a morcellator with a protective obturator connected to a stability cap according to the present invention.
Figure 42:
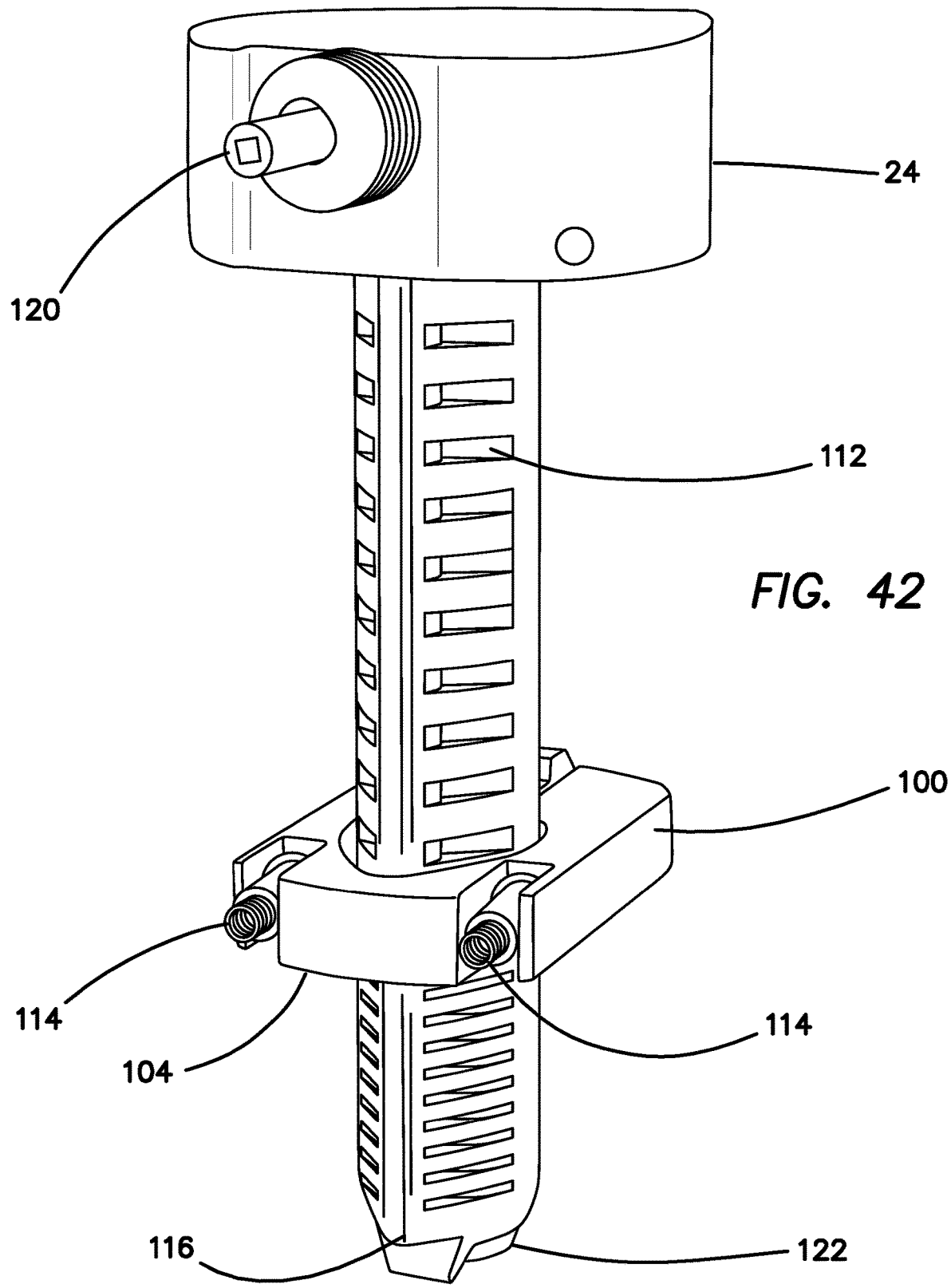
FIG. 42 is a top perspective view of a morcellator connected to a stability cap according to the present invention.

Turning now to FIGS. 40-41, the stabilizer 100 is shown connected to a power morcellator 24. The system of FIGS. 40-41 includes a ratcheting mechanism that includes a toothed bar on the morcellator 24 configured to engage with a pawl (not shown) inside the central portion 104 of the stabilizer 100. Buttons 114 are shown on the stabilizer 100 to release and engage the pawl in order to unlock and lock the stabilizer 100 from the morcellator 24 to free or arrest their relative vertical translation. The morcellator 24 includes an integrated scope and illuminator 116, an insufflation port 118 and a mechanical drive connection 120 to rotate the morcellator blade 122. The stabilizer 100 includes a lower flange 102 that extends outwardly to engage a bag or retractor or guard as described above. In one variation, the stabilizer 100 is configured such that activation of the morcellator 24 is prevented if the pawl of the stabilizer is within a certain range of the toothed bar 112 providing a safety shut-off mechanism so that the morcellator 24 is not activated when in a position that is too distal, or beyond the range of the guard and, therefore, would threaten inadvertent contact with the bag. Another variation of the stabilizer 100 is shown in FIGS. 42-43 wherein like numbers are used to describe like parts. The stabilizer 100 has a different shape and the pawl elements 122 are visible in FIG. 43.

Figure 44:
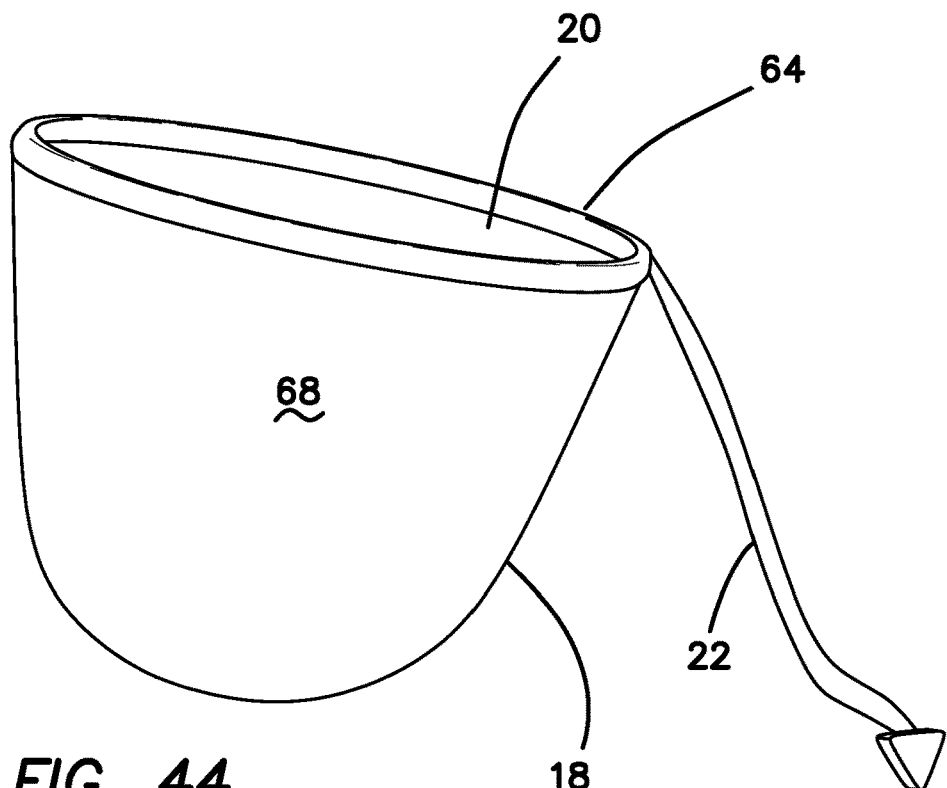
FIG. 44 is a top perspective view of a containment bag according to the present invention.
Figure 45:
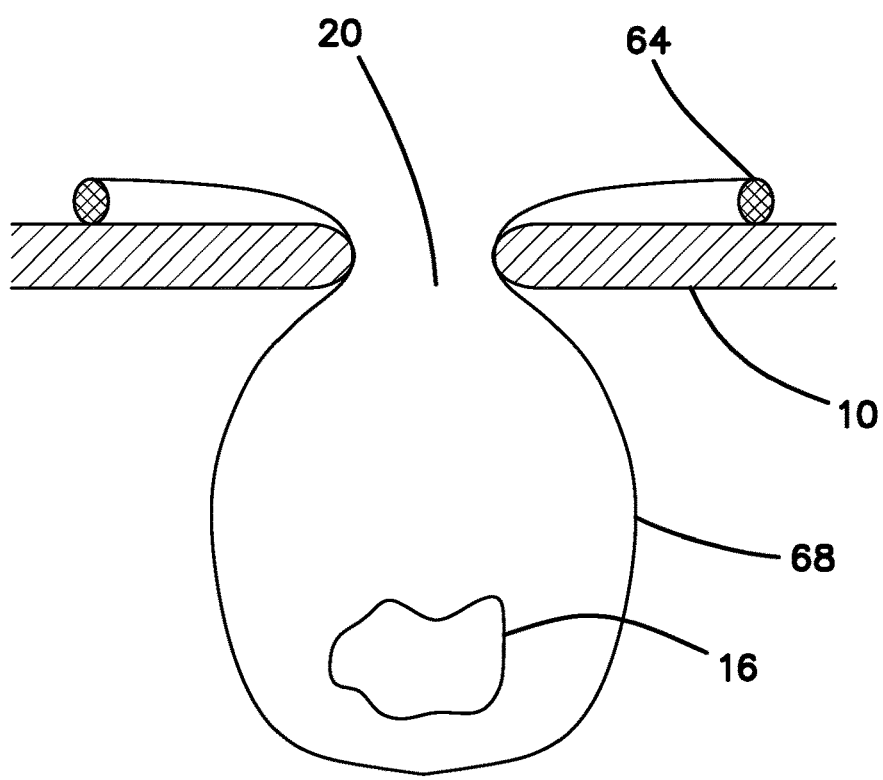
FIG. 45 is a cross-sectional side view of a tissue specimen inside a containment bag placed across a body wall according to the present invention.

FIGS. 44-45 illustrate a bag 18 having a tether 22 and a flexible ring 64 at the opening 20. The bag material can be clear or opaque and the ring 64 is compressible for insertion through a small incision. The sidewall 68 can be rolled about the first ring 64 to reduce the bag height and, therefore, raise the specimen closer to the opening and, thereby, make the specimen more accessible for morcellation.

Figure 46:
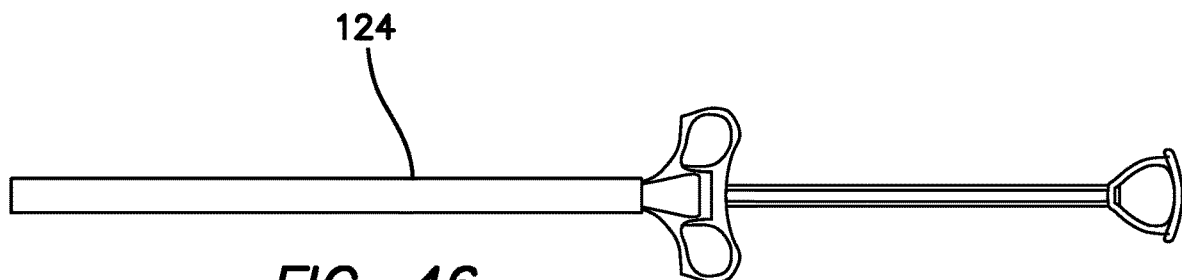
FIG. 46 is a side view of a containment bag deployment instrument according to the present invention.
Figure 47:
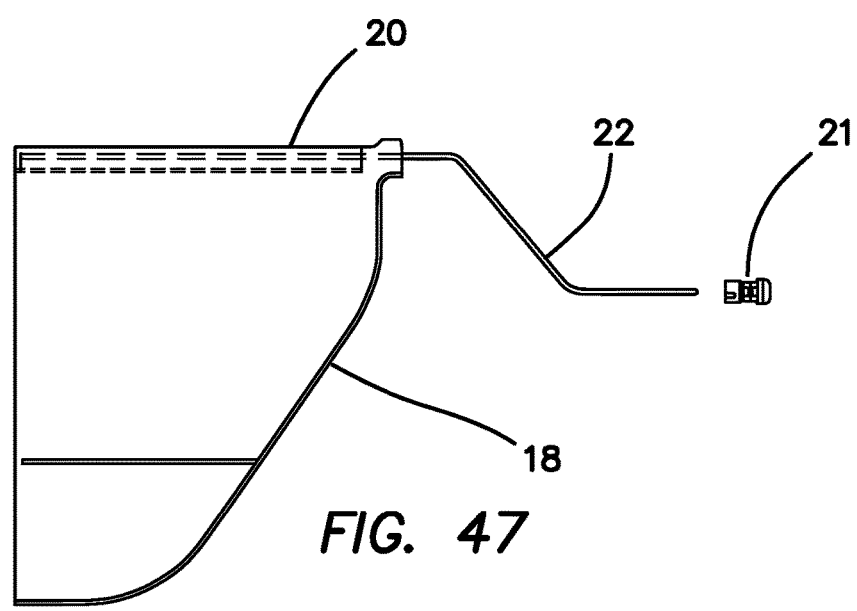
FIG. 47 is a side view of a containment bag and deployment cap according to the present invention.

FIGS. 46-47 illustrate a bag deployment instrument 124 for the bag 18 of FIG. 47. The instrument 124 may be inserted through a trocar. The bag 18 includes an opening 20, tether 22 and deployment cap 21.

Figure 48:
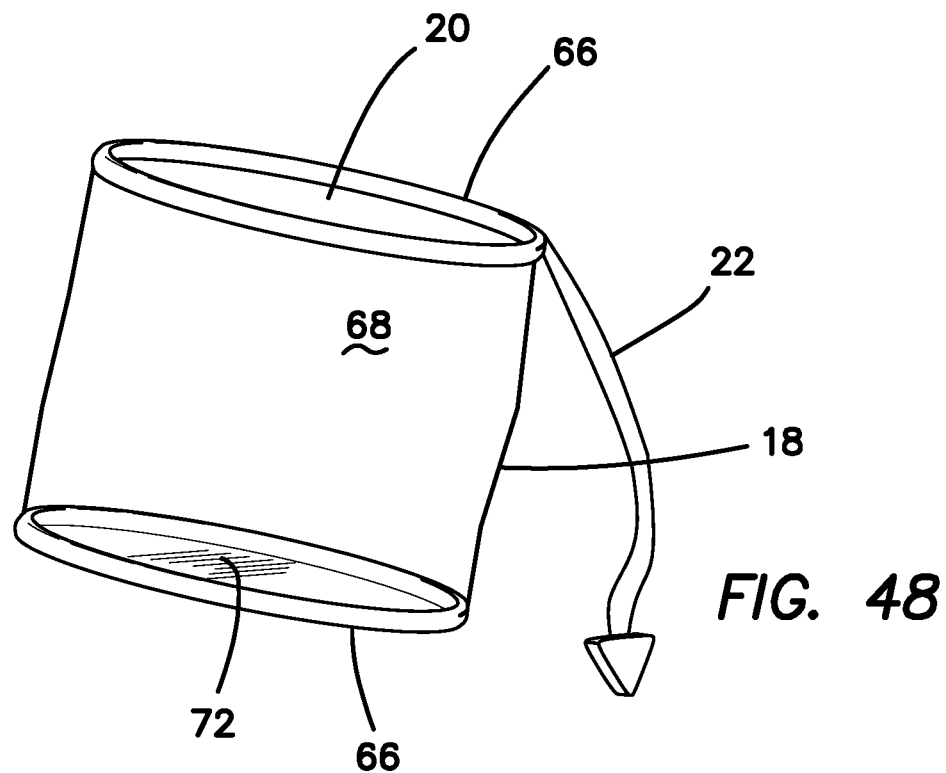
FIG. 48 is a top perspective view of a containment bag according to the present invention.
Figure 49:
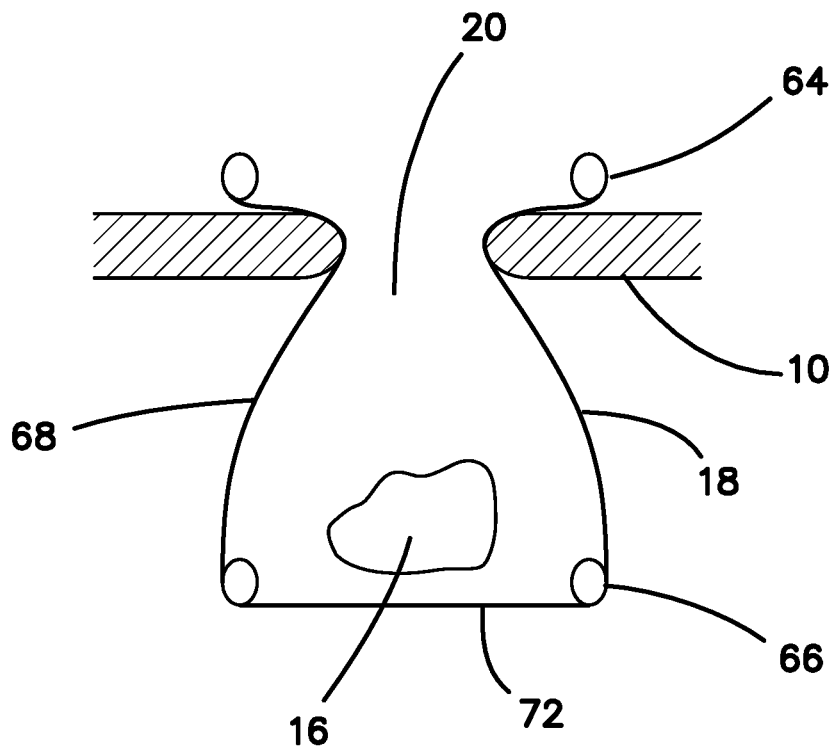
FIG. 49 is a cross-sectional side view of a tissue specimen inside a containment bag placed across a body wall according to the present invention.

FIGS. 48-49 illustrate another bag variation having a first ring 64, a second ring 66 and a sidewall 68 therebetween and a base 72. A resilient second ring 66 located at the bottom of the bag 18 causes the bag to flare open when disposed inside the body cavity 12 and helps prevent material from clinging to the specimen 16. After a specimen is placed into the bag 18, the first ring 64 is pulled to the surface of the abdominal wall 10 as shown in FIG. 49.

Figure 50:
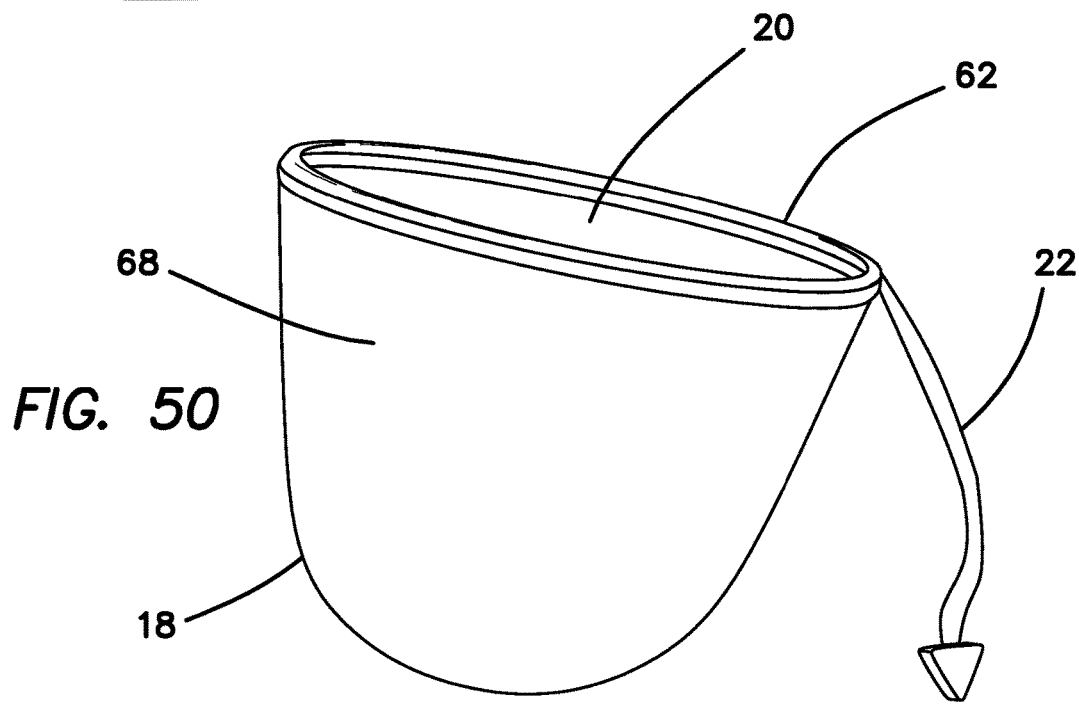
FIG. 50 is a top perspective view of a containment bag according to the present invention.

FIG. 50 illustrates a bag 18 having a first ring 64 made of nitinol to allow for easier insertion through a small incision while providing support to keep the bag 18 open inside the abdominal cavity 12.

FIGS. 50A to 50D illustrate a bag 18 in accordance with various embodiments in a non-collapsed state or expanded or partially expanded state. As shown, the bag 18 includes a closed end 126 and at least one open end 128. The open end 128 in accordance with various embodiments comprises a tether or drawstring 130 that encircles the open end 128 of the bag 18. Manipulation of the tether 130 closes the open end 128 of the bag 18. The bag 18 as illustrated includes a plurality of preformed folds 132 or a predefined deformation pattern in the wall 134 of the bag 18 between the closed end 126 and the open end 128 of the bag 18. The bag 18 in accordance with various embodiments is formed to provide a tendency of the bag 18 to be in a collapsed and flat state providing a minimal height with the open end 128 facing up or towards the opening in the body cavity and having a maximum width, diameter or opening dimension and the closed end 126 facing away from the opening in the body cavity and arranged to lay flat and stable along the body cavity. In accordance with various embodiments, when force is applied in one direction, the height of the wall 134 of the bag 18 increases to capture or surround a specimen within the bag 18. The folds 132 or deformation pattern ensures that the increase of the bag 18 occurs linearly in the direction in which the force is being applied. In accordance with various embodiments, a weight, the specimen or an opposite force is applied to the bag 18 to further assist in the increase in the bag 18 or in particular the linearly directed increase in the bag 18.

In one embodiment, the bag 18 is folded flat or in an accordion fashion prior to deployment into the patient's body. The bag 18 when deployed lays flat with the open end 128 of the bag 18 on the top and the closed end 126 on the bottom. The closed end 126 for example lays on the bottom the patient's body cavity. As such, the open end 128 of the bag 18, due to the pattern formed on the wall 134 of the bag 18, remains open and thus does not need to be held open. Additionally, due to the pattern, the open end 128 is biased open and resists closing. The difficulty and time expended to place the specimen on and/or within the bag is thereby reduced.

The surgeon places the specimen on the top of the bag 18 on or over the open end 128 of the bag 18. By pulling the tether 130, the wall 134 of the bag 18 is pulled up and around the specimen thereby containing the specimen. The opposite forces of the pull on the tether 130 and the weight of the specimen on the bag 18 cause the deformation pattern along the wall 134 of the bag 18 to unfold or straighten. In one embodiment, the bottom or closed end 126 of the bag 18 includes a weight or an attachable weight to ensure sufficient opposite force is provided to straighten the wall 134 of the bag 18 as the tether 130 is being pulled. In one embodiment, one or more tabs 136 or portions of the bag 18 around the open end 128 of the bag 18 are provided to ensure that forces pulling the bag 18 out or towards the opening in the body cavity also cause the wall 134 or one or more folds 132 of the wall 134 of the bag 18 to unfold.

In one embodiment, when the weight of the specimen pulls the bag 18 down it causes the shorter sides of the bag 18 to pull downward decreasing the overall containment size. In accordance with various embodiments, to compensate or reduce the decrease in overall containment size, one or more tabs 136 are provided at the open end 128 of the bag 18 that lies on the flat side of the bag 18 and prevent the bag 18 from decreasing in its overall containment size. As such, in one embodiment, when the bag 18 is flattened, the distance along the edge of the bag 18 is greater than the distance along the cross-section of the bag 18. The tether 130 in one embodiment is threaded through the tabs 136.

Figure 50A:
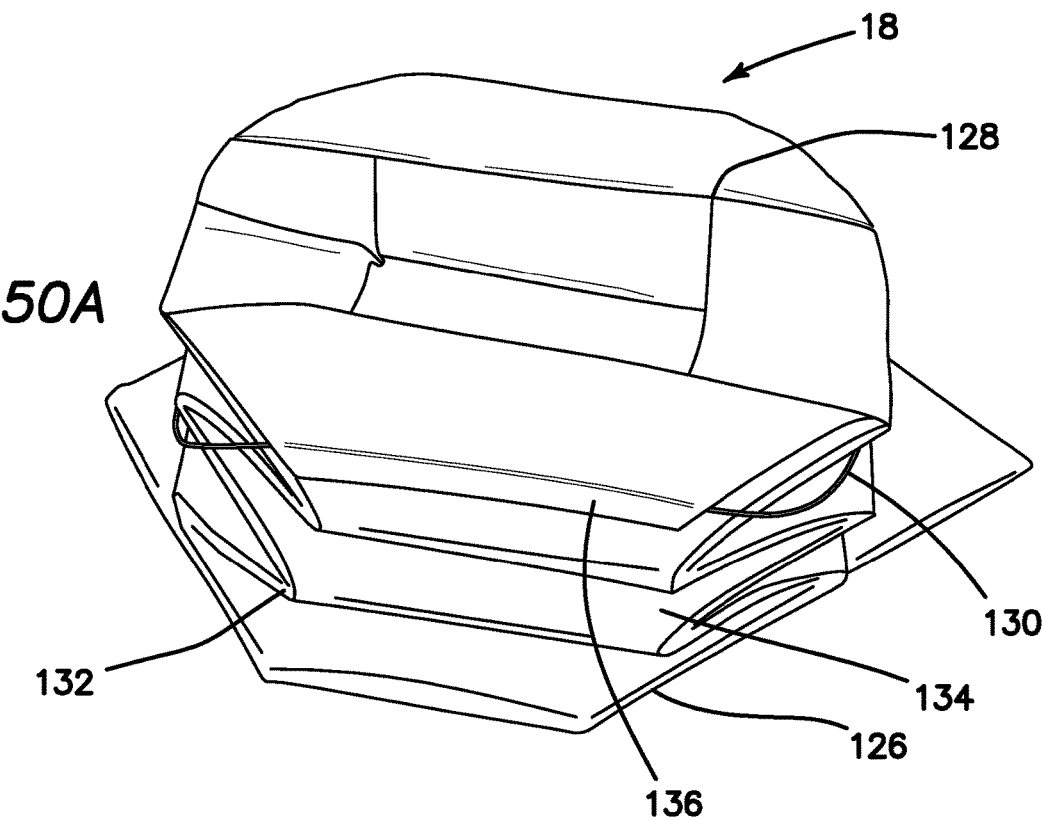
FIG. 50A is a top perspective view of a containment bag according to the present invention.
Figure 50B:
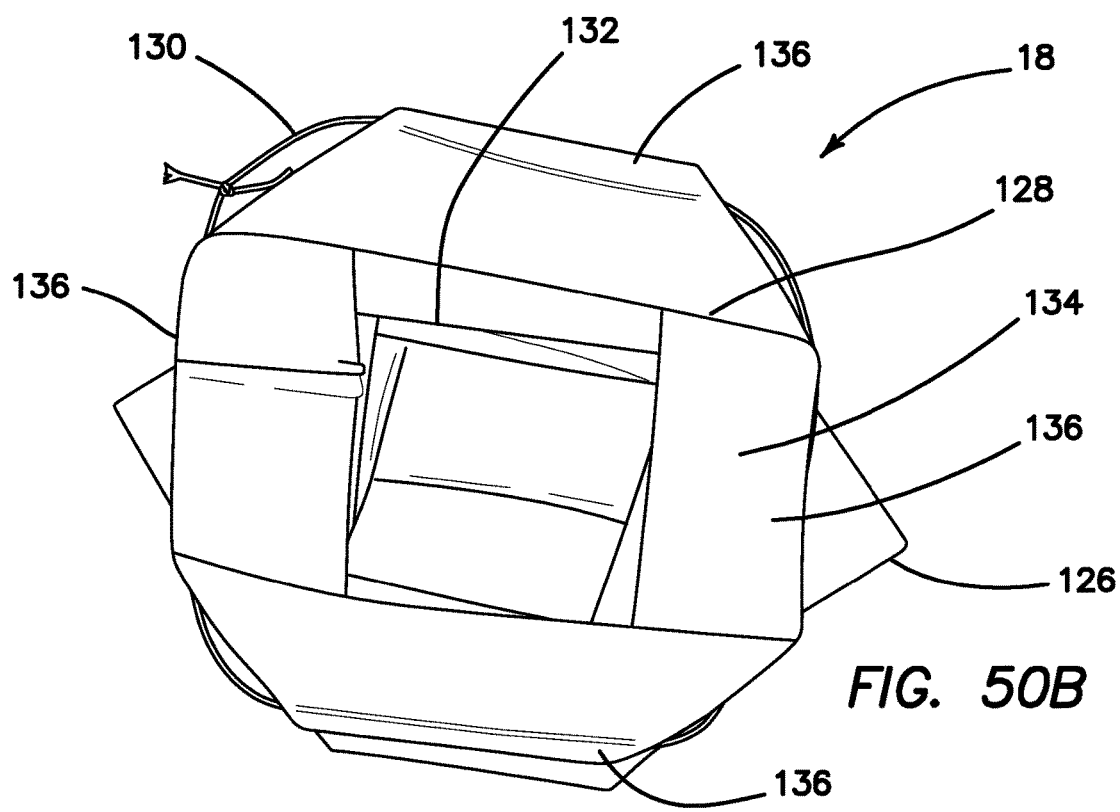
FIG. 50B is a top view of a containment bag according to the present invention.
Figure 50E:
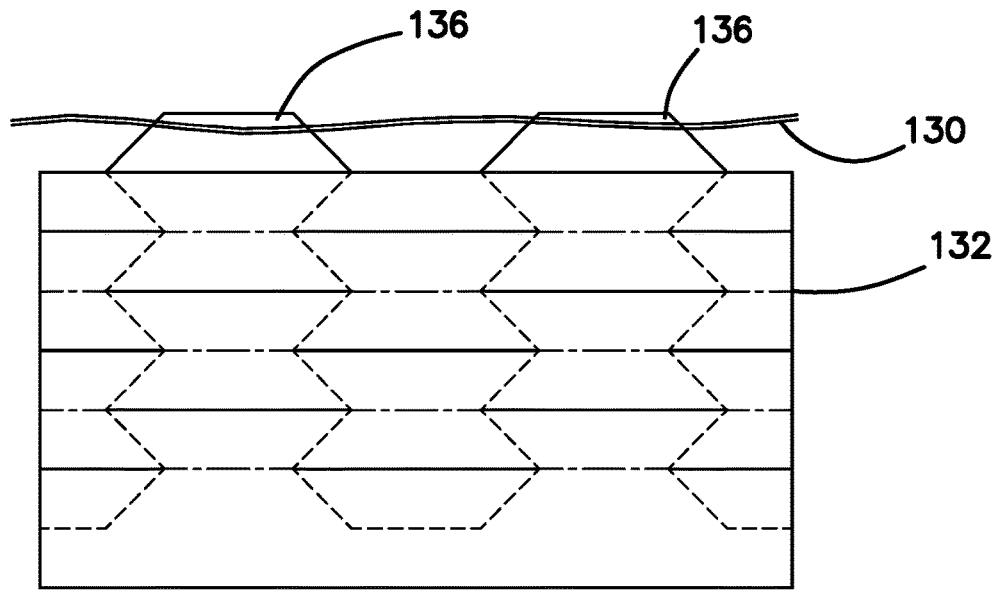
FIG. 50E is a top view of a pattern for a containment bag wherein solid lines depict a valley folds and dashed lines depict mountain folds according to the present invention.
Figure 50F:
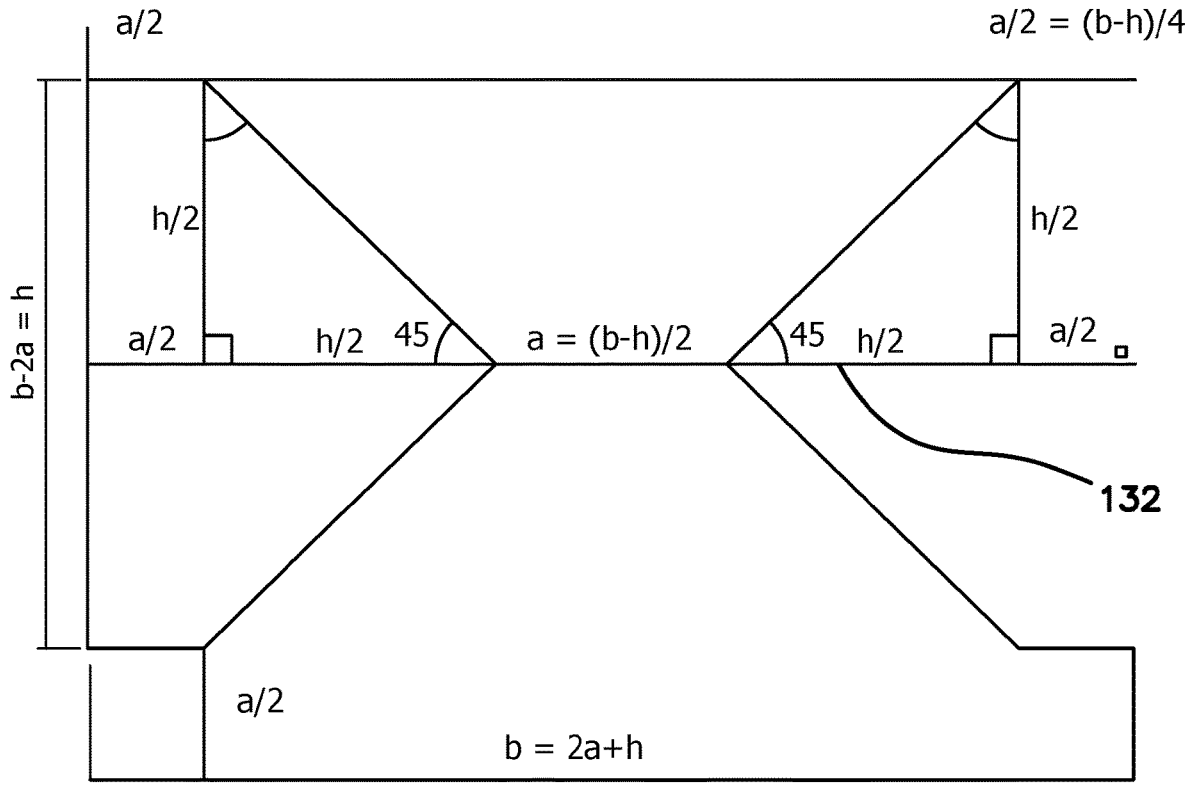
FIG. 50F is a partial top view of a pattern with dimensions for a containment bag according to the present invention.

For a particular desired height and/or width of the bag 18, the pattern as shown in FIGS. 50E-50F is used to optimally create the wall pattern to ensure the proper deployment and operation (e.g., straightening and containment). In one embodiment, the bag 18 is pre-formed with the illustrated pattern and the bag 18 is then heated to maintain the flat and patterned state. A tether 130 is attached or threaded through tabs 136 at the open end 128 of the bag 18. As such, the heat, pressure or preformed condition to place the bag 18 in an initial flat, stabled and patterned state assists in keeping the deformation pattern and causes or biases the bag 18 to the collapsed and deformed state when placed inside the body cavity. A downward force applied to the center of the bag 18 assists in causing the folds 132 to straighten or unfold and thereby expand or lengthen the height of bag 18 to engulf the specimen. As shown, the valley and/or mountains of the pattern can have the same height and/or width to further ensure a linear and constant or measured size increase. In various embodiments, the valleys or mountains of the pattern can have different dimensions and apply equal force on the inside walls of a cylindrical deployment device which lowers the force needed to deploy the bag 16.

In accordance with various embodiments, the top or open end and bottom or closed end of the bag are twisted in alternating directions causing spiral patterns on the wall of the bag. The bag and/or spirals are heated or compressed to keep their shape. The spiral folds assist in keeping the bag flat after being inserted into the body. After the specimen placed on the open end of the bag, the pulling of the tether encircling the open end of the bag causes the wall of the bag to unfold or untwist. As such, opposite forces of the pull on the tether or open end of the bag and the weight of the specimen and/or attached or added weight at the closed end or bottom of the bag causes the bag to untwist and engulf the specimen as the bag is pulled towards the opening in the body cavity. In accordance with various embodiments, the open end includes a first ring and/or the closed end includes a second ring. The first and/or second ring may be reinforced or include a wire or rod to bias the open end in an open or enlarged state to receive a specimen, increase the tendency for the bag to remain in a flat or unexpanded condition or to provide weight to assist in expansion of the bag or stability in the placement of the bag or the receiving and capturing of the specimen.

In accordance with various embodiments, the top or open end and bottom or closed end of the bag are collapsed directly towards each other. The wrinkles or folds in the wall of the bag between the open and closed end of the bag are heated or compressed to keep their pattern/shape and assist in keeping the bag flat after being inserted into the body. After the specimen placed on the open end of the bag, the pulling of the tether encircling the open end of the bag causes the wall of the bag to un-wrinkle or straightens. As such, opposite forces of the pull on the tether or open end of the bag and the weight of the specimen and/or attached or added weight at the closed end or bottom of the bag causes the bag to straighten and engulf the specimen as the bag is pulled towards the opening in the body cavity. In accordance with various embodiments, the open end includes a first ring and/or the closed end includes a second ring. The first and/or second ring may be reinforced or include a wire or rod to bias the open end in an open or enlarged state to receive a specimen, increase the tendency for the bag to remain in a flat or unexpanded condition or to provide weight to assist in expansion of the bag or stability in the placement of the bag or the receiving and capturing of the specimen.

Figure 50G:
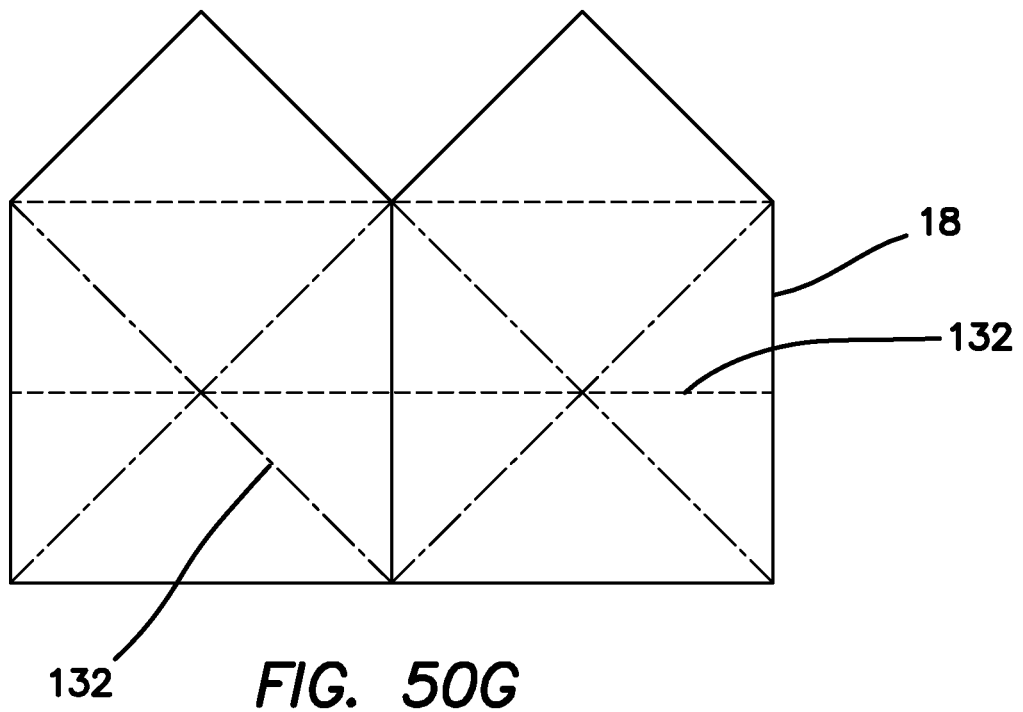
FIG. 50G is a top view of a pattern for a containment bag that is substantially square when viewed from the top according to the present invention.
Figure 50H:
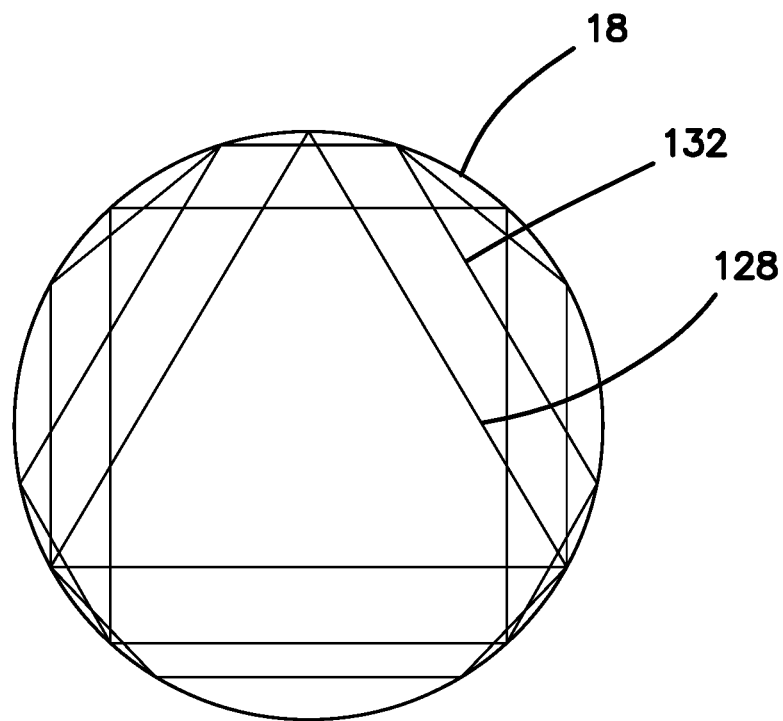
FIG. 50H is a top view of a containment bag having a triangular open end according to the present invention.

As shown in FIG. 50G and FIG. 50H, the bag 18 can have various upper, base and overall shapes including but not limited to cubes, prisms, cylinders, spheres, dodecahedrons, hemispheres, cones, cuboids, polygons and so on and is enclosed with one or more openings and including various deformation wall patterns to cause the bag to tend to remain in a collapsed or substantially flat shape and to expand in linear or controlled fashion when manipulated to contain and engulf the specimen within.

Various examples of access systems to be included or integrated into the morcellation system in which the entire access systems, portions of the access systems or combinations of access systems and/or components thereof arranged to provide a channel and/or a protective region in accordance with various embodiments of the present invention are described in U.S. patent application Ser. No. 13/865,854, filed Apr. 18, 2013; 61/880,641, filed Sep. 20, 2013; Ser. No. 12/578,422, filed Oct. 13, 2009, 61/104,963, Oct. 13, 2008; Ser. No. 12/358,080, filed Jan. 22, 2009; Ser. No. 11/374,188, filed Mar. 13, 2006; Ser. No. 11/683,821, filed Mar. 8, 2007; Ser. No. 12/396,624, filed Mar. 3, 2009; Ser. No. 14/209,161, filed Mar. 13, 2014; Ser. No. 12/873,115, filed Aug. 31, 2010; Ser. No. 12/840,989, filed Jul. 21, 2010; Ser. No. 11/548,758, filed Oct. 12, 2006; Ser. No. 10/516,198, filed Nov. 30, 2004; and Ser. No. 10/666,579, filed Sep. 17, 2003; the entire disclosures of which are hereby incorporated by reference as if set forth in full herein.

Figure 51:
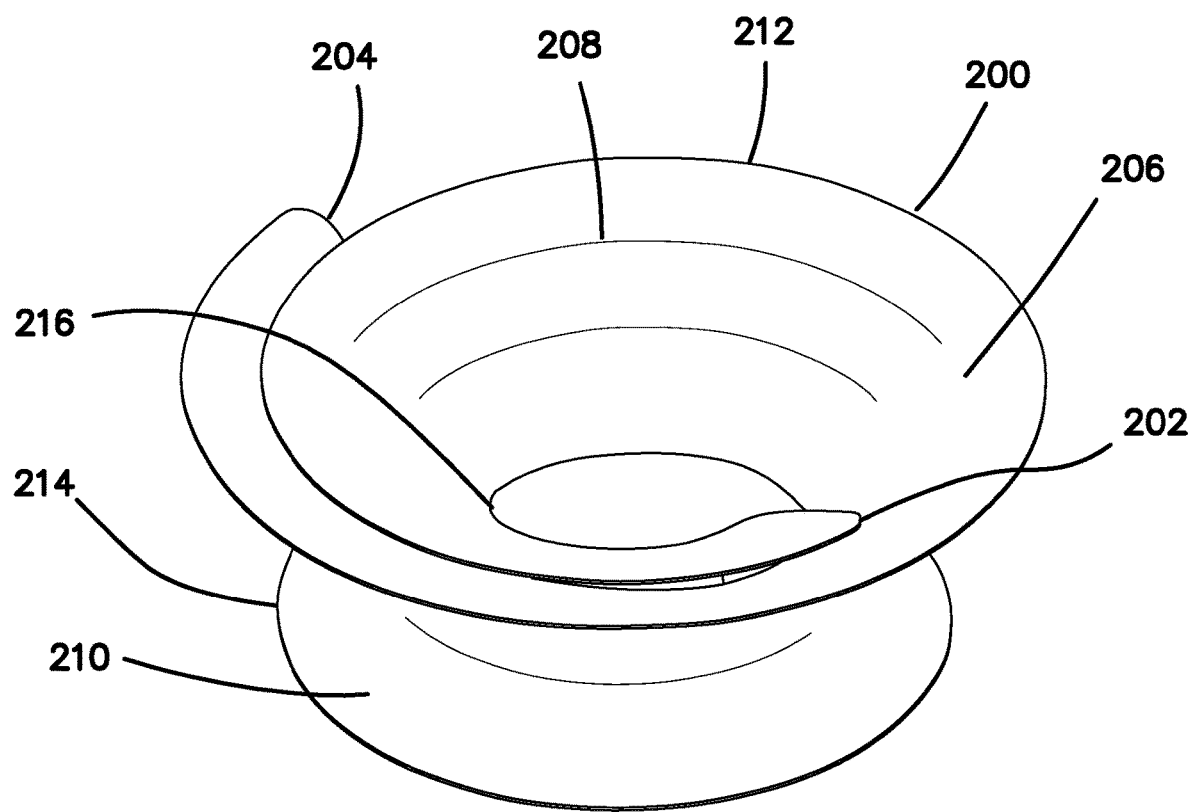
FIG. 51 is a top perspective view of a guard according to the present invention.
Figure 53:
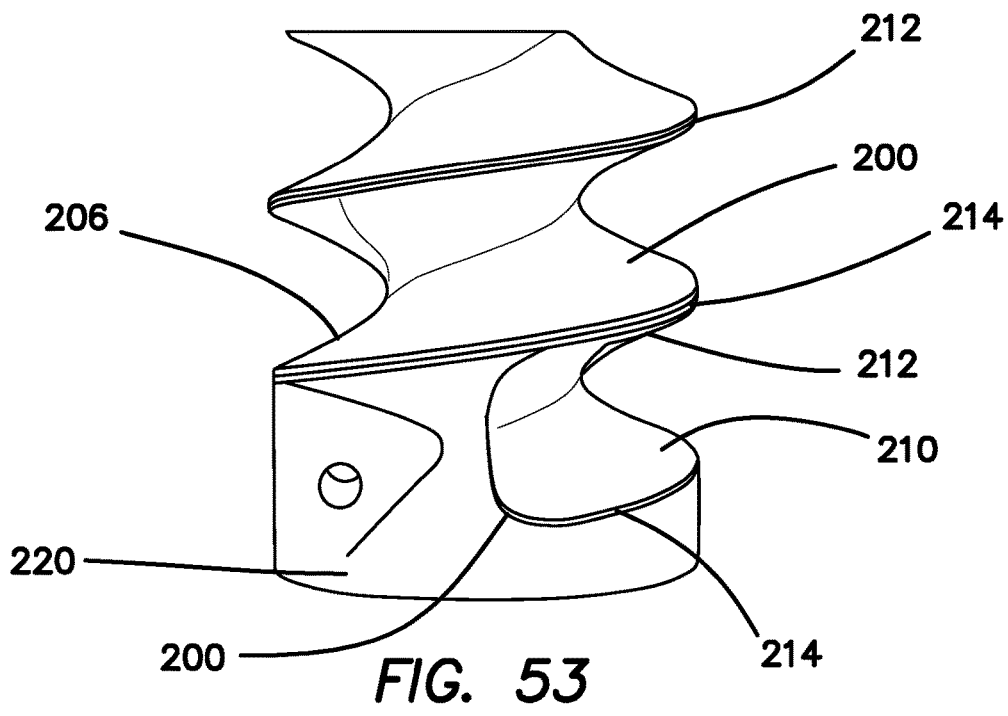
FIG. 53 is a top perspective view of a guard on a mold according to the present invention.
Figure 52:
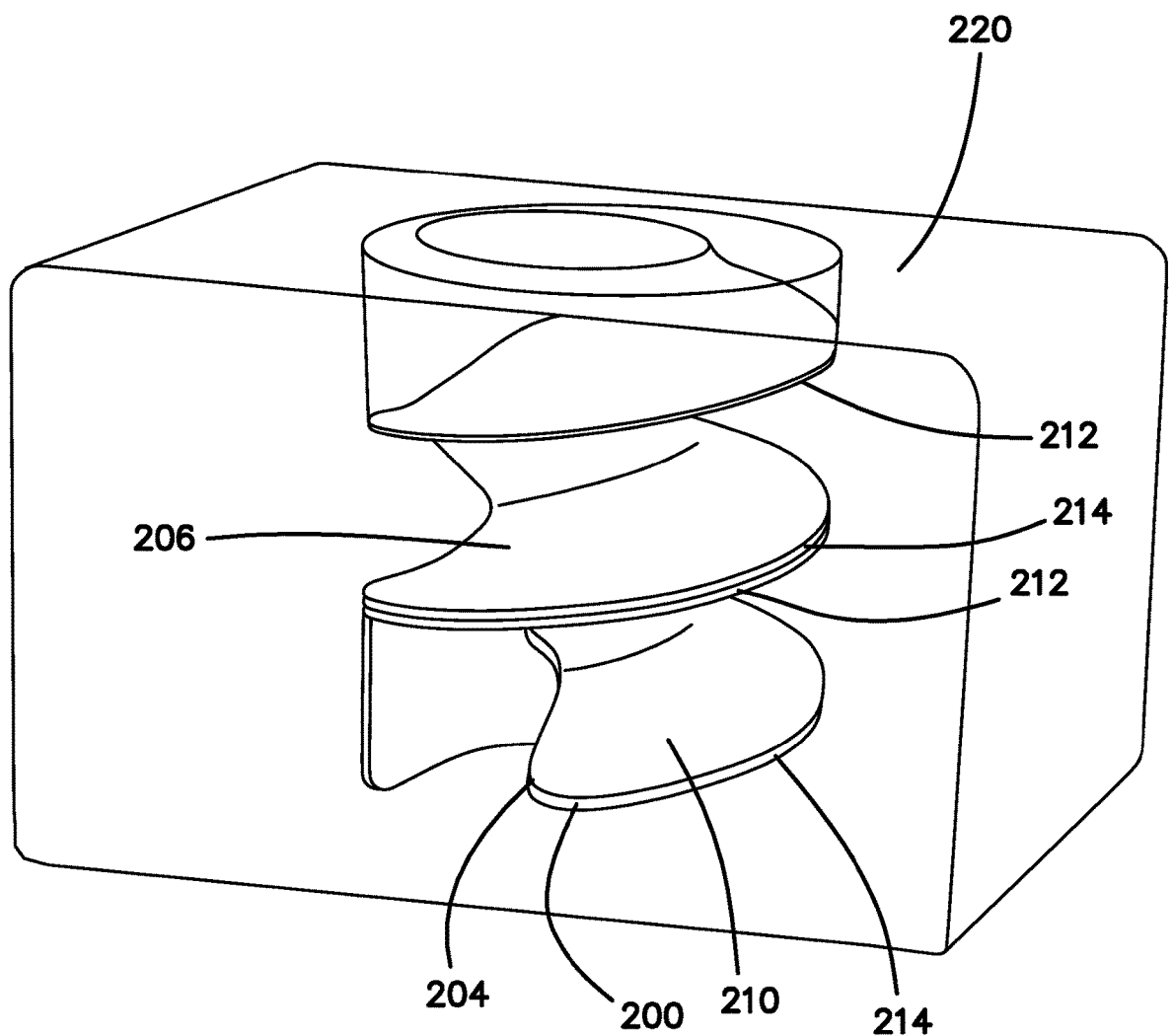
FIG. 52 is a top perspective view of a guard inside a mold according to the present invention.
Figure 54:
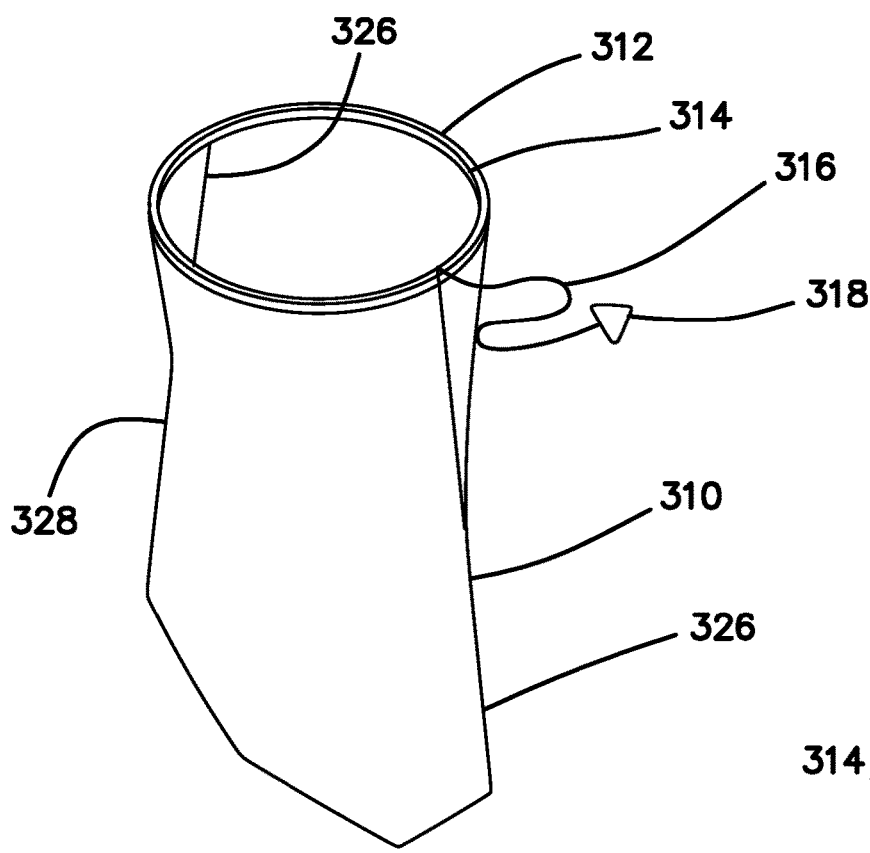
FIG. 54 is a top perspective view of a containment bag according to the present invention.

Turning now to FIGS. 51-53, there is shown another variation of the guard or shield 200 according to the present invention. The guard 200 has a general shape of a spiral. The guard 200 includes a first inner end 202 and a second outer end 204. The first end 202 and the second end 204 are interconnected by a central portion 206 also called a leaf or band. The guard 200 has an inner surface 208 and an outer surface 210 interconnected by a top end 212 also called a trailing end or proximal end and a bottom end 214 also called a leading end or distal end and by the first inner end 202 and the second outer end 204. The central portion 206 or band has a concave outer surface 210 and the inner surface 208 forms a conforming surface that is convex when viewed from within the spiral. The concavity of the band is parabolic in one variation with the inflection point being midway between the top end 212 and the bottom end 214 although the invention is not so limited and the inflection point may be anywhere between the top end 212 and the bottom end 214 and even coincident or nearly coincident with the top end 212 or bottom end 214. The band 206 may also not have a concavity and may be simply curved or straight along at least a portion of the guard 200 between the top end 212 and the bottom end 214. The guard 200 is shown to be symmetrical having a top end that has the same outer diameter as the bottom end. In another variation, the guard 200 is asymmetrical in shape and may have a top end larger or smaller in diameter relative to the bottom end. The guard 200 is also vertically symmetrical; however, the invention is not so limited and the guard 200 may have a central axis that is angled with respect to a reference horizontal plane. The guard 200 has a spiral shape such that a portion of the band overlaps another portion of the band in a curved, circular or elliptical fashion. In particular, at least a portion of the outer surface 210 of the band 200 overlaps and faces at least a portion of the inner surface 208 of the band 200 such that the concavity of part of the band 200 is adjacent or juxtaposed to a concavity of another part of the band seating and nesting a part of the band within the other part of the band. The spiral is shown to have a resting and mechanically unstressed configuration having one and a half turns with a circumferential length of approximately 37R where R is the radius taken perpendicular to the longitudinal axis of the guard 200. The invention is not limited to the guard 200 having precisely 1.5 turns and may have more or less turns as desired according to its size, shape and desired force distribution for a particular incision size and function such as a retractor function and/or retention function. A particular advantage of the spiral guard 200 is that its shape and size and be changed, expanded or reduced. In essence, the band can slide relative to itself to form a larger spiral form having a larger diameter or a smaller spiral form having a smaller diameter. The spiral guard 200 includes a central lumen 216 formed by the spiral which can also be enlarged as the spiral is expanded or opened up. The size of the central lumen 216 may also be reduced as the spiral is closed or reduced in size by sliding the band into a tighter curl upon itself producing a greater number of turns versus a larger curl that would produce a larger diameter with a smaller number of turns. The central lumen 216 is substantially circular in shape; however, the invention is not so limited and the central lumen 216 may be elliptical or irregular in shape. As such, the spiral shield 200 is adjustable when inserted into the wound of a patient or an incision or a bag placed inside a patient as described above with the other guards. Depending on the size of the incision, the spiral shield 200 can be adjusted larger or smaller by opening or closing the spiral shape, curling the guard onto itself make more turns to fit the wound opening or bag accordingly. Furthermore, the spiral shield 200 may be molded with a predetermined bias for a particular resting or normal diametrical position, shape and size. For example, if an incision of approximately one inch is made into the patient, a spiral shield 200 having a resting diameter of approximately two inches may be reduced in size by twisting the shield onto itself to increase its windings upon itself, thereby, decreasing its diameter. While in the reduced configuration, the spiral shield 200 is inserted into the one inch incision and then released. Whereas because of the bias molded into the spiral shield 200, the spiral shield 200 will tend towards its normal configuration and, therefore, expand from its reduced configuration and advantageously retract the incision at the same time as well as seal or force against the incision holding the spiral shield 200 and anything between the shield 200 and the incision such as a bag in position with respect to the patient. Alternatively, the shield 200 may advantageously be reduced under force of the tissue when inserted into the incision. The force of the tissue upon the shield may reduce the diametrical size of shield. Because the shield is adjustable, the central opening or lumen 216 may be increased in size by opening up the spiral for the removal of larger specimens. This adjustability advantageously reduces the strain on surrounding tissue, keeps the incision site as small as possible, reduces the risk of infection and at the same time allows the incision size to be retracted and increased by opening up the spiral as needed to pull the specimen out of the body. Sometimes the size of the tissue to be removed is unpredictable and this adjustability advantageously allows for ease of removal of a wider range of tissue specimens without creating difficulties for the doctor.

The position of the spiral shield 200 is further advantageously retained with respect to the incision site or natural orifice such as the vagina with the help of the curvature or concavity of the band. In particular, the top end 212 forms a top lip also called a top flange that at least in part circumferentially extends onto the upper surface of tissue. The bottom end 214 forms a bottom lip or bottom flange that at least in part circumferentially extends onto the under surface of the tissue inside the patient cavity, abdominal wall or surgical working space advantageously retracting tissue away from the shield 200 cutting surface which is generally the inner surface 208 of the band. The tissue is received against the outer surface 210 of the band and is seated within the concavity or curved shape of the outer surface 210 keeping the shield and containment bag in place with the flanges preventing the shield from slipping down into the patient or slipping up and out of the patient. Of course, the shield 200 is placed directly within a surgical incision/orifice or within any one or more of the containment bags and wound retractors described above. Morcellation can proceed in any technique or fashion chosen by the surgeon including employing the inner surface 208 of the shield 200 as a cutting board against which a blade may be used to cut tissue pulled through or into the central lumen 216 with a grasper. As the tissue to be morcellated is pulled up through the central lumen 216, it can be positioned against the inner surface 208 of the guard 200 and a blade or scalpel can be used to cut the tissue against the shield 200. The shield 200 is manufactured of a suitable material such as any polymer or metal. One suitable material is ultra-high molecular weight polyethylene plastic. Another suitable material is low linear density polyethylene. The shield material has a thickness optimized for protecting the tissue without being punctured or severed easily when tissue is cut against it. When morcellation is completed, the spiral shield 200 can be reduced in diameter by winding the shield upon itself into a reduced configuration for easy removal from the surgical site. Alternatively, the shield 200 can be removed by pulling the shield 200 vertically or along the longitudinal axis of the shield.

FIGS. 52-53 illustrate the spiral shield 200 on a core pin of a forming mold 220 that has a helical shape. To manufacture the spiral shield 200 by injection molding, the shield 200 is molded onto a helical mold 220. Once unwound off the core-pin of the mold 220, the shield 200 can be conformed into its functioning spiral form by tucking one end in front of or behind the adjacent winding. Because the shield 200 is initially molded into a helix, and then conformed into a spiral, it has some spring-back tension memory within it making it want to assume a helical shape instead of staying as a perfect spiral. If the shield 200 has an undesirable and excessive amount of spring-bias tension, an annealing process can be performed by placing the shield 200 into an oven at the appropriate temperature for an allotted time and then removed and, thereby, reducing or alleviating any remnant tension in the shield 200. However, in one variation of the shield 200, some remaining tension is advantageously desirable as the tendency of the shield 200 to expand along a longitudinal axis facilitates removal of the device from the incision site. A tab (not shown) may be formed on one end of the shield 200 such as the proximal end, inner end or outer end and/or a hole may be formed near one end of the shield through which a pull string may be attached so that the string or tab may be pulled by the practitioner to easily remove the shield 200 from the incision site. The tab or hole may indicate a directional preference for inserting the shield so that the helical tension may be taken advantage of when removing the device with the tab/hole residing proximal to the surgeon outside the patient. In one variation, the first inner end 202 that is conformed to the inside of the winding would be tabbed or holed for this removal feature. During removal when the inner end 202 is pulled in a vertical direction, the band of the shield will progressively uncoil out of the incision site.

As an alternative to injection molding, the spiral shield 200 may be manufactured from plastic sheet stock, die cut and thermoformed into shape. Also, instead of injection molding the shield 200 into a helix, the spiral shield 200 may be injection molded in the shape of the spiral directly.

Figure 71A:
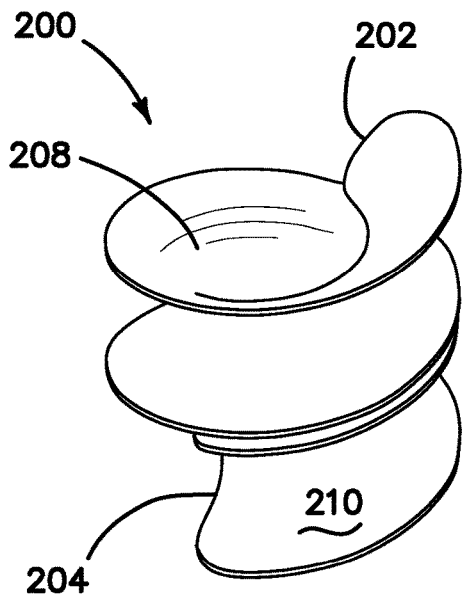
FIG. 71A is a top perspective view of a guard according to the present invention.
Figure 71B:
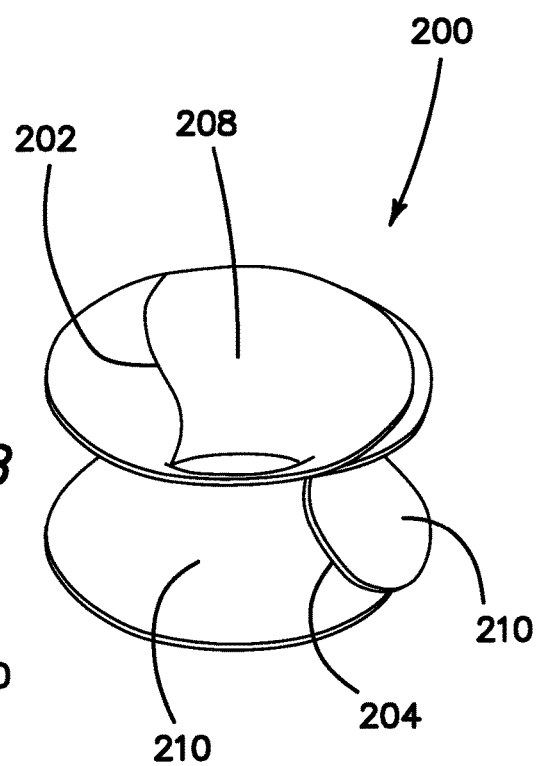
FIG. 71B is a top perspective view of a guard according to the present invention.
Figure 72:
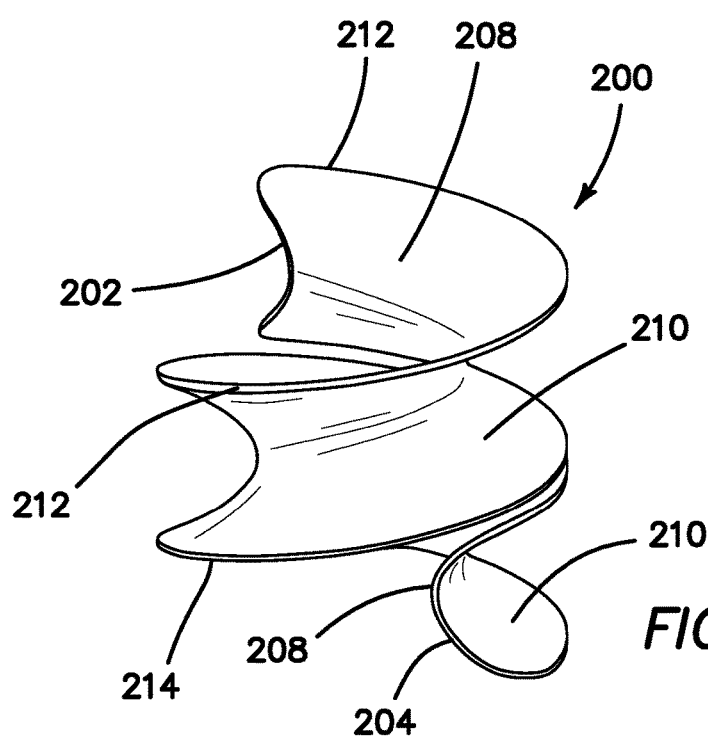
FIG. 72 is a top perspective view of a guard according to the present invention.
Figure 73:
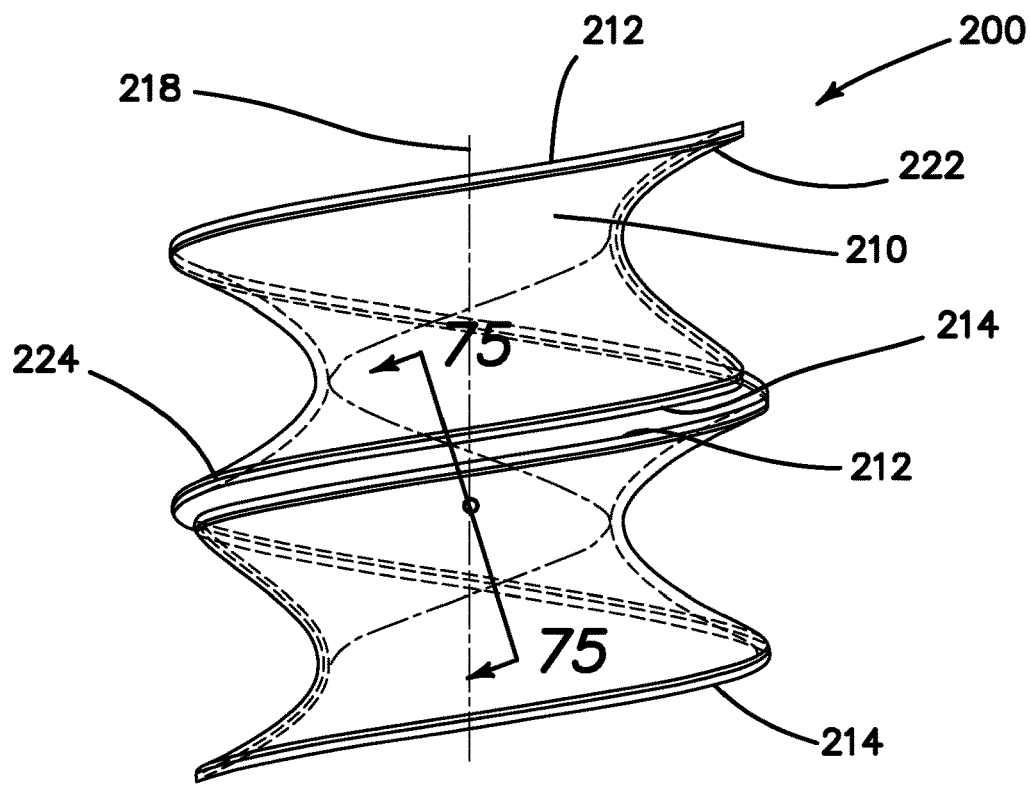
FIG. 73 is a semi-transparent side view of a guard according to the present invention.
Figure 74:
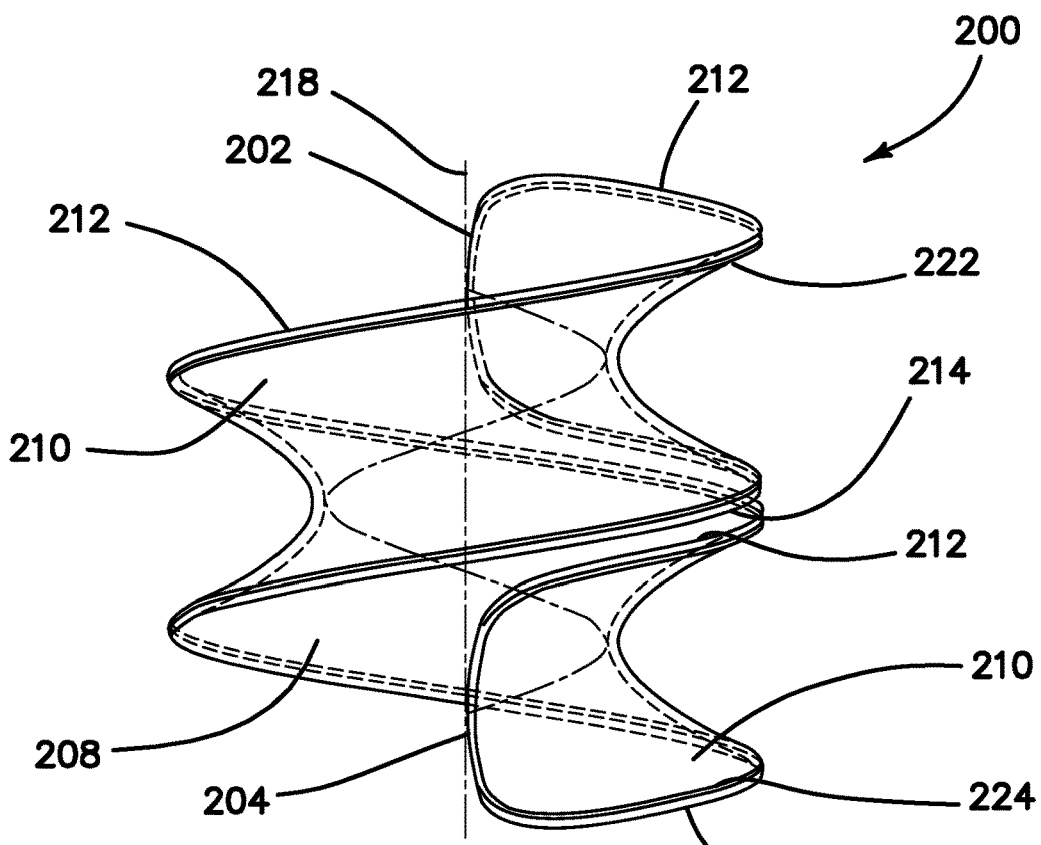
FIG. 74 is a semi-transparent side view of a guard according to the present invention.
Figure 77:
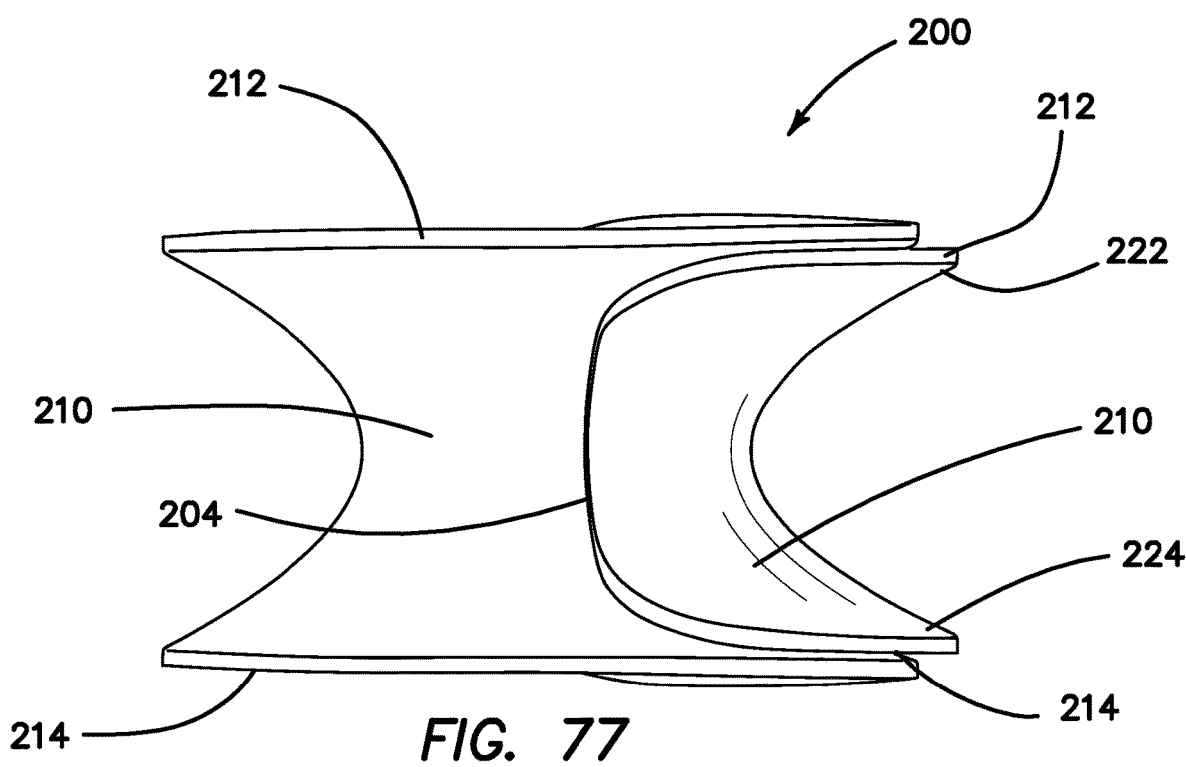
FIG. 77 is a side view of a guard according to the present invention.
Figure 78B:
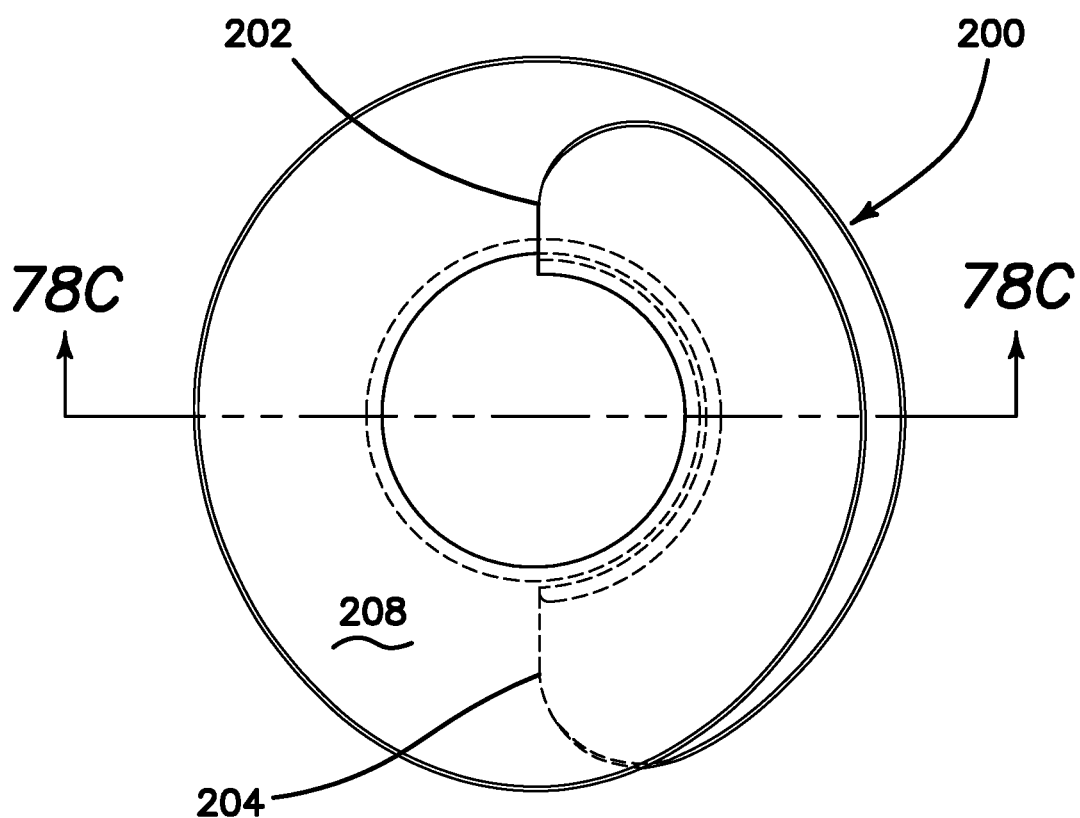
FIG. 78B is a semi-transparent top view of a guard according to the present invention.
Figure 78C:
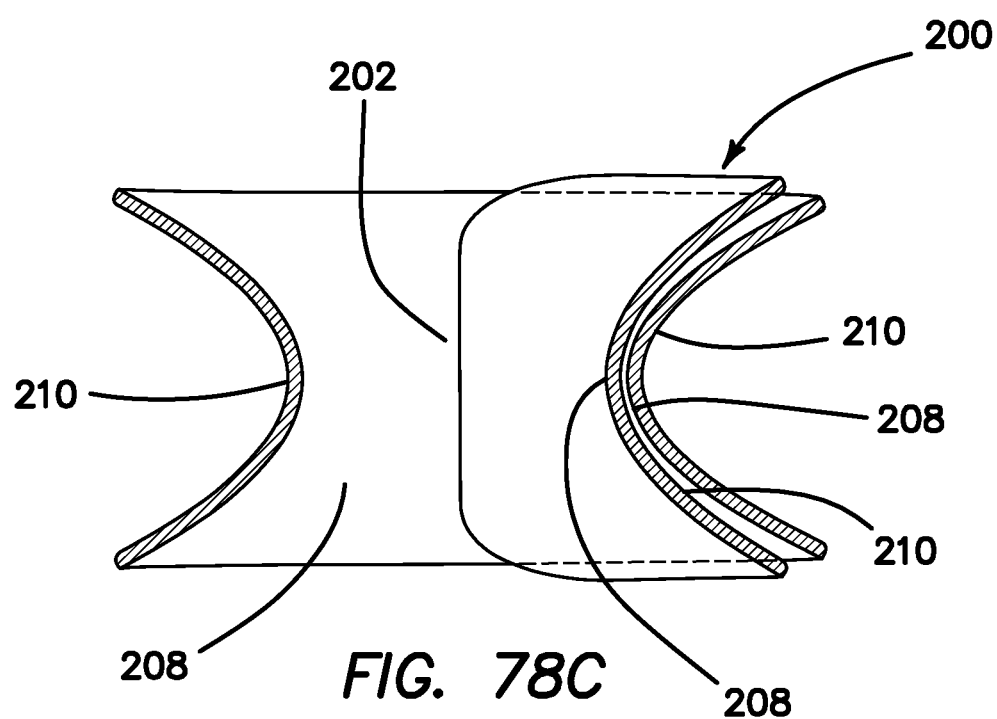
FIG. 78C is a cross-sectional view taken along line 78C-78C of FIG. 78B of a guard according to the present invention.

Turning now to FIGS. 71A and 71B, there is shown a shield 200 in an expanded elongate configuration and a compressed or unexpanded configuration, respectively. The expanded configuration of the shield 200 is also illustrated in greater detail in FIGS. 72-74. The shield 200 in the expanded configuration is convertible into the compressed configuration by overlapping the inner surface 208 onto the outer surface 210. The compressed configuration of the shield 200 is also illustrated in FIGS. 76-79. At least part of the shield 200 overlaps itself in the unexpanded configuration as shown clearly in FIGS. 78A-78C. In FIG. 78C, the nesting of one part of the shield 200 in the concavity of the outer surface 210 of an adjacent overlapping portion of the shield 200 is shown. The shield 200 is adapted to be rolled or curled at least in part around the longitudinal axis 218. The shield 200 is adapted to be rolled or curled at least in part around the longitudinal axis 218 onto itself such that a portion of the shield 200 overlaps or lies in juxtaposition or in contact with another portion of the shield 200. When in the unexpanded configuration of FIG. 71B, the shield 200 has a relaxed or normal lateral configuration in addition to a compact configuration in which the unexpanded configuration is rolled into a tighter roll having a reduced diametrical or lateral dimension suitable for insertion into a wound or orifice. The shield 200 has a bias towards the relaxed or normal lateral configuration and will tend toward this bias after insertion into a wound or orifice providing some retraction forces on the tissue as the shield 200 expands from the compact configuration to a larger configuration depending on the material used for the shield 200 and the forces exerted by the surrounding tissue in response to the inserted shield 200. If the wound or orifice is tight, the shield 200 may not expand from its reduced lateral insertion configuration or may only slightly expand in the lateral dimension unrolling slightly as it tends towards its normal relaxed configuration or the shield 200 may expand all the way to its normal relaxed configuration.

The vertically expanded configuration of the shield 200 shown in FIG. 71A is a result of it being molded onto a helical mold 220. The shield 200 defines a longitudinal axis 218 about which the shield 200 is centered. The shield 200 is made of a material that is biased at least in part toward the vertically expanded position. The shield 200 may also be made of shape-memory material or include parts made of shape-memory material. When in the vertically compressed configuration, the bias to the vertically expanded position will not result in shield 200 springing into the vertically expanded configuration because the concavity of the outer surface forms a top lip also called a top flange 222 and a bottom lip also called a bottom flange 224 such that at least a portion of the top flange 222 abuts an adjacent overlapping top flange 222 while in the compressed configuration and at least a portion of the bottom flange 224 abuts an adjacent overlapping bottom flange 224 while in the compressed configuration preventing the vertically compressed configuration from easily popping into a vertically expanded configuration. At least one of the top flange 222 and bottom flange 224 serve as a stop preventing the shield 200 from expanding from the compressed configuration to the expanded configuration. The bias towards the expanded configuration imparts some friction onto the device itself which helps to adjust the lateral dimension or diametrical expansion of the shield 200. When in the compressed configuration, the shield 200 can be rolled/curled about the longitudinal axis to reduce the diametrical or lateral dimension; thereby, reducing the size of the shield 200 as well as reducing the diameter of the central lumen 216 making it easier to insert through small minimally invasive incisions or orifices.

Figure 80:
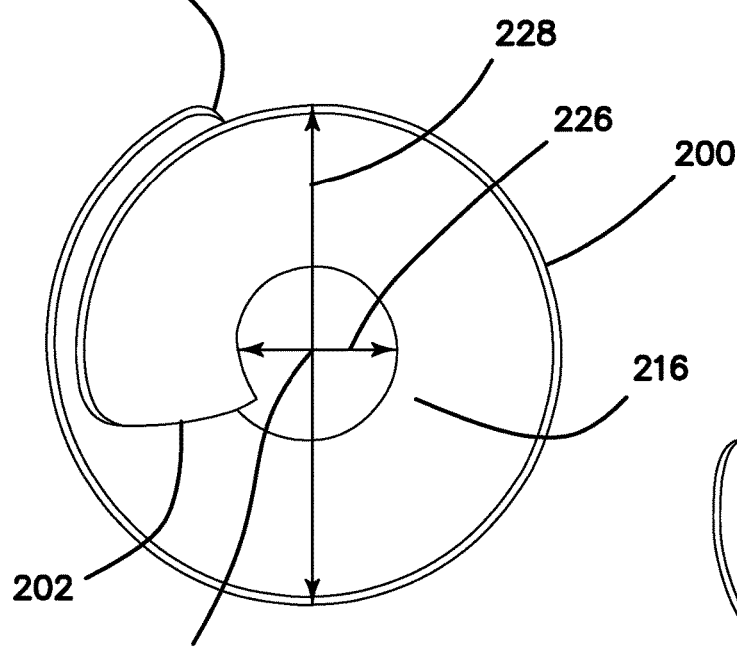
FIG. 80 is a top view of a guard according to the present invention.
Figure 81:
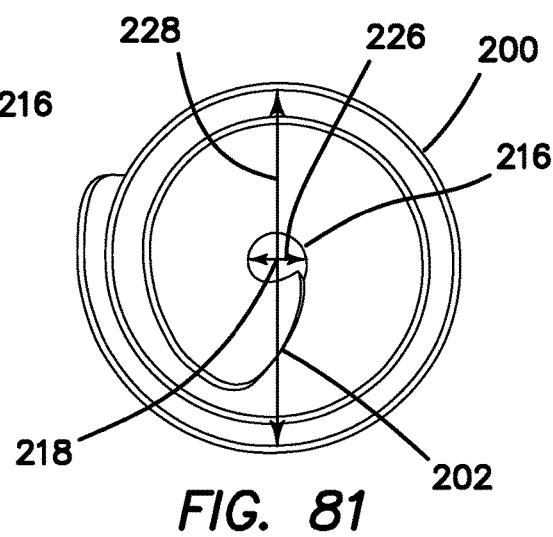
FIG. 81 is a top view of a guard according to the present invention.

FIG. 80 illustrates the shield 200 in a relaxed or normal lateral configuration having approximately 1.25 times the circumference circumferential windings showing the central lumen 216 with a shield inner diameter or lumen diameter 226, and shield diameter 228 or outer diameter either of which serve as a lateral or diametrical dimension for the shield 200. FIG. 81 illustrates a top view of the shield 200. In FIG. 81, the shield 200 is in a compact configuration suitable for insertion into an incision/orifice in which the shield 200 is rolled into a tighter roll onto itself. The shield 200 in FIG. 81 has equal to or greater than approximately 2.25 times the circumference circumferential windings and a reduced lumen diameter 226 and shield diameter 228 relative to the relaxed, normal configuration of FIG. 80. The overlapping portions of the shield 200 contact each and act to slightly frictionally retain the reduced lateral dimension position; however, since the bias of the lateral dimension is towards the unstressed or relaxed radial normal configuration, the shield 200 will tend to the normal configuration. The compact configuration having a reduced lateral dimension is suitably adapted for insertion into a wound or orifice. From the compact configuration, the shield 200 will expand from a reduced lateral dimension position towards a normal, unstressed lateral dimension configuration when released when outside the wound or orifice. This expansion in situ may be limited by forces exerted by the tissue in response to the forces imparted by the inserted shield 200. Although the shield 200 includes a central lumen 216 having a circular shape and diameter, the invention is not so limited and variations include a shield 200 having an elongate lumen 216 having a length that is greater than its width such as an oval or ellipse. As such, the outer perimeter of the shield 200 may or may not have a corresponding shape. In a variation in which the outer perimeter of the shield 200 has a shape that corresponds to the shape of the central lumen 216, where the lumen 216 is circular, the outer perimeter of the shield 200 is also circular or if the central lumen 216 has an oval or elliptical shape, the outer perimeter of the shield also has an oval or elliptical shape.

Figure 79:
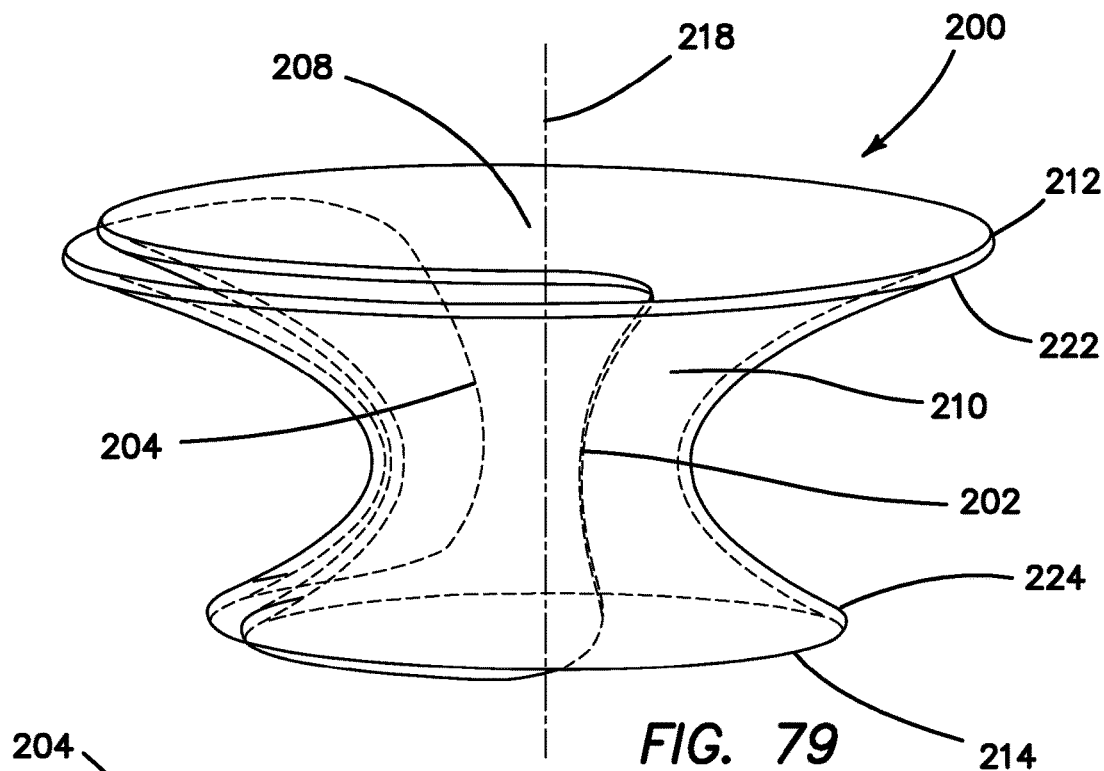
FIG. 79 is a semi-transparent top perspective view of a guard according to the present invention.

As described above, the shield 200 includes a top flange 222 and a bottom flange 224 as part of the concave outer surface 210 of the shield 200. While in a vertically unexpanded configuration, the shield 200 is generally symmetrical about a plane perpendicular to the longitudinal axis 218 in which case the top flange 222 and bottom flange 224 extend an approximately equal distance radially outwardly from the longitudinal axis 218 as shown in FIG. 77. Turning to FIG. 79, there is shown a variation of the shield 200 in which the shield 200 is not symmetrical about a plane perpendicular to the longitudinal axis 218. In FIG. 79 the top flange 222 extends radially outwardly from the longitudinal axis 218 a distance greater than the bottom flange 224 extends radially outwardly from the longitudinal axis 218. The shield 200, thereby, forms an enlarged top flange 222 relative to the bottom flange 224. The enlarged top flange 222 advantageously provides a larger surface area of protection for the surround tissue and/or containment bag as well as provides a larger cutting board surface for the surgeon to use when morcellating/reducing tissue.

Figure 82:
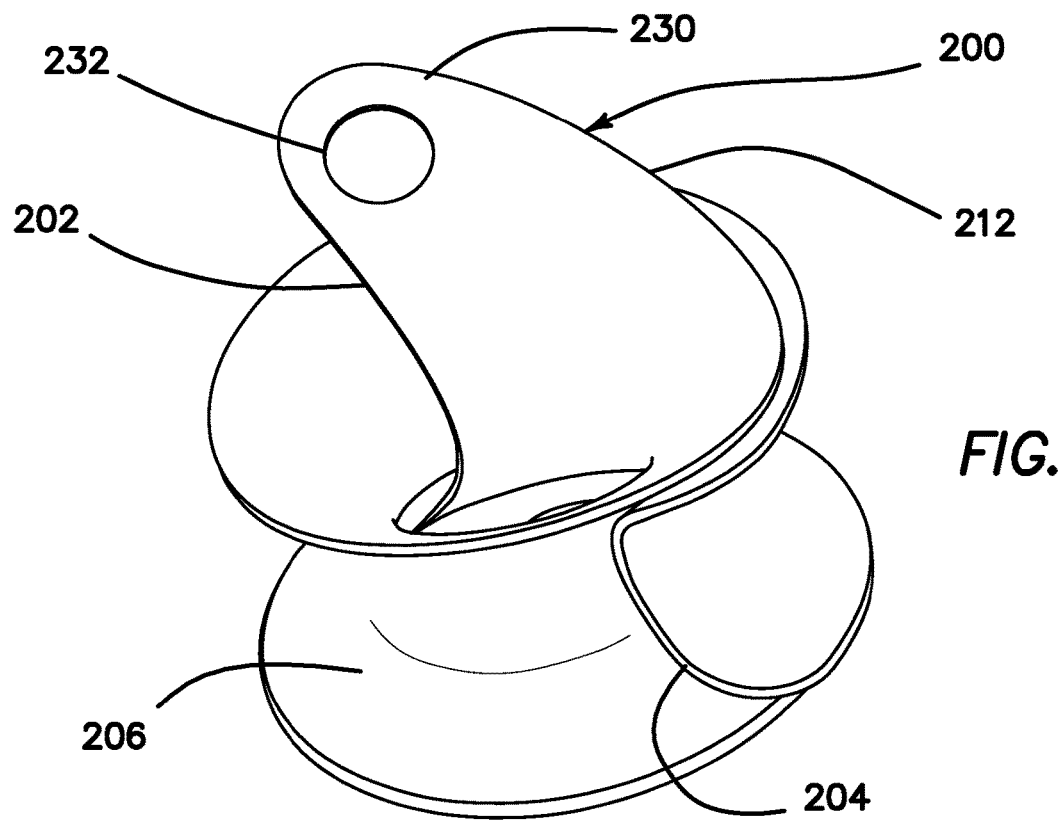
FIG. 82 is a top perspective view of a guard according to the present invention.

Turning to FIG. 82, there is shown a variation of the shield 200 having a finger pull or tab 230. The tab 230 is shown integrally formed at or near the first inner end 202 of the shield 200. The tab 230 extends from first inner end 202 and from the top end 212 of the shield 200 forming an extension adapted to be easily grasped by the user either with the user's fingers or with an instrument such as a grasper. In one variation, the tab 230 includes an aperture 232 configured to provide a location for the insertion of an instrument or finger. In another variation, there is no aperture 232. The tab 230 is configured such that when it is pulled generally in the upwardly or proximal direction, the shield 200 will convert from the unexpanded configuration to the expanded configuration. Upwardly directed force applied at the first end 202 via the tab 230 results in the bottom flange 224 of the first end 202 being unhooked or dislodged from the adjacent lower flange 224 of the shield 200 separating the first end 202 from a nested position with the overlapping curvature of the adjacent shield 200 portion. As the proximal end of the tab 230 is being pulled upwardly it will lead the vertical expansion of the shield 200, first resulting in the first inner end 202 moving out from the unexpanded configuration and leading the rest of the shield 200 progressively out of a nested juxtaposition of the unexpanded configuration and into a the spiral shape of a shield 200 in an expanded configuration. FIG. 82 illustrates a shield 200 in an unexpanded configuration and the tab 230 integrally formed with the shield 200. In another variation, the tab 230 is a separate element attached by adhesive, staple or other fastener to the first end 202 of the shield 200. In yet another variation, the tab 230 includes a tether attached to the shield 200 and in another variation the tab 230 is a tether and not an extension of the shield 200.

Figure 83:
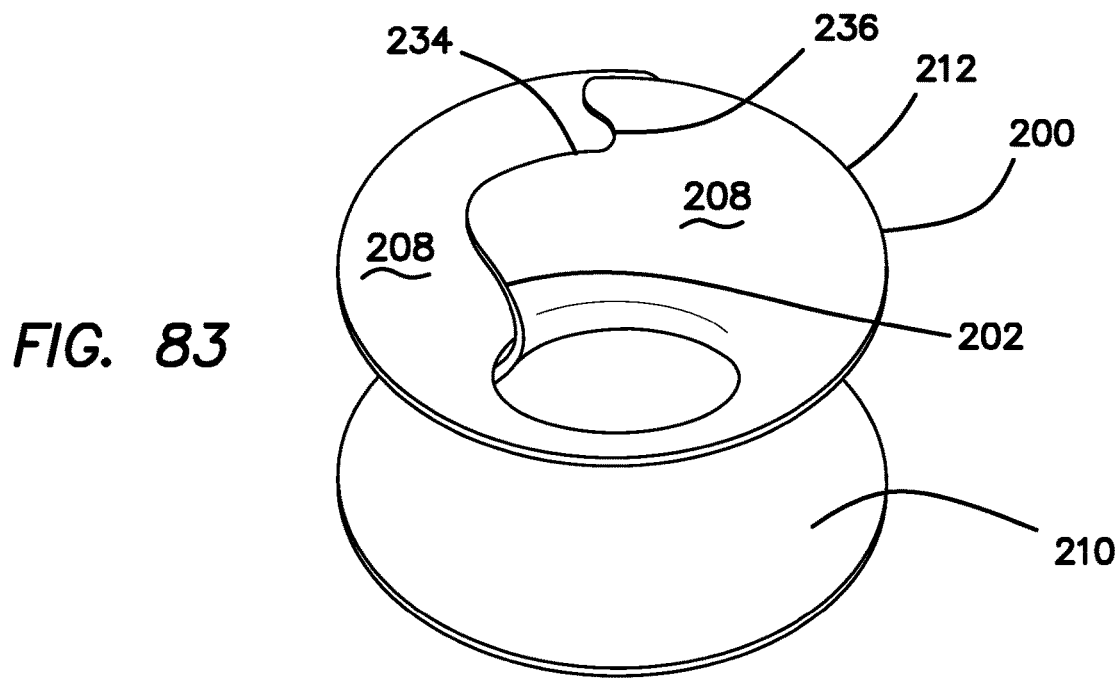
FIG. 83 is a top perspective view of a guard according to the present invention.
Figure 84:
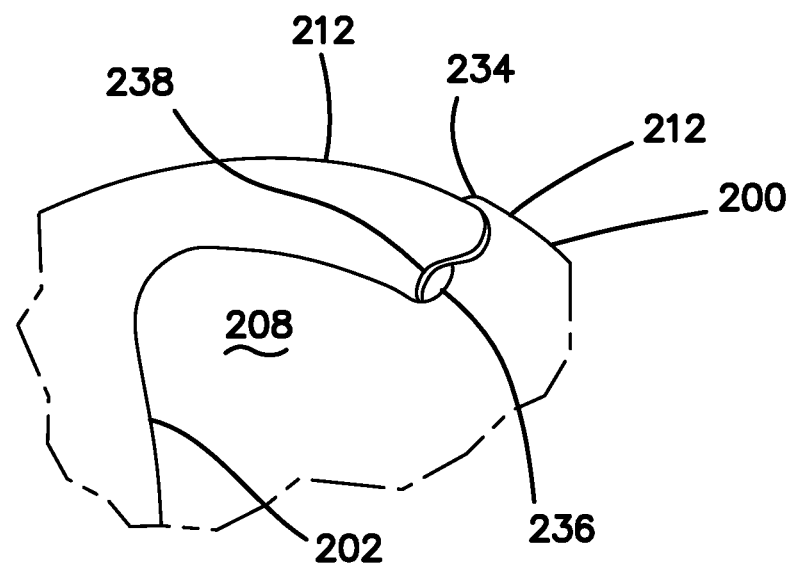
FIG. 84 is a sectional top view of a guard according to the present invention.

Turning now to FIGS. 83-84, there is shown a shield 200 with a lock 234. The lock 234 is configured to lock the lateral or diametrical dimension of the shield 200 while it is in the unexpanded configuration. When the shield 200 is placed in situ, the forces of the surrounding tissue may force the lateral or diametrical dimension of the shield 200 to be smaller than desired. Although the shield 200 may include a relaxed normal configuration while in the unexpanded configuration, the built-in bias of the shield 200 may not be sufficient to overcome the forces of the surround tissue or may otherwise be less than surgeon preference for a particular procedure or for a particular instrument to be passed through the central lumen 216 or for a particularly large specimen of target tissue. In either case, the lock 234 is configured to lock and hold the lateral or diametrical dimension of the shield 200 substantially fixed and, in particular, to prevent reduction of the lateral or diametrical dimension because of force from the surrounding tissue. For example, if the shield 200 is to be inserted into an incision or orifice that is relatively smaller than the lateral dimension of the shield 200, it is first reduced into a compacted configuration such as shown in FIG. 81. While in the compacted configuration, the shield 200 is inserted into the wound or orifice. The forces of the surrounding tissue in response to the inserted shield 200 may be greater than the bias tending to return the shield 200 to an unstressed, relaxed normal configuration. In such a case, the surgeon may desire a larger central lumen 216 for the shield 200 or to retract the surrounding tissue. The surgeon will then unroll the shield 200 into a larger lateral or larger diametrical configuration and lock that position with the lock 234 provided on the shield 200. In one variation, the lock 234 comprises a first notch 236 located a distance proximal from the first inner end 202 of the shield 200 and near the top end 212 and a second notch 238 located a distance proximal from the second outer end 204 of the shield 200 and near the top end 212. The notches 236, 238 are located in the proximity of where one end 202 of the shield 200 overlaps with the other end 204 of the shield 200 in the unexpanded configuration. The shield 200 is shown in an unlocked configuration in FIG. 83. To lock the shield 200, the shield 200 is expanded in the lateral dimension by unrolling the shield 200 to create a larger central lumen 216. The first notch 236 is overlapped with the second notch 238 to lock the shield 200 in a fixed diametrical/lateral dimension position with the remainder of the shield 200 maintaining some degree of overlap circumferentially around the perimeter of the shield 200. FIG. 84 shows the first notch 236 overlapped or interlocked with the second notch 238 in a locked configuration. While in a locked configuration, at least a portion of the first end 202 is located exterior to at least a portion of the second end 204 such that a portion of the inner surface 208 of the first notch 236 faces the outer surface 210 of the second notch 238. To unlock the shield 200, the notches 236, 238 are unhooked from each other.

As described above, the shield 200 can be inserted into the wound or orifice by winding and/or squeezing it into a smaller diameter and then inserting it into the wound or shield. Insertion of the shield 200 may be facilitated with common surgical instruments such as a clamp or grasper. Once inserted, the shield 200 naturally opens slightly and the tissue yields to the outside of its form. In one variation, the shield includes a lock 234 that enables the shield 200 to be locked at a slightly larger diameter than it would naturally occlude to. The lock 234 includes notches 236, 238 along the outer edge of the shield 200 near the first and second ends 202, 204 where the spiraled material overlaps. These notches 236, 238 overlap when in the locked configuration such that at least part of an inner end of the shield 200 is snapped to reside outside the outer end of the shield 200. The exposed tabs of the lock 234 could be pinched into an overlapping condition which would provide the mechanical interlock point.

Figure 85:
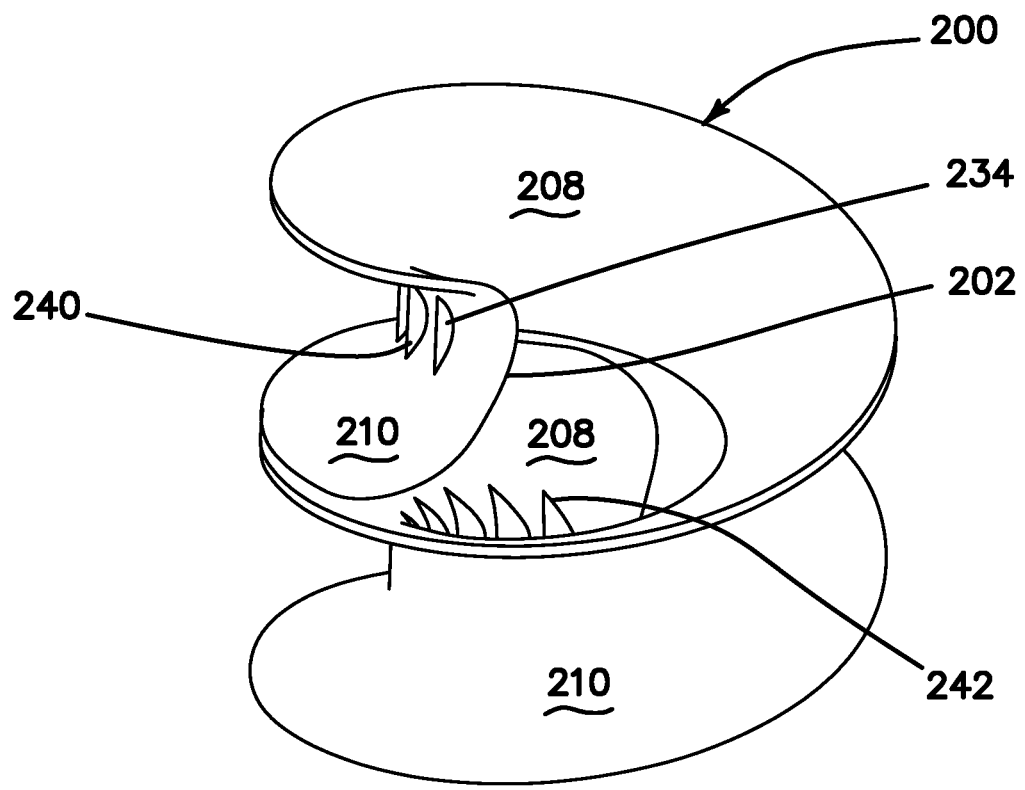
FIG. 85 is a perspective top view of a guard according to the present invention.
Figure 86:
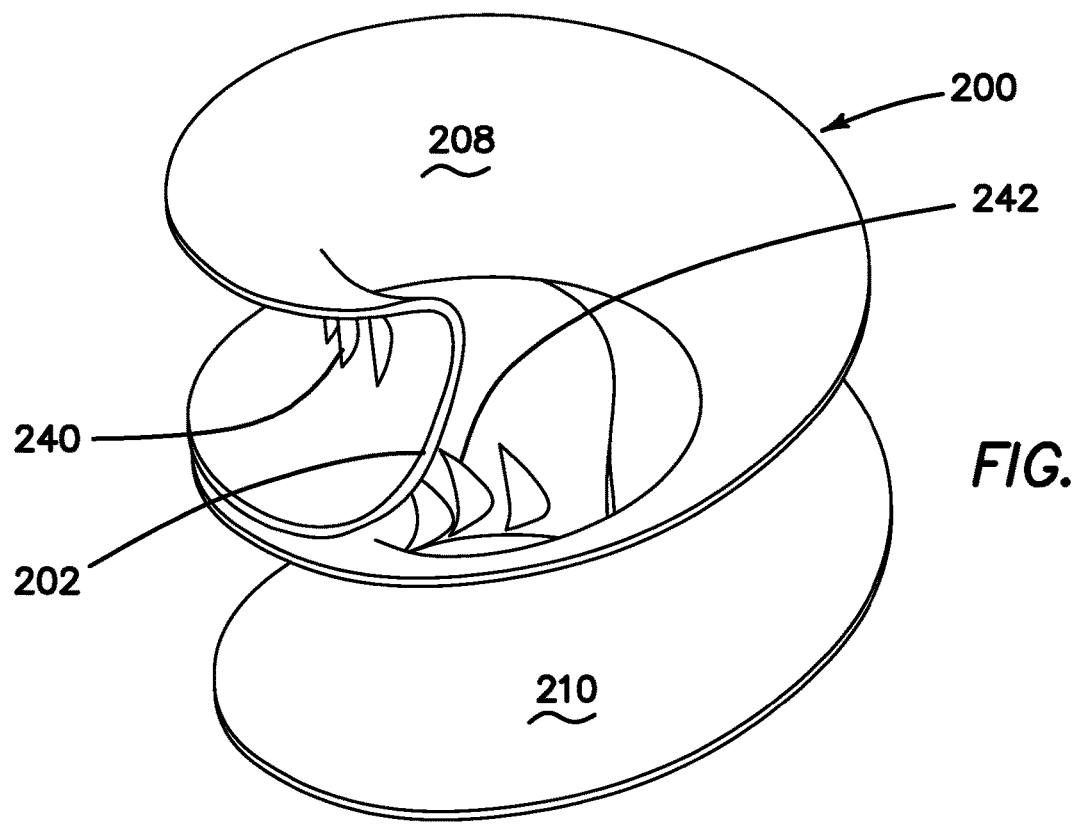
FIG. 86 is a perspective top view of a guard according to the present invention.

Turning now to FIGS. 85-86, there is shown another variation of a lock 234 on the shield 200. The lock 234 includes interlocking teeth. In particular, a first set of outer teeth 240 are formed on the outer surface 210 near the first inner end 202 of the shield 200 and a second set of inner teeth 242 are formed on the inner surface 208 near the second outer end 204 of the shield 200. The first set of outer teeth 240 are located in the concavity near the first inner end 202 and extend substantially vertically. The second set of inner teeth 242 are located in the convexity near the second outer end 204 and extend substantially vertically. The outer teeth 240 and the inner teeth 242 may also be angled. In one variation, the teeth 240, 242 are angled such that that they may more readily slide or ramp over each other when moving from a reduced lateral dimension to an increased lateral dimension. The angle of the teeth locks the ends together and prevents the shield 200 from being reduced in the lateral direction by force of tissue at the wound or orifice. The outer teeth 240 and the inner teeth 242 are configured to interlock with each other in order to prevent reduction of the lateral dimension of the shield 200. A plurality of inner teeth 240 and a plurality of outer teeth 242 are formed along at least a portion of the perimeter near the first and second ends 202, 204 so that the position at which the shield 200 is locked can be adjusted as needed and, hence, the lateral dimension can be fixed as desired. While the teeth 240, 242 are shown located in the midline perpendicular to the longitudinal axis 218, the invention may include teeth provided anywhere along the vertical dimension.

In another variation of lock on a shield 200, the shield 200 is provided with a protuberance that extends from the inner surface. The protuberance may be shaped like a hook and configured to engage a notch or opening formed in an adjacent portion of the shield 200. In one variation, the protuberance is near one of the first inner end 202 and second outer end 204 and the notch or opening is formed near the other one of the first inner end 202 and second outer end 204.

Figure 75:
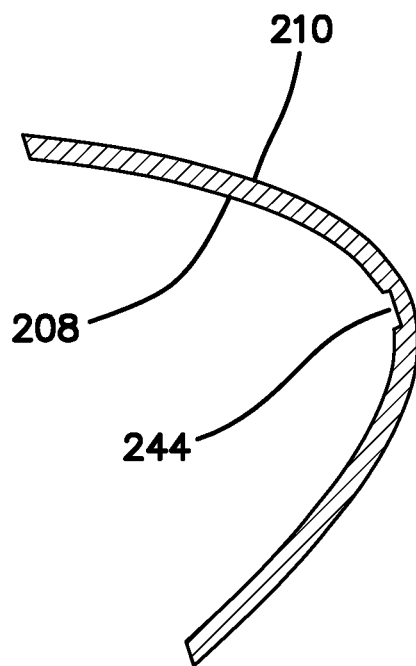
FIG. 75 is a cross-sectional view of a sidewall of a guard according to the present invention.
Figure 78A:
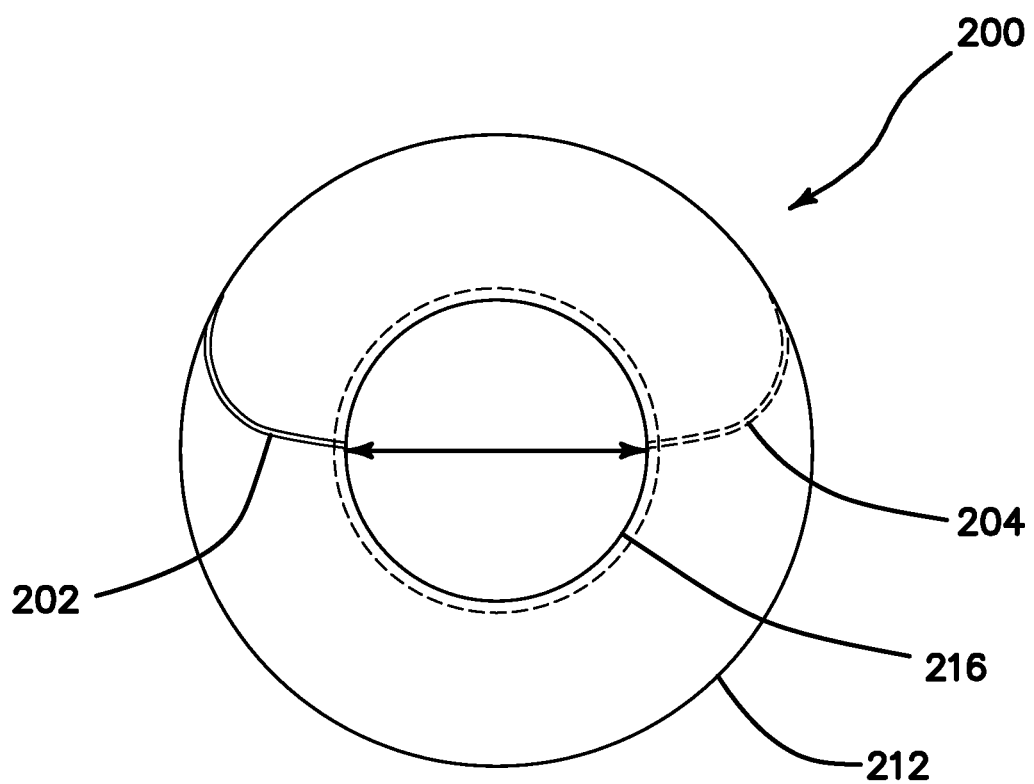
FIG. 78A is a semi-transparent bottom view of a guard according to the present invention.
Figure 76:
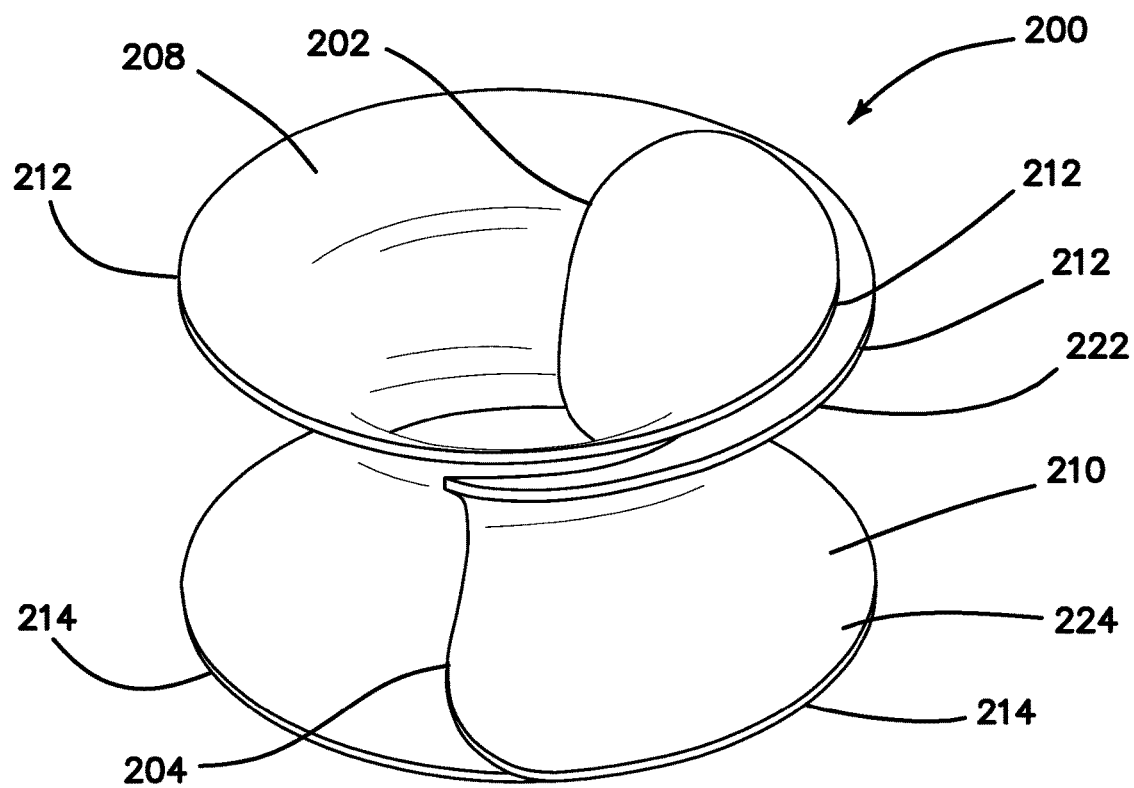
FIG. 76 is a top perspective view of a guard according to the present invention.

The shield 200 guards the tissue surrounding a wound or orifice in the body from sharp objects such as blades and morcellators during surgery. The terms wound, orifice, incision, body opening are used interchangeably in the specification. The wound is generally a minimally invasive incised wound that penetrates through the abdominal wall for laparoscopic or other types of surgery. The shield 200 is a spiral spring in the expanded configuration comprising a ribbon of material formed into a spiral that when inserted into a wound or orifice generates an outward force. The shield 200 also retracts tissue within the wound or orifice providing an opening across the abdominal wall or through an orifice via the central lumen 216 which is generally circular in shape when viewed along the longitudinal axis 218. In one variation of the shield 200, the shield 200 is not curved but made by winding a ribbon of generally flat material into a cylindrical or conical form. In another variation, the curved ribbon shield 200 has a C-shape vertical profile when viewed from the side. The proximal and distal edges also called the top end 212 and the bottom end 214 are larger in diameter than the mid portion of the shield 200 forming a top flange 222 and a bottom flange 224, respectively. This C-shape configuration advantageously cups the tissue at the wound opening and provides anchor-like securement so the shield 200 does not easily dislodge axially from the wound or orifice during normal use. In one variation, the C-shape is parabolic as shown in FIG. 75. The vertex of the parabola is located in a plane perpendicular to the longitudinal axis 218. In another variation, the vertex is between the top end 212 or bottom end 214 and the vertical midline.

Removing the shield 200 from the wound or orifice is accomplished by first disengaging any interlocking features 234 and then gripping the exposed inner corner of the shield 200 and curling it inwardly in the direction of the material's spiral and then pulling it upwardly along the longitudinal axis and out of the wound or orifice. The shield 200 advantageously cork-screws out into a helical form of the expanded configuration. The shield 200 may be pulled out by hand with fingers or with the aid of common surgical instruments such as a clamp or grasper. One variation of the shield 200 is made from cut-resistant, yet pliable plastic material. The material choice and thickness provide the protection features. The shield 200 is pliable enough to be inserted and removed yet rigid enough to remain secured and provide protection.

The shield 200 provides several advantageous features. One important feature provided by the shield 200 is that it protects surrounding tissue from sharp objects such as blades, scalpels and morcellators. The shield 200 also provides protection for a containment bag in which it is placed, thereby, preventing the containment bag from being pierced or cut by sharp objects ensuring that the containment of biological specimens is maintained with reduced risk of leakage. The top flange 222 provides a wide base or cutting-board like protection for tissue and bag surfaces surround the wound or orifice. The top flange 222 overlays, covers and protects tissue margin and/or the containment bag. The middle portion of the shield 200 also shields tissue at the wound or orifice and also protects the containment bag in which it is placed if a containment bag is employed. The middle portion further advantageously allows surgeons to reach deeply with a blade and cut tissue specimen closely at the midline horizontal plane perpendicular to the longitudinal axis or above and even reach distally beyond the midline plane of the shield 200 to cut the tissue specimen as the entire vertical length of the shield 200 provides protection to the surrounding tissue and containment bag.

Another advantage of the shield 200 is that it includes an anchoring feature. The shield 200 is advantageously configured to anchor itself within the wound and orifice via the C-shape design. The anchoring features makes morcellation procedures dramatically easier and faster because it does not require sutures or another hand to hold the shield 200 in place during a normal procedure. A dual-flange (top and bottom 222, 224) is provided for anchoring the shield 200 capturing tissue or the abdominal wall within the concavity of the C-shape. The shield has a distal anchoring member for location within a wound interior and a proximal anchoring member for location externally of a wound opening. A single flange, either a top or bottom, is also within the scope of the present invention. Furthermore, although the top flange 222 and the bottom flange 224 are shown to extend around the entire circumference of the top end 212 and the bottom end 214, respectively, the invention is not so limited and either one or more of the top and bottom flange 222, 224 may extend around at least a portion of the circumference. In such a variation, finger-like extensions may be formed in lieu of a circumferential bottom flange 224. The fingers may easily flex along the longitudinal direction for easy insertion and then spring radially outwardly into an anchoring position under an abdominal wall or other tissue structure or orifice. Also, the top flange 222 may extend radially outwardly a greater distance than the bottom flange 224 as shown in FIG. 79 and vice versa to provide a larger cutting-board-like surface.

Furthermore, the shield 200 is advantageously adapted for easy insertion and removal into and out of a wound or orifice. The shield 200 includes vertically expanded and vertically unexpanded configurations imparting the shield 200 with vertical variability. This makes the shield 200 easy to remove by simply pulling one end of the shield 200 proximally such that the shield 200 unhooks from adjacent and overlapping flanges and/or concavities and corkscrews into an expanded spiral shape from a nested unexpanded configuration. A tab, hole, and/or tether 230 is provided to help with grasping the shield 200 to pull vertically. Furthermore, while in the nested or unexpanded configuration, the shield 200 is movable into a compact configuration by rolling or curling the shield 200 onto itself to form a smaller or tighter circle and more revolutions about itself. The shield 200 advantageously moves from the laterally compact configuration by releasing the compacted configuration whereupon it assumes the normal relaxed configuration which has a relatively greater lateral dimension. A further increased configuration is also provided by shield 200 wherein a lateral or diametrical position larger than the normal or relaxed configuration can be locked in position via a lock 234 formed in the shield 200. The lateral variability of the shield 200 allows the lateral dimension to be reduced for easy insertion into the wound or orifice. Also, from a locked, diametrically-increased position, the shield 200 may be unlocked and reduced in size in the lateral direction by simply unlocking the shield and/or unlocking the shield and then curling the shield upon itself into a tighter configuration making it easy to remove from the wound or orifice.

Also, the shield 200 is advantageously self-deploying. After curling the shield 200 into a compacted lateral configuration, the shield 200 is easily inserted into the wound or orifice and then released whereupon it tends to increase in size due to its spring bias. This spring-back action in the lateral direction helps to automatically seat the shield 200 within the wound or orifice with little effort while at the same time providing protection and retraction to the tissue and/or containment bag keeping both out of the way of sharp objects that may be encountered in a normal procedure.

Furthermore, while in the vertically unexpanded configuration, the shield 200 has a C-shaped or hourglass overall outer shape wherein the proximal end flares radially outwardly from the longitudinal axis and the distal end of the shield 200 flares radially outwardly from the longitudinal axis with the waist being the narrowest lateral dimension along a plane between the proximal end and the distal end of the shield. The flare at the distal end of the shield 200 advantageously provides a ramped surface or funnel that facilitates guiding and moving targeted tissue into and through the shield 200.

The flexibility of the shield 200 allows it to excel at insertion, deployment, removal and being an anchor due to expansion. The flexibility is advantageously balanced against its ability to provide protection to the surrounding tissue and/or containment bag. The protection that the shield 200 provides is sufficient for manual morcellation procedures when performed properly while affording the surgeon freedom to employ personal morcellation techniques. The shield 200 is inserted into the mouth of a containment bag and may also be placed in the neck of a containment bag or in the main receptacle of the containment bag. The containment bag surrounds the shield 200 and is captured between the tissue/orifice and the shield 200. The shield 200 serves to retract the surround tissue as well as the surrounding containment bag material. The shield 200 exerts sufficient force onto the containment bag such that the containment bag is kept in position substantially fixed such that it does not slide into the wound or orifice. A sufficient amount of the proximal end of the bag is located proximal to the shield and overlays the external surface, such as the abdomen, of the patient forming a blanket that helps prevent contamination. The shield 200 is configured to hold the mouth of the containment bag in an accessible, open configuration and receive and support a manual or power morcellator device.

In another variation, the shield 200 is adapted for insertion into the vaginal canal and as such is longer in length as shown. The shield 200 may also include shape-memory parts to assist in deployment. The shield 200 provides for a reliable and safe removal of endogenic samples and is easy to use reducing operating time and costs. The shield 200 in combination with a containment bag aids in reducing the risk of contaminating healthy tissue by possibly malignant cells during the tissue sampling and removal operations.

With reference to FIGS. 54-59, a bag 310 according to the present invention will now be described. The bag 310 includes a single opening or mouth 312. At or near the mouth 312 of the bag, a semi-rigid, compressible plastic ring 314 is connected into the bag 310. The ring 314 can be compressed from a circular or large configuration into an oval or smaller configuration such that the bag 310 can be inserted through the small incision. Once inside the patient, the resilient ring 314 expands to its original uncompressed, larger configuration opening the mouth 312 of the bag 310 along with it. When laid flat inside the patient, the ring 314 clearly defines the opening 312 of the bag 310 which without a ring 314 may be difficult to see under laparoscopic observation. Sometimes the opening 312 to the bag 310 may be difficult to find. The opening 312 must then be oriented inside the patient so that tissue can be clearly placed into it and not placed past the opening 312. In the present invention, the expanded ring 314 when laid on top of the bag 310 ensures that the any tissue placed within the ring 314 will end up inside the bag 310 when the ring 314 is lifted toward the incision. The empty bag 310 lies flat on a flat surface and the ring 314 falls naturally above the bag 310. The resilient ring 314 allows the bag 310 to remain open without assistance inside the abdominal cavity to ease the capture of tissue.

After a tissue specimen is placed inside the ring 314, the ring 314 is pulled up toward the incision. A tether 316 is provided near the mouth 312 of the bag 310 to assist the surgeon in pulling the bag 310 up towards the incision. The tether 316 may have a tag 318 at the proximal end which is retained outside the patient when the bag 310 is placed inside the patient. The tag 318 is also easily found inside the patient. The large tag 318 helps to quickly locate and pull the tether 16 when needed. The tether 316 may also be configured to cinch the bag 310 closed in order to prevent the contents of the bag 310 from spilling out. Alternatively, there may be an additional cinch string connected to the bag 310 and located beneath or above the ring 314 such that the cinch string circumferentially closes the bag. Other ways to close or seal may also be provided such as a press fit or zipper.

When the bag 310 is pulled and located near the incision, the ring 314 is compressed from its expanded configuration to its compressed configuration so that it can be pulled through the small incision. The ring 314 is compressed with a grasper or by hand through the incision opening. After the ring 314 is pulled through the incision, a sufficient amount of the bag 310 is pulled along with it so as to be laid over and cover a portion of the patient's abdomen. Hence, the bag 310 must be pretty large in order to create an apron effect around the incision outside the patient. With the ring 314 and part of the bag 310 outside the patient, the remainder of the bag 310 and tissue specimen remains inside the patient.

The cross-section of the ring 314 may be circular and may have a hollow center to impart flexibility. In one variation, the ring 314 has an elliptical, elongate or oval cross-section. In the variation shown in the figures, the ring 314 has a shape resembling the number eight or having two connected circular cross-sections which result in a small valley 320 between the circles. In general, the cross-section of the ring 314 has a length greater than its width. This elongated cross-section allows the ring 314 to be rolled or flipped over itself by inverting the ring 314 outwardly or inwardly to roll up the bag 310 onto the ring 314 itself. The ring 314 can be rolled in the opposite direction to unfurl the bag 310 from the ring 314. The elongate cross-section of the ring 314 advantageously keeps the bag 310 sidewall rolled-up onto the ring 314. If the cross-section were circular, the ring 314 may more easily roll and, thereby, unravel the rolled-up sidewall of the bag 310. The rolling of the ring 314 about itself draws the bag 310 upwardly and brings the specimen inside the bag 310 closer to the incision opening. The rolling action of the bag 310 reduces the volume of the bag 310 located inside the patient and also creates a nicely-formed and taut apron outside the patient. If the bag 310 is retracted too tightly, the ring 314 may warp. The tissue specimen is then pulled from the bag 310 by morcellating it with a blade or electronic morcellator into a size and shape that can be passed through the small incision and removed from the bag 310. The sidewall 328 of the bag 310 may be rolled up onto itself to form a roll 330 located adjacent to the ring 314 for ease of deployment as shown in FIG. 59. The ring 314 would be squeezed such that the compressed length of the ring 314 is aligned with the length of the roll 330 for easy insertion.

With particular reference to FIGS. 55-56, the ring 314 is a formed from a single elongate piece 322 of plastic formed into a circle or other shape by bonding the free ends together. In another variation, the ring 314 is made of two or more pieces such as two semi-circles that together define a circle of the same radius. The ends are not connected but are retained in a normal curved configuration inside a sleeve at the mouth of the bag 310. The multi-piece ring 314 makes compressing the ring 314 into a smaller configuration easier. A ring 314 is approximately 0.38 inches in height and 0.18 inches wide and approximately 38 inches long. The thickness of the material forming the ring 314 is approximately 0.18 inches.

Figure 57A:
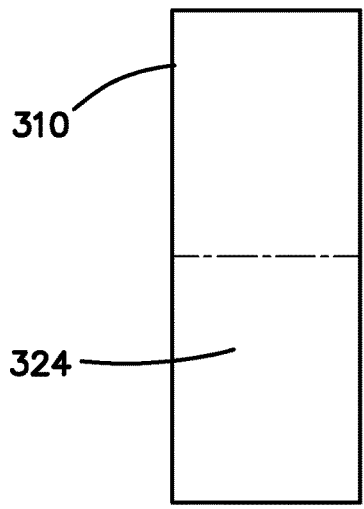
FIG. 57A is a top view of a containment bag sidewall according to the present invention.
Figure 57B:
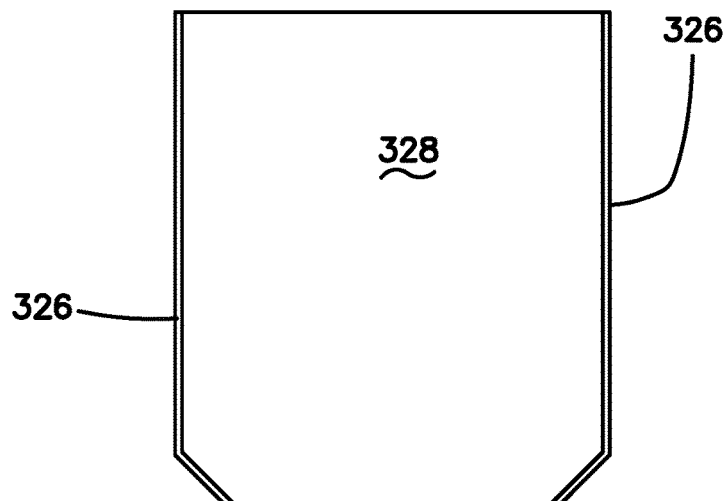
FIG. 57B is a side view of a containment bag sidewall according to the present invention.
Figure 58A:
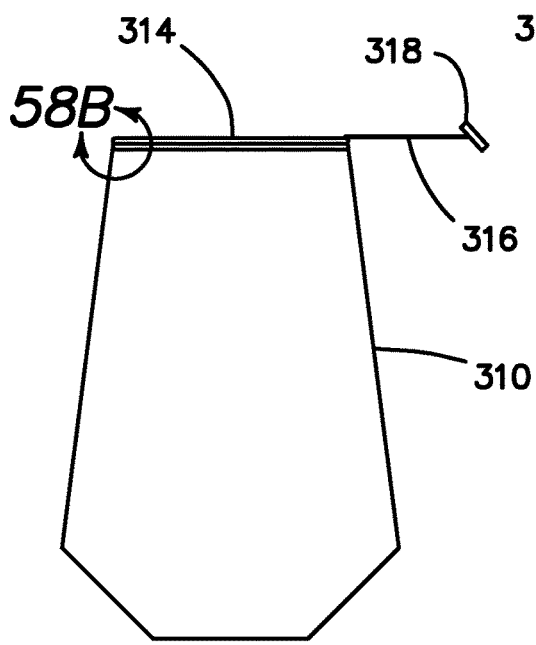
FIG. 58A is a side view of a containment bag according to the present invention.
Figure 58B:
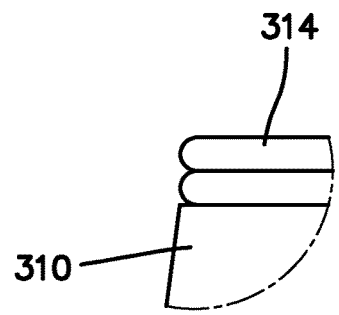
FIG. 58B is a sectional view taken along section 58B of FIG. 58A of a containment bag according to the present invention.

With particular reference to FIGS. 57-59, the bag 310 is formed from a single sheet 324 of material. The sheet 324 of material is folded lengthwise and heat sealed on the sides to form seams 326. The weakest part of any bag 310 is the area around the weld seams 326. As can be seen in FIG. 57, there is no weld seam 326 at the bottom of the bag 310 where forces are most likely to concentrate when removing a specimen which makes the bag 310 have a greater critical strength. Also, the material of the bag 310 is made of 4.2 mil Inzii® film which is clear and allows the surgeon to see through the side of the bag 310 during surgery. Visibility through the bag 310 eliminates the need to puncture the side of the bag 310 to achieve visualization. The film is elastic and gives the bag 310 good retraction. The bag 310 may also be made of U-5746 rip-stop nylon with a polyurethane coating. The polyurethane coating makes the film air tight and heat sealable. The U-5746 is a military grade material that is stronger than the Inzii® film but has less retraction and is opaque. The bag 310 is approximately 16 inches long and 12 inches wide at the mouth 312. The bottom of the bag 310 forms an angle of approximately 45 degrees with the sidewall 328 at a distance of approximately 12.4 inches from the mouth 312. The bag 310 has a thickness of approximately 0.2 inches and at the seams 326, the bag 310 is approximately twice as thick. In another variation, the bag 310 is a double bag having one bag located inside another bag to provide greater resistance to accidental punctures. In another variation, only a bottom portion of the bag 310 is reinforced with a double-walled construction. The bag 310 is leak-proof and prevents viral penetration.

As previously described, a shield may be provided and used in conjunction with the bag 310. The shield that is inserted into the mouth 312 of the containment bag 310 after the bag 310 is placed inside the patient and pulled through the incision. The shield is made of thicker plastic and protects the plastic bag 310 from being inadvertently cut by the blade used by the surgeon to morcellate the target tissue. The shield may also serve as a cutting board against which a surgeon may cut the target tissue if needed. The bag 310 may also be used with a retractor as described above wherein when the bag 310 is pulled through the incision, a retractor is placed inside the mouth 312 of the bag 310 and the tissue and bag 310 at the location of the incision is retracted before a shield is placed inside the retractor and the specimen removed.

Figure 60:
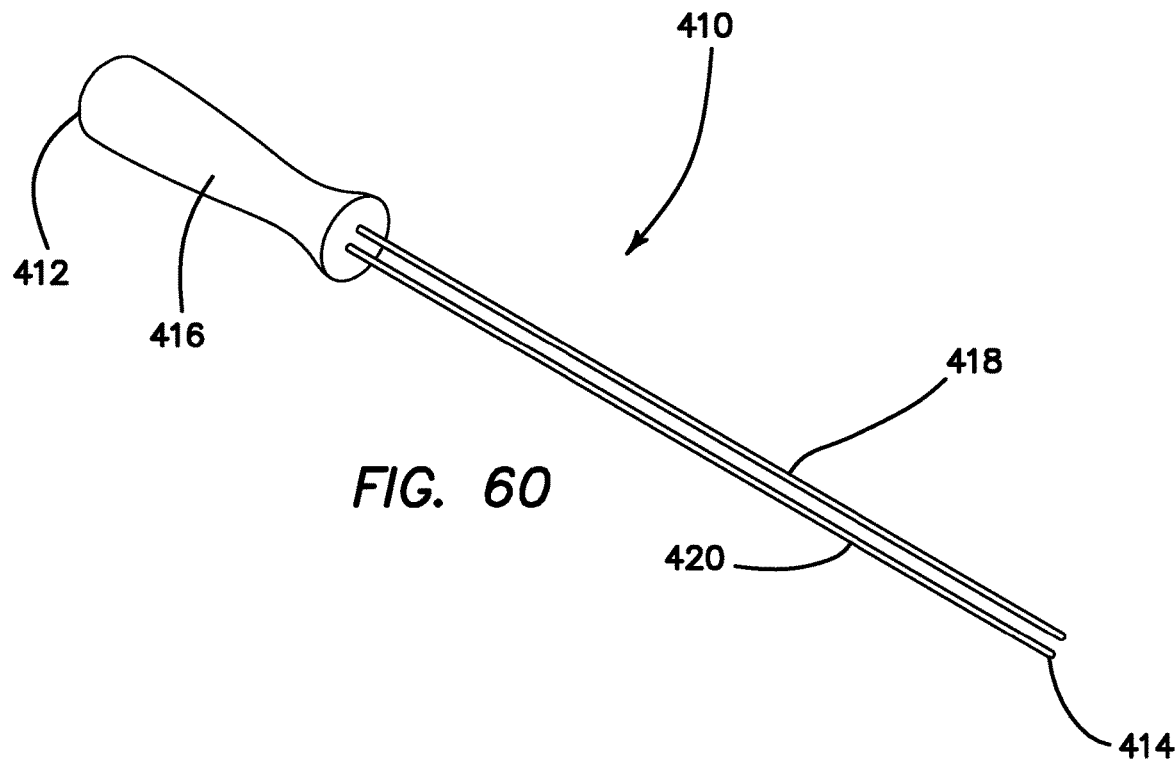
FIG. 60 is a top perspective view of a bag introducer according to the present invention.
Figure 61:
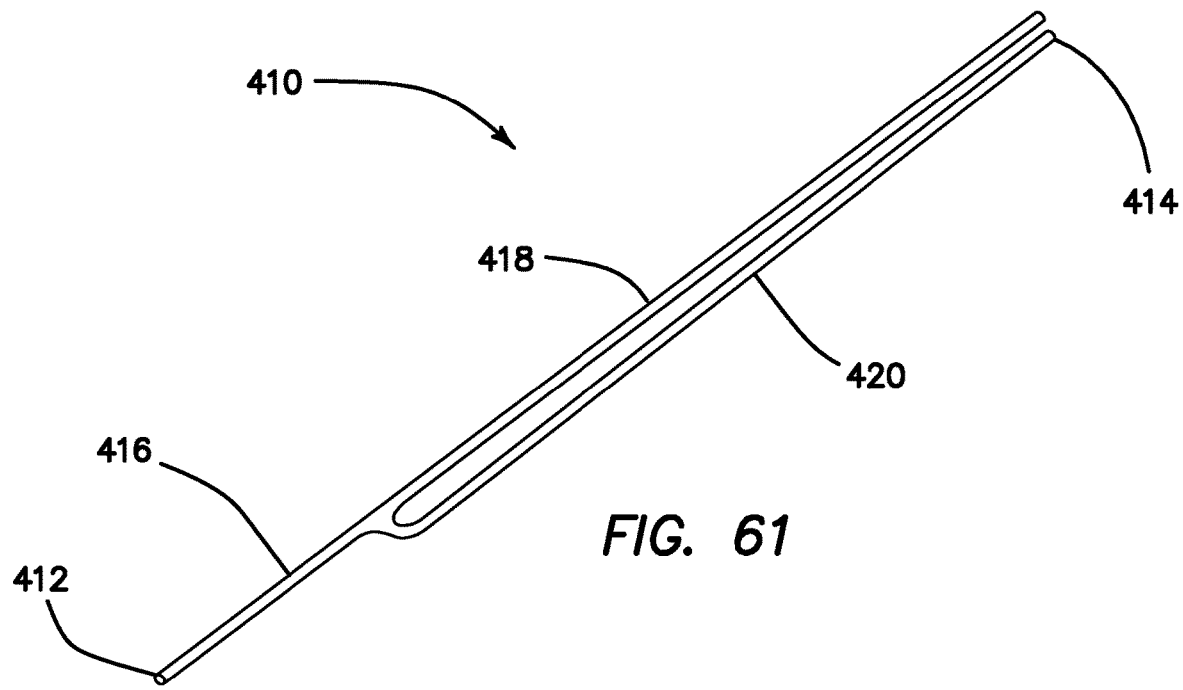
FIG. 61 is a top perspective view of a bag introducer according to the present invention.

With reference to FIGS. 60-63, a bag introducer or fork 410 is used to introduce a containment bag 310 into a body cavity of a patient through a small incision. The introducer 410 facilitates placement of a bag 310 into the surgical field. The fork 410 has a proximal end 412 and distal end 414. A handle 416 is provided at the proximal end 412. A first prong 418 and a second prong 420 extend distally from the handle 416 forming a substantial fork-like configuration. The prongs 418, 420 are of equal length. The prongs 418, 420 may have any suitable cross-section and are spaced apart from each other by a sufficient distance. The prongs 418, 420 are made of stainless steel and are connected to an injection molded plastic or metal handle 416 as shown in FIG. 60. In this design, the steel rods comprising the prongs 418, 420 are inserted into and connected to an injection molded handle 416 which allows for a fork 410 with a small profile but is more expensive to and takes longer to produce. In FIG. 61, the fork 410 is made from a single piece of material wherein both the handle 416 and prongs 418, 420 are injection molded to form a unitary structure. This design is the easiest and least expensive to manufacture at the cost of a larger profile and weaker design.

Figure 62:
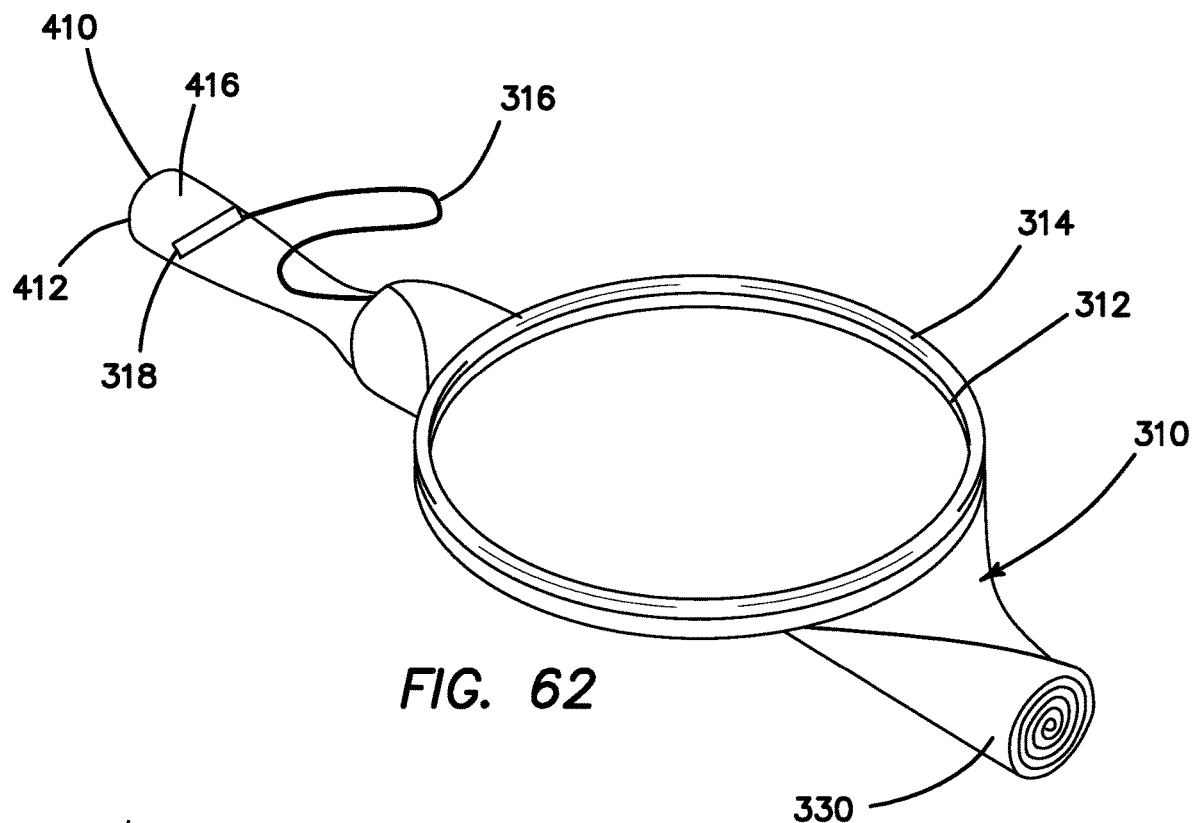
FIG. 62 is a top perspective view of a containment bag and bag introducer is a top perspective view of a bag introducer according to the present invention.
Figure 63:
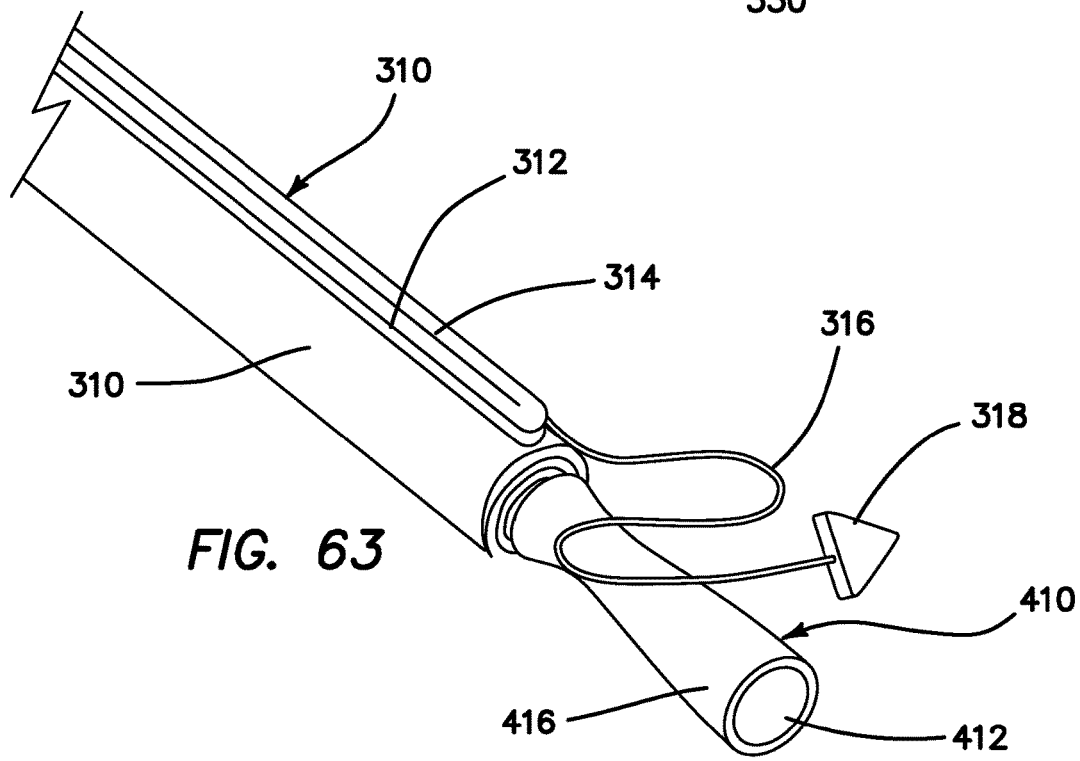
FIG. 63 is a top perspective view of a containment bag and bag introducer is a top perspective view of a bag introducer according to the present invention.

In use, and with particular reference to FIGS. 62-63, the bottom of the containment bag 310 is placed between the prongs 418, 420 with the tether 316 and tag 318 placed near the handle 416. The bottom edge of the bag 310 is folded over the prongs 418, 420 with the prongs extending slightly past the end of the bag 310. Hence, the prongs 418, 420 are slightly longer than the width of the bag 310. The handle 416 is grasped and rotated allowing the bag 310 to roll up evenly into a tubular roll 330 until resistance is met. The bag 310 is reduced to a minimum size for introduction in the incorporeal region. The resilient ring 314 is squeezed and the bag 310 is rolled up until it is taut and located next to the ring 314. Under visualization, the bag 310 and fork 410 combination is inserted through the incision ensuring the opening 312 of the ring 314 is positioned upwards. The bag 310 is inserted until it is approximately three-quarters into the incision. The fork 410 is rotated in the opposite direction to slightly loosen the bag 310. The bag 410 is loosened to reduce the tension on the bag to make it easier for tissue to fall into the bag 310. The fork 410 allows the bag 310 to be easily deployed while controlling how tight of the bag 310 is wound during insertion and the direction of the ring opening 312. If the bag 310 is wound too tightly, then the tissue will not fall easily into the bag 310 when the ring 310 is lifted inside the patient. Rotation of the introducer 410 in the opposite direction before removal of the introducer 410 facilitates ease of tissue insertion into the bag 310.

The fork 410 is separated from the bag 310 by pulling the handle 416 proximally. The remaining quarter section of the bag 310 is pushed into the incision. After the bag 310 is fully deployed in the abdominal cavity, an access port and scope are placed and the cavity is insufflated. The bag 310 is positioned such that the ring 314 lies on top of the bag 310. The access port may be placed in the same incision or in a secondary incision. Under visualization, the tissue to be morcellated and removed from the patient is placed into the bag 310. A lateral access port can be used to visualize and confirm that the tissue is inside the bag 310. The access port is removed and the removal of the bag 310 out of the patient is commenced. A secondary access port need not be removed and may be used to continue observation of the removal and subsequent morcellation. The tag 318 may be resident outside of the patient. It is pulled to draw the bag 310 up toward the incision. If the tag 318 is inside the cavity, visualization through the access port and a grasper may be employed to grab the tag 318. The tether 316 and tag 318 are pulled-up through the incision until part of the ring 314 is through the incision. The ring 314 is pulled until the entire ring 314 is outside of the incision. The bag 310 is retracted by rolling/flipping the ring 314 over itself to roll the bag 310 around the ring 314. This rolling of the ring 314 not only retracts tissue slightly, but also, reduces the volume of the bag 310 inside the patient drawing the tissue inside the patient closer to the surface. The tissue is then morcellated.

Alternatively, a retractor having a central lumen is placed inside the mouth of the bag 310 at the incision and tissue along with the bag 310 is retracted enlarging the opening and then the tissue is morcellated with the bag 310 in place. The retractor having a central lumen is placed inside the mouth of the bag 310 in the location of the incision and a shield as previously described is provided and used in conjunction with the bag 310 and the retractor. The shield is placed inside the central lumen of the retractor. Of course, the shield may be used without the retractor. If a retractor is not used, the shield is placed into the mouth 312 of the bag 310 in the location of the incision. The shield is inserted into the mouth 312 of the containment bag 310 after the bag 310 is placed inside the patient and pulled through the incision. The shield is made of thicker plastic and protects the plastic bag 310 from being inadvertently cut by the blade or other instruments used by the surgeon to morcellate the target tissue. The shield may also serve as a cutting board against which a surgeon may cut the target tissue if needed. The shield itself may also function as a retractor having a first reduced dimension and a second expanded dimension. The second expanded dimension serving to retract tissue.

If a retractor is used inside the bag 310, the retractor advantageously not only retracts the tissue but also retracts part of the bag, keeping the bag out of the way of a morcellating blade and, thereby, protecting the bag from cuts and punctures. A typical retractor includes a top ring and bottom ring with a flexible sidewall connected therebetween. The bottom ring is inserted through the incision and resides inside the patient whereas the top ring of the retractor resides above the patient. The top ring is rolled/flipped over itself like the bag to pull the lower ring of the retractor closer and the sidewall into a taut relation between the rings. The lower ring of the retractor advantageously retracts the portion of the bag 310 inside the patent and away from potential damage arising from punctures and tears from the blade.

The tissue is morcellated in a fashion desired by the surgeon. Generally, a small part of the target tissue is pulled to the outside of the patient while the larger portion of the target tissue remains inside the patient. The surgeon will take a blade and make a circumferential cut of approximately 180 degrees or 360 degrees around the circumference of the protruding tissue without severing the protruding tissue from the remainder of the target tissue. Keeping the protruding tissue intact with the larger piece inside the patient permits the surgeon to continue to grasp the tissue without losing it inside the bag. The surgeon pulls the grasped tissue little-by-little out of the patient making periodic circumferential cuts of any size so that more of the tissue can be pulled out until the entire piece of target tissue is removed. The result is a single elongated piece of removed target tissue instead of multiple small pieces. If not removed in one piece, the target tissue is removed in fewer pieces and in a more controlled manner. The bag 310 may be further retracted in between morcellations to bring the specimen closer to the surface. Once the tissue remaining in the bag 310 is small enough to easily fit through the incision, the bag 310 is completely removed.

Figure 64:
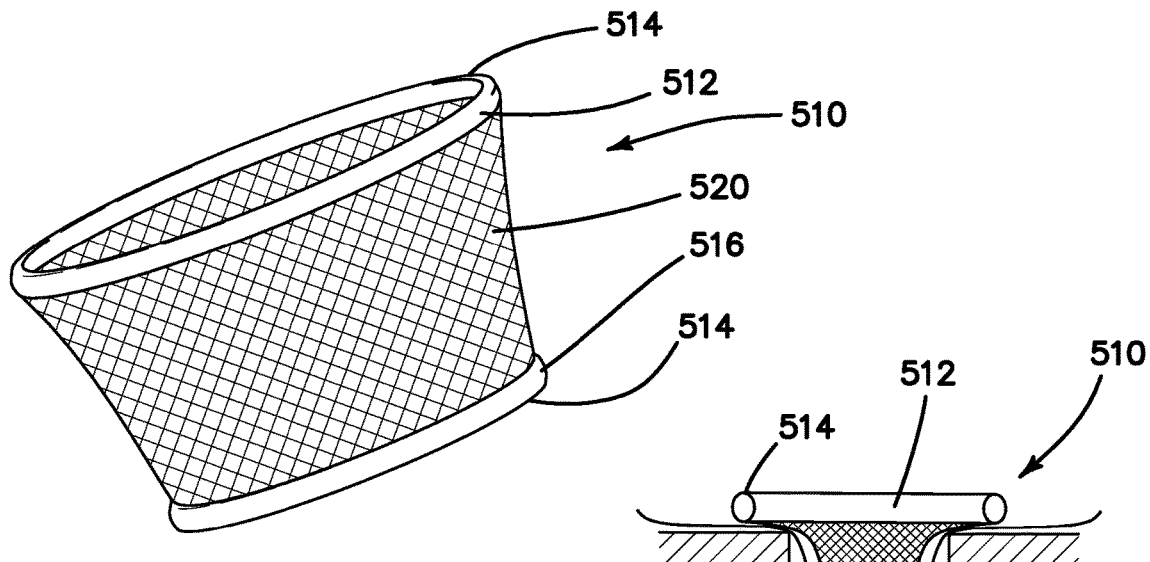
FIG. 64 is a top perspective view of a guard is a top perspective view of a bag introducer according to the present invention.
Figure 65:
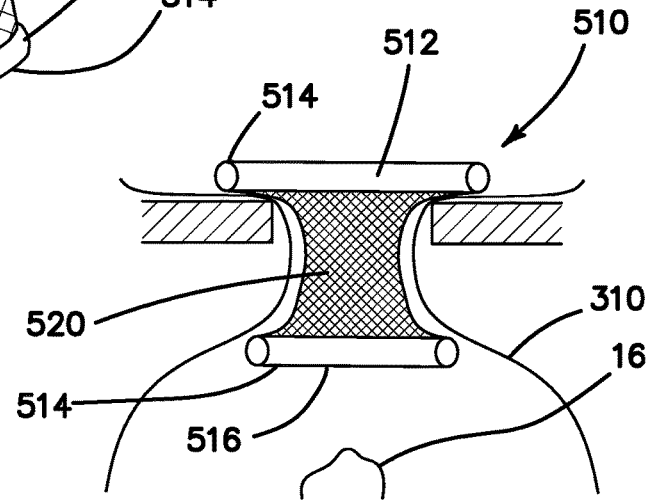
FIG. 65 is a cross-sectional side view of a tissue specimen inside a containment bag and a guard placed across a body wall according to the present invention.

Turning now to FIGS. 64-65, there is shown another shield 510 according to the present invention. The shield 510 comprises a first ring 512 at the proximal end 514 and a second ring 516 at a distal end 518. The rings 512, 516 are substantially parallel to each other and are interconnected by a sidewall 520. The sidewall 520 is a fabric, sheath material that can be made of flexible textile or polymer. The material can be Kevlar®, Dyneema®, rip-stop nylon, or polymer blend material. The sidewall 520 is heat sealed or bonded to the rings 512, 516. The first and second rings 512, 516 are semi-rigid and compressible between a normal, high-profile, large configuration and a compressed, low-profile, elongate configuration. The rings 512, 516 are generally circular in their normal configuration or can be elliptical. The rings 512, 516 can be compressed from a circular or large configuration into an oval or smaller configuration such that the shield 510 can be inserted into a small incision, in particular, into the mouth of a containment bag to protect it. In one variation, only the second ring 516 is compressible for insertion into an incision and the first ring 512 is rigid such that the first ring 51 is intended for residency outside or proximally relative to inside the patient. The rigid proximal first ring 512 may be larger and wider in order to serve as a larger shield or cutting board for morcellation. The second or distally placed ring 516 is of flexible suitable for compression and easy insertion into a bag and may be slightly smaller in diameter than the first ring 512.

Figure 55B:
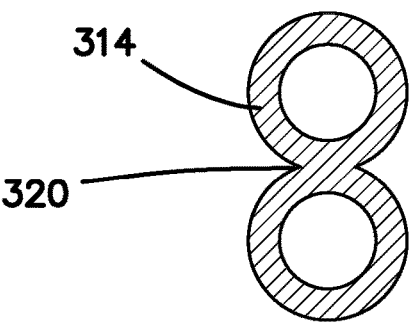
FIG. 55B is a cross-sectional view taken along line 55B-55B of FIG. 55A of a ring of a containment bag according to the present invention.
Figure 55A:
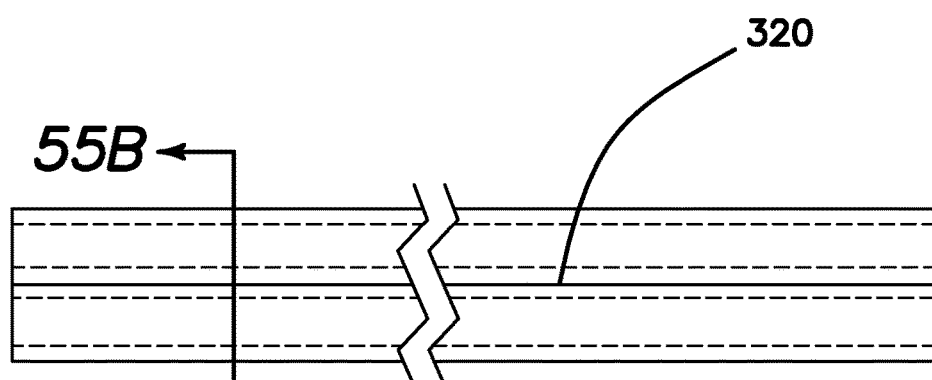
FIG. 55A is a side view of a ring of a containment bag according to the present invention.

The cross-section of one or more of the rings 512, 516 may be circular. The rings 512, 516 have a hollow center to impart flexibility. In one variation, the rings 512, 516 have an elliptical, elongate or oval cross-section with a hollow center. In another variation, the rings 512, 516 have a shape resembling the number eight having two connected circular cross-sections which result in a small valley between the circles as shown in FIGS. 55A-55B. In general, the cross-section of the rings 512, 516 has a length greater than its width. This elongated cross-section allows each ring 512, 516 to be rolled or flipped over itself by inverting the ring 512, 516 outwardly or inwardly to roll up the sidewall 520 onto the ring 512, 516. In one variation, only the first ring or proximal ring 512 is configured for rolling up the sidewall 520. In another variation, both of the rings 512, 516 are configured for rolling making the shield 510 bi-directional, that is either the first ring 512 or the second ring 516 can be placed proximally relative to the incision/orifice and rolled. The shield 510 is inserted by compressing one or more of the rings 512, 516. While both rings 512, 516 may be compressed into the low-profile configuration for easy insertion through the incision, generally only the distal ring needs to be compressed with the proximal ring residing outside of the patient not needing to be compressed. Also, only the proximal ring need be configured for rolling the sidewall 520 as the distal ring resides inside the patient. The one or more rings 512, 516 configured for rolling can be rolled in the opposite direction to increase the length of the sidewall 520. When one of the rings 512, 516 is rolled, the length of the sidewall 520 is taken up onto the ring shortening the length of the shield 510. The elongate cross-section of the ring advantageously keeps the sidewall 520 rolled-up onto the ring. If the cross-section were circular, the ring may more easily roll in-situ and, thereby, unravel the rolled-up sidewall 520. The rolling of the ring about itself draws the opposite ring upwardly and closer to it.

The rings 512, 516 are formed from a single elongate piece of plastic formed into a circle or other shape by bonding the free ends together. In another variation, the rings 512, 516 are made of two or more pieces such as two semi-circles that together define a circle for each ring. The ends are not connected but are retained in a normal curved configuration. A multi-piece ring makes compressing the ring into a smaller low-profile configuration easier. A ring is approximately 0.38 inches in height and 0.18 inches wide and approximately 38 inches long. The thickness of the material forming the ring 314 is approximately 0.18 inches. FIG. 65 illustrates the shield 510 placed inside a bag 310 and retracted by rolling the proximally located first ring 512 until the proximal rigid ring 512 is flush with the outer surface or abdomen of the patient. The cut resistant material of the rings 512, 516 as well as the sidewall 520 protects the bag 310. Retraction by rolling the proximal first ring 512 advantageously causes the incision to stretch. The resulting larger incision allows for greater ease of manual morcellation. In another variation, the shield 510 is not configured to permit rolling of one or more of the rings 512, 516 to reduce the length of the shield 510 and the sidewall of the shield 510 is made of protection material.

Figure 66:
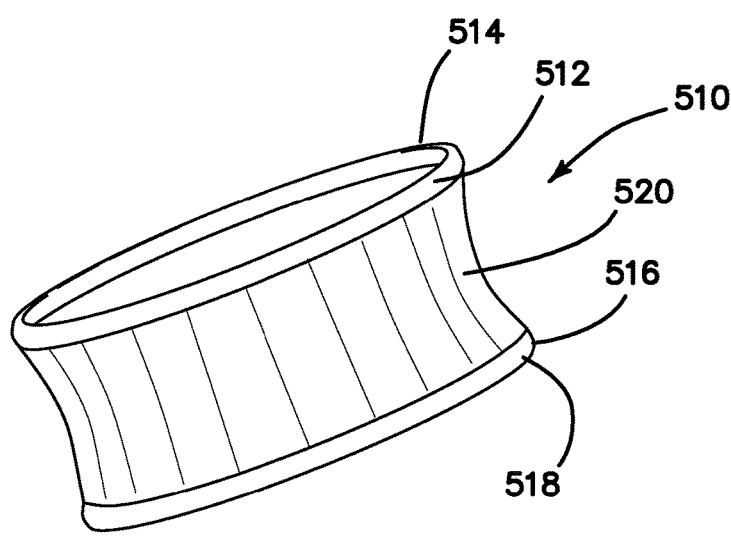
FIG. 66 is a top perspective view of a guard according to the present invention.
Figure 67:
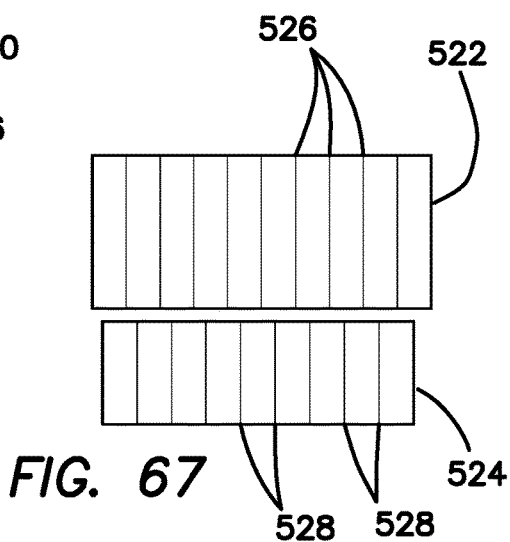
FIG. 67 is a side view of a two sidewall components of a guard according to the present invention.

Turning now to FIGS. 66-67, there is shown another shield 510 according to the present invention. This shield 510 is similar to the shield of FIGS. 64-65 in that it comprises a first ring 512 at the proximal end 514 and a second ring 516 at the distal end 518 interconnected by a flexible sidewall 520. The sidewall 520 of the variation depicted in FIGS. 66-67 comprises a first layer 522 and a second layer 524 shown separated and laid flat in FIG. 67. The first layer 522 includes a plurality of vertical slits 526 and the second layer 524 includes a plurality of vertical slits 528. The first layer 522 is placed adjacent or in juxtaposition to the second layer 524 to form the lantern-like sidewall 520 such that the slits 526 of the first layer 522 and the slits 528 of the second layer 524 are offset such that they do not meet to create a break through the shield 510. Instead, the overlapping layers 522, 524 with their offset slits 526, 2528 create a flexible yet strong sidewall 520 that resists penetration. Each of the first layer 522 and second layer 524 is a flexible or semi-flexible sheath that bends easily but is cut resistant. The layers 522, 524 are flexible enough to ease insertion yet capable of retraction when placed inside the bag in the incision with or without flipping of the rings 512, 516 as described above. In another variation, the slits 526, 528 are not perpendicular to the top and bottom edges of the layers 522, 524 as shown in FIG. 67. Instead, slits 526, 528 are angled with respect to the top and bottom edges. The overall height of the shield 510 is approximately 0.5-2.0 inches and the sidewall 520 is made of protection material.

Figure 68:
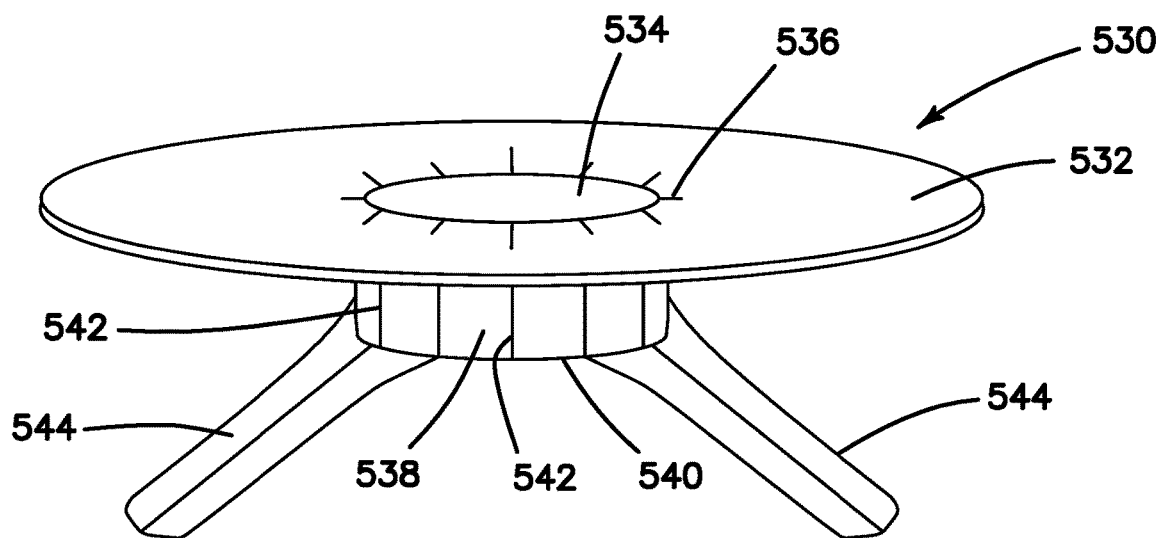
FIG. 68 is a top perspective view of a guard according to the present invention.
Figure 69:
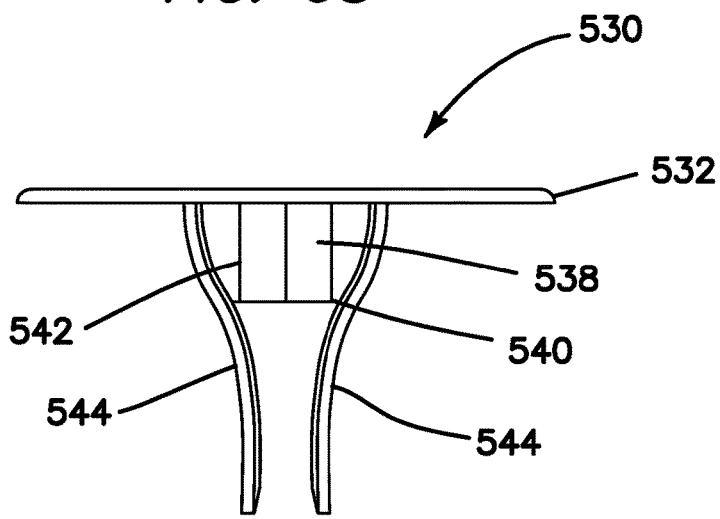
FIG. 69 is a side view of a guard according to the present invention.
Figure 70:
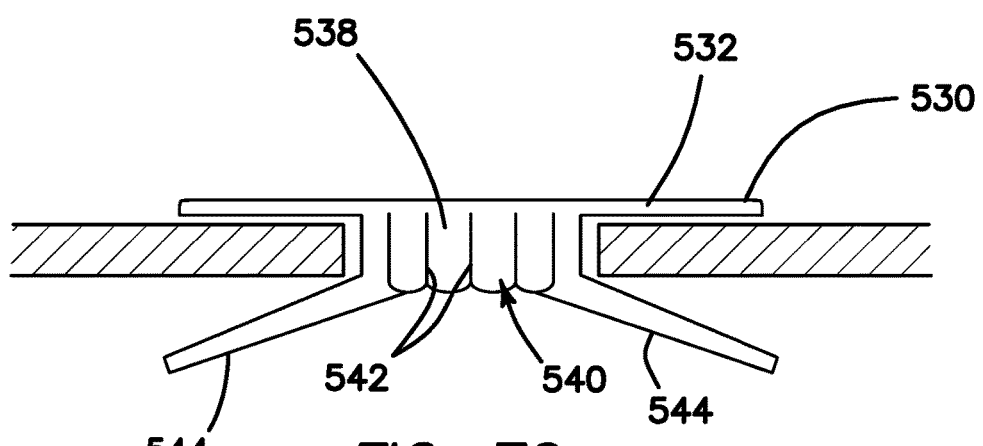
FIG. 70 is a side view of a guard in a body opening according to the present invention.

Turning now to FIGS. 68-70, there is shown another variation of a shield 530 according to the present invention. The shield 530 is made of flexible or semi-rigid plastic. The shield 530 includes a flange 532 is substantially planar and includes an opening 534 in the middle. From the opening 534, a plurality of slits 536 extends from the circumference of the opening 534 outwardly into the flange 532 to increase the flexibility of the corner intersection. The flange 532 is sized and configured to fit inside a retractor if one is used. In particular, the flange 532 snaps under the top ring of a retractor to help hold the shield 530 in position.

The flange 532 is connected to a central tubular section 538. The tubular section 538 includes a central lumen that extends between the opening 534 at the proximal end and extends to an opening 540 at the distal end. The tubular section 538 may also include a plurality of slits 542 that extend upwardly from the distal opening 540. The shield 530 further includes two fingers, or elongate extensions 544, extending downwardly from the tubular section 538 at an oblique angle defining a first configuration for the fingers 544. The fingers 544 include a second configuration that is a reduced or compressed configuration as shown in FIG. 69 in which the fingers 544 are pressed together or folded toward the longitudinal axis to assume a lateral dimension that is the same size or smaller than the lateral dimension of the central tubular section 538. The reduced configuration makes it easy to insert the shield 530 into an incision or orifice. When inserted past the abdominal wall, as shown in FIG. 70, the fingers 544 are configured to advantageously spring back to the first configuration in which the fingers 544 spread outwardly at an angle. In this first configuration, inside the incision, the fingers 544 advantageously retract not only tissue, but also, the bag (not shown) into which it is inserted. The slits 542 impart further flexibility to the distal end of the central portion 538 allowing it to assume a narrower configuration when placed into the incision and then also snap back to its normal configuration which aids in the retraction of the bag and tissue. The height of the flange 532 and the central portion 538 is approximately 0.5-2.0 inches and the shield 530 is made of HDPE, LDPE, HYTREL®, or other suitable polymer or metal. Also, the shield 530 may include more than two fingers 544.

Turning now to FIGS. 87-90, there is shown a morcellation system 600. The morcellation system 600 is device that allows for the bulk removal of body tissue or organs through a limited surgical opening in a safe way. The morcellation system 600 is substantially a closed system that prevents contamination of surrounding tissue with potentially cancerous cells resident in the target tissue during morcellation and extraction procedures. The morcellation system 600 includes a morcellator 602, a containment bag (not shown), a tenaculum 606 and a shield 608.

The containment bag may be any of the bag embodiments described herein. Generally, the containment bag includes a polymer pouch having a mouth or opening that is attached to a ring such that the ring encompasses the mouth opening. The ring is flexible and configured to be biased in an open configuration such that the mouth of the bag is held open by the ring to facilitate insertion of a specimen into the bag. The ring is flexible such that it can be compressed into a low-profile state making it easily insertable into a wound or orifice. The ring maintains an opening and allows the bag to be retracted by rolling the ring about itself to wrap the sidewall of the bag around the ring. A tether is attached to the ring or proximal end of the bag. The tether includes an attached tag for grasping with a surgical instrument.

The morcellation system 600 further includes a morcellator 602. The morcellator 602 is a power morcellator. The morcellator 602 includes a cutting ring or annular blade 610 having a sharp distal end adapted to sever tissue. The annular blade 610 is mounted on a hollow cylinder 612. The cylinder 612 is connected to a pneumatic or electric motor (not shown) via gears and configured to rotate about the longitudinal axis. The morcellator 602 includes an inner cylinder 614 having a flared or funnel-like proximal end that is connected to the morcellator housing 616. The distal end 620 of the inner cylinder 614 extends to a location proximal to the annular blade 610. The inner cylinder 614 defines a working channel or central lumen 618 of the morcellator 602. The inner cylinder 614 prevents tissue that is pulled into the central lumen 618 from spinning within the morcellator 602. The morcellator 602 further includes an outer cylinder 622. The outer cylinder 622 coaxially encompasses the cutting cylinder 612. The outer cylinder 622 has a proximal end that connects to or forms part of the housing 616. The distal end 624 of the outer cylinder extends to a location proximal to the distal end of the blade 610. The outer cylinder 622 includes an extension 626 at the distal end 624 of the outer cylinder 622. The extension 626 extends slightly beyond the distal end of the blade 610. The extension 626 prevents coring of the specimen that is morcellated.

The morcellation system 600 further includes a shield 608. The shield 608 can be any of the shields 608 described herein and, in one variation, of the like described with respect to FIGS. 51-53 and 71-86. The shield 608 has a general shape of a spiral when in a vertically expanded configuration. The shield 608 is collapsible into a low-profile, unexpanded configuration. The shield 608 can be moved from the expanded configuration to the unexpanded configuration and vice versa repeatedly as needed. The shield 608 is a band of flexible plastic having the form of a spiral in an expanded configuration. The shield 608 may also be made of thin flexible metal or other suitable material that prevents sharps from penetrating the shield 608. The band extends between a first end and a second end and a top or proximal end 628 and a bottom or distal end 630. The distance between the proximal end 628 and the distal end 630 is approximately the overall length 638 of the shield 608 while in the unexpanded or low-profile configuration. The shield 608 has an inner surface 632 and an outer surface 634 interconnected by a proximal end 628 and the distal end 634 and by the first end and the second end. The outer surface 634 is concave and the inner surface 632 forms a conforming surface that is convex when viewed from within the shield 608. The outer surface 634 is substantially parallel to the inner surface 632. The shield 608 defines a central lumen 636. When in the low-profile, unexpanded configuration, the shield 608 is capable of being reduced laterally in size to have a relatively smaller lateral dimension. As described above, the shield 608 includes a relaxed normal position having a first lateral or diametrical dimension while in the low-profile, unexpanded configuration. The shield 608 also includes a reduced configuration while in the low-profile unexpanded configuration having a second lateral or diametrical dimension. The second lateral or diametrical dimension is less than the first lateral or diametrical dimension. The reduced configuration when in the unexpanded configuration is achieved by curling the shield 608 onto itself into a tighter and smaller configuration. This curling action reduces the size of the central lumen 636. This reduced configuration is held fixed by hand or by a lock. Insertion of the shield 608 into a small incision or orifice is greatly facilitated by curling the shield 608 onto itself into a reduced configuration. When inserted into the incision or orifice, the shield 608 is then released and allowed to unwind from a tight curl toward the relaxed, normal position having a larger lateral dimension. However, forces from surrounding tissue may prevent the shield 608 from reaching the first lateral or diametrical dimension and, therefore, the shield 608 may reach a dimension that is equal to the second lateral dimension or equal to the first lateral dimension or have a dimension anywhere between the first lateral dimension and second lateral dimension. Furthermore, the shield 608 may be uncurled into an enlarged configuration having a third lateral or diametrical dimension. The third lateral or diametrical dimension is larger than the first lateral or diametrical dimension. The enlarged configuration may be locked in position with the shield 608 by way of any of the locks described herein that fix the position and the lateral or diametrical dimension of the shield 608. This enlarged configuration may serve to retract tissue and enlarge the opening of the orifice or wound. The reduced configuration as well as the relaxed normal configuration and any position between the reduced configuration to the enlarged configuration may serve to retract tissue and hold the wound and orifice open while providing a working channel through the central lumen 636.

Figure 87:
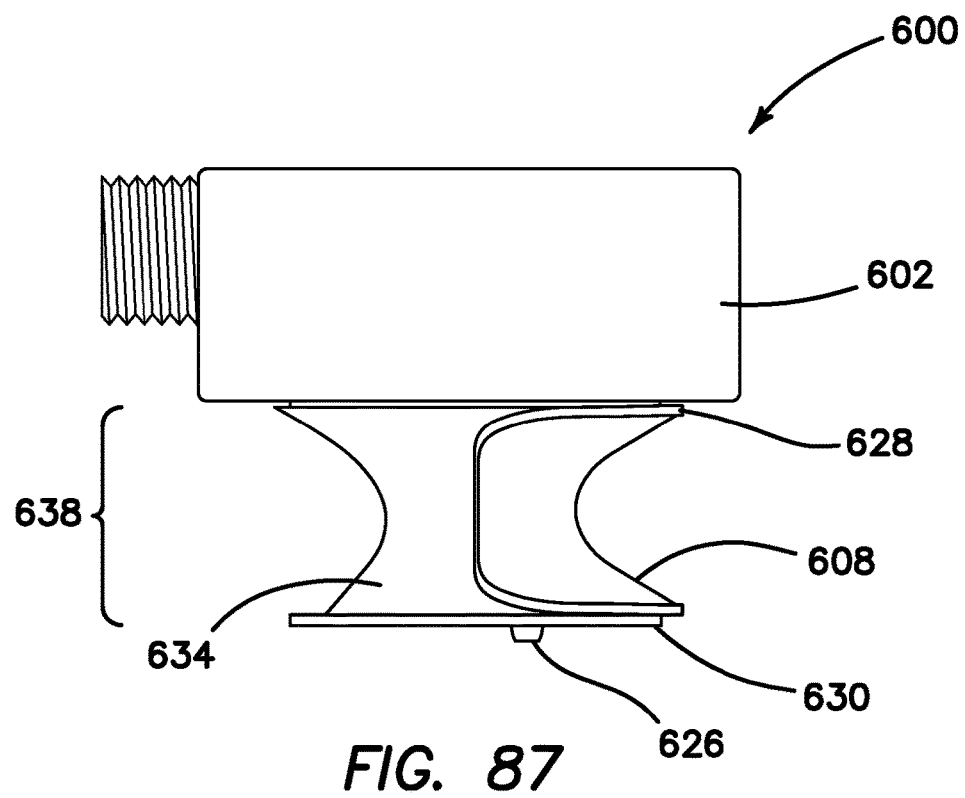
FIG. 87 is a side view of a morcellator and guard according to the present invention.
Figure 88:
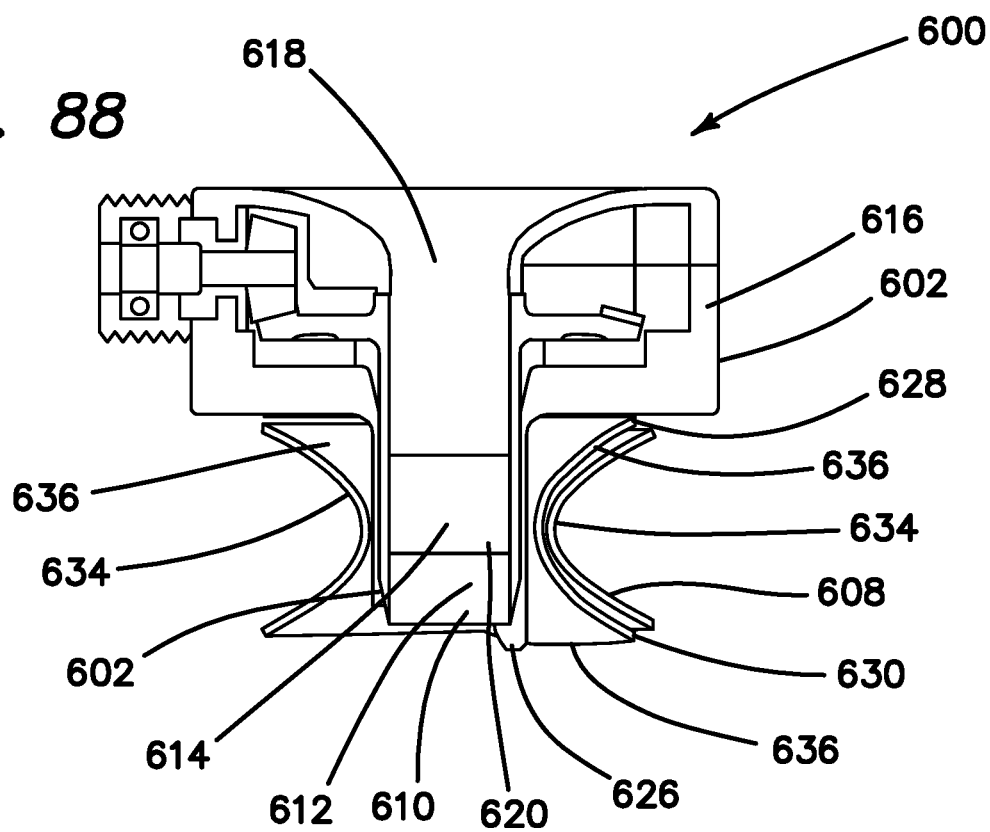
FIG. 88 is a cross-sectional side view of a morcellator and guard according to the present invention.

With particular reference to FIGS. 87 and 88, the morcellator 602 is shown inserted into the central lumen 636 of the shield 608. The distal end of the morcellator housing 616 abuts the proximal end 628 of the shield 608. The length 640 of the morcellator 602 that extends downwardly from the housing 616 and includes the blade cylinder 612, the inner cylinder 614 and the outer cylinder 622 is approximately equal to the length 638 of the shield 608. In one variation, the length 638 of the shield 608 is shorter than the extension 626 that protrudes from the outer cylinder 622. FIG. 87 illustrates the extension 626 extending beyond the length of the shield 608. In such a variation, the distal end of the shield 608 is just proximal to the extension 626. In another variation, the length 638 of the shield 608 is equal to the distal end of the annular blade 610. In another variation, the length 638 of the shield 608 is extends slightly distally beyond the blade 610. In another variation, the length 638 of the shield 608 is distal to the extension 626. The length 638 of the shield 608 is adapted to encompass the depending portion of the morcellator 602, in particular, the blade 610. By encompassing the blade 610, the shield 608 and guards the blade 610 from inadvertent contact with the surrounding tissue and containment bag.

In use, a tissue containment bag is placed through a small incision in the abdomen or small orifice or opening in the body. This is accomplished by compressing the flexible ring of the bag into a low-profile configuration and inserting the bag through a small incision/opening. The flexible ring is allowed to spring open inside the body cavity and expand the mouth portion of the bag making it easy to place a severed piece of target tissue into the bag. The targeted tissue is placed into the bag while the bag is inside the abdominal body cavity. A retractor may be employed and placed inside the incision. The tether on the bag is then used to pull the ring of the bag through the incision. The ring on the bag is rolled over itself to roll the bag sidewall around the ring reducing the length and size of the bag and, thereby, to draw the specimen inside the bag closer to the incision/opening. The specimen inside the bag is visualized with the naked eye near the mouth of the bag. The shield 608 is rotated to minimize its size while outside the patient by rolling or curling the shield 608 onto itself into a tighter form. While in the reduced configuration, the shield 608 is placed into the bag within the incision/opening and allowed to expand on its own or is enlarged diametrically to maximize the incision opening by reversing the rotation of the shield 608. The enlarged position may be fixed with a lock of the type described herein. The shield 608 is uncurled into a larger dimension. The C-shaped outer surface 634 of the shield 608 anchors nicely within the incision such that the abdominal wall is seated within the concavity of the "C". A tenaculum 606 is advanced through the central lumen 618 of the morcellator 602 and is used to grasp the targeted tissue during visualization of the targeted tissue with the naked eye. Once the tissue is properly grasped, it is held by the tenaculum 606 and the morcellator 602 is moved or slid down the length of the tenaculum 606 such that the depending portion of the morcellator 602 including the blade cylinder 612, inner cylinder 614 and outer cylinder 622, is passed into the central lumen 636 of the shield 608 until the distal end of the morcellator housing 616 abuts the proximal end 628 of the shield 608. The tenaculum 606 may be pulled proximally such that the specimen comes into contact with the blade 610 of the morcellator 602. The morcellator 602 is activated to rotate the blade cylinder 612 at a high speed. The tenaculum is withdrawn in the proximal direction while still grasping the specimen. The tenaculum is used to pull the grasped tissue into the cutting blade of the morcellator 602. The extension 626 on the outer cylinder 622 prevents the full circumference of the blade 610 from cutting through tissue at the same time. This prevents coring and allows the blade 610 to migrate along the specimen yielding a greater portion of the specimen that is extracted in one piece. After all of the tissue has been removed or reduced to pieces having a size that may fit through the incision, the shield 608 and bag are removed. The shield 608 advantageously protects and retracts the adjacent tissue at the incision and guards against adjacent portions of the containment bag from contacting the cutting blade 610 accidentally. Also, the present invention avoids making secondary openings made in the containment bag in order to insert a scope and visualize the morcellation procedure. The secondary openings which may compromise the closed containment system are advantageously avoided by this morcellation system 600. Morcellation within a body cavity may spread potentially harmful fragments of the specimen being morcellated. As such, morcellation within a closed system is desired. Placing the specimen in a containment bag creates a closed system when the opening of the bag is brought to the surface through an incision, thereby, isolating the specimen inside the bag and from coming into contact with tissue in the body cavity. Previous solutions for visualization have necessitated creating another opening the bag to place a laparoscope through the opening, thereby, no longer maintaining a closed system. Alternatively, a scope may be placed through the same incision as the morcellator, however, this results in poor visibility and triangulation needed for optimum viewing. The shield 608 advantageously permits a cutting mechanism including a power morcellator to be used within a closed system while preventing a potential breach to a contained system. The morcellation system 600 allows for visibility of the specimen without a laparoscope by bringing the specimen to the surface when the bag is retracted. The morcellation system 600 maintains and ensures a closed system throughout the morcellation procedure by mitigating damage to the tissue containment bag through the use of the shield 608 with a corresponding short morcellator. The shield 608 length is approximately equal to the length of the protruding portion of the morcellator 602. The shield 608 surrounds the blade 610 and lies between the bag and the morcellator 602. The shield 608 opens and retains the incision opening so that the specimen may be easily visualized and removed. The shield 608 protects the bag and the tissue at the incision site from being damaged by the cutting blade 610 or tenaculum 606. The outer cylinder 622 of the morcellator is encompassed by the shield 608 which prevents incidental contact of the blade 610 with the containment bag that would possibly result in a breach of the closed system. The shield 608 forms a protective cage around blade ensuring safe morcellation. In one variation, the length 638 of the shield 608 in the unexpanded configuration is approximately one inch and the length 640 of the morcellator cylinder is also approximately one inch.

Figure 89:
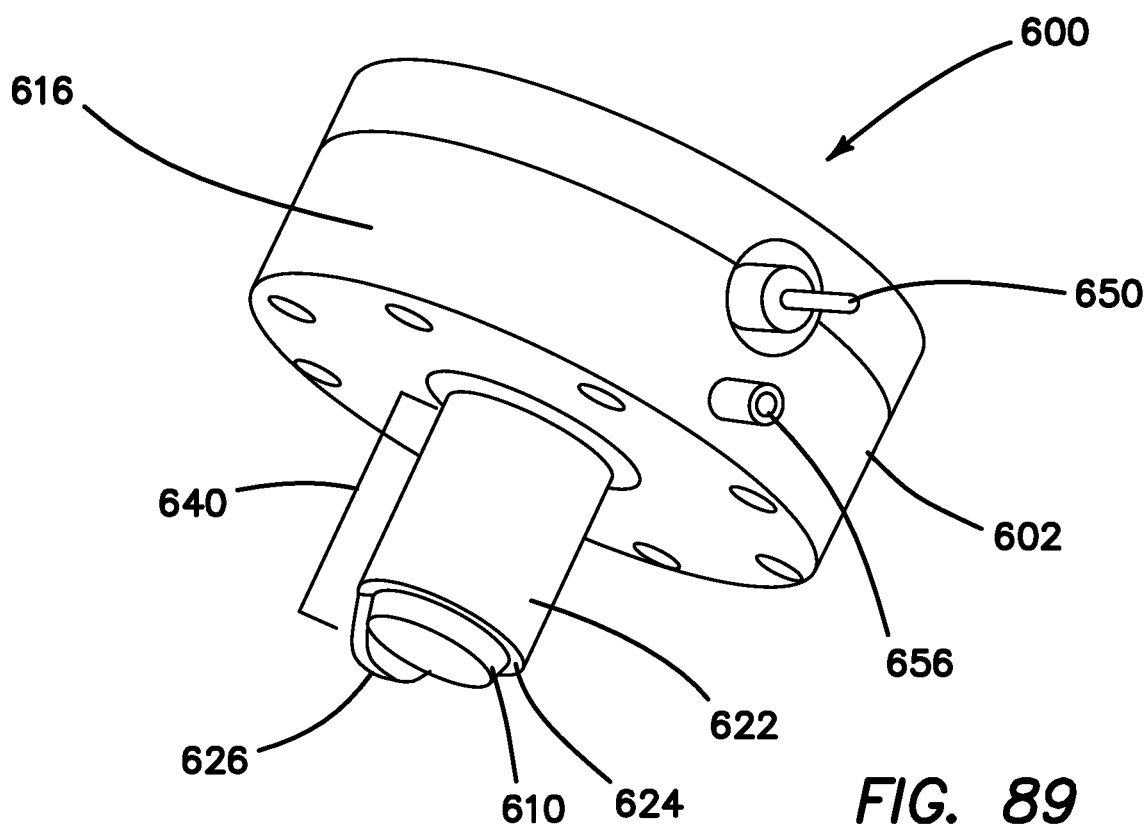
FIG. 89 is a bottom perspective view of a morcellator according to the present invention.
Figure 90:
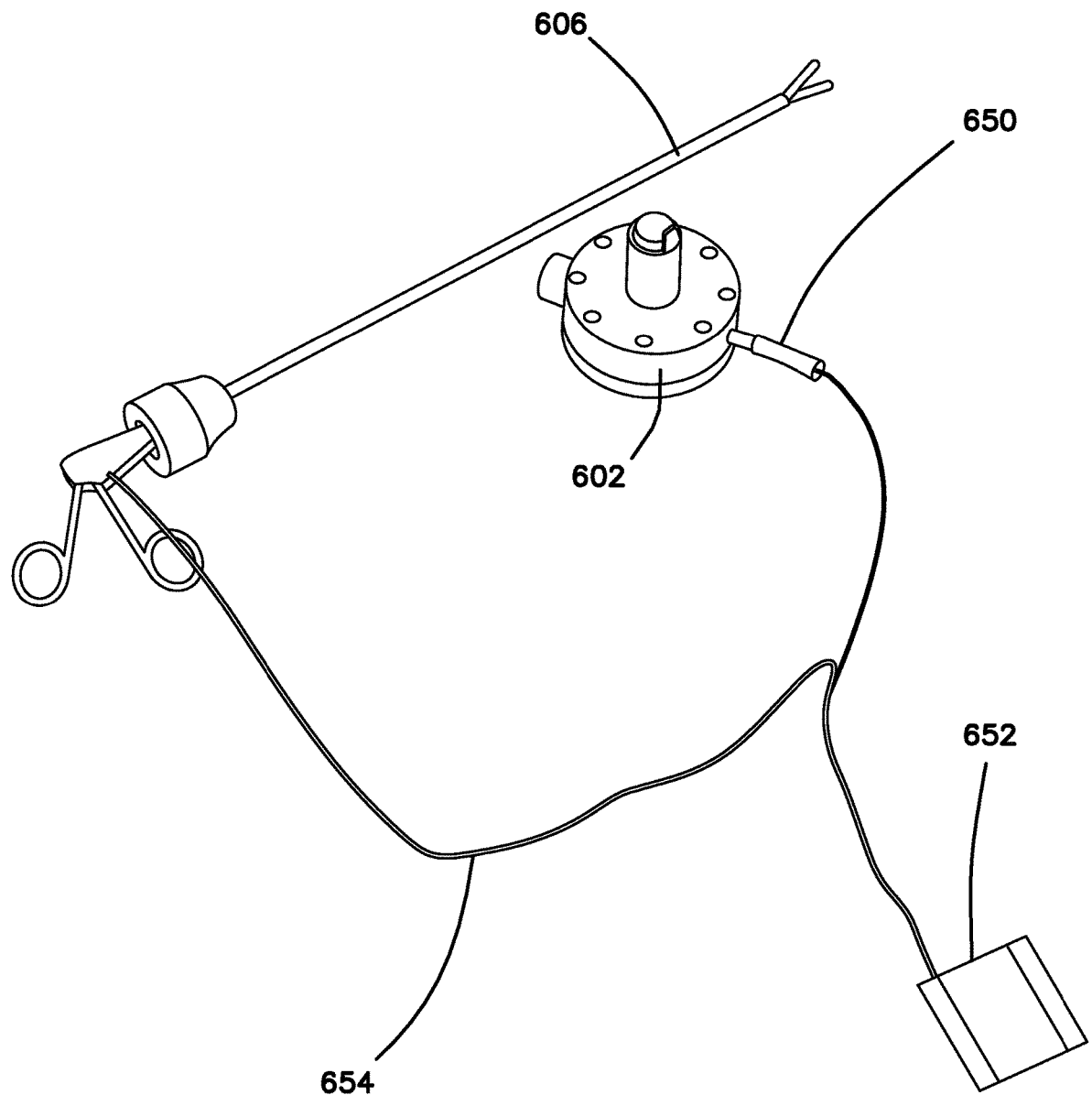
FIG. 90 is a top perspective view of an energy morcellator and graspers according to the present invention.
Figure 91:
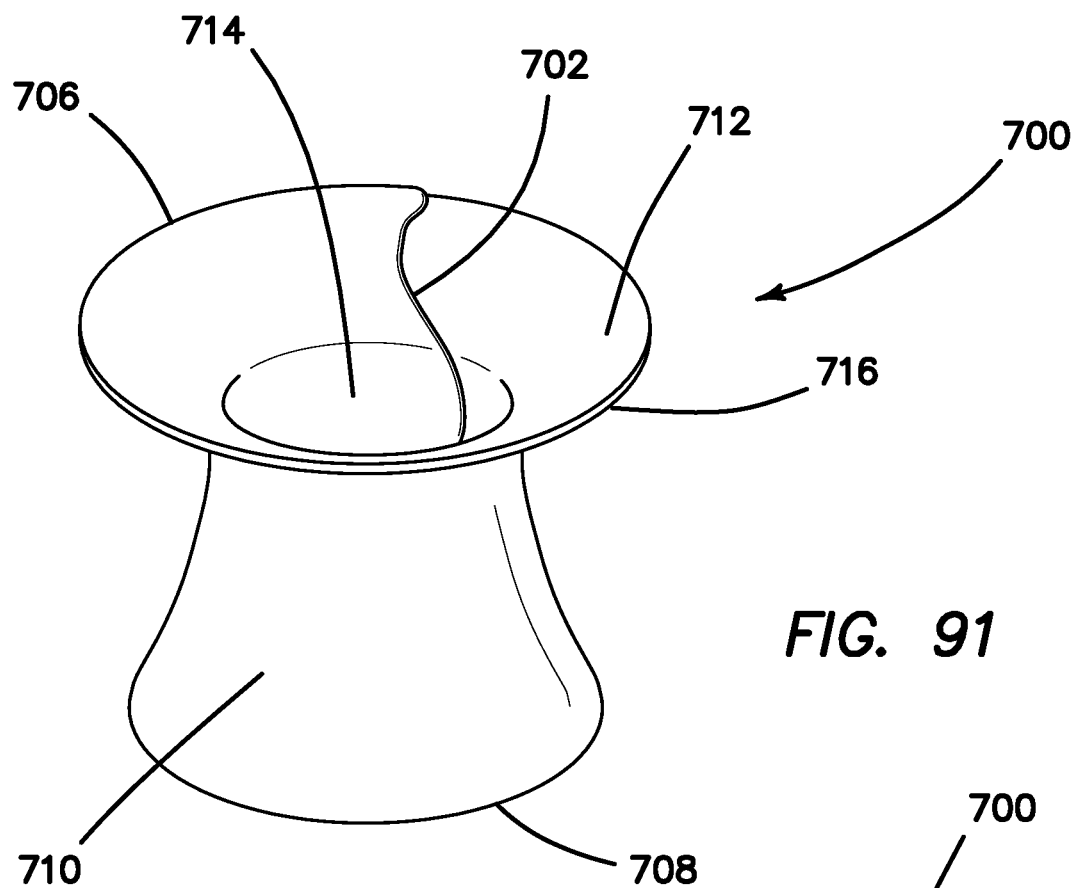
FIG. 91 is a top perspective view of a guard according to the present invention.
Figure 92:
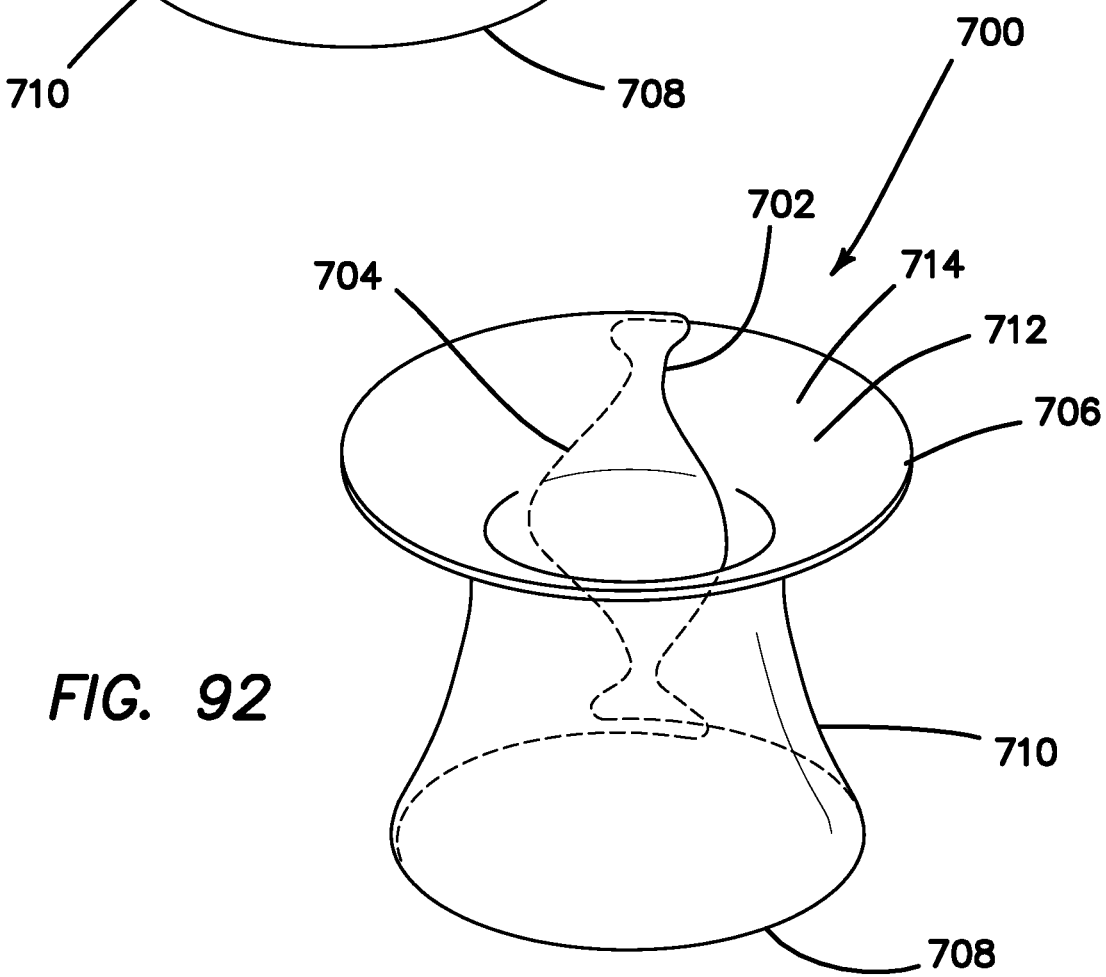
FIG. 92 is a semi-transparent, top perspective view of a guard according to the present invention.

Turning now to FIGS. 89-90, there is shown a morcellation system 600 that uses an energy-based morcellator 602. The energy-based morcellation system utilizes the tissue containment bag, tenaculum, shield 608 in the same manner as described above. Rather than rotating the blade 610 to cut tissue, a circular blade 610 remains stationary. The blade 610 and cylinder 612 of the morcellator 602 are connected via an energy input 650 to the output of a monopolar energy system 652. The tenaculum 606 is connected to a plug 654 leading to a ground on the monopolar energy system 652. When the target tissue is grasped by the tenaculum 606 and brought to the blade 610, the monopolar energy is engaged, cutting the tissue. The extension 626 serves the same purpose as mentioned previously. An evacuation port 656 is provided on the housing 616 to prevent inhalation of smoke from the cutting process.

Turning now to FIGS. 91-103, there is shown a shield 700 adapted for placement within the vaginal canal. The shield 700 has a similar shape to the shields described herein. The shield 700 is substantially cylindrical/tubular in shape formed from a band of material having an inner first end 702 and an outer second end 704 interconnected between a proximal end 706 and a distal end 708. The shield 700 includes an outer surface 710 and an inner surface 712. The inner surface 712 defines a central lumen 714 that extends from the proximal end 706 to the distal end 708 along a longitudinal axis. The central lumen 714 is shown to be circular in shape and, in another variation, may also have an elliptical or elongate oval oblong shape. The proximal end 706 defines a radially outwardly extending proximal flange 716 that forms a funnel-like entryway to the central lumen 714. The outer surface 634 is concave and flares progressively radially outwardly toward the distal end 708. At least a portion of the shield 700 overlaps onto itself when in a relaxed normal configuration. The shield 700 can be curled onto itself to reduce a lateral dimension for ease of insertion into the vagina or other orifice or wound incision. The overlapping portions of the shield 700 conform and nest with each other. The shield 700 is configured such that one end such as the first end 702 slides against the second end 704. The shield 700 is capable of having a first reduced lateral or diametrical dimension suitable for easy insertion into the vagina or other body opening. The reduced lateral position is achieved by curling the shield 700 onto itself into a tighter and smaller configuration. The shield 700 also includes a relaxed normal position having a second lateral or diametrical dimension. The second lateral or diametrical dimension is greater than the first lateral/diametrical dimension. The shield 700 is molded with a bias towards the normal relaxed position such that when reduced to the first diametrical position the shield 700 will tend to automatically expand or spring open, or uncurl towards its relaxed and normal position having the approximate second lateral or diametrical dimension. The shield 700 may be provided with a lock of the kind described herein that fixes the lateral or diametrical position. The shield 700 also includes an enlarged configuration having a third lateral or diametrical dimension. The third lateral or diametrical dimension is larger than the second lateral or diametrical dimension. The enlarged configuration is achieved by curling the shield 700 in the opposite direction or uncurling the shield 700 to open up the central lumen 714. Any of the positions and any intermediate position of the shield 700 lateral dimension may be locked in position via the lock. The shield 700 and, particularly, the enlarged configuration of the shield 700 serves to retract tissue and open the orifice or wound to provide a safe working channel for surgical procedures.

Figure 93:
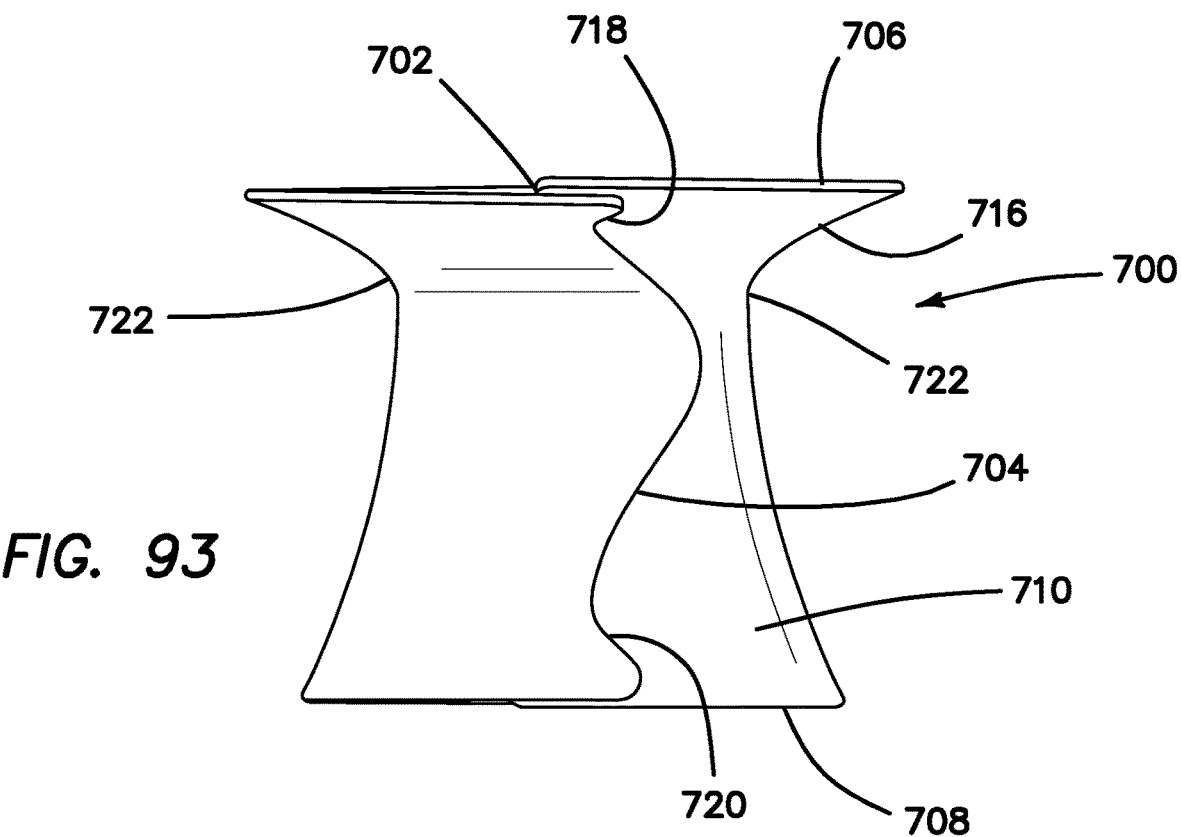
FIG. 93 is a side view of a guard according to the present invention.
Figure 94:
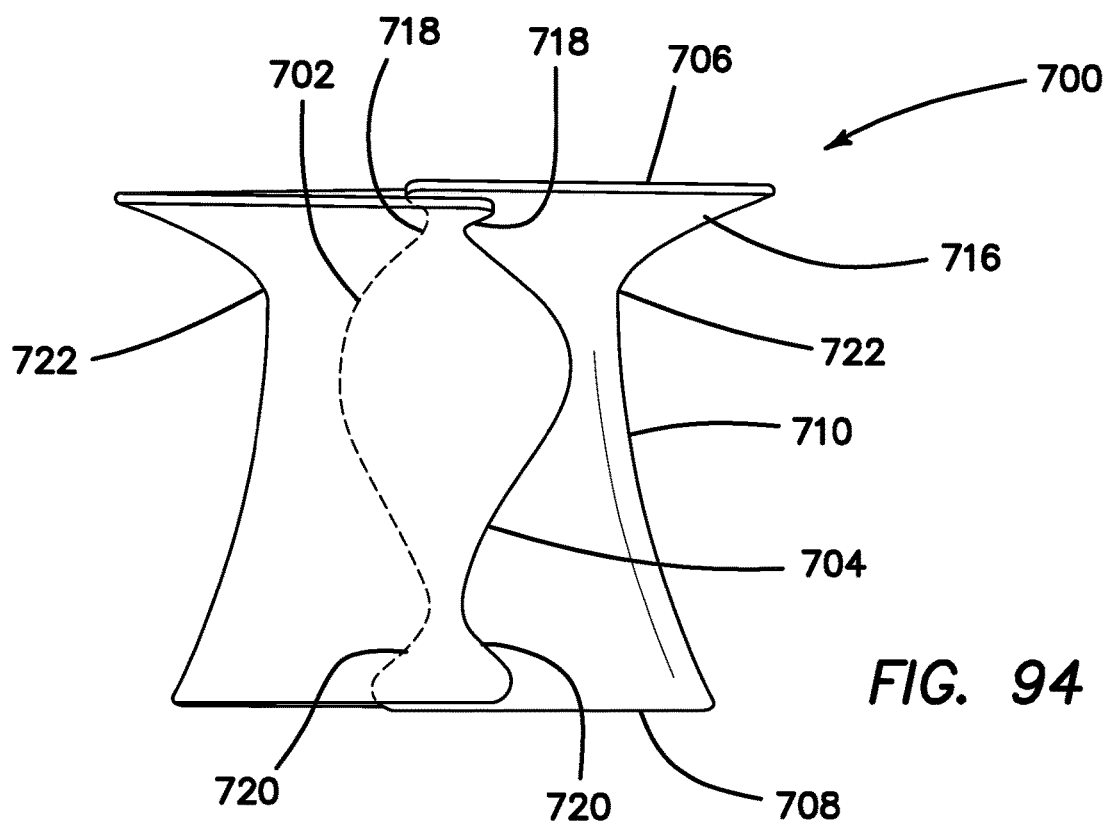
FIG. 94 is a semi-transparent, side view of a guard according to the present invention.
Figure 95:
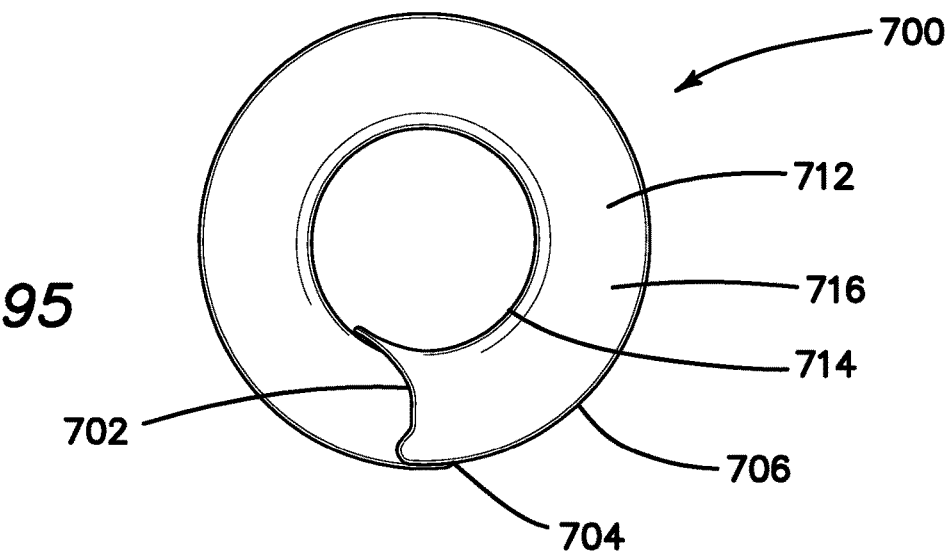
FIG. 95 is a top view of a guard according to the present invention.
Figure 96:
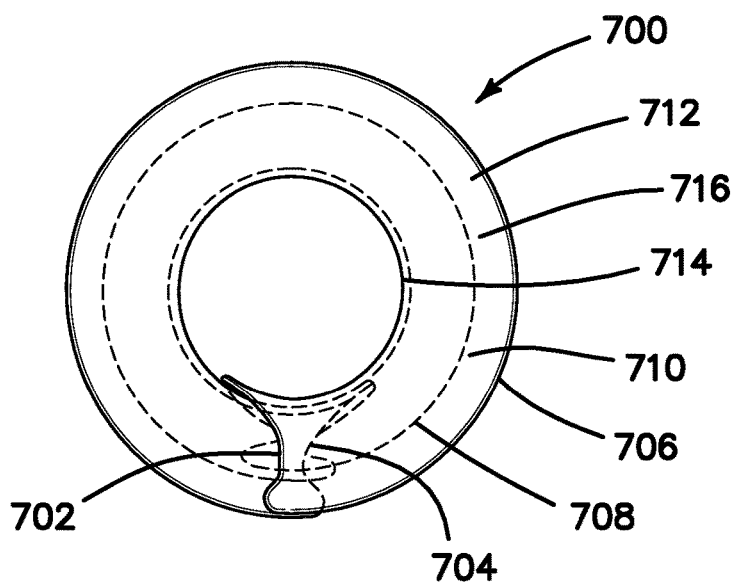
FIG. 96 is a semi-transparent, top view of a guard according to the present invention.
Figure 97:
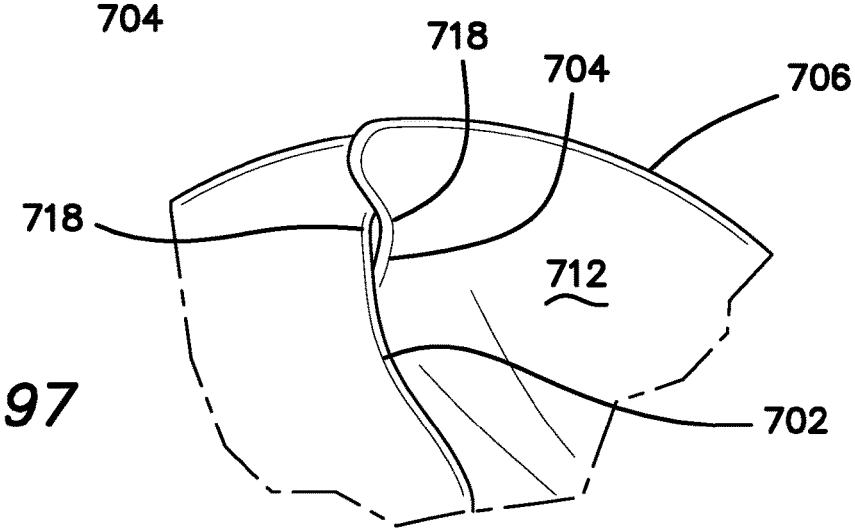
FIG. 97 is a sectional top view of a guard according to the present invention.
Figure 98:
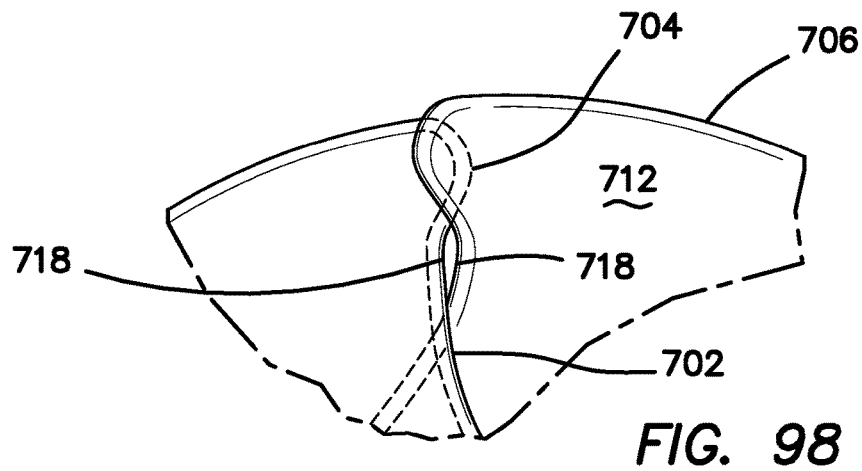
FIG. 98 is a semi-transparent, sectional top view of a guard according to the present invention.
Figure 99:
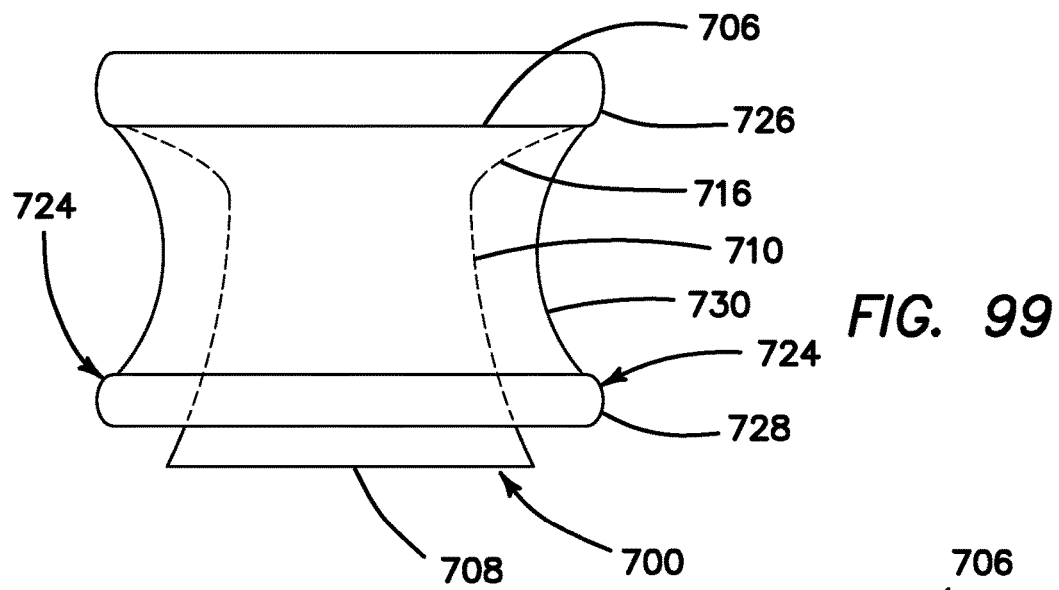
FIG. 99 is a semi-transparent, side view of a retractor and guard according to the present invention.
Figure 100:
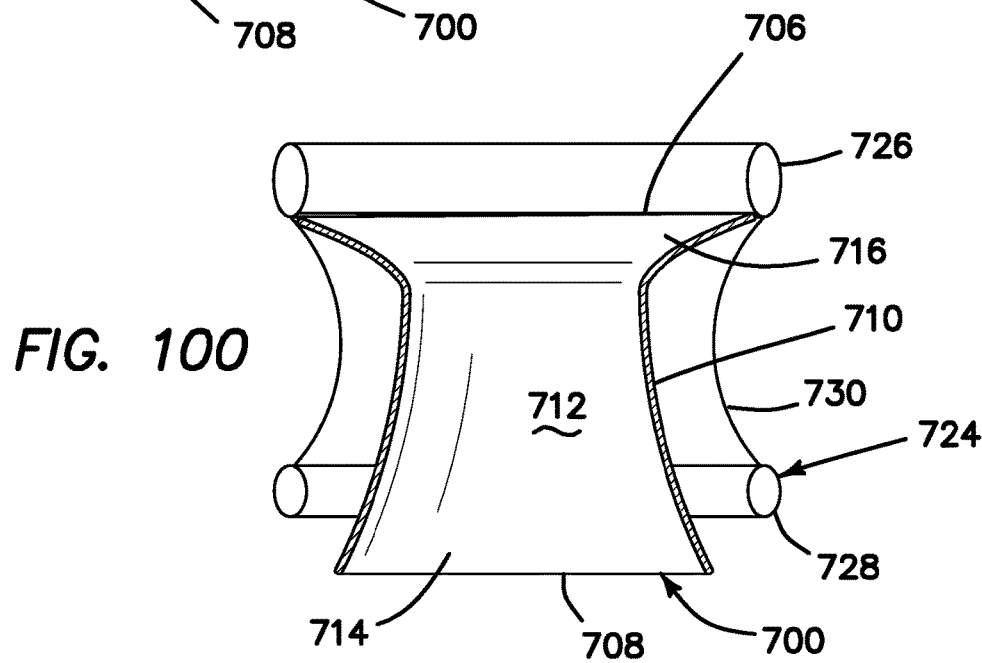
FIG. 100 is a cross-sectional side view of a retractor and guard according to the present invention.
Figure 101:
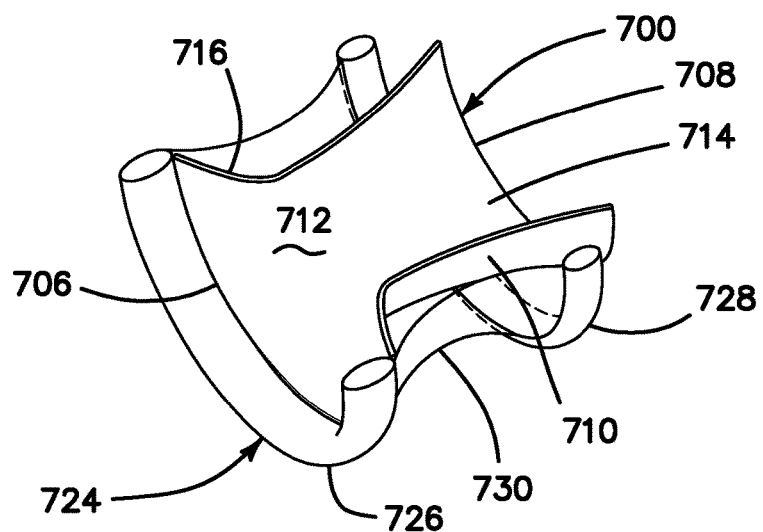
Figure 102:
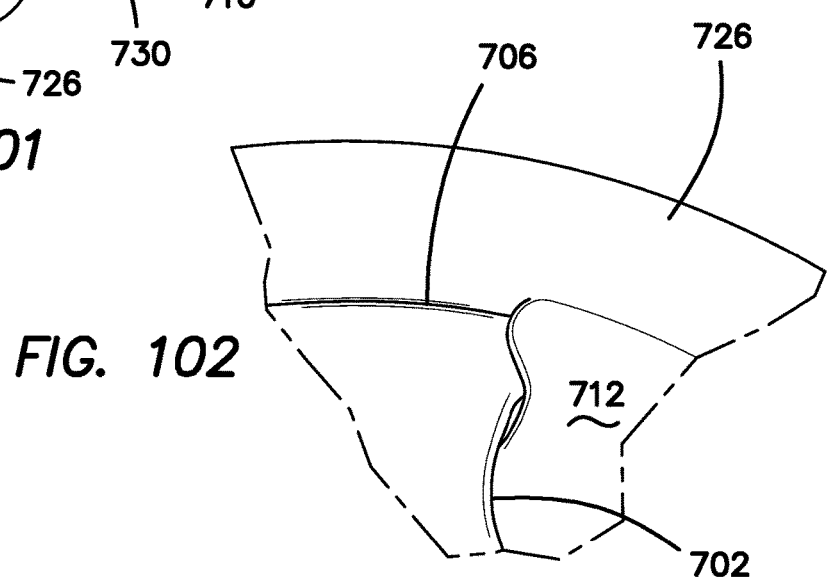
Figure 103:
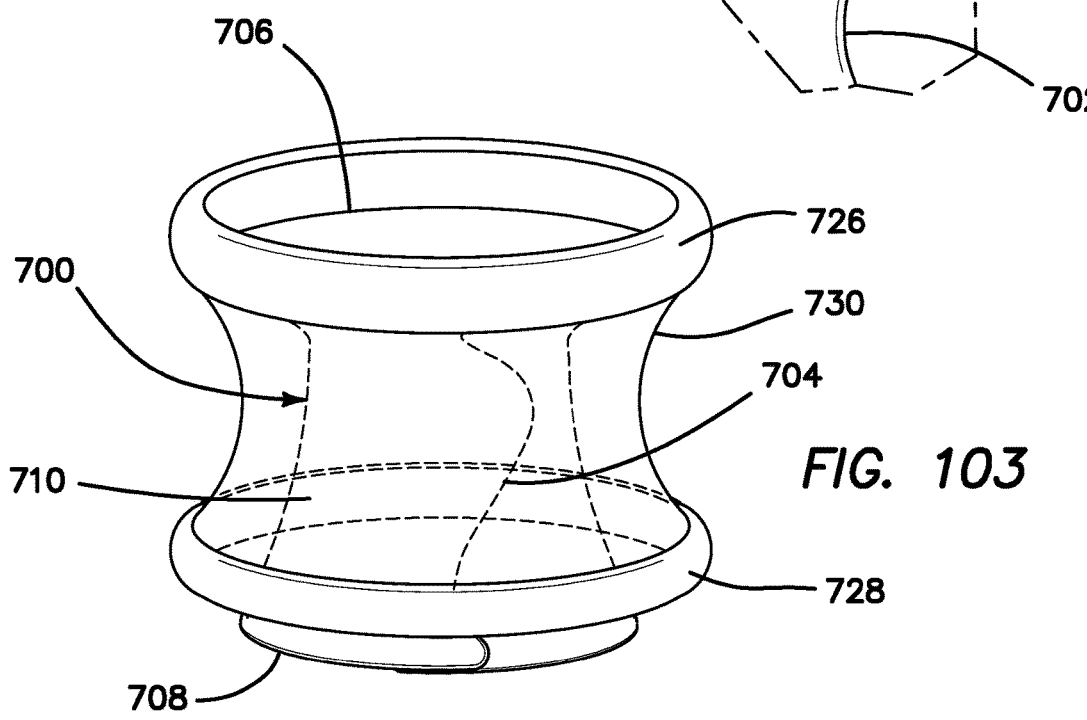
Figure 104:
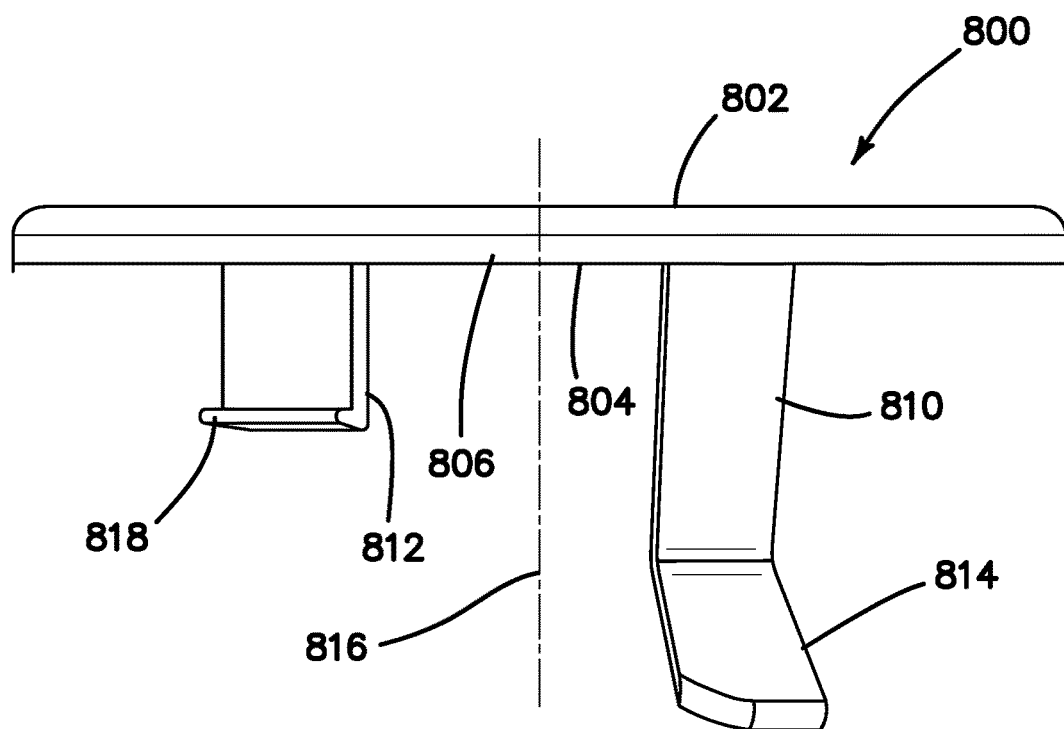
Figure 105:
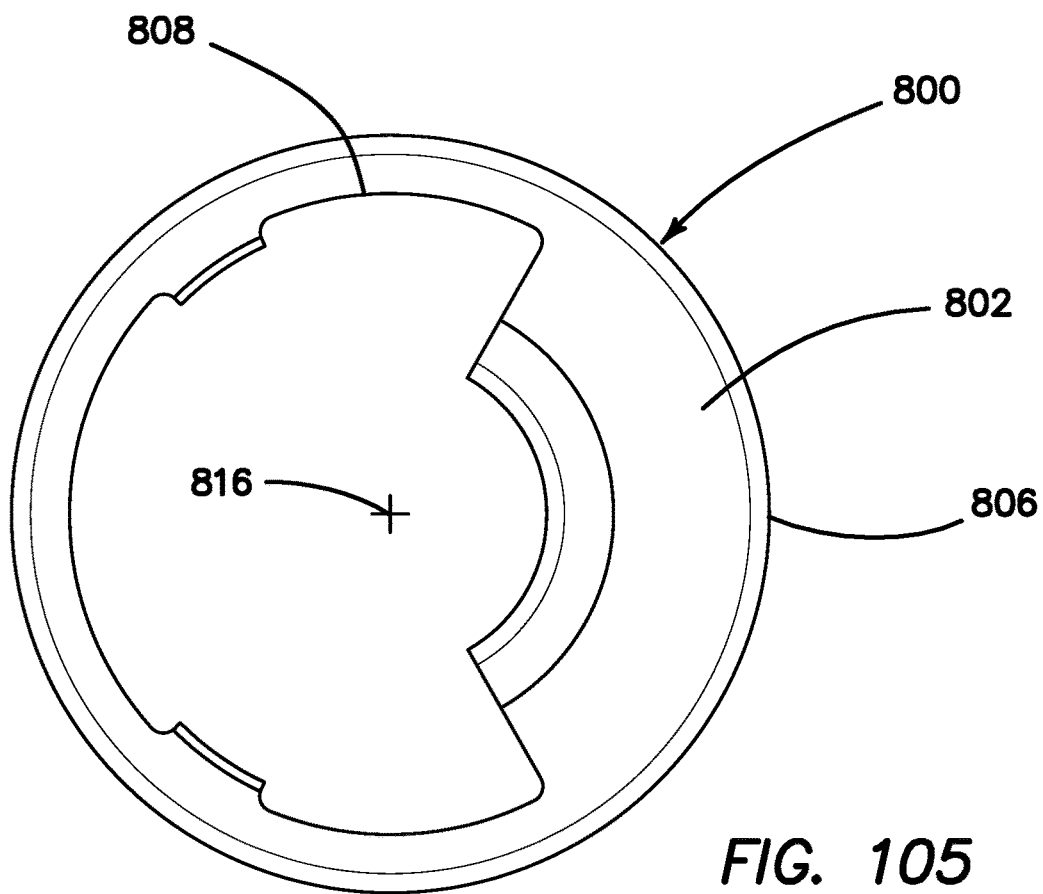

As can be seen in FIGS. 93-94, the first end 702 and the second end 704 each have an S-shape curvature that overlaps onto an outer surface 710 of an adjacent shield portion. The S-shape transitions into notches 718, 720 near the proximal end 706 and the distal end 708, respectively. The notches 718, 720 form the lock configured to fix the lateral dimension of the shield 700. The notches 718, 720 are shown in an unlocked position in FIGS. 93-94 and in a locked position in FIGS. 97-98. The notches 718, 720 form finger-like extensions that are configured to mate with each other to lock the shield 700 in position. In FIGS. 97-98, the finger-like extension near notch 718 of the outer second end 704 overlaps the inner first end 702 to lock the shield 700. As described above, the outer surface 710 of the shield 700 forms a concave surface having a point of inflection 722 visible in FIGS. 93-94. The inflection point 722 is located near the proximal flange 716 above the mid-plane taken perpendicular to the longitudinal axis. The proximal flange 716 serves as a protective surface that guards a containment bag, retractor 724 and vaginal canal tissue at the insertion location. The shield and/or the flange is made of hard, rigid, or semi-rigid, plastic or cut-resistant material. The proximal flange 716, in particular, the inner surface 712 of the proximal flange 716 provides a cutting-board like surface against which sharps such as scalpels or blades can be advantageously used to cut and reduce targeted tissue for extraction and removal without fear of cutting the containment bag, adjacent tissue or retractor.

With particular reference now to FIGS. 99-103, there is shown the shield 700 employed in combination with a retractor 724. The retractor 724 is the same retractor 62 as described with respect to FIGS. 18-19. The retractor 724 includes a first ring 726 and a second ring 728 interconnected by a flexible sidewall 730. The sidewall 730 defines a central opening extending along the longitudinal axis of the retractor 724. The second ring 728 can be compressed and inserted through the vaginal canal where it expands to create a securement against the vagina. The first ring 726 resides above the entrance to the vagina outside the patient where it can be rolled down to retract and enlarge the vaginal canal.

In a hysterectomy, the uterus is detached from the body via instruments inserted through abdominal ports. After the uterus has been detached, the shield 700 may be inserted directly into the vaginal canal. In such a variation, the shield 700 is curled upon itself into a reduced configuration to aid in the insertion of the shield 700 and when in position, the shield 700 is allowed to expand to its normal, relaxed configuration while inside the vaginal canal, thereby, expanding and retracting the vaginal opening. The proximal flange 716 resides near the entrance to the vagina. The detached uterus would be gasped and pulled into the central lumen 714 of the shield 700 against which it may be morcellated with a blade permitting the uterus to be reduced in size or pieces and completely removed through the vaginal canal.

In another variation, a containment bag is placed inside the abdominal cavity either through an abdominal port or through the vaginal canal. The removed uterus is placed into the containment bag. The tether of the containment bag is pulled through the vaginal canal. The ring of the containment bag is compressed into a low-profile configuration to facilitate pulling the proximal end of the containment bag through the vaginal canal. The ring of the containment bag is pulled outside the body and allowed to expand into an open configuration, thereby, opening the mouth of the containment bag. The ring of the containment bag resides outside the entrance to the vagina. The ring of the containment bag may be rolled-down to roll the sidewall of the bag onto the ring of the containment bag. This action brings the removed uterus inside the bag closer to the vaginal opening. The shield 700 is then inserted into the mouth of the containment bag and into the vaginal canal. The shield 700 may be curled down into a compact configuration to aid insertion. The proximal flange 716 resides at or near the entrance to the vagina. In one variation, the proximal flange 716 of the shield 700 is snapped under the ring of the containment bag. The removed uterus is gasped with a grasper and pulled into the central lumen 714 of the shield 700 where morcellation can commence.

The distal end of the shield 700 is funnel-shaped having a progressively increasing radial dimension from the point of inflection 722 toward the distal end 708 of the shield 700. This funnel-like shape advantageously helps to move the detached uterus into the shield 700. The uterus is morcellated with a blade while it is at least partially resident within the shield 700 before being completely removed in whole or in parts. The shield 700 advantageously protects the surrounding vaginal canal as well as the containment bag from the sharp blade helping to maintain the integrity of the containment bag and the closed morcellation system.

In another variation, the same procedure is carried out as in the previous paragraph but a retractor 724 is inserted into the mouth of the containment bag after the uterus has been placed into the containment bag and after the ring of the containment bag is pulled to outside the body. The second ring 728 of the retractor 724 is compressed for easy insertion into the mouth of the containment bag and then allowed to expand into an open configuration inside the containment bag in a location distal to the vaginal canal inside the abdominal cavity. The first ring 726 of the retractor 724 that is resident outside the body is rolled about itself to roll the sidewall 720 of the retractor 724 onto the first ring 726. This action retracts not only the vaginal canal but also retracts the containment bag out of the way clearing the vaginal canal for insertion of the shield 700. The containment bag is captured between the retractor and the vaginal canal keeping it in place and preventing its migration into or out of the vaginal canal. The shield 700 is then inserted into the central lumen of the retractor 724 that is residing inside the containment bag. The shield 700 may be curled down into a compact configuration if needed and then allowed to expand to self-anchor the shield 700 into position. The shield 700 is then connected to the first ring 726 of the retractor 724 by snapping the proximal flange 716 of the shield 700 under the first ring 726 as shown in FIGS. 99-103. The uterus can then be grasped with a surgical instrument and pulled from the pouch of the containment bag into the central lumen 714 of the shield 700 where the uterus is morcellated with a blade while it is at least partially resident within the shield 700 before being completely removed in whole or in parts. The shield 700 advantageously protects the surrounding vaginal canal as well as the containment bag from the sharp blade helping to maintain the integrity of the containment bag and the closed morcellation system while providing the surgeon with a mechanism to perform morcellation safely and quickly.

In another variation, the same procedure is carried out in the same way as in the previous paragraph except that the retractor 724 is placed into the vaginal canal before the containment bag with the specimen inside is pulled through the vaginal canal. In this variation, the removed uterus is placed inside the containment bag located inside the abdominal cavity and the tether attached to the proximal end of the containment bag is pulled with a grasper through the central lumen of the retractor bringing the ring of the containment bag and mouth to the outside of the patient. The ring of the containment bag may then be rolled down to bring the detached uterus closer to the opening. Afterwards, the shield 700 is reduced in size laterally by curling the flexible retractor 700 onto itself into a compact configuration and then releasing the shield 700 allowing it to expand due to its bias tending it to expand laterally from the compact configuration. As the shield 700 expands it self-anchors and retracts the containment bag creating a working channel though the central lumen 714 of the shield 700 for moving and morcellating the detached uterus. The proximal flange 716 of the shield 700 may be snapped under the ring of the containment bag or first ring 726 of the retractor 724. The containment bag is captured between the retractor 724 and the shield 700 keeping it from slipping proximally or distally during the procedure. The flange 726 may also serve as a cutting-board-like surface against which a sharp blade can be used to cut the uterus for removal. For all of the above hysterectomy procedures, the containment bag and retractor combination of FIG. 20 may be used in lieu of one or more of the containment bag and retractor 724.

In yet another variation, the shield 700 is employed with a retractor 724 as shown in FIGS. 99-103. In such a variation, the retractor 724 is placed into the vaginal canal. The uterus is detached employing standard techniques either before or after the retractor 724 has been placed in position. The second ring 728 of the retractor 724 is compressed for easy insertion into the vaginal canal and then allowed to expand into an open configuration in a location distal to the vaginal canal inside the abdominal cavity. The first ring 726 of the retractor 724 that is resident outside the body is rolled about itself to roll the sidewall 720 of the retractor 724 onto the first ring 726. This action retracts the vaginal canal. The shield 700 is then inserted into the central lumen of the retractor 724. The shield 700 may be curled down into a compact configuration if needed and then allowed to expand to self-anchor the shield 700 into position. The shield 700 is then connected to the first ring 726 of the retractor 724 by snapping the proximal flange 716 of the shield 700 under the first ring 726 as shown in FIGS. 99-103. The uterus can then be grasped with a surgical instrument and pulled into the central lumen 714 of the shield 700 where the uterus is morcellated with a blade while it is at least partially resident within the shield 700 before being completely removed in whole or in parts. The shield 700 advantageously protects the surrounding vaginal canal as well as the retractor 724 from the sharp blade while providing the surgeon with a mechanism to perform morcellation safely and quickly.

Figure 106:
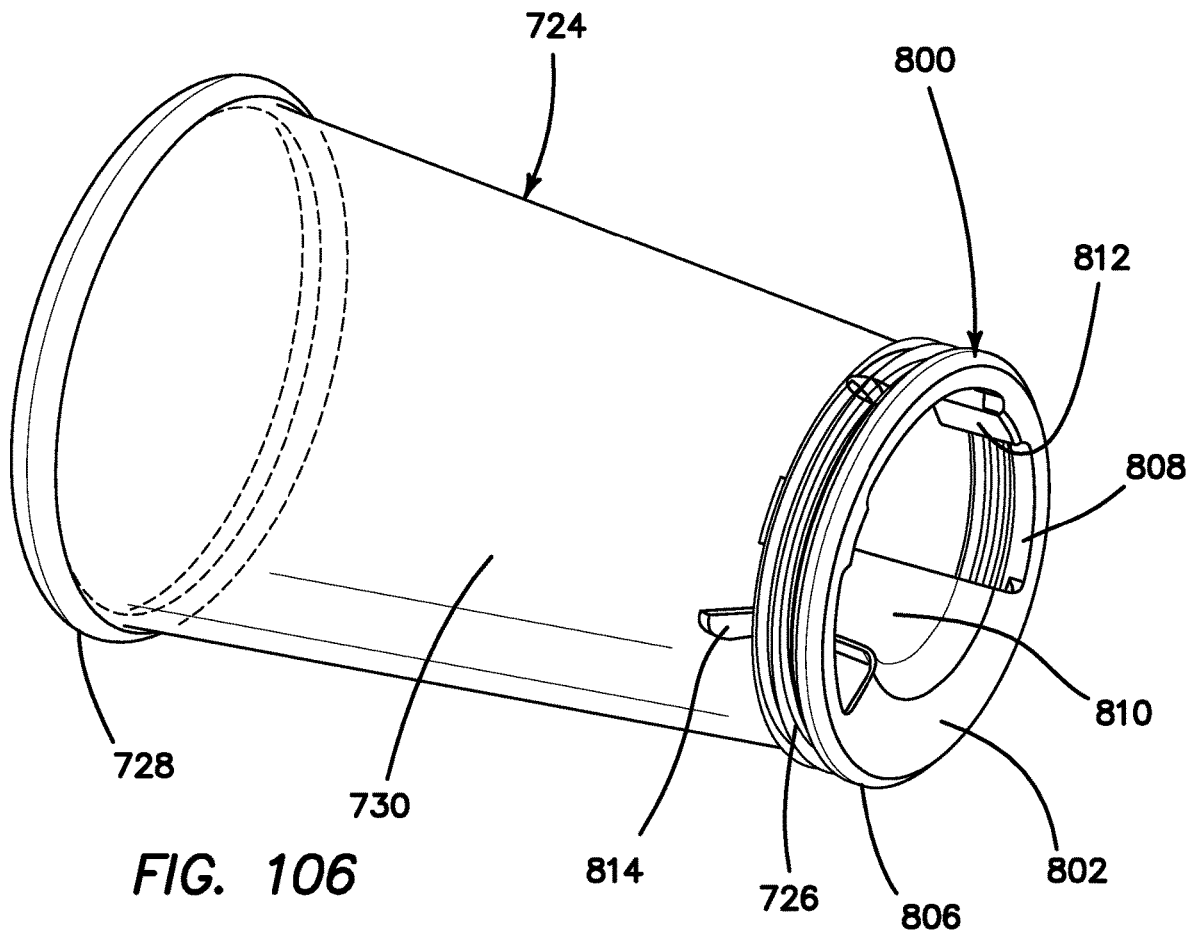
Figure 107:
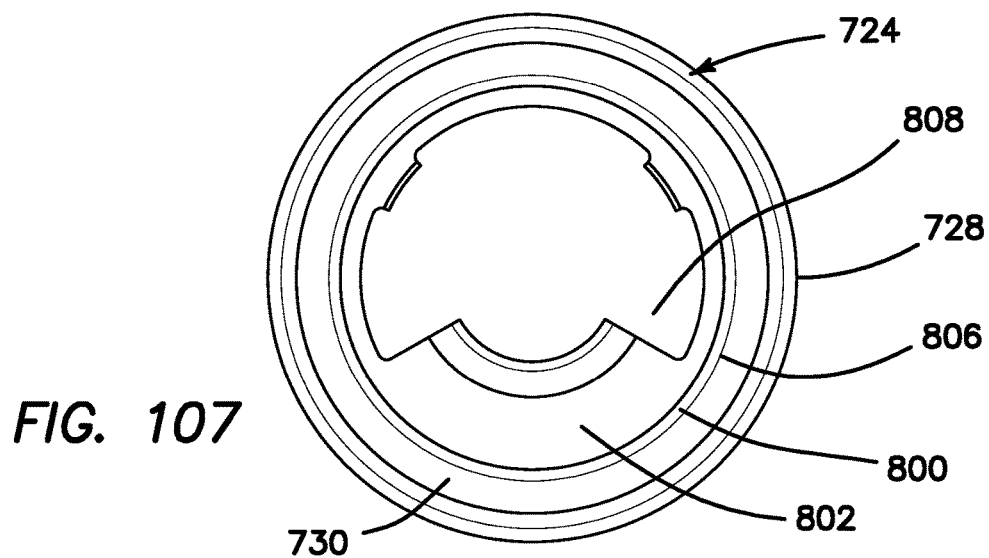

Turning now to FIGS. 104-107, there is shown another variation of a shield 800 adapted for use in the vaginal canal. The shield 800 includes a top end 802 and a bottom end 804 interconnected by a sidewall 806. An opening 808 is formed in the shield 800 that extends through the top end 802 and the bottom end 804. The shield 800 further includes a first flange 810 and a second flange 812. The first flange 810 extends from the bottom end 804 in the distal direction. The first flange 810 is curved forming an elongate surface that is concave towards the longitudinal axis 816. The first flange 810 may also be substantially flat elongate surface. The first flange 810 includes a distal end 814 that is angled away from the longitudinal axis 816. The second flange 812 extends from the bottom end 804 in the distal direction. The second flange 812 includes a hook 818 that is configured to attach to a ring of a containment bag or a proximal ring of a retractor by snapping under the ring. FIGS. 106-107 illustrate the shield 800 connected to a retractor 724. The retractor 724 is the same retractor as described above with respect to FIGS. 18-19 and FIGS. 99-103. The retractor 724 includes a first ring 726 and a second ring 728 interconnected by a flexible sidewall 730. The sidewall 730 defines a central opening extending along the longitudinal axis of the retractor 724. The second ring 728 can be compressed and inserted through the vaginal canal where it expands to create a securement against the vagina cavity. The first ring 726 resides above the entrance to the vagina outside the patient where it can be rolled down to retract and enlarge the vaginal canal.

The shield 800 will now be described in use during a surgical procedure such as a hysterectomy even though the invention is not limited to use in a hysterectomy and can be applied to the removal or morcellation procedure of any targeted tissue. In a hysterectomy, the uterus is detached from the body via instruments inserted through abdominal ports.

In one variation, the shield 800 is employed with a retractor 724 as shown in FIGS. 106-107. In such a variation, the retractor 724 is placed into the vaginal canal. The uterus is detached employing standard techniques either before or after the retractor 724 has been placed in position. The second ring 728 of the retractor 724 is compressed for easy insertion into the vaginal canal and then allowed to expand into an open configuration in a location distal to the vaginal canal inside the abdominal cavity. The first ring 726 of the retractor 724 remains resident outside the body and is rolled about itself to roll the sidewall 720 of the retractor 724 onto the first ring 726. This action retracts the vaginal canal. The shield 800 is then inserted into the central lumen of the retractor 724 and connected to the retractor 724. The shield 800 is connected to the first ring 726 of the retractor 724 by snapping the second flange 812 of the shield 800 under the first ring 726 from the inside of the first ring 726 as shown in FIGS. 106-107. Additional hooks for connecting the shield 800 to the retractor 724 may be provided. The shield 800 covers or caps onto the first ring 726 of the retractor 724 and the one or more hook 818 hooks under the first ring 726 to secure the shield 800 to the retractor 724. The uterus can then be grasped with a surgical instrument and pulled in the proximal direction and placed onto or in juxtaposition to the first flange 810. The first flange 810 of the shield 800 is curved and advantageously cradles the detached uterus preventing it from slipping off the first flange 810 while a surgeon uses a blade to cut the uterus to reduce it in size for removal through the vaginal canal. The first flange 810 advantageously serves as a cutting-board like surface against which a blade can be safely employed to cut tissue resting near or in contact with the first flange 810. The angled distal end 814 of the first flange 810 provides additional vaginal dilation and provides a ramp for moving and guiding the uterus into the vaginal canal and proximally toward the vaginal opening. At the proximal end of the shield 800, the ring-like portion of the shield 800 advantageously retracts the labia safely out of the way of the morcellating blade. The uterus is morcellated with a blade while it is at least partially resident within the shield 800 before being completely removed in whole or in parts. The shield 800 advantageously protects the surrounding vaginal canal, the labia as well as the retractor 724 from the sharp blade while providing the surgeon with a mechanism to perform morcellation safely and quickly.

In another variation, a containment bag is placed inside the abdominal cavity either through an abdominal port or through the vaginal canal. The removed uterus is placed into the containment bag. The tether of the containment bag is pulled through the vaginal canal. The ring of the containment bag is compressed into a low-profile configuration to facilitate pulling the proximal end of the containment bag. The ring of the containment bag is pulled outside the body and allowed to expand into an open configuration opening the mouth of the containment. The ring of the containment bag resides outside the entrance to the vagina. The ring of the containment bag may be rolled down to roll the sidewall of the bag onto the ring of the containment bag. This action brings the removed uterus inside the bag closer to the vaginal opening. The shield 800 is then inserted into the mouth of the containment bag and into the vaginal canal and connected to ring of the containment bag by hooking the second flange 812 onto the ring to secure the shield 800 to the bag. The removed uterus inside the bag is gasped with a grasper and pulled onto the first flange 810 of the shield 800. The angled distal end 814 of the first flange 810 helps guide and ramp the uterus into position and cradles the uterus for morcellation. The uterus is morcellated with a blade while it is at least partially located adjacent to the first flange 810 before being completely removed in whole or in parts. The shield 800 advantageously protects the surrounding vaginal canal as well as the containment bag from the sharp blade helping to maintain the integrity of the containment bag and the closed morcellation system.

In another variation, the same procedure is carried out as in the previous paragraph but a retractor 724 is inserted into the mouth of the containment bag after the uterus has been placed into the containment bag and after the ring of the containment bag is pulled to outside the body. The second ring 728 of the retractor 724 is compressed for easy insertion into the mouth of the containment bag and then allowed to expand into an open configuration inside the containment bag in a location distal to the vaginal canal inside the abdominal cavity. The first ring 726 of the retractor 724 is rolled about itself to roll the sidewall 720 of the retractor 724 onto the first ring 726. This action retracts not only the vaginal canal but also retracts the containment bag out of the way clearing the vaginal canal for insertion of the shield 800. The containment bag is thereby captured between the retractor 724 and the vaginal canal keeping it in place and preventing its migration proximally or distally along the vaginal canal. The shield 800 is then inserted into the central lumen of the retractor 724 residing inside the containment bag. The shield 800 is connected to the first ring 726 of the retractor 724 by snapping the second flange 812 of the shield 800 under the first ring 726 of the retractor 724. The uterus can then be grasped with a surgical instrument and pulled from the pouch of the containment bag into juxtaposition with first flange 810 of the shield 800 where the uterus is morcellated with a blade while it is at least partially in contact with the first flange 810 before being completely removed in whole or in parts. The shield 800 advantageously protects the surrounding vaginal canal as well as the containment bag and retractor 724 from the sharp blade helping to maintain the integrity of the containment bag and the closed morcellation system while providing the surgeon with a mechanism to perform morcellation safely and quickly. For all of the above hysterectomy procedures, the containment bag and retractor combination of FIG. 20 may be used in lieu of one or more of the containment bag and retractor 724. It is also understood that the invention is not limited to hysterectomy procedures and can be applied for the morcellation, reduction and removal of any tissue or organ.

Figure 108:
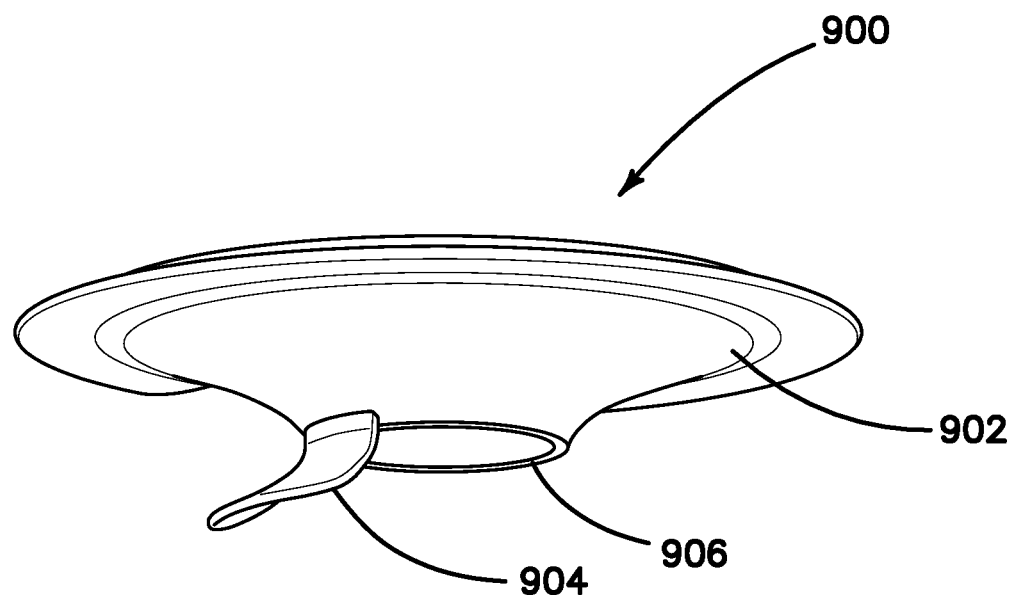

Turning now to FIGS. 108-109, there is shown a variation of a shield 900 that includes a funnel 902 having a retraction finger 904 at a distal end. The funnel 902 defines a central opening 906. The proximal end of the shield 900 defines a funnel-like entry to the central opening and forms a proximal flange surface circumferentially surrounding the central opening 906. The shield 900 is inserted into an orifice or wound incision by inserting the retraction finger 904 first and then inserting or angling the central portion of the funnel 902 into the opening. The proximal end of the funnel 902 is laid on top of the abdomen or other outer surface of the body. The proximal flange provides a cutting-board location against which tissue can be morcellated. The retraction finger 904 serves to retract the incision or orifice and helps keep the shield 900 anchored in position. The retraction finger 904 forms a distal flange that extends only around a portion of the circumference of the distal end of the central opening 906. The retraction finger 904 is curved such that the side profile of the shield 900 in the location of the retraction finger 904 is substantially C-shaped wherein the upper part of the letter "C" extends laterally a greater distance relative to the lower part of the "C". Also, the funnel 902 provides protection to the surrounding tissue and containment bag and retractor if employed together with the shield 900. For example, a containment bag may be inserted through the orifice or incision and the mouth of the bag pulled back out of the incision after a specimen has been inserted into the bag. The proximal end of the bag is laid over the abdomen and the shield 900 is inserted into the mouth of the bag and anchored with the retraction finger 904. A grasper is inserted into the central opening 906 and the specimen inside the bag is pulled towards the central opening 906. A blade is then used to reduce the specimen for removal in whole or in parts through the small incision/orifice. The shield 900 is made of firm plastic of a sufficient thickness to prevent and reduce that potential for penetration by the blade and protect the adjoining tissue and maintain the integrity of the containment bag.

In another variation, the shield 900 is employed with a retractor of the like described above. The retractor is placed inside the incision either before or after the bag is placed and then the shield 900 is inserted into the mouth of the bag and retractor. In one variation, the proximal end of the shield 900 is sized and configured to mate with the proximal ring of the retractor or bag by capping or snapping with the proximal ring of the bag or retractor. A variation of the shield 900 that is adapted to cap onto the proximal ring of a retractor or bag is shown in FIGS. 109B and 109C having an oval-shaped central lumen 906 and a circular-shaped central lumen 906, respectively. The shield 900 in FIGS. 109B and 109C have at least one hook 905 configured for attaching to the retractor or bag ring.

With particular reference now to FIG. 109, the funnel 902 includes a circumferential rim 908 that is raised from the inner surface. The rim 908 is configured to connect with a blade and will be described in greater detail below. Also, the funnel 902 includes a raised portion 910. The raised portion 910 is configured to retain a second shield 912. A second shield 912 is shown in FIG. 110. The second shield 912 is similar to the shield described with respect to FIGS. 71-86 as well as to other shields described herein. In one variation, the second shield 912 is spiral in shape and collapsible and expandable in the vertical direction as described above. In the variation shown in FIG. 110, the second shield 912 is not spiral-shaped but substantially cylindrical having a concave outer surface and a gap 914 to create a C-shaped shield. The second shield 912 includes a proximal flange 916 and a distal flange 918 interconnected by a central portion 920. The proximal flange 916 may include a tab or finger pull to aid its removal from the orifice/incision. The second shield 912 has a reduced configuration in which a lateral dimension is smaller than a normal relaxed configuration shown in FIG. 110. The reduced configuration is optimal for insertion into a wound or orifice and for connecting the second shield 912 to the first shield 900. The second shield 912 is made of flexible plastic having properties sufficient prevent penetration by a blade or other sharp object or instrument under normal use to protect adjacent tissue.

Turning now to FIG. 111, there is shown the first shield 900 connected to the second shield 912. The C-shaped second shield 912 is placed inside the first shield 900 such that the proximal flange 916 of the second shield 912 overlays at least a portion of the inner surface of the funnel 902 of the first shield 900. The raised portion 910 of the shield 900 is received within the gap 914 of the second shield 912. The connection with the raised portion 910 prevents the second shield 912 from moving around inside the funnel 902. The first shield 900 provides protection along part of the lower circumference in the location of the retraction finger 904 and the second shield 912 completes the circumferential protection at the distal end. The second shield 912 provides 360 degree circumferential protection at the distal end which is placed in the incision/orifice. Also, the distal flange 918 provides a funnel-like entry into the central lumen 922 of the second shield 912 which helps to move tissue into shields 900, 912 and out of the body while providing protection for the surrounding tissue, containment bag and retractor if employed. The shields 900, 912 may be employed with manual bladed morcellation or with a short power morcellator of the like described above with respect to FIGS. 87-90.

Turning now to FIGS. 112-113, there is shown a blade carrier 926 connected to the first shield 900 that is in turn connected to a second shield 912 to comprise another variation of the shield system. The blade carrier 926 includes a funnel 928 defining a central opening 930, a blade receiver 932 and a blade 934. The funnel 928 includes a funnel-like shape and a circumferential hook configured to cap, snap on and connect to the first shield 900. In particular, as shown in FIG. 113, the circumferential hook of the funnel 928 connects directly with the raised circumferential rim 908. In one variation, the blade carrier 926 snaps with the first shield 900 such that it is vertically retained yet permitted to rotate relative to the first shield 900. The blade receiver 932 contains the blade 934 within a blade channel 936. The blade 934 is connected to a blade handle 938 via a pin 940 that connects the blade 934 to an inner rod 942. Details of the blade housing 932 are also shown in FIGS. 114-115. In one variation, the inner rod 942 to which the blade 934 is pinned via the pin 940 reciprocates with respect to the blade handle 938. The reciprocating action may be provided manually by moving the inner rod 942 at the proximal end back-and-forth with respect to the blade handle 938 to effect back-and-forth movement of the blade 934 at the distal end. The reciprocating action may be provided by an electric motor (not shown) located in blade handle 938 at the proximal end in a removable and reusable handle attachment. The blade receiver 932 may be provided in two parts, a first part and a second part. The first part includes a blade channel 936 having a slot 944 configured to receive the pin 940 and configured to guide the translation of the blade 934 inside the blade channel 936. One end of the pin 940 is connected to the blade 934 and the other end of the pin 940 is connected to the distal end of the inner rod 942 which is housed in the second part of the blade receiver 932 which together house the blade 934. The blade receiver 932 is connected to the funnel 928 of the blade carrier 926. The inner rod 942 is moved distally to expose the blade 934 for cutting tissue when in an exposed position. With the blade 934 exposed, the blade carrier 926 may be rotated relative to the first shield 900 to cut tissue circumferentially along at least a part of the interior of the central lumen. The blade 934 can be retracted into a retracted position in which the blade 934 is at least partially concealed inside the blade receiver 932. When in the retracted position, the sharp sides of the blade 934 are substantially concealed making the blade carrier 926 safe to handle. The blade 934 can be moved from the retracted position to the exposed position manually or automatically to cut tissue. This reciprocal cutting motion can be selectively engaged by the user manually or automatically when tissue cutting is desired or engaged to reciprocate in a continuous manner. Also, the reciprocal cutting action can be performed simultaneously with rotation of the blade carrier 926 with respect to the first shield 900 or performed intermittently with the rotation of the blade carrier 926. Moving the blade 934 from a retracted position to an exposed position moves the blade 934 into a plane containing the distal end of the central opening 930 at an angle with respect to the plane or substantially perpendicular to the plane. This plane may also be defined as the plane perpendicular to the longitudinal axis of the device or longitudinal axis of the central lumen. The amount that the blade 934 is exposed may be selected by the user to effect selective cutting. For example, the blade 934 may be exposed halfway from a completely retracted position in which case, the blade 934 may not cross the plane containing the distal end of the central opening 930. The blade 934 is configured to extend beyond the distal end of the central opening 930 of the blade carrier 926 but not beyond the distal end of the second shield 912, thereby, ensuring that the blade 934 and the blade pathway is always encompassed and surrounded by either one or more of the first shield 900, second shield 912, and blade carrier 926. In another variation, the distal end of the blade 934 is permitted to extend slightly beyond the distal end of the second shield 912.

In one variation, the blade 934 is fixed with respect to the blade receiver 932 and does not reciprocate with respect to the blade carrier 926 and only rotates with respect to the first shield 900. In another variation, the blade carrier 926 is fixed with respect to the first shield 900 in the sense that it does not rotate with respect to the first shield 900 but is configured such that the blade 934 reciprocates with respect to the blade carrier 926. The rotational cutting action aims to increase the chances that the specimen will be removed as a single extraction instead of multiple pieces while ensuring protection to the surrounding tissue. Also, the blade 934 is illustrated in the figures to curve downwardly into central opening. In other variations, the blade 934 extends radially inwardly in a plane perpendicular to the central lumen and has a configuration similar to a guillotine or cigar-cutter. It is within the scope of the present invention for the blade 934 to have an approach angle of zero to less than 180 degrees wherein a zero approach angle would be the blade 934 crossing the plane perpendicular to the longitudinal axis of the central lumen parallel to the longitudinal axis at a twelve o'clock position. An approach angle of less than 180 degrees would be the blade 934 crossing the plane that is perpendicular to the longitudinal axis from beneath the plane at approximately 5 and 7 o'clock positions.

FIG. 116 illustrates the blade 934 of the blade carrier 926. The blade 934 has a sharp tip and sharp sides configured to pierce tissue as well as to cut tissue.

Turning now to FIGS. 117-119, there is shown the shield assembly 950 including the blade carrier 926, first shield 900, and second shield 912. The blade 934 is shown connected to a blade handle 938 having motor housed inside a detachable handle extension 946. The first shield 900 includes a cutout 948 visible in FIGS. 109, 111, 117 and 118. The cutout 948 facilitates separation and removal of the blade carrier 926 from the first shield 900 by providing a location for a finger to snap the blade carrier 926 away from the first shield 900.

Turning now to FIGS. 120-126, there is shown another variation of the shield assembly. The shield assembly includes a first shield 900, a second shield 912 and a blade carrier 926. The blade carrier 926 comprises a blade receiver in two parts 932a, 932b, a blade 934, an inner rod 942, a pin 940, and a blade handle 938. The length of the blade handle 938 is not shown to scale and is drawn for illustrative purposes to include a variation where a reusable handle extension 946 can be attached to the proximal end of the blade handle 938 in a construct in which the shield assembly is disposable. The variation of FIGS. 120-126 is substantially similar to the variation shown in FIGS. 109-119 with several modifications. The second shield 912 is of a spiral nature described above instead of a cut cylinder. The second shield 912 is shown in a compressed configuration in FIG. 120. The first shield 900 includes an outer rim 908 located at the top periphery of the first shield 900. The funnel 928 of the blade carrier 926 snaps under the outer rim 908 in the variation shown in FIGS. 120-126.

In another variation of the shield, the shield is molded about a helicoid whose cross-section normal to the helical guide path is parabolic. Once taken off the mold, the helicoid is compressed upon itself into the shape of a catenoid in which it will stay during its resting state. The parametric equations below cover variations of the shield.

$$x(u,v)=\beta[\cos(\alpha)\sin h(v)\sin(u)+\sin(\alpha)\cos h(v)\cos(u)] \quad (1)$$

$$y(u,v)=\gamma[-\cos(\alpha)\sin h(v)\cos(u)+\sin(\alpha)\cos h(v)\sin(u)] \quad (2)$$

$$z(u,v)=\delta[u \cos(\alpha)+v \sin(\alpha)] \quad (3)$$

The value α is a constant, fixed parameter that changes the state of progression in the deformation of a helicoid into a catenoid. For α=0, a helicoid is generated; for α=π/2 a catenoid is generated. Variations of the shield have a value of a that is greater than 0 and less than π/2 which can be considered on the open interval of (0, π/2). Other variations of the shield have a value of a that is greater than 0 and less than or equal to π/2 which can be considered on the open interval of (0, π/2). Other variations of the shield have a value of a that is equal to or greater than 0 and less than or equal to π/2 which can be considered on the open interval of (0, π/2). The parameters β, γ, δ are also fixed constants. For β, γ, δ∈R\{0}, for β<0, γ<0, δ<0 the rotation will flow counterclockwise. If for any β, γ, δ>0 the rotation will flow clockwise. By means of the parametric equations, the surface is constructed on the u-v plane. Values for vectors u and v can be considered for u∈(-π,+π) and v∈(-∞,+∞).

Turning now to FIG. 127, there is shown another variation of a containment bag 1000 according to the present invention. The bag 1000 includes a sidewall 1002 that defines an opening 1004 at the proximal end. The bag 1000 has a longitudinal axis that is substantially perpendicular to the opening 1004. The sidewall 1002 may form any shape for the bag 1000 such as cylindrical, elongate, spherical and the like and may or may not include a base or bottom panel from which the sidewall 1002 extends towards the proximal end. The sidewall 1002 may extend downwardly to define the base with or without a seam. For example, the bag 1000 may be formed by a planar length of material that is folded and joined along the sides such that the seams are not formed along the base, but instead, are located at the sides of the bag 1000 and extend upwardly substantially perpendicular to the longitudinal axis.

Still referencing FIG. 127, the containment bag 1000 includes at least a first ring 1006 located at or near the opening 1004 of the bag 1000. The first ring 1006 is connected to the bag 1000. A second ring 1008 is shown in FIG. 127. The second ring 1008 is located a distance below the first ring 1006 and is connected to the bag 1000. The first ring 1006 and second rings 1008 are resilient and compressible from an expanded configuration that is circular or oval in shape into a collapsed elongate configuration having a reduced lateral dimension suitable for passing into a small incision, body orifice or through the lumen of a trocar. In one variation, the second ring 2008 is not employed. The bag 1000 is collapsible along the longitudinal axis of the bag 1000 to a shorter length. The collapsed bag 1000 is then subsequently easily compressed in a lateral direction by squeezing the first ring 1006 and the second ring 1008, if a second ring 1008 is employed, into their collapsed elongate configurations and deployed into the abdominal cavity. Inside the abdominal cavity, the compressed rings 1006, 1008 are allowed to return to their original expanded open configurations. With the rings 1006, 1008 in their expanded configurations inside the abdominal cavity, the bag 1000 is easily oriented within the abdominal cavity. The location within the perimeter of the rings 1006, 1008 provides a target for the placement of an excised tissue or organ. In one variation, the bag 1000 in a collapsed configuration does not have a right side up because either side can be used to place the specimen within the boundaries of the first/second rings 1006, 1008. The first ring 1006 serves as a perimeter guide for specimen placement within the perimeter of the first ring 1006 and, hence, the first ring 1006 may be brightly colored or contrast colored with the rest of the bag 1000 or its intended surroundings so that it can be easily observed with a laparoscope. After the excised tissue or organ is placed inside the perimeter of the first ring 1006, the first ring 1006 is moved towards the exit incision or orifice. The lifting of the ring 1006 results in the excised tissue moving or falling deeper into the bag's interior space 1010. Movement of the bag towards the exit opening results in the tissue specimen becoming seated within interior space 1010 of the bag 1000. The first ring 1006 is compressed into the reduced elongate configuration and pulled through the exit orifice, opening or exit incision. Once passed the opening, the first ring 1006 is allowed to self-expand and spring back to an open enlarged configuration residing above the abdominal wall or outside the patient near and overlaying the exit orifice, opening or exit incision. The first ring 1006 is rolled or flipped over itself by inverting the first ring 1006 outwardly or inwardly to roll the bag 1000 onto the first ring 1006. The first ring 1006 can be rolled in the opposite direction to unfurl the bag 1000 from the first ring 1006. In one variation, the first ring 1006 has a cross-section that has a length greater than its width. The elongate cross-section of the first ring 1006 advantageously keeps the bag sidewall 1002 rolled-up onto the first ring 1006. If the cross-section of the first ring 1006 is circular, the first ring 1006 may more easily roll and un-roll to roll or un-roll the sidewall 1002 with respect to the first ring 1006. The rolling of the first ring 1006 about itself draws the bag 1000 upwardly and brings the specimen inside the bag 1000 closer to the opening. With the rolling of the first ring 1006 the distance of sidewall 1002 between the first ring 1006 and the second ring 1008 is reduced which brings the second ring 1008 into closer proximity to the first ring 1006 resulting in the abdominal wall being anchored between the first ring 1006 and the second ring 1008 securing the bag 1000 to the patient for the ensuing morcellation. The rolling action of the bag 1000 reduces the volume of the bag 1000 and also creates a nicely-formed and taut protective apron at the opening as well as outside the patient surrounding the opening. The rolling action may also serve to retract the tissue at the opening conveniently enlarging the opening for easy tissue extraction from inside the bag 1000. The tissue specimen is then pulled from the bag 1000 by morcellating it manually with a blade or automatically with an electronic morcellator into a size and shape that can be passed through the opening and removed from the bag 1000. After the tissue specimen is extracted from the bag 1000, the first ring 1006 is unrolled loosening the space between the two rings 1006, 1008 if it is necessary to do so. Then, the second ring 1008 is compressed into its reduced elongate configuration and pulled outside of the patient through the opening and the bag 1000 is removed from patient.

The bag 1000 and/or the sidewall 1002 of the bag 1000 is made of a material that is extremely cut-resistant to sharp objects such as scalpel blades and blades used in electronic morcellators. In one variation, the bag 1000 is made of an extremely cut-resistant woven material like DYNEEMA® fiber. The cut-resistant material is an ultra-high-molecular-weight polyethylene (UHMWPE) also known as high-modulus polyethylene or high-performance polyethylene. In one variation, the bag 1000 is made of DYNEEMA® coated with an elastomer to prevent fluids from traversing the material plane. In one variation, the entire bag 1000 is made of the cut-resistant material. In another variation, only select portions of the bag 1000 are made of the cut-resistant material. In one variation, at least a portion the sidewall 1002 of the bag 1000 that is located between the first ring 1006 and the second ring 1008 is made of the cut-resistant material. In another variation, only part of the bag 1000 is made of the cut-resistant material in areas where cutting is expected. In another variation, the bottom portion of the distance between the two rings 1006, 1008 is made of the cut-resistant material, leaving the top portion of the distance between the two rings 1006, 1008 available for rolling onto the first ring 1006. In another variation, the top portion of the distance between the two rings 1006 is made of the same cut-resistant material but has a thickness or fiber thickness that is smaller than the thickness of the sidewall or fiber thickness of the bottom portion. In variations, where part of the bag 1000 is made of cut-resistant material, the other remaining portions are made of suitable polymer material described above. In one variation, use of the bag 1000 made of cut-resistant material eliminates the need for a retractor described above to be used in conjunction with the bag 1000 in a morcellating procedure. Hence, the bag 1000 advantageously not only provides cut resistance and safety shielding during morcellation but also serves to retract the opening in which it is inserted. Because the bag 1000 is cut-resistant, it may be employed without a shield/guard of the types described above. The absence of a shield or guard may advantageously provide for a larger working space.

Embodiments of the bag 1000 comprise sheets, membranes, fibers, and/or strands of one or more materials that endow the sheath with abrasion and puncture resistance in addition to cut resistance. Suitable sheets, membranes, fibers, and/or strands comprise at least one of natural polymers, semi-synthetic polymers, synthetic polymers, metal, ceramic, glass, carbon fiber, carbon nanotubes, and the like. Suitable natural polymers include cellulose, silk, and the like. Semi-synthetic fibers include nitrocellulose, cellulose acetate, rayon, and the like. Suitable synthetic fibers include polyester, aromatic polyester, polyamide (NYLON®, DACRON®), aramid (KEVLAR®), polyimide, polyolefin, polyethylene (SPECTRA®), polyurethane, polyurea, polyvinyl chloride (PVC), polyvinylidene chloride, polyether amide (PEBAX®), polyether urethane (PELLETHANE®), polyacrylate, polyacrylonitrile, acrylic, polyphenylene sulfide (PPS), polylactic acid (PLA), poly(diimidazopyridinylene-dihydroxyphenylene) (M-5); poly(p-phenylene-2,6-benzobisoxazole) (ZYLON®), liquid crystal polymer fiber (VECTRAN®), and the like, and blends, copolymers, composites, and mixtures thereof. Suitable metals include stainless steel, spring steel, nitinol, super elastic materials, amorphous metal alloys, and the like. The bag 1000 includes retractor integration providing both specimen containment and tissue retraction features. Additional retraction features and materials and construction that are incorporated into the bag 1000 in variations of the present invention are described in U.S. Patent Application Publication 2011/0054260A1 which is incorporated herein by reference in its entirety.

Currently available morcellators generally cut tissue with an exposed, unprotected device such as a sharp blade or energy tip in the body cavity. For most morcellators this causes added danger because the exposed blade/tip could easily contact unintended areas causing damage to organs, tissue, vessels, etc. Since current morcellators sever tissue in open areas, it's possible for smaller pieces of cut tissue to be left behind after the tissue removal procedure. These pieces can lead to endometriosis in females where uterus cells attach themselves to other organs or tissue walls. The pieces can also contain cancer cells which must be completely removed. Currently, if tissue is expected to be cancerous then the entire mass is removed openly instead of laparoscopically which increases the risk of infection for the patient, as well as increased recovery time. Even if all the pieces are found, there is still an increase in surgery time due to the extra step of searching the body cavity for the smaller members of tissue. Furthermore, current morcellators require two people to perform the procedure. One person pulls the tissue through the morcellator with a tenaculum while another person has to hold the remaining tissue mass close to the tip of the rotating blade from inside the body cavity. As the procedure is performed the specimen is usually dropped or tears away from the instrument holding it in place during morcellation. This causes added time as the person in charge of positioning the specimen in front of the morcellator has to find the tissue and re-clamp their instrument to it before placing the specimen in front of the morcellator again. Hence, morcellation in containment such as a bag is desirable; however, the bag itself is subject to potential puncture and spilling of contents. The specimen bag of one variation of present invention has a protective inner layer of material to resist punctures from the tenaculum jaws and rotating morcellator blade. Also, since the morcellator is locked into a stationary position with the use of any of the aforementioned stabilizers, the likelihood of the blade contacting the bag is greatly reduced. With a specimen bag, the entire tissue sample will be contained so even if small pieces fall off from the larger specimen during morcellation they will be removed when the bag is pulled out of the patient. This increases patient safety and reduces surgery time for the morcellation procedure since there is no need to search for left behind tissue pieces. The specimen bag will support the tissue and keep it in place. This allows one person to perform the morcellation procedure instead of two. It also reduces time required to continually relocate and re-clamp the specimen.

With reference now to FIGS. 128-134, the tissue morcellator 3000 is a multi-component medical device used to capture tissue specimens such as a uterus inside the human body under laparoscopic surgical conditions and reduce it in size for removal though small incisions, orifices, openings that may or may not include laparoscopic ports. The morcellator 3000 includes a gear housing 3016 containing a gear train, as can be seen clearly in FIG. 133, connected to a flexible transmission shaft 3018 connected at the proximal end to a motor to turn the morcellator blade 3010. The morcellator 3000 has a central working channel lumen 3020 that extends through the length of the morcellator 3000. The inner and outer tubes of the morcellator 3000 are stationary and non-rotating relative to the moving blade 3010 to provide no moving surfaces against the tissue as it is being removed through the lumen 3020. In one variation, the morcellator 3000 includes a camera 3022. The camera 3022 may be integrally formed with the rest of the morcellator 3000 or comprise a separate add-on that slides over the morcellator shaft and connects to the morcellator 3000 as shown in FIG. 134. As also seen in FIG. 132 the distal end of the morcellator shaft includes a fixed protruding appendage that covers at least part of the blade extending distally to interrupt the morcellation of tissue to prevent tissue from rotating relative to the instrument.

Still referencing FIGS. 128-134, the morcellation system further includes a tenaculum 3012 having an elongated shaft 3028, a jaw-like grasper at the distal end controlled at a handle 3024 at the proximal end to open and close the jaws 3026 to grasp tissue. The shaft 3028 and jaws are configured to fit inside the working channel 3020 of the morcellator 3000 and extend and protrude out the distal end of the morcellator shaft. The tenaculum handle 3024 is designed to be held vertically in either the left or right hand and the ergonomic design is meant to optimize the movement of the hand and arm pulling upwards. The handle 3024 includes a lever 3030 that is squeezed toward the handle 3024 to close the jaws 3026 as shown in FIG. 129. Alternatively, the lever 3030 may be squeezed to open the jaws 3026. The lever 3030 is under spring tension so that the lever 3030 springs open away from the handle 3024 which may define the closed configuration of the jaws 3026 allowing the user to then focus on pulling the tenaculum 3012 upwardly to extract tissue. Alternatively, the trigger is under spring tension so that the lever 3030 will spring away from the handle 3024 to open the jaws 3026.

With particular reference now to FIGS. 130-132, the tenaculum jaws 3026 include a distal tip 3032 that is curved. The jaws 3026 include an upper jaw and a lower jaw hinged together. Each of the upper and lower jaw includes a rounded and curved distal end that does not have any sharps along a curve that is traced by the distal end 3032 in the opening and closing of the jaws 3026. In a closed configuration shown in FIGS. 130-131, the curved distal tip 3032 presents no exposed sharp points or edges that may pose a danger to tissue or bag integrity when in an open or closed configuration. The inside of the upper and lower jaws includes teeth 3034. Also, the distal tip 3032 includes interlocking teeth 3034 from the upper and lower jaw that providing a positive purchase on grasped tissue while providing a smooth curved outer surface to protect any surrounding tissue and/or bag. FIG. 132 illustrates the jaws 3026 in an open configuration showing the pathway 3036 followed by the distal end 3032 in the opening and closing of the tenaculum. The curved distal end 3032 advantageously protects the bag in which morcellation is taking place from being punctured as tissue is grasped. Even when the jaws 3026 are fully opened the curved distal end 3032 of the jaws are capable of protecting the bag from unwanted punctures.

Turning now to FIGS. 135A-135D and FIGS. 136A-136B, the morcellation system includes a specimen retrieval receptacle bag 3002. The morcellation system described may be adapted for use with a power morcellator as described above or can also be employed with manual morcellation. The bag 3002 is shown flat in FIG. 135A and rolled up in FIGS. 135B and 135C. The bag 3002 includes a bag ring 3004 that encompasses the opening or mouth of the bag 3004. FIG. 136A illustrates a tissue specimen 3006 captured inside the bag 3002 with the bag ring 3004 being pulled to the outer surface. FIG. 136B illustrates the bag ring 3004 pulled completely through the body opening to expose the interior of the bag 3002 to the exterior of the body for removal of the specimen 3006 inside the bag 3002. In FIG. 136B, a tissue guard 200 is shown ready for insertion into the body opening. Although, the tissue guard 200 is shown any tissue guard according to the present invention may be employed.

With reference to FIGS. 137A-137C and FIGS. 138A-138C, another variation of the bag 3002 is shown. The bag 3002 includes a bag ring 3004 having an elongated cross-section such as the cross-section shown in FIG. 137C. The bag 3002 of FIGS. 137A-137C is configured to be rolled down to wrap the sidewall of the bag 3002 around the bag ring 3004. FIG. 138A illustrates a bag 3002 with a specimen of tissue 3006 inside its interior. The bag ring 3004 is being pulled through the body opening to the surface of the body. FIG. 138B illustrates the bag ring 3004 completely pulled to the surface and FIG. 138C illustrates the bag ring 3004 being rolled or flipped about itself as shown by the arrows in FIG. 138C and as previously described in this specification to reduce the length of the sidewall of the bag and bring the contents of the bag closer to the surface where it can be more easily morcellated. The bag ring 3004 is not limited to having the cross-section of FIG. 137C and any cross-section that permits the bag to be rolled about the bag ring is within the scope of the present invention. The bag ring 3004 is both flexible so as to be capable of being squeezed and compressed into an elongate shape so that it can be inserted and removed through a small incision or body opening. The resilient bag ring 3004 expands when released to assume its open mouth configuration enabling easy placement of specimen 3006 into the interior of the bag 3002. The bag 3002 has an open top with a semi-rigid bag ring 3004 attached at the top at or near the mouth of the bag 3002. The bag 3002 can be deployed into the body such as into the abdomen via a trocar or other deployment instrument. The bag 3002 can be manipulated with graspers. The specimen 3006 is loaded into the bag 3002 and the bag 3002 is retrieved through the body wall 3056 such as the abdominal wall. The entire bag 3002 does not pass through the small laparoscopic incision due to the large size of the specimen 3006. The semi-rigid bag ring 3004 is the only portion that is allowed to surface with the rest of the bag remaining inside the abdominal body cavity. The cross-section of the semi-rigid ring allows for the bag 3002 to be shortened by a rolling method. This not only shortens the bag 3002 but helps in wound retraction. The tissue 3004 sample acts as an anchor to allow retraction of the wound opening allowing greater access to the tissue 3006 with power or manual morcellation instrument(s). Once the bag 3002 is in place, morcellation can begin. As the tissue sample 3006 decreases in size the semi-rigid bag ring 3004 can be rolled more to bring the tissue 3006 closer to the surface and allow easier access for morcellation. Once enough of the tissue 3006 is removed, the bag 3002 can then be withdrawn from the patient. FIG. 138C, illustrates a tissue guard 200 ready to be inserted into the body opening and into the bag 3002.

With reference to FIGS. 139A-139C, the bag 3002 is connected to a delivery shaft 3038 configured to open and close the mouth of the bag 3002. The delivery shaft 3038 is used to conveniently scoop the specimen 3006 when in an open mouth configuration. The delivery shaft 3038 is manipulated to close the mouth of the bag 3002 after the specimen 3006 has been captured to bring the bag ring 3004 through the opening in the body and to the surface for morcellation and removal of the specimen 3006. The bag 3002 has an open top with a semi-rigid bag ring 3004 attached at the top. The bag 3002 is attached to a two fork shaft 3038. The forks are made of a semi-rigid material such as spring steel. The purpose of the delivery shaft 3038 is to allow the bag to be manipulated with greater accuracy and ease. The system can be deployed into the abdomen via a trocar cannula 3044. The specimen 3006 is loaded into the bag 3002 and the bag 3002 is retrieved through the abdominal body wall 3056. To retrieve the bag 3002 the forked shaft 3038 is pulled through the trocar cannula 3044 until the corner of the bag 3002 is leading into the distal tip of the trocar cannula 3044. Once the bag 3002 has engaged the trocar cannula 3044, the bag 3002 can be drawn up to the surface through the wound opening. The entire bag 3002 does not pass through. The semi-rigid bag ring 3004 is the only portion that is allowed to the surface. Once at the surface the forked deliver shaft 2038 can be removed from the semi-rigid bag ring 3004. The cross-section of the semi-rigid bag ring 3004 allows for the bag 3002 to be shortened by a rolling method. This not only shortens the bag 3002 but helps in wound retraction. The tissue sample 3006 acts as an anchor to allow retraction of the wound opening allowing greater access to the tissue 3006 with morcellation instruments. Once the bag 3002 is in place, morcellation can begin. As the tissue sample 3006 decreases in size the semi-rigid bag ring 3004 can be rolled more to bring the tissue 3006 closer to the surface and allow easier access for the morcellation instruments and blades. Once enough of the tissue 3006 is removed the bag 3002 can then be withdrawn from the patient. In an alternative arrangement, the bag 3002 is provided with a second bag ring 3040. The second bag ring 3040 is attached to the bag 3002 approximately mid distance down the bag 3002. This second bag ring 3040 serves as an anchor to allow the bag 3002 to be shortened while simultaneously retracting the wound to its largest potential opening. The bag 3002 is attached to a two fork delivery shaft 3038. The forks are semi-rigid. With the first bag ring 3004 residing outside the patient, the first bag ring 3004 is rolled/flipped about itself. The cross-section of the semi-rigid first bag ring 3004 allows for the bag 3002 to be shortened by a rolling method. This not only shortens the bag 3002 but helps in wound retraction. The second bag ring 3040 that is midway down the bag 3002, acts as an anchor to allow maximum retraction of the wound opening. This allows greater access to the tissue 3006 with the various morcellation instruments. Once the bag 3002 is in place, morcellation can begin. Once enough of the tissue 3006 is removed the bag 3002 can then be withdrawn from the patient.

Turning now to FIGS. 140A-140B and 141A-141D, there is shown another variation of the bag 3002 according to the present invention. The bag 3002 includes a sidewall defining an interior and a mouth. A first bag ring 3004 and a second bag ring 3040 are provided. The second bag ring 3040 is spaced distally apart from the first bag 3004 and interconnected by the sidewall. The bag 3002 includes a balloon 3042 located at the bottom of the bag 3002. The balloon 3042 forms at least part of the base of the bag and has a deflated condition and an inflated condition. The interior of the balloon 3042 is interconnected to a source of inflation pressure providing positive pressure into the balloon 3042. The source of inflation pressure may also provide a negative pressure to remove inflation fluid to deflate the balloon 3042 as desired by the user. The source of inflation pressure is actuated by the user manually or automatically. The balloon 3042 at the base of the bag 3002 is spaced distally from the second bag ring 3040 as shown in FIG. 140A. FIG. 141A illustrates the bag 3002 inserted into the body through a body wall 3056 with the first bag ring 3004 pulled to reside outside the body to provide access to the interior of the bag 3002 such that the specimen 3006 located therein may be extracted from the bag 3002. FIG. 141B illustrates the proximal end and mouth of the bag 3002 being pulled until the second bag ring 3040 substantially engages the undersurface of the body wall 3056. FIG. 141C illustrates the first bag ring 3004 being rolled about itself to wrap the sidewall of the bag 3002 around the first bag ring 3004. As the first bag ring 3004 is being rolled, the length of the sidewall located between the first bag ring 3004 and the second bag ring 3040 is reduced. Such reduction in the length of the sidewall brings the base of the bag 3002 and the specimen located inside the bag 3002 closer to the surface opening in the body. FIG. 141D shows the balloon 3042 in the inflated condition which further raises the specimen 3006 closer to the opening for ease of visualization, morcellation and removal. The balloon 3042 advantageously provides an added protective interface or barrier between the interior and the exterior of the bag 3002. For example, if a morcellation instrument such as a scalpel, power morcellator or grasper accidentally breaches the proximal end of the balloon 3042 that is facing the interior of the bag 3002, the balloon 3042 may deflate but the overall integrity of the bag 3002 is not breached as a containment barrier to the exterior or sidewall of the bag remains intact. In essence, the balloon 3042 provides a double-wall that provides added protection in a location of the base which is likely to encounter sharp instruments in the course of morcellation. The inflatable base of the bag 3002 also provides a pedestal effect for the tissue specimen 3006 even if the tissue 3006 is not centrally located atop the balloon 3042. Also, the inflatable base of the bag 3002 when in the inflated condition provides a moat-like location for bodily fluid such as blood to drain away from the specimen 3006. When inflated, the balloon 3042 interior wall is spaced significantly further apart from the exterior wall in the double-wall arrangement of the base, thereby, keeping the exterior wall safely away from impinging instruments and more likely to remain intact in the case of a breach in the interior wall. The double-wall sidewall may be employed throughout the bag 3002 and not just in the location of the base. Breach and the resulting subsequent deflation of the balloon 3042 provides visual notice to the user that a sharp instrument has impinged the balloon and alerts the user to employ extra care to ensure safety of the exterior wall when continuing with the extraction. This is in contrast to a single-walled configuration in which a breach of the sidewall means a breach to the exterior of the bag 3002 without warning. After the specimen 3006 is raised to the surface, the specimen 3006 can be easily visualized from outside the body through the mouth of the bag 3002 and morcellation can proceed more easily. The balloon 3042 can be any inflatable member and can be integrated into the floor of the bag 3004. As morcellation is carried out, the tissue is reduced in size. This can result in the specimen becoming lost in the bag 3002 and harder to find with the morcellator and instruments. By inflating the balloon 3042, the tissue 3006 is raised up closer to the end of the morcellator and instruments allowing greater ease of access to the tissue sample 3006.

Turning now to FIGS. 142A-142C and 143A-143D, there is shown another variation of a containment bag 3002 having an inflatable sidewall. The bag 3002 has a sidewall formed to have an open top serving as a mouth or entryway into the interior of the bag 3002. The bag 3002 includes a first semi-rigid bag ring 3004 attached at the top near the opening. There is also a second bag ring 3040 that is attached approximately mid distance down the bag 3002. The second bag ring 3040 serves as an anchor to allow the bag 3002 to be shortened and retract the wound to its largest potential opening. The bag 3002 utilizes air channels 3008 to aid in expanding the lower portion of the bag 3002 that contains the specimen. By expanding the lower portion the visibility of the specimen from the top side is greatly increased. It also aids in the speed at which morcellation can be carried out. The bag 3002 is attached to a two fork delivery shaft 3028. The forks are semi-rigid. The purpose of the delivery shaft 3028 is to allow the bag 3002 to be manipulated with greater accuracy and ease. The system can be deployed across a body wall 3056 into the abdomen or other location or orifice of the body. The tissue specimen 3006 is loaded into the bag 3002 and the bag 3002 is retrieved through the abdomen body wall. To retrieve the bag 3002 the forked shaft 3028 is pulled through the trocar until the corner of the bag 3002 is leading into the trocar. Once the bag 3002 has engaged the trocar, the bag can be drawn up to the surface as shown in FIG. 143A. Once at the surface, the forked shaft can be removed from the first semi-rigid bag ring 3004. The entire bag 3002 does not pass through. The semi-rigid first ring 3004 and part of the sidewall is allowed to surface. The cross section of the semi-rigid first ring 3004 allows for the bag 3002 to be shortened by a rolling method illustrated by the arrows in FIG. 143C. This not only shortens the bag 3002 but helps in wound retraction as shown in FIG. 143C. The second bag ring 3040 that is midway down the bag 3002, acts as an anchor to allow maximum retraction of the wound opening. This allows greater access to the tissue 3006 with the morcellator. The bag 3002 serves both containment and retraction functions. Once the wound has been retracted, the air channels 3008 can be inflated as shown in FIG. 143D and an optional tissue guard 200 may be employed. The air channels 3008 will expand outward creating free space around the tissue 3006. This allows the tissue 3006 to be in more of a free space. By being in more of a free space, the tissue 3006 can tumble and move as it is being morcellated. Once the bag is in place, morcellation can begin. Once enough of the tissue 3006 is removed, the bag 3002 can then be withdrawn from the patient. In an alternative variation, the base of the bag 3002 may be also inflatable such as described with respect to FIGS. 140-141.

Turning now to FIGS. 144A-144C and 145A-145D, there is shown another variation of a containment bag 3002 having an inflatable sidewall without a second bag ring 3040 and only a first bag ring 3004. The bag 3002 has an open top with a semi-rigid first bag ring 3004 attached at the top. The bag 3002 utilizes air channels 3008 to aid in expanding the lower portion of the bag 3002 that contains the specimen 3006. The air channels 3008 are circumferentially located around the bag perimeter at the lower portion of the bag. The air channels 3006 are interconnected and connectable to a source of inflation pressure. Positive inflation pressure inflates the channels and negative pressure acts to actively deflate the channels 3008. A deflated configuration is shown in FIG. 145A and an inflated configuration is shown in FIG. 145B-145D. In one variation, the air channel closest to the opening of the bag which is the proximal-most air-channel, is annular and is larger than the other air channels. The air channels 3008 are tubular ring-shaped lumens that may be fluidly connected with one or more adjacent tubular ring-shaped lumens and configured to be connectable to a source of inflation fluid. This proximal-most, first annular ring-shaped air channel lumen provides a reaction force on the underside of the abdominal wall to allow greater retraction as the upper bag ring 3004 is rolled down causing retraction. Therefore, the first annular ring-shaped lumen acts similarly to the second bag ring 3040 of the previous variation. Also, by expanding the lower portion the visibility of the specimen 3006 from the top side is greatly increased. It also aids in the speed at which morcellation can be carried out. The bag 3002 is attached to a two-fork delivery shaft 3038. The forks are semi-rigid. The purpose of the delivery shaft 3038 is to allow the bag to be manipulated with greater accuracy and ease. The system can be deployed into the abdomen body via a trocar. The specimen 3006 is loaded into the bag 3002 and the bag 3002 is retrieved through the abdomen body wall. To retrieve the bag 3002 the forked shaft is pulled through the trocar until the corner of the bag is leading into the trocar. Once the bag 3002 has engaged the trocar the bag can be drawn up to the surface. The entire bag does not pass through. The semi-rigid bag ring 3004 and a portion of the bag sidewall is the only portion that is allowed to surface as shown in FIGS. 145A-145D. Once at the surface the forked shaft can be removed from the semi-rigid bag ring 3004. The cross section of the semi-rigid bag ring 3004 allows for the bag 3002 to be shortened by a rolling method shown by the arrows in FIG. 145D. This rolling action not only shortens the bag 3002 by rolling the sidewall of the bag up but helps in wound retraction. The bag 3002 is then inflated. The bag 3002 may also be inflated prior to rolling as shown in the figures. The first annular air channel 3008 that is approximately midway down the bag and acts as an anchor to allow maximum retraction of the wound opening. This allows greater access to the tissue with the morcellator. The air channels 3008 will expand outward creating free space around the tissue 3006. This allows the tissue 3006 to be in more of a free space. By being in more of a free space, the tissue 3006 can tumble and move as it is being morcellated. Once the bag 3002 is in place, morcellation can begin. Once enough of the tissue 3006 is removed, the bag 3002 can then be withdrawn from the patient. In an alternative variation, the base of the bag 3002 may be also inflatable such as describe with respect to FIGS. 140-141.

Many different types of materials can be used for the bag and semi-rigid ring. Multiple materials may be desirable on the same bag such as hybrid between polymers and woven textiles. The semi-rigid ring can be made from a multitude of flexible polymer materials including but not limited to pellethane, silicone, KRATON polymer, IROGRAN polyester-based thermoplastic polyurethane, metal, polymer, plastic, rubber, and the like.

Any of the containment bags described in the present invention, including inflatable bags 3002, can be used with a guard or shield configured for placement within the bag 3002 to protect the bag sidewall and the adjoining tissue margin from sharp manual or power morcellation instruments. Additional examples of guards are shown in FIGS. 146-148. FIGS. 146A-146B, illustrate a cylindrical rigid guard 3047 having a circular-shaped proximal end 3048 and an outwardly flared funnel-like distal end 3050. The funnel-shaped guard 3047 acts to concentrate or funnel the tissue toward the cutting blade blade. The central lumen of the guard 3047 enlarges in the distal direction. The funnel shape also assists in spreading the sidewall of the bag 3002 away providing clearance for morcellation and prevents the specimen bag from engaging the blade. The guard 3047 may also include a spring loaded guard feature that prevents the blade from being exposed unless the tissue is engaged. This makes for safer handling of the morcellator. The blade guard can be adapted to work with the spring loaded guard.

With reference to FIGS. 148A-148B, the guard 3047 has a reversed funnel at the distal end or lead-in guard wherein the central lumen decreases towards the distal end 3050. The lead-in guard 3047 allows for easier coring of tissue 3006. The blade guard 3047 is cone-shaped with the narrow end 3050 pointing in the same direction as the leading edge of the blade of the morcellation tool. The guard 3047 pushes the surrounding tissue away and to the side once the blade is engaged with the tissue 3006.

Turning now back to FIGS. 147A-147B, there is shown another variation of the guard 3047 that includes anti-rotation studs 3052 that extend from the inner surface of the guard 3047 into the central lumen. The inwardly-projecting anti-rotation studs 3052 keep lumped mass tissue 3006 from catching in the rotating blade and rotating tube and spinning together when a power morcellator is used. If the tissue 3006 is spinning with the blade, then there is no relative blade movement; therefore, it will not cut the tissue. The anti-rotation studs 3052 can also be located on the outside of the guard 3052 extending outwardly from the outer surface of the guard 3047. These projections would arrest rotation of the guard 3047. The anti-rotation studs 3052 on the inside also help guide and lead tissue 3006. The studs 3052 can have various shapes and sizes. This feature can be adapted to work with every guard. In another variation, a bipolar perpendicular tissue separator may be included with the guard. The bipolar perpendicular tissue separator feature functions to sever cores of tissue from the lump mass. This alleviates the problem of coring and not being able to separate the morcellated core from the large mass. This feature can be adapted to work with every blade guard. Also, a light may be included with the guard 3047 and integrally formed with it. The purpose of the light source such as a LED is to enhance and improve visibility inside the tissue bag 3002 for greater scope visibility. This feature can be adapted to work with every blade guard. The variation of FIGS. 147A-147B further includes a plurality of holes 3054 extending across the guard 3047. These holes 3054 serve as vacuum bypass holes 3054 configured to prevent the bag 3002 from being drawn into the blade when vacuum is employed to draw tissue 3006 out of the bag 3002 such as with a vacuum power morcellator system. This is achieved by always having a radial hole 3054 exposed around the guard 3047. Once tissue is engaged with the blade the vacuum bypass holes will not affect the vacuum interface with the tissue. This feature can be adapted to work with every blade guard used under vacuum.

Morcellation is performed manually by the surgeon with a scalpel or electrosurgical instrument. Instead of utilizing a power morcellator, any bag variation described herein is employed with manual morcellation. The bag is inserted into the body cavity through an incision. Target tissue is placed into the bag and the opening of the bag is pulled through the incision. A bag guard of the like described herein is inserted into the bag and retained near the bag opening and optionally connected to the proximal end of the bag such that the bag opening is kept in an open position. The surgeon grasps the tissue with a grasper and pulls it toward the opening and into the location of the guard. Then, the surgeon uses a scalpel instead of a power morcellator to cut the tissue into smaller pieces and pull them out of the body. The cutting is performed in the location of the guard and/or against the guard so that the bag is not accidentally perforate by the scalpel. The bag with smaller pieces of tissue or no tissue at all is removed from the body cavity along with the bag guard.

The system includes a specimen retrieval receptacle bag 3002 attached to a shaft. The bag 3002 can be deployed inside the body and capture the desired tissue 3006 after it has been detached. Once the specimen 3006 has been placed inside the bag 3002, there is a semi-rigid ring 3004 attached to the bag opening that can be pulled outside of the body through the laparoscopic wound, incision, opening, orifice access site. After the bag opening ring 3004 has been pulled outside the patient, the lower bag portion that remains in the body cavity with the specimen 3006 contains air channels 3008 that are inflated to create a structure which counteracts the internal pneumoperitoneum pressure and provides an internal anchoring mechanism for the bag 3002. Then the outer bag opening ring 3004 can be rolled down to retract the wound opening in the same manner as described above. The inflated portion of the bag 3002 that remains inside the body cavity with the specimen 3006 is now exposed to the surface. Once the specimen bag 3002 is retracted in place, the morcellator device 3000 with a center, hollow, spinning blade tube 3010 is attached to the bag opening ring. The morcellator 3000 is locked into a stationary position with the blade tube 3010 inserted down through the wound and into the lower area of the bag 3002 where the specimen 3006 is located. At that point the morcellator 3000 is turned on to allow the blade tube 3010 to rotate. Once the tube 3010 is rotating a tenaculum 3012 is inserted through the hollow blade tube 3010 to grasp the tissue and pull it up into the spinning blade 3010 which reduces the large specimen 3006 into smaller core pieces that can be removed through the small laparoscopic wound site. The morcellator 3000 also contains a camera 3014 at the distal tip of the morcellator 3000 for visualization inside the specimen bag 3002. When the tissue 3006 has been completely removed or reduced enough in size to pull through the wound site, the morcellator 3000 is detached from the bag ring, the bag 3002 is deflated, and then finally the bag 3002 is pulled through the laparoscopic wound completing the procedure.

Turning now to FIG. 149, there is shown a system including a power morcellator 4000 and bag 4002 connected to the side of the morcellator shaft 4004. With additional reference to FIGS. 150A-150D, the morcellator 4000 includes a handle 4006 connected to the shaft 4004 with one or more rotating blades 4008 at the distal end of the shaft 4004. The morcellator 4000 further includes a motor 4010 located in the handle 4006. The motor 4010 is connected to and configured to rotate a gear pinion 4012. The gear pinion 4012 is further connected to a gear train including a gear inner tube 4014 and a gear outer tube 4016. The gear outer tube 4016 is further connected to a spacer 4018 which is in turn connected to an outer shaft 4020. The distal end of the outer shaft 4020 is connected to a blade 4008. The gear inner tube 4014 is connected to an inner shaft 4026 which in turn is connected to a second blade 4022. The gear outer tube 4016 and gear inner tube 4014 are configured to rotate in opposite directions to create counter-rotating blades at the distal end. With counter rotating tubes there are two tubes. One tube is inside the other. The inner tube is rotating in one direction and the outer tube is rotating in the opposite direction. In one variation, the blade is attached to the end of the outer tube. The concept of counter rotating tubes is to double the relative velocity that the tissue experiences when compared from the perspective of the blade. Every tube configuration can have an outer most tube that retains a blade guard configuration. In another variation, the inner tube is stationary with a rotating outer tube. The outer tube has the blade attached at the end and is allowed to rotate. The concept of a stationary inner tube is to create a slick member that will allow for easier tissue advancement up the working channel. In another variation, a single outer tube rotates and there exists only one tube with the blade attached at the end. The inside of the tube is featureless and smooth. In another variation, there are three tubes in which the inner tube and outer tube are stationary and a middle tube rotates. The blade is attached to the end of the middle rotating tube and protrudes past the inner and outer tubes. The stationary outer tube is to protect anything from being rubbed by the rotating middle tube. The stationary inner tube is to facilitate easier tissue advancement up the tube. In another variation, a riffled tissue advancement tube is provided in a configuration for any tube that is rotating and has unobstructed contact with the tissue on its inside surface. A riffling pattern is formed on the inside surface of the rotating tube which places an axial force on the morcellated tissue causing it to advance upward away from the blade. In yet another variation, an auger-type tissue advancement tube is provided for any rotating inner tube configuration. The tube has multiple flutes traveling the length of the inside of the tube. The ends of the flutes grab the tissue and advance it up the flutes away from the blade. As can be seen in FIG. 150C, counter rotating tubes 4020, 4026 are driven from a single gear 4012 and over molded seals or quad ring seals 4046 are provided to seal them as shown in FIG. 150B. The entire electric motor is enclosed in the handle 4006 and may be powered by a battery or connected to an external power source.

A spring loaded blade guard 4024 operates to cover and uncover the blades 4008, 4022 and a trigger 4028 operates to activate the motor 4010. The spring loaded blade guard 4024 operates to only allow the blades 4008 to be exposed once tissue is contacting the end of the blade guard for added safety. The blade guard 4024 shaft with opening(s) and proximal knob may be detachable and the blade guard 4024 may be non-rotating. The inner and outer shafts 4026, 4020 are concentric and define a working channel 4030 down the middle. At the proximal end, a conical funnel 4032 is provided for easing the insertion of instruments such as graspers into the working channel 4030. The proximal end of the morcellator 4000 may also be adapted for connection to a specimen receptacle 4034, shown in FIG. 151, and a vacuum source for the extraction of morcellated specimen. The specimen receptacle 4034 is a transparent container that includes an inlet port 4038 and a port 4040 for connecting to a vacuum source located on the removable lid. The port 4040 for connected to a vacuum source may include a valve to turn the vacuum on or off and may be configured to be activated electronically. The proximal end of the morcellator 4000 may also be adapted for connecting with a seal assembly 4042 as shown in FIG. 150D. The seal assembly 4042 may include a zero seal and a septum seal for sealing against an inserted instrument into an opening at the proximal end of the seal assembly 4042. The seal assembly 4042 may further include a port 4044 for connection to a source of fluid under pressure. The blade guard 4024 includes at least one lateral slot or side window opening 4036 configured to expose the blades through the side for receiving tissue to be morcellated through the side of the morcellator 4000 and into the working channel 4030. The blade guard 4024 can be rotated or retracted to cover and close the side opening or to expose the blades at the distal opening for receiving tissue to be morcellated into the working channel 4030 at the distal end opening.

Turning now to FIG. 152, a bag 4002 configured for attachment to a morcellator shaft 4004 having a side opening 4036 will now be described. In one variation of the bag 4002, the bag 4002 has an open top 4048 with a means for closure 4050. The morcellator shaft 4004 has a rounded end and is adapted for connection with the bag 4002. The side of the morcellator shaft 4004 has a windowed opening 4036. The specimen retrieval system is introduced into the body via a trocar, for example, or via an open wound or body orifice. The bag 4002 is then opened and the tissue specimen is placed into the bag 4002. The bag 4002 is then sealed with the closure means 4050. The morcellator shaft 4004 may be attached to the morcellator 4000 and morcellation begins. Alternatively, a bag tube 4066 is provided and the morcellator 4000 is easily attached to the bag tube 4066 by sliding the morcellator shaft 4004 into the bag tube 4066 as shown in FIGS. 152 and 159. The bag 4002 may be pre-attached to the bag tube 4066. Once the specimen is reduced the specimen retrieval system is withdrawn from the patient. An example of a morcellator is described in U.S. patent application Ser. Nos. 12/102,719 and 13/659,462, filed Apr. 14, 2008 and Oct. 24, 2012, respectively, and incorporated by reference in their entireties as if set forth in full herein.

Turning now to FIGS. 153-157, various bag closure means will be described. In FIGS. 153A-153B, a drawstring 4052 located at the bag top 4048 is employed to close the open top 4048. In FIGS. 154A-154B, a zip-lock or zippered-style 4054 closure is provided in which a slider can be used to lock and unlock two sides of the closure means to open and close the top 4048. In FIGS. 155A-155C, another closure means includes a grommet 4056 formed in the bag 4002 near the bag top 4048. A grasper 4058 or other instrument is inserted into the grommet 4056 opening and then twisted as shown in FIG. 155C to roll the bag 4002 down and close the open top 4048. In FIGS. 156A-156B, the top 4048 is provided with a hook-and-loop type fastener 4060. The opposite sides of the hook-and-loop type fastener are contacted to close the open bag top 4048. In FIGS. 157A-B, the bag top 4048 includes a plurality of grommet openings 4062. In particular, four openings 4062 are provided. An instrument such as a grasper 4058 is used to grasp all of the openings 4062 and then twisted to roll the opening closed as shown in FIG. 157B.

In order to protect the bag 4002 and prevent it from entering the lateral slot 4036 on the morcellator shaft 4004 and making contact with the rotating blade 4008, a plastic guard 4064 is provided as shown in FIGS. 158A-158E. The plastic guard 4064 is made of one piece of semi-rigid plastic and configured to fold and be inserted into the morcellator slot 4036. The plastic guard 4064 is made of material stiffer than the bag 4002 and configured to surround the lateral opening 4036 and provide a trough-like or funnel like opening to spread the bag 4000 away from the opening 4036. The bag 4002 is attached to the distal end of the morcellator shaft 4004. The bag 4002 has an open top 4048 with a means for closure 4050. The bag 4002 also has a semi-rigid structure at the lateral opening 4036 of the morcellator shaft 4004 to allow the tissue to be loaded into the bag 4002 more easily. The specimen retrieval system is introduced into the body via a trocar or open wound or orifice or other delivery mechanism. The bag 4002 is then opened and the tissue specimen is placed into the bag 4002. The bag 4002 is then sealed via the closure means 4050. The morcellator 4000 is attached to the proximal end of the morcellator shaft 4004 and morcellation begins. Alternatively, a bag tube 4066 is provided and the morcellator 4000 is easily attached to the bag tube 4066 by sliding the morcellator shaft 4004 into the bag tube 4066 as shown in FIG. 159. The bag 4002 may be pre-attached to the bag tube 4066 with or without a plastic guard 4064 or reinforced rigid section near the distal opening of the bag tube 4066. The morcellator shaft 4004 and the bag tube 4066 are held together by friction via a knob that is attached to the bag tube 4066. The knob interferes with the morcellator handle in a snap or friction fit engagement. Once the specimen is reduced the specimen retrieval system is withdrawn from the patient. The semi-rigid structure of the guard 4064 can be made of spring steel, nitinol or molded plastic. All three variations in the material would permit closure of the bag 4002 by using a drawstring method or pinching the ends and rolling the structure to close the bag 4002. In another variation shown in FIG. 160, the bag 4002 is attached to a bag tube 4066. The bag 4002 has closed ends. The opening 4068 of the bag 4002 is on the side of the bag 4002. The bag 4002 also has a semi-rigid structure at the opening to allow the tissue to be loaded into the bag more easily. The bag tube 4066 has a rounded end. The side of the bag tube 4066 has a windowed section 4070. The specimen retrieval system is introduced into the abdomen body via a trocar or open wound. The bag 4002 is then opened and the tissue specimen is placed into the bag 4002. The bag is then sealed, the morcellator 4000 is attached and morcellation begins. Once the specimen is reduced the specimen retrieval system is withdrawn from the patient. The side opening 4068 can include a reinforcement of spring steel, nitinol or molded plastic located mid-sidewall of the bag 4002. The side opening 4068 springs open to an oval shape to facilitate easier tissue insertion of the specimen into the bag 4002. All three variations in the material would close the bag by using a drawstring method or pinching the ends and rolling the structure to close the bag 4002. In another variation, spring steel, nitinol or molded plastic is located near the bag tube 1066 as shown in FIG. 161.

In another variation shown in FIGS. 162A-162C, the bag 4002 is a separate component from the bag tube 4066. The bag 4002 has two open ends 4072, 4074. One opening 4072 is larger than the other. The larger end 4072 is semi-rigid by means of spring steel, nitinol or a plastic member. Different means for closure 4050 such as a drawstring 4052 or pinch and roll down method can be used to seal the large end 4072 of the bag 4002. The smaller end 4074 has a spring steel or nitinol clamp 4076 that attaches to the bag tube 4066. The clamp 4076 attaches around the rigid blade guard 4064. The taper of the rigid blade guard 4064 helps the clamp 4076 to seat on the rim and keep from sliding off the bag tube 4066. The bag tube 4066 has a rounded end. The side of the bag tube 4066 has a windowed section 4070. The bag 4002 is first introduced into the abdomen body through an opening, orifice or open wound via trocar, delivery shaft, instrument or other deployment method. The large end of the 4072 bag is then opened and positioned around a tissue sample 4078. The large end 4072 of the bag 4002 is then sealed. The bag tube 4066 is then introduced into the body. The bag 4002 is then attached to the bag tube 4066 by means of the clamp 4076. The morcellator 4000 is attached and morcellation begins. Once the specimen 4078 is reduced the retrieval system is withdrawn from the patient.

In another variation shown in FIGS. 163A-163C, the bag 4002 is attached to a bag tube 4066 named bag tube. The bag 4002 has an open end. The bag tube 4066 has a rounded end. The bag tube 4066 has an over sheath. The sheath tip has two holes to facilitate a nitinol or other flexible semi-rigid drawstring 4052 for opening and closing a semi-rigid bag opening 4068. The sheath also has two channels parallel to the axis of the tube to facilitate the nitinol retrieval. The side of the tube has a windowed section 4070. The specimen retrieval system is introduced into the body through an opening as shown in FIG. 163B. The bag 4002 is then opened by deploying the drawstring 4052 and the tissue specimen 4078 is retrieved by surrounding the specimen 4078 with the net created by the nitinol and bag 4002. This can be done with or without the assistance of a grasper or dissector. Once the tissue 4078 is surrounded the nitinol can be retrieved proximally via the drawstring 4052 and this causes the bag 4002 to close around the tissue sample 4078 and seal the bag 4002. The morcellator is attached and morcellation begins. Once the specimen 4078 is reduced the retrieval system is withdrawn from the patient.

In another variation, the bag 4002 has an open top with a semi-rigid ring attached at the top. The bag 4002 can be rolled tightly then deployed into the abdomen via a trocar. The bag 4002 can then be opened inside by manipulation with graspers. The specimen 4078 is loaded into the bag 4002 and the bag 4002 is retrieved through the abdominal wall. The entire bag 4002 does not pass through. The semi-rigid ring is the only portion that is allowed to surface. Morcellation can begin. Once enough of the tissue 4078 is removed, the bag 4002 can then be withdrawn from the patient.

The tissue guard described herein is typically employed with a containment bag. The bag is placed inside the body through a body opening. The body opening refers to any entranceway into the patient and may include and is not limited to incision sites and natural orifices. The target specimen is typically too large to be safely removed through the body opening and requires to be manipulated such as by cutting with a blade in order to extract the target specimen through the body opening. The minimally invasive, laparoscopic body opening is generally smaller than the target specimen size. The target specimen is placed inside the bag and the mouth of the bag is pulled to the outside of the patient. The guard is placed inside the mouth of the bag and anchored across the body opening and the target specimen is pulled into the lumen of the guard. While in the lumen of the guard, the target specimen is in a protected morcellation zone wherein the surgeon may reach in with a blade to cut the target specimen for extraction. The guard protects against the stray blade and also provides a direct cutting surface against which tissue may be placed for reduction. The entire length of the guard typically defines the length of the morcellation zone protecting the bag and the tissue at the margins of the body opening. Additionally, a retractor may be employed. The retractor may be integrally formed with the bag or be a separate stand-alone device. A typical retractor described herein is a two-ringed retractor with a flexible sidewall material located between the two rings. The sidewall of the retractor is configured to be capable of being rolled about the first ring to retract the tissue at the margin of the body opening. If a retractor is employed it may be placed between the marginal tissue and the bag or inside the bag between the bag and the guard. The above description describes different variations of use of the guard, bag and retractor that is employed in manual morcellation. For power morcellation, the guard is inserted inside the bag and morcellation is carried out. In another variation for power morcellation, a stability cap is connected to the proximal ring of the bag or to the proximal end of the guard and power morcellation is carried out. The stability cap serves to locate the vertical position of the blade ensuring that the blade does not extend beyond the predetermined morcellation zone inside the guard or at a short distance safely beyond the distal end of the guard. In another variation for power morcellation, a retractor is employed in which case the retractor is located between the marginal tissue and the bag or between the bag and the guard as previously described and power morcellation is carried out. In the previous variation, a stability cap may be employed in such a manner that it connects to the proximal ring of the retractor, the proximal ring of the bag, or to the proximal end of the guard and morcellation is carried out. In addition to the above variations, any one of the following approaches may be employed in conjunction with any of the variations above when performing a procedure such as a hysterectomy. In one variation, the bag is placed in through the vagina, the target specimen (e.g. uterus) is placed inside the bag while the bag is inside the body cavity, and then the mouth of the bag is pulled through an abdominal incision wherein the guard is inserted into the mouth of the bag, and morcellation, extraction and bag removal take place at the abdominal opening. In another variation, the bag is placed in through the vagina, the target specimen (e.g. uterus) is placed inside the bag while the bag is inside the body cavity, and then the mouth of the bag is pulled back through the vaginal canal wherein the guard is inserted into the mouth of the bag, and morcellation, extraction and bag removal take place at the vagina. In yet another variation, the bag is placed in through an abdominal incision, the target specimen (e.g. uterus) is placed inside the bag while the bag is inside the body cavity, and then the mouth of the bag is pulled through the vaginal canal wherein the guard is inserted into the mouth of the bag, and morcellation, extraction and bag removal take place at the vagina. In one other variation, the bag is placed in through an abdominal incision, the target specimen (e.g. uterus) is placed inside the bag while the bag is inside the body cavity, and then the mouth of the bag pulled back through the abdominal incision wherein the guard is inserted into the mouth of the bag, and morcellation, extraction and bag removal take place at the vagina. In another approach to morcellation of the uterus or other target specimen, the bag may be omitted. In such a case, an incision is made in the abdominal wall, the guard is placed across the incision in the abdominal, the uterus or target specimen is detached and pulled through the central lumen of the guard with morcellation and extraction taking place at the abdominal incision. Alternatively, the target specimen (e.g. uterus) is approached through the vagina, the guard is placed inside the vaginal canal, the target specimen is detached and pulled through the central lumen of the guard with morcellation and extraction taking place at the vagina. As a further variation of the abdominal approach without a bag, the procedure may be observed via a laparoscope inserted through the vagina. As a further variation of the vaginal approach without a bag, the procedure may be observed via a laparoscope inserted through an incision in the abdomen.

In some cases, the guard is not employed. In one such variation without a guard, a bag is placed inside the body cavity via the vaginal canal and the target specimen is placed inside the bag and the mouth of the bag is pulled through an incision in the abdomen, a retractor may be placed inside the bag across the abdominal incision, and morcellation, extraction and bag removal take place at the abdominal incision. In another variation without a guard, a bag is placed inside the body cavity via the vaginal canal and the target specimen is placed inside the bag, and the mouth of the bag is pulled back through the vaginal canal, a retractor may be placed inside the bag inside the vaginal canal, and morcellation, extraction and bag removal take place at the vagina. In another variation without a guard, a bag is placed inside the body cavity via an abdominal incision and the target specimen is placed inside the bag, and the mouth of the bag is pulled through the vaginal canal, a retractor may be placed inside the bag inside the vaginal canal, and morcellation, extraction and bag removal take place at the vagina. In another variation without a guard, a bag is placed inside the body cavity via an abdominal incision and the target specimen is placed inside the bag, the mouth of the bag is pulled through the abdominal incision, a retractor may be placed inside the bag inside the vaginal canal, and morcellation, extraction and bag removal take place at the abdominal incision. In any of the variations without a guard that employ a retractor, employing any of the heretofore mentioned cut-resistant retractors is preferred. Also, in any of the variations without a guard that employ a retractor, the retractor may be placed between the bag and the tissue margin. Also, in any of the variations without a guard that do or do not employ a retractor, employing any of the heretofore mentioned cut-resistant bags is preferred. Power morcellation may also be employed with any of the methods that do employ a guard. In such cases, a stability cap is employed and connected to the proximal end of the bag or proximal ring of the retractor.

In a variation without a guard that employs a retractor, a cut-resistant retractor is provided. The retractor has a first ring and compressible second ring interconnected by a webbing or sidewall. The retractor being configured such that the webbing can be rolled up around the first ring to reduce the length of the retractor and to retract the tissue margin. The bottom ring is inserted through the body opening and resides inside the patient whereas the top ring of the retractor resides above the patient. The top ring is rolled/flipped over itself like the bag to pull the lower ring of the retractor closer and the sidewall into a taut relation between the rings. The lower ring of the retractor advantageously retracts the portion of the bag inside the patent and away from potential damage arising from punctures and tears from the blade. At least part of the webbing is made of puncture-resistant, cut-resistant material. The retractor is configured for insertion into the containment bag and into the body opening to retract the bag and the tissue margin with the first ring of the retractor and mouth of the containment bag residing outside the patient and the second ring of the retractor and the remainder of the containment bag residing inside the patient. This placement of the bag between the retractor and the tissue margin at the body opening anchors the bag with respect to the patient's body. In one variation, only the distal portion of approximately four inches of length of the webbing is cut-resistant being made of KEVLAR, DYNEEMA or other cut-resistant material and the proximal portion of the webbing is not made of cut-resistant material and is made of polyurethane or other flexible film. This arrangement permits the proximal end of the webbing to be more easily rolled around the first ring during retraction. As the length of the webbing is reduced by rolling, the distal cut-resistant portion of the webbing is brought closer to the proximal end or first ring of the retractor and into position for protect morcellation to proceed. With less cut-resistant material, that can be thick and bulky, the retractor is less expensive, and also easier to flip and roll the first ring as less cut-resistant material will be rolled about the first ring. In another variation, the entire webbing is made of cut-resistant material. In another variation for use in the vagina, for example, only the proximal portion of approximately five inches of length of the webbing is cut-resistant being made of KEVLAR, DYNEEMA or other cut-resistant material and the distal portion of the webbing is not made of cut-resistant material and is made of polyurethane or other flexible film for greater flexibility and anchoring at the distal end. In a vaginal surgical procedure, such as a total laparoscopic hysterectomy, the first ring at the proximal end does not have to be rolled down as much. Therefore, the proximal end of the webbing is made of cut-resistant material compared to an abdominal surgical procedure where the webbing is rolled around the first ring quite a bit, the proximal end is not made of cut-resistant material.

According to one aspect of the invention, a contamination prevention system for manual or power in-situ morcellation is provided. The system includes a containment bag having a mouth and a shield configured to be removably inserted into the mouth of the bag. The shield has a central lumen that provides a working channel for morcellation and protects the bag and surrounding tissue.

According to another aspect of the invention, a device for safely removing a tissue specimen from a body cavity through a body opening that is smaller than the tissue specimen is provided. The device includes a removable shield configured to be anchored in the body opening. The device further includes a bag or retractor located between the body opening and the shield.

According to another aspect of the invention, a shield having a sidewall defining a central opening is provided. The shield includes a C-shaped, concave outer surface for anchoring the shield in a body opening.

According to another aspect of the invention, a shield having a sidewall defining a central opening is provided. The shield includes a C-shaped, concave outer surface for anchoring the shield in a body opening. The shield is split such that one part of the shield is nested within another part of the shield and the shield is expandable from a reduced lateral configuration to an enlarged lateral configuration and vice versa by varying the nested portion of the shield.

According to another aspect of the invention, an expandable shield having a sidewall defining a central opening is provided. The shield is movable between a first configuration and a second configuration. The first configuration having a dimension larger than the dimension when in the second configuration wherein the dimension is a vertical and/or a lateral dimension.

According to another aspect of the invention, a system for preventing the potential spreading of cancerous cells when removing a large tissue specimen from a small opening in the body is provided. The system includes a container and a morcellation zone. The morcellation zone is insertable into and removable from the container. The morcellation zone protects the container from penetration by morcellating instruments.

According to another aspect of the invention, a shield is provided. The shield includes a blade connected to the shield. The blade is movable along a predetermined pathway with respect to the shield and the shield surrounds at least part of the predetermined pathway to protect tissue surrounding a body opening.

Turning now to FIGS. 164-167, a shield 5000 according to the present invention is shown. The shield 5000 includes a band of flexible, cut-resistant material. The shield 5000 has an inner surface 5002 and an outer surface 5004 interconnected by a top end 5006 and a bottom end 5008 and a first end 5010 and a second end 5012. The band is configured to define a central lumen having a longitudinal axis. The central lumen has a lumen diameter that is perpendicular to the longitudinal axis. The lumen diameter may vary along the longitudinal axis. For example, the inner surface 5002 defines a shape such as a convex shape wherein the lumen diameter is larger at the top end 5006 and bottom end 5008 relative to the lumen diameter at the center or waist of the band as shown in FIGS. 164-167. In one variation, the inner surface 5002 defines a constant lumen diameter from the top end 5006 to the bottom end 5008, or an angled or funnel-like shape or other curve or shape. The outer surface 5004 substantially matches the inner surface 5002 in shape to define a band of substantially uniform thickness; however, the invention is not so limited and the outer surface 5004 may take a shape that is different from the inner surface 5002 and/or have a band thickness that is different along the longitudinal axis. A curved, funnel-like or C-like, concave shape of the outer surface 5004 as discussed above in this specification helps to anchor the shield 5000 at the tissue margin when inserted into a body orifice, incision site or other opening. Also, the larger diameter shape at the top end 5006 assists in providing a cutting board surface for performing manual morcellation and protecting the surrounding tissue. For example, a flatter and more planar orientation of the top end 5006 in which the inner surface 5002 faces upwardly and perpendicularly or nearly perpendicularly to the longitudinal axis and the outer surface 5004 faces downwardly onto the tissue such as downwardly onto the abdominal wall forms a larger protective overlay or larger cutting board-like surface. As shown in the variation of FIGS. 164-167, the outer surface of the band has a concavity or curvature along the longitudinal axis from the top end 5006 to the bottom end 5008 and extending circumferentially around the guard from the first end 5010 to the second end 5012. The shield 5000 is made of flexible, resilient material such as plastic and is molded to have a resting configuration defining a resting lumen diameter. The resting configuration is shown in FIGS. 164-166 wherein a gap is defined between the first end 5010 and the second end 5012. The gap is approximately 5-10 degrees having an arc length of approximately 4-6 mm. The resting lumen diameter at the waist is approximately 40 mm. Because the shield 5000 is resilient and flexible, its lumen diameter is adjustable by flexing and turning the band inwardly to reduce the gap, and to overlap the first end 5010 and second end 5012 of the band to reduce the lumen diameter or by flexing and bending the band outwardly to increase the gap and increase the lumen diameter relative to the resting lumen diameter. From an increased or reduced lumen diameter relative to the resting lumen diameter, the band will tend to spring back toward approximately the resting configuration and resting lumen diameter because of its resilient nature. In one variation, the resting configuration does not have a gap. As the band is reduced in diameter, the first end 5010 will overlap the second end 5012 to form a spiral shape when viewed from the top or bottom. The outer surface 5004 of the band at the first end 5010 will face at least a portion the inner surface 5002 of the band at the second end 5012 resulting in part of the band near the first end 5010 being nested within part of the band near the second end 5012. To accommodate the nested first end portion of the band, the second end portion is configured to jog outwardly by a distance 5014 approximately equal to the width of the band wall, that is, the width of material between the inner surface 5002 and the outer surface 5004, which is approximately 1-3 mm such that, when the band is nested, the inner surface 5002 retains a larger inner diameter that is not reduced by the overlapped segment of the band in the location of the overlap and such that the inner surface is substantially flush at the intersection with the overlapping location as can be seen in FIG. 167. An inner ridge surface 5016 is formed in the shield 5000 by an outwardly extending jog or irregularity in the inner surface of the band defined by an increased lumen diameter. The increased lumen diameter extends along a portion of the circumference of the band from the ridge 5016 to the second end 5012. The inner ridge 5016 is formed approximately 127 degrees from the second end 5012. The inner ridge 5016 is formed with respect to the inner surface 5002 and extends substantially perpendicularly from the inner surface 5002 in a vertical fashion from the top end 5006 to the bottom end 5008. The inner ridge 5016 forms a corresponding outer ridge 5018 as the band is molded to create the jog at the inner ridge 5016 where the band increases in inner diameter by a segment distance 5014 of approximately 127 degrees around the circumference from the inner ridge 5016 to the second end 5012. Between the inner ridge 5016 and the second end 5012, at least one abutment is formed extending along the longitudinal axis between the top end 5006 and the bottom end 5008.

A first inner abutment 5020 is formed on the inner surface 5002. The surface of the first inner abutment 5020 faces the second end 5012 and is substantially perpendicular to the inner surface 5002 and extends outwardly from the inner surface 5002 and along the longitudinal axis between the top end 5006 and the bottom end 5008. The first inner abutment 5020 has a height from the inner surface 5002 approximately equal to or greater than the thickness of the band material between the inner surface 5002 and the outer surface 5004. When the first end 5010 overlaps the second end 5012 such that the outer surface 5004 at the first end 5010 overlays and faces the inner surface 5002 at the second end 5012 in a first reduced configuration, the first end 5010 is configured to contact the first inner abutment 5020 to lock and prevent further reduction in the size of the inner diameter. This configuration serves to lock the shield 5000 in a fixed diametrical/lateral dimension position with the shield 5000 maintaining some degree of overlap circumferentially around a portion of the perimeter of the shield 5000. This lock is particularly useful when the shield 5000 is located inside a body orifice or incision where forces of the tissue would tend to collapse the central lumen and further reduce the inner diameter. The central lumen serves as a working channel and the lock is created when at least a portion of the shield 5000 contacts the first inner abutment 5020. The first inner abutment 5020 is located approximately 30 degrees from the second end 5012. When the first end 5010 contacts the first inner abutment 5020, the inner diameter is approximately 36 mm.

The shield 5000 further includes a second inner abutment 5022 located a greater distance from the second end 5012. In particular, the second inner abutment 5022 is located approximately 65 degrees from the second end 5012. The second inner abutment 5022 is formed on the inner surface 5002. The surface of the second inner abutment 5022 faces the second end 5012 and is substantially perpendicular to the inner surface 5002 and extends outwardly from the inner surface 5002 and along the longitudinal axis between the top end 5006 and the bottom end 5008. The second inner abutment 5022 has a height from the inner surface 5002 approximately equal to or greater than the thickness of the band material between the inner surface 5002 and the outer surface 5004. The first inner abutment 5020 and the second inner abutment 5022 are substantially parallel. When the first end 5010 overlaps the second end 5012 such that the outer surface 5004 at the first end 5010 overlays and faces the inner surface 5002 at the second end 5012 in a reduced diametrical/lateral configuration, the first end 5010 is configured to contact either the first inner abutment 5020 or the second inner abutment 5022 to lock and prevent further reduction in the size of the inner diameter. The second inner abutment 5022, like the first inner abutment 5020 serves to lock the shield 5000 in a fixed diametrical/lateral dimension position with the shield 5000 maintaining some degree of overlap circumferentially around the perimeter of the shield 5000. This lock is particularly useful when the shield 5000 is located inside a body orifice or incision where forces of the tissue would tend to collapse the central lumen and further reduce the inner diameter. The central lumen serves as a working channel and the lock is created when at least a portion of the shield 5000 contacts the second inner abutment 5020. When the first end 5010 contacts the second inner abutment 5022, the inner diameter is approximately 33 mm. When the first end 5010 contacts the second inner abutment 5022, the first inner abutment 5020 is located against the outer surface 5004. To accommodate the first inner abutment 5020, a first outer abutment 5024 or receiving area 5024 is formed in the outer surface 5004. In one variation as shown, the receiving area 5024 includes an abutment formed therein and in another variation, the receiving area is not configured to have an abutment surface. The first outer abutment 5024 is located approximately 30 degrees from the first end 5010. The first outer abutment 5024 is formed on the outer surface 5004. The surface of the first outer abutment 5024 faces the first end 5010 and is substantially perpendicular to the outer surface 5004 and extends inwardly from the outer surface 5004 and along the longitudinal axis between the top end 5006 and the bottom end 5008. The first outer abutment 5024 has a height with respect to the outer surface 5004 approximately equal to or greater than the thickness of the band material between the inner surface 5002 and the outer surface 5004. The first outer abutment 5024 and the first inner abutment 5020 and second inner abutment 5022 are substantially parallel. When the first end 5010 overlaps the second end 5012 such that the first end 5010 contacts the second inner abutment 5022, the first inner abutment 5020 faces and contacts the first outer abutment 5024 to lock and prevent further reduction in the size of the inner diameter.

The shield 5000 further includes a third inner abutment 5026 located a greater distance from the second end 5012. In particular, the third inner abutment 5026 is located approximately 100 degrees from the second end 5012. The third inner abutment 5026 is formed on the inner surface 5002. The surface of the third inner abutment 5026 faces the second end 5012 and is substantially perpendicular to the inner surface 5002 and extends outwardly from the inner surface 5002 and along the longitudinal axis between the top end 5006 and the bottom end 5008. The third inner abutment 5026 has a height from the inner surface 5002 approximately equal to or greater than the thickness of the band material between the inner surface 5002 and the outer surface 5004. The first inner abutment 5020, the second inner abutment 5022 and the third inner abutment 5026 are substantially parallel and approximately equally spaced apart around the circumference of the inner surface 5002. When the first end 5010 overlaps the second end 5012 such that the outer surface 5004 at the first end 5010 overlays and faces the inner surface 5002 at the second end 5012 in a reduced diametrical/lateral configuration, the first end 5010 is configured to contact either the first inner abutment 5020, the second inner abutment 5022, or the third inner abutment 5026 to variably adjust the inner diameter and then to lock and prevent further reduction in the size of the inner diameter. The third inner abutment 5026, like the first inner abutment 5020, and the second inner abutment 5022 serves to lock the shield 5000 in a fixed diametrical/lateral dimension position with the shield 5000 maintaining some degree of overlap circumferentially around the perimeter of the shield 5000. This lock is particularly useful when the shield 5000 is located inside a body orifice or incision where forces of the tissue would tend to collapse the central lumen and further reduce the inner diameter. When the first end 5010 contacts the third inner abutment 5026, the inner diameter is approximately 30 mm. When the first end 5010 contacts the third inner abutment 5024, the first inner abutment 5020 and the second inner abutment 5022 are located against the outer surface 5004. To accommodate the first inner abutment 5020 and the second inner abutment 5022, a first outer abutment or receiving area 5024 is formed is in the outer surface 5004 and a second outer abutment or receiving area 5028 is formed in the outer surface 5004. In one variation, the receiving area is provided with an abutment surface and, in another variation, the receiving area is sized and configured to accommodate the inner abutments in a flush manner. The second outer abutment 5028 is located approximately 65 degrees from the first end 5010. The second outer abutment 5028 is formed on the outer surface 5004. The surface of the second outer abutment 5028 faces the first end 5010 and is substantially perpendicular to the outer surface 5004 and extends outwardly from the outer surface 5004 and along the longitudinal axis between the top end 5006 and the bottom end 5008. The second outer abutment 5028 has a height from the outer surface 5004 approximately equal to the height of the inner abutments or the thickness of the band material between the inner surface 5002 and the outer surface 5004. The second outer abutment 5028, the first outer abutment 5024 and the first inner abutment 5020, the second inner abutment 5022, and the third inner abutment 5026 are substantially parallel. When the first end 5010 overlaps the second end 5012 such that the first end 5010 contacts the third inner abutment 5026, the first inner abutment 5020 faces and contacts the second outer abutment 5028 and the second inner abutment 5022 faces and contacts the first outer abutment 5020 to lock and prevent further reduction in the size of the inner diameter.

The shield 5000 further includes a third outer abutment 5030 located a greater distance from the first end 5010 than the second outer abutment 5028. In particular, the third outer abutment 5030 is located approximately 100 degrees from the first end 5010. The third outer abutment 5030 is formed on the outer surface 5004. The surface of the third outer abutment 5030 faces the first end 5010 and is substantially perpendicular to the outer surface 5004 and extends inwardly from the outer surface 5004 and along the longitudinal axis between the top end 5006 and the bottom end 5008. The inward extension of the outer abutments creates ramp-like surfaces on the inner surface 5002. The third outer abutment 5030 has a height from the outer surface 5004 approximately equal to or greater than the thickness of the band or inner abutments. The third outer abutment 5030 is configured to accommodate and receive the first inner abutment 5020 when the first end 5010 abuts the inner ridge 5016 as shown in FIG. 167. In another variation, first end 5010 abuts a fourth inner abutment that is not configured as an inner ridge 5016 as described herein. The first inner abutment 5020, the second inner abutment 5022 and the third inner abutment 5026 are substantially parallel. When the first end 5010 overlaps the second end 5012 such that the outer surface 5004 at the first end 5010 overlays and faces the inner surface 5002 at the second end 5012 in a reduced diametrical/lateral configuration, the first end 5010 is configured to contact either the first inner abutment 5020, the second inner abutment 5022, the third inner abutment 5026 or the inner ridge 5016 to variably adjust the inner diameter and then to lock and prevent further reduction in the size of the inner diameter. In one variation, all of the inner abutments including the inner ridge are substantially equally spaced apart. The first end 5010 is shown contacting the inner ridge 5016 in FIG. 167 to configure a shield 5000 having the smallest relative inner diameter of approximately 28 mm. When the first end 5010 contacts the inner ridge 5016, the first inner abutment 5020, the second inner abutment 5022, and the third inner abutment 5026 are located against the outer surface 5004 and, in particular, received in or against the third outer receiving area or abutment 5030, second outer receiving area or abutment 5028 and the first outer receiving area or abutment 5024, respectively. To unlock the shield 5000, the inner-nested segment of the shield 5000, the first end 5010 is moved toward the longitudinal axis to release the abutting surfaces. The first end 5010 is demarcated with a marker 5032 such as a tab, grip having a textured surface, or a contrast colored area such as near the top end 5006 or bottom end 5008 to serve as an indicator to the user which end of the shield 5000 is to be nested within the shield 5000 so that the abutments interlock accordingly. Also, the marker 5032 facilitates withdrawal or release of the shield 5000 from the locked configuration by providing a textured location to pull or grasp the shield. The marker 5032 may further serve a directional purpose indicating to the user which side of the shield is up if the shield is asymmetrical along the longitudinal axis.

Although three inner abutments 5020, 5022, 5026, three outer abutments 5024, 5028, 5030 and one inner ridge 5016 have been described having certain spacings and angular relationships, the invention is not so limited and any number of inner abutments may be provided to provide the variable locking configurations to achieve the desired inner diameter of the working channel. Furthermore, although the gap is shown to be approximately 8 degrees in the relaxed configuration, the invention is not so limited, and the shield 5000 may have a larger gap, smaller gap or no gap. As described above, the shield 5000 is designed such that the first end 5010 serves as a functional locking edge that contacts an abutment, in particular, one or more inner abutments 5020, 5022, 5026 and/or one or more inner ridge 5016 at a time to variably select and fix the inner diameter. In another variation, the first end 5010 does not serve as a functional edge and instead an outer abutment serves as a functional locking edge as it contacts and abuts one or more inner abutments 5020, 5022, 5026. And in yet another variation of the shield as described above, the first end 5010 and one or more outer abutments 5024, 5028, 5030 serve as functional locking edges wherein one or more than one abutment are simultaneously in contact at a fixed diametrical position. Each inner abutment forms a triangular-like ramped protrusion from the inner surface 5002 and the outer abutments form correspondingly shaped, yet larger triangular-like ramped indentations or protrusions into the outer surface 5004 configured to receive the smaller inner abutments such that the one or more inner abutment surfaces come into contact with the one or more outer abutments or are simply received in receiving areas without contact against outer abutments. In one variation, the shapes of the inner and outer abutments may further include friction-fit or snap-fit configurations to further enhance locking ability where features include ridges that provide the increased frictional lock, ledge or gate. The ramped protrusion at the inner surface 5002 facilitates expansion of the shield from a reduced configuration to an enlarged configuration. For example, when inserting the shield into an incision/orifice, the shield 5000 is first curled into a reduced configuration so that it can fit into a small incision/orifice and then the shield 5000 is uncurled into a larger diameter configuration. As the reduced configuration is uncurled into a larger diameter configuration, portions of the outer surface 5004 will ramp up and over the ramped protrusions on the inner surface 5002. After the outer surface ramps over the inner surface, the inner abutments will come into contact with the outer abutments to create a first stop or locked position. The shield 5000 can then be uncurled further and the outer surface ramped over an inner surface protrusion in the location of the outer abutment to then come to another locked position wherein the inner abutments and the outer abutments come into contact with each other and so forth. As such, the expansion of the shield is performed in a ratchet-like fashion in which the diametrical dimension increases by degrees in a stepwise manner between locking interaction with one or more abutment. In one variation, the shield 5000 does not have an outer abutment formed in the outer surface. Instead, the shield 5000 has a receiving area for receiving the inner abutments over which the outer surface overlays to provide a flush locking position wherein the locking function is performed when an inner abutment contacts the first end 5010 or, in one variation, one or more outer abutment formed in one or more receiving area. As such, the receiving area that is not configured for abutment formed in the outer surface 5004 can have any shape at the outer surface. The inner surface in the location opposite from the receiving area may have the ramped configuration or other curved configuration that facilitates movement of the shield between a reduced configuration and an enlarged configuration. This ramping feature advantageously makes the shield 5000 easy to use because uncurling the shield into a larger diameter does not require a separate step to mechanically unlock a locked configuration. Instead, the shield is simply curled or otherwise moved circumferentially to ramp over an inner protrusion to enter an adjacent locked position of abutment in ratchet-like fashion.

The shield 5000 shown in FIGS. 164-167 is adjustable to have four distinct inner diameter sizes. When inserted inside an incision or body orifice the shield 5000 provides protection and can conform to incisions of approximately one inch and smaller. Of course, a larger shield 5000 can be made to be placed inside larger incisions/orifices such as the vaginal canal. Such a shield may also be made to have a length that is longer than the one shown in FIGS. 164-167. The shield 5000 provides retraction of tissue at the incision/orifice. When inserted into an incision/orifice, the shield 5000 is curled into a reduced configuration to be inserted into a small incision/orifice and then the shield 5000 is uncurled into a larger diameter configuration with a plurality of locking positions available to customize the locking position of the shield. As such, the shield 5000 serves the function of retraction, enlarging the incision or orifice simultaneous with the enlargement of the shield diameter and working channel. With the shield 5000 of FIGS. 164-167, the shield provides retraction and can conform to incisions up to approximately 1.5 inches in diameter. The retraction of surrounding tissue will increase the working space and provide better stability for the user.

Furthermore, the shield 5000 locking mechanism is unique as it relies on radial pressure exerted onto the shield 5000 from the outside and onto the outer surface 5004. Hence, the shield 5000 and, in particular, the locking mechanism of the shield, in one variation, functions when the shield is inserted into an incision size equal to or less than the inner diameter of the smallest reduced configuration of the shield. The surrounding tissue will exert a radial force circumferentially around the outer perimeter of the shield 5000 that forces the first end 5010 into abutment with one or more of the inner abutments or inner ridge and/or forces one or more inner abutment into abutment with one or more outer abutment. The surrounding tissue margin exerts a compressive force onto the shield. The shield is configured to take advantage of the force component that is tangential to the circumference of the shield to move the perpendicular abutments both inner and/or outer, and/or ridge and/or first end into contact with one or more other abutment or ridge, first end or other perpendicular structure, thereby, preventing the collapse of the shield while at the same time providing a locking feature. The structures of the shield that are perpendicular to the circumferential surfaces such as the abutments/ends/ridges support the structure and reinforce it making the shield stronger. Variations of the shield having locking positions and configurations in which more than one pair of abutment surfaces are in contact simultaneously for a giving locking position make the shield stronger and more capable of withstanding forces tending to collapse a retracted tissue position. To further increase the radial strength of the shield while retracting tissue and subject to tissue pressure surrounding the shield when inside a tissue opening any one or more of the abutments/ridges/ends that form contact surfaces that serve a locking function extend from the top end 5006 or nearly the top end 5006 to the bottom end 5008 or nearly the bottom end 5008, or at least equal to or greater than 50 percent surface length of shield in order to provide strength and substantially uniform reinforcement along the a length of the shield from the top to the bottom. The tissue pressure onto the shield while it is located in an incision/orifice forces the leading edge and the outer abutments into the corresponding inner abutments and also allows the overlapping faces of the shield to sit flush within the shield due to the ridge and jog formed in the shield, the distance of which equals the width of the shield wall. Without the tissue pressure onto the shield, a shield that is configured into a reduced configuration in which surfaces are in abutment will not remain in the reduced and locked configuration because the shield is molded and biased towards a larger resting configuration. Hence, the lock is a living lock requiring tissue pressure to effect a locked configuration in one variation. The tissue pressure at the locus of incision/orifice cooperates to bring the abutment surfaces into a locking configuration and keeping it there. In use, the shield is placed into a reduced configuration from a resting configuration by first closing the gap and bringing the first end of the band into an overlapping configuration with at least part of the second end of the band. The overlapping portion is increased by curling down the band to further reduce the inner diameter to a size that will fit into an incision/orifice. The shield is inserted into the incision/orifice and released inside the incision/orifice and is subjected to pressure from the surrounding tissue arising from the incision/orifice diameter being smaller than the reduced configuration of the shield or arising from increasing the size of the shield by uncurling it from the reduced configuration. The shield is curled in a reverse direction to increase the inner diameter of the shield. Increasing the inner diameter will tend to retract tissue at the margin of the incision/orifice. The retraction of tissue will increase the bias force of the tissue back onto the shield. Reducing the amount of overlapping shield will ratchet the abutments into consecutive locked positions in which one or more abutments are in contact with each other or with an end or ridge. Contact with the abutments will prevent collapse of the shield and will fix the inner diameter. When viewed from the top along the longitudinal axis of the shield, the shield will form a spiral shape in a plane perpendicular to the longitudinal axis when it is in a reduced configuration. When in a resting configuration, the shield forms an open circle or open ellipse in one variation. In another variation, the first end of the shield slightly overlaps at the second end of the shield. The locking mechanism in cooperation with the tissue pressure serves to anchor the shield within the incision/orifice. An aggressive C-shaped curvature of the outer surface is not as necessary to help anchor the shield into the incision/orifice because of the lock. Without a lock, wedging a lower flange of an aggressive C-shaped outer surface into the incision/orifice and resting an upper flange against the tissue surface helps to anchor the shield with respect to the patient. The locking mechanism advantageously allows the working channel and inner diameter to be maximized without it being decreased by an aggressive C-shaped curvature to the sidewall of the band. In one variation, the shield does not have a curved profile or only a very slightly curved profile in order to maximize the inner diameter with greater reliance on the locking mechanism to anchor the shield with respect to the patient. The outward jog at the second end of the band further maximizes the inner diameter in the location where one portion of the band overlaps with another portion of the band creating a uniform and flush inner diameter instead of the inner diameter being reduced in the location of the overlap. In one variation, the shield does not have outer abutments, but instead, has receiving areas sized and configured to receive the inner abutments when the shield is spiraled to overlap inner abutments. The receiving areas prevent the overlapping band from buckling inwardly toward the central lumen. Instead, the inner abutments are received within the receiving areas to maximize the inner diameter and to create a flush arrangement of the band around the inner diameter even in the location of the overlapping portion of the band. In the most reduced configuration, in which the shield has the smallest inner diameter, the first end contacts the inner ridge and all of the inner abutments are either received in the receiving areas or are in contact with corresponding outer abutments.

Turning now to FIG. 168, there is shown another shield 5000 to illustrate another locking mechanism according to the present invention wherein like reference numbers are used to describe like parts. The first end 5010 includes a projection 5034 sized and configured to fit inside a slot 5036 formed in the second end 5012. The abutment of the projection 5034 against the slot 5036 creates a locking configuration and prevents further reduction in the inner diameter. As seen in FIG. 168, the slot 5036 is substantially vertically orientated and the slot 5034 is curved to conform to the curvature of the shield band. Although one slot 5036 is shown, a plurality of slots 5036 may be provided to afford variability in locking diameters.

Turning now to FIGS. 169-170, there is another variation of a locking shield 5000. The shield 5000 includes a first end 5010 configured to slide into a slot 5036 formed at the second end 5012. A plurality of slots 5036 is provided to afford variability in locking diameters. Each slot 5036 is substantially C-shaped forming a tongue 5038 behind which the first end 5010 is inserted to fix the inner diameter. The shield 5000 is unlocked by increasing the diameter by pulling apart the interlocked segments of the band.

Turning now to FIG. 171, there is another variation of a shield 5000 having a locking mechanism. The shield 5000 includes one or more vertical slots 5036 formed at the second end 5012. A plurality of slots 5036 is provided to afford the shield 5000 with variable locking positions. The first end 5010 includes a projection 5034 having an outwardly extending hook 5040 that is sized and configured to be received inside any one of the slots 5036. The hook 5040 abuts the slot 5036 openings to restrain reduction or expansion of the inner diameter. The lock is released by flexing the first end 5010 inwardly to remove the hook 5040 from the slot 5036 opening.

Turning now to FIGS. 172-174, there is shown another variation of a shield 5000 having a locking mechanism. The shield 5000 includes a first end 5010 provided with one or more apertures 5042. A plurality of apertures 5042 is provided to afford variable locking positions along the band to adjust the inner diameter and lock it into place as desired. The second end 5012 of the shield 5000 includes a projection 5034. The projection 5034 includes a circular head connected to a neck portion 5044. The projection 5034 extends radially inwardly from the inner surface 5002 of the band. Each aperture 5042 has two parts. The first part of the aperture 5042 includes an opening that is shaped to correspond to the head of the projection 5034 and sized to permit the head of the projection 5034 to pass into the aperture 5042 as shown in FIG. 172. As shown in FIG. 174, the projection 5034 is then moved into the second part of the aperture 5034 that forms a channel for the neck portion 5044 and a constraint for the head portion such that when the projection 5034 resides inside the second part of the aperture 5034, the head portion cannot be removed unless the head portion is aligned with the first part of the aperture 5034 and passed therethrough. The slot-lock fixes the head portion of the projection 5034 at the second end 5012 in one of the apertures 5042 along the first end 5010 to fix and lock the inner diameter and prevent it from being expanded or reduced in size.

Turning now to FIG. 175, there is shown another variation of a shield 5000 having a locking mechanism. The lock includes a projection 5034 extending outwardly from the outer surface 5004 near the first end 5010. The projection 5034 is vertically oriented. The second end 5012 includes one or more correspondingly-shaped, vertically oriented slots 5036. A plurality of slots 5036 is provided for variability in the adjustment of the size and inner diameter of the shield 5000. The first end 5010 is flexed inwardly and nested inside the second end 5012 to spiral the shield 5000 into a smaller inner diameter. When the desired inner diameter is achieved for the particular surgical purpose, the projection 5034 is aligned with the desired slot 5036 for the desired inner diameter and the projection 5034 is inserted into the slot 5036. The projection 5034 abuts the slot 5036 preventing the expansion or reduction in size and inner diameter of the shield 5000, thereby, locking the inner diameter of the shield 5000 in the desired configuration. To unlock the shield 5000, the projection 5034 is reversed and pushed back out of the slot 5036 by flexing the first end 5010 inwardly or the second end 5012 outwardly to release the projection 5034 from the slot 5036. In the unlocked configuration, the inner diameter may be reduced in sized so that it can be easily pulled out of the incision or body orifice. The shield 5000 may be readjusted to have an increased or decreased inner diameter and re-locked as desired while resident in the incision/orifice.

Turning now to FIG. 176, there is shown another variation of a shield 5000 having a locking mechanism. The lock includes one or more projection 5034 extending outwardly from the inner surface 5002 near one of the first end 5010 and second end 5012. The projection 5034 is oriented horizontally, perpendicular to the inner surface 5002 and/or the longitudinal axis. In FIG. 176, one projection 5034 is located near the top end 5006 and another projection (not shown) is located near the bottom end 5008. The second end 5012 includes one or more correspondingly-shaped, horizontally oriented slots 5036 that are sized and configured to receive the one or more projections 5034. A plurality of slots 5036 is provided along the circumference of the shield 5000 to provide variability in the adjustment of the size and inner diameter and locking positions of the shield 5000. The first end 5010 is flexed inwardly and nested inside the second end 5012 to spiral the shield 5000 into a smaller inner diameter. When the desired inner diameter is achieved for the particular surgical purpose, size of incision, orifice or tissue to be extracted, the one or more projection 5034 is aligned with a corresponding one or more slot 5036 for the desired inner diameter. Each projection 5034 is inserted into the corresponding slot 5036. The projection 5034 abuts the slot 5036 preventing the expansion or reduction in size and inner diameter of the shield 5000, thereby, locking the inner diameter of the shield 5000 in the desired configuration. The top end 5006 and the bottom end 5008 are uniformly locked with respect to each other. To unlock the shield 5000, the projection 5034 is pushed back out of the slot 5036 by flexing the first end 5010 inwardly or the second end 5012 outwardly to release the projection 5034 from the slot 5036 to achieve an unlocked configuration. In the unlocked configuration, the inner diameter may be reduced in sized so that it can be easily pulled out of the incision or body orifice. The shield 5000 may be readjusted to have an increased or decreased inner diameter and re-locked as desired while resident in the incision/orifice.

Turning now to FIG. 177, there is shown another variation of a shield 5000 having a locking mechanism. The lock includes at least one abutment 5020 extending outwardly from and perpendicular to the inner surface 5002 near the second end 5012. The abutment 5020 is vertically oriented extending between the top end 5006 and the bottom end 5008. A plurality of abutments 5020 is provided and each is spaced apart from each other from the second end 5012 to provide variability in the adjustment of the size and inner diameter of the shield 5000. The plurality of abutments 5020 form a step-like arrangement of a plurality of curved steps along the inner surface 5002 against which the first end 5010 is configured to abut. The first end 5010 is a curved edge that corresponds to the curvature of the shield 5000. Any size and shape abutment may be provided at one location together with a correspondingly shaped abutment such as the first end 5010 on the other side of the shield 5000 or other location along the inner or outer surface of the shield. The first end 5010 is flexed inwardly and nested inside the second end 5012. The shield is spiraled into a smaller inner diameter. When the desired inner diameter is achieved for the particular surgical purpose, the first end 5010 or other abutment at or near the first end 5010 is aligned and placed into contact with one of the abutments 5020 near or at the other side or the second end 5012 of the shield 5000. The contact of the first end 5010 with the abutment 5020 creates a lateral/diametrical lock that prevents reduction in the size of the shield and its inner diameter. This lock configuration, however, permits expansion of the lateral/diametrical dimension. If expansion occurs, the first end 5010 may be moved into contact with an adjacent abutment 5020 and snap against it to create another locking position. To release the lock, the first end 5010 is moved out of contact with the abutment 5020 to free the variability of shield size. In the unlocked configuration, the inner diameter may be reduced in sized so that it can be easily pulled out of the incision or body orifice. The shield 5000 may be readjusted to have an increased or decreased inner diameter and re-locked as desired.

Turning now to FIG. 178, there is shown another variation of a shield 5000 having a locking mechanism. The lock includes at least one abutment 5020 extending outwardly from and perpendicular to the inner surface 5002 near the second end 5012. The abutment 5020 is vertically oriented extending between the top end 5006 and the bottom end 5008. A plurality of abutments 5020 is provided and each is spaced apart from each other from the second end 5012 to provide variability in the adjustment of the size and inner diameter of the shield 5000. The plurality of abutments 5020 form a step-like arrangement of a plurality of curved steps along the inner surface 5002 against which the first end 5010 is configured to abut. The first end 5010 is a curved edge that corresponds to the curvature of the shield 5000. Any size and shape abutment may be provided at one location together with a correspondingly shaped abutment such as the first end 5010 on the other side of the shield 5000 or other location along the inner or outer surface of the shield. The shield 5000 further includes one or more projection 5034 extending outwardly from the inner surface 5002 and located adjacent to the at least one abutment 5020. One projection 5034 is provided adjacent to each abutment 5020. In the variation, shown in FIG. 178, three abutments 5020 are shown and three projections 5034 are shown adjacent to each abutment 5020. The projection 5034 is cylindrical in shape but can be any shape. The abutments 5020 and the projections 5034 are associated with the second end 5012 of the band. The band includes one or more apertures 5042 formed at or near the first end 5010. The apertures 5042 are sized and configured to receive the projections 5034 and spaced apart such that in one diametrical arrangement of the shield 5000, all of the projections 5034 are insertable into corresponding apertures 5042. The first end 5010 is flexed inwardly and nested inside the second end 5012. The shield is spiraled into a smaller inner diameter. When the desired inner diameter is achieved for the particular surgical purpose, the first end 5010 or other abutment at or near the first end 5010 is aligned and placed into contact with one of the abutments 5020 near or at the other side or the second end 5012 of the shield 5000. In doing so, the corresponding one or more projections 5034 is passed through the corresponding aperture 5042 to lock the shield into place. The contact of the first end 5010 with the abutment 5020 creates a lateral/diametrical lock that prevents reduction in the size of the shield and its inner diameter. The abutment of the projection 5034 against the aperture 5042 further creates a lateral/diametrical lock that prevents the increase as well as the reduction in the size of the shield and its inner diameter. To release the lock, the one or more projection 5034 of the second end 5012 is moved out of the one or more apertures 5042 of the first end 5042 and the first end 5010 is moved out of contact with the abutment 5020 to free the variability of shield size. In the unlocked configuration, the inner diameter may be reduced in sized so that it can be easily pulled out of the incision or body orifice. Of course, the shield 5000 may be readjusted to have an increased or decreased inner diameter and re-locked as desired.

Turning now to FIGS. 179-180, there is shown another variation of a shield 5000 having a locking mechanism. The shield 5000 includes a plurality of corrugations 5046 around band or in at least near the first end 5010 and near the second end 5012. The variation in FIGS. 179-180 includes corrugations all the way around the circumference of the shield 5000. The corrugations 5046 are vertically oriented folds that extend along the longitudinal axis. The folds form a plurality of peaks 5048 alternating with valleys 5050 around the circumference of the shield 5000. The peaks 5048 project inwardly into the central lumen toward the longitudinal axis and the valleys 5050 are located between the peaks 5048. The valleys 5050 project outwardly away from the longitudinal axis and away from the central lumen. The peaks 5048 and valleys 5050 are correspondingly shaped such that each peak 5048 is received or nested in an interlocking fashion within each valley 5050. A peak 5048 is formed by a bend in the band. The corrugations 5046 are vertical folds or bellows that extend along the longitudinal axis. The corrugations 5046 facilitate reduction of the diametrical/lateral dimension of the shield 5000 by providing a plurality of hinge locations around the circumference. A peak 5048 at the inner surface 5002 forms a valley 5050 at the outer surface 5004. The first end 5010 or second end 5012 is flexed inwardly and nested inside the other of the first end 5010 or second end 5012. The shield 5000 is spiraled or curled into a smaller inner diameter. When the desired inner diameter is achieved, one or more peaks 5048 are nested within one or more valleys 5050 to create a locking configuration, as shown in FIG. 180, in which the reduction and expansion of the lateral/diametrical dimension of the shield 5000 is fixed. One or more peaks 5048 at the inner surface 5002 at the second end 5012 are nested into tangential, circumferential abutment within one or more valleys 5050 at the outer surface 5004 of the first end 5010. To release the lock, the one or more peaks 5048 are removed from abutment within the one or more valleys 5050. In the unlocked configuration, the inner diameter may be reduced in sized so that it can be easily pulled out of the incision or body orifice. Of course, the shield 5000 may be readjusted to have an increased or decreased inner diameter and re-locked as desired.

Turning now to FIG. 181, there is shown another variation of the shield 6000. The shield 6000 is made of rigid material such as plastic or metal or other material. The shield 6000 includes a first end 6002 interconnected with a second end 6004 between an outer perimeter 6006 and an inner perimeter 6008. Between the outer perimeter 6006 and the inner perimeter 6008, the shield 6000 defines an inflection line that extends between the first end 6002 and the second end 6004. The inflection line in FIG. 181 is a curve; however, the invention is not so limited. The shield 6000 includes a flange 6010 having an upper surface 6012 opposite from a lower surface 6014 defining a thickness therebetween. The flange 6010 is substantially planar and provides a cutting-board like surface for performing manual morcellation and protecting adjoining tissue. The flange 6010 is interconnected with a depending portion 6016. The depending portion 6016 includes an inner surface 6018 that is contiguous with the upper surface 6012 of the flange 6010. The depending portion 6016 includes an outer surface 6020 that is contiguous with the lower surface 6014 of the flange 6010. The depending portion 6016 is curved. In one variation, the arc defined between the first end 6002 and the second end 6004 is less than or equal to approximately 180 degrees. In another variation, the arc defined between the first end 6002 and the second end 6004 is between approximately 45 degrees and 290 degrees. The shield 6000 is configured such that the depending portion 6016 is insertable into an incision or orifice or other body opening to partially circumferentially retract the tissue margin at the incision. The depending portion 6016 serves as a hook for securing the flange 6006 at the incision site and providing protection to the surrounding tissue. The shield 6000 is rigid and cut resistant such that the surgeon can safely morcellate against the flange 6012. The shield 6000 of FIG. 181 can be used by itself and inserted directly into an incision/orifice or employed in combination with a retractor and/or containment bag of the like describe in this specification. A two ring retractor with webbing therebetween is inserted into the incision site or orifice and the tissue margin is retracted by rolling to top ring to wrap the webbing around the top ring as described herein. After the incision/orifice is retracted, the shield 6000 is placed inside the retractor to protect the surrounding tissue and the retractor webbing from inadvertent incision during a morcellation procedure. The flange 6010 is large enough to overlay the outer tissue such as the abdominal wall to provide a shelf/apron of protection for the patient. Although the depending portion 6016 is shown to be curved, the invention is not so limited and the depending portion may be flat or C-shaped. A C-shaped depending portion may assist in hooking the shield 6000 at the incision site. All of the methods described in this application for a guard and/or shield are interchangeable and applicable to all of the guards and shields described herein including but limited to their use with or without containment bags and/or retractors and/or other devices described herein or known to a person having ordinary skill in the art.

It is understood that various modifications may be made to the embodiments disclosed herein. Therefore, the above description should not be construed as limiting, but merely as exemplifications of preferred embodiments. Those skilled in the art will envision other modifications within the scope and spirit of the present disclosure.

We claim:

1. A system for removing a tissue specimen through a body opening defining a tissue margin, the system comprising:
   a shield including a band made of flexible cut-resistant material; the band having an inner surface and an outer surface interconnected by a top end and a bottom end and by a first end and a second end; the band being configured to define a central lumen having a longitudinal axis; the central lumen having a lumen diameter that is perpendicular to the longitudinal axis; and
   a locking mechanism configured to fix the lumen diameter; the locking mechanism includes at least one inner abutment formed on the inner surface; the at least one inner abutment extending along the longitudinal axis along at least a portion of the band between the top end and the bottom end; the first end being configured to contact the at least one inner abutment to prevent reduction of the lumen diameter in a locked configuration,
   wherein the band is split such that the band is movable into a reduced configuration where at least a portion of the outer surface at the first end overlaps and is in juxtaposition with the inner surface at the second end to form a spiral and define an overlapping portion,
   wherein the band includes a resting configuration defining a resting lumen diameter; the band being configured to have no overlapping portion when in the resting configuration, and
   wherein the shield is configured to have a variable lumen diameter by varying the overlapping portion.

2. The system of claim 1 wherein the band is further configured to spring back toward the resting configuration and resting lumen diameter from an increased or reduced lumen diameter.

3. The system of claim 1 wherein a portion of a band between the top end and the bottom end is at least equal to or greater than 50 percent of a surface length of the shield.

4. The system of claim 1 wherein the locking mechanism is configured to further function in conjunction with tissue pressure when inserted inside a body opening or orifice to effect the locked configuration.

5. The system of claim 4 wherein when in the locked configuration, the shield is configured to retract the tissue margin when inserted inside the body opening or orifice and the locked configuration prevents reduction in a locked lumen diameter.

6. The system of claim 5 wherein the shield is configured to remain in the locked configuration only when placed into the body opening or orifice and subject to circumferential pressure exerted by the tissue margin onto the shield.

7. The system of claim 1 wherein in the reduced configuration at least a portion of the outer surface of the band overlaps and faces at least a portion of the inner surface of the band such that the inner surface of one part of the band is nested in the outer surface of the band.

8. The system of claim 1 wherein the at least one inner abutment comprises a plurality of inner abutments being spaced around the inner surface of the band to provide multiple releasable locking positions to variably fix the lumen diameter.

9. The system of claim 8 wherein the outer surface of the band comprises a plurality of outer abutments or receiving areas; each of the plurality of outer abutments or receiving areas being sized and configured to receive one of the plurality of inner abutments.

10. The system of claim 1 wherein the top end includes a top flange that extends radially outwardly forming a funnel-like shape in which the lumen diameter increases toward the top end and the bottom end includes a bottom flange that extends radially outwardly forming a funnel-like shape in which the lumen diameter increases toward the bottom end.

11. A system for removing a tissue specimen through a body opening defining a tissue margin, the system comprising:
- a shield including a band made of flexible cut-resistant material; the band having an inner surface and an outer surface interconnected by a top end and a bottom end and by a first end and a second end; the band being configured to define a central lumen having a longitudinal axis; the central lumen having a lumen diameter that is perpendicular to the longitudinal axis; wherein the band is split such that the band is movable into a reduced configuration where at least a portion of the outer surface at the first end overlaps and is in juxtaposition with the inner surface at the second end to form a spiral and define an overlapping portion; the shield being configured to have a variable lumen diameter by varying the overlapping portion; and
- a locking mechanism configured to fix the lumen diameter; the locking mechanism includes a plurality of inner abutments formed on the inner surface and a plurality of outer abutments formed on the outer surface; each of the plurality of inner abutments being configured to contact one of the plurality of outer abutments or the first end to prevent reduction of the lumen diameter in a locked configuration,
- wherein a portion of the band is adapted for jogging outwardly to form a ridge in the inner surface defining an increased lumen diameter; the increased lumen diameter being the lumen diameter increased by a segment distance that extends along a portion of the band from the ridge to the second end.

12. The system of claim 11 wherein the portion of the band is displaced outwardly by a distance equal to a width of the band defined between the inner surface and outer surface of the band.

13. The system of claim 11 wherein the ridge is configured to contact the first end of the band in the locked configuration having a smallest locked lumen diameter.

14. The system of claim 11 wherein the plurality of inner abutments are disposed between the ridge and the second end.

15. The system of claim 11 wherein the ridge comprises an inner ridge surface and a corresponding outer ridge surface; the inner ridge surface being configured such that the inner surface of the band is substantially flush at an intersection with the overlapping portion of the band.

16. The system of claim 11 wherein the locked configuration prevents reduction and expansion of the lumen diameter.

17. The system of claim 11 wherein the plurality of inner abutments and the plurality of outer abutments extend along the longitudinal axis along at least a portion of the band between the top end and the bottom end.

18. The system of claim 17 wherein a portion of the band between the top end and the bottom end is at least equal to or greater than 50 percent of a surface length of the shield.

19. The system of claim 11 wherein the locking mechanism is configured to further function in conjunction with tissue pressure when inserted inside a body opening or orifice to effect the locked configuration, wherein when in the locked configuration.

20. The system of claim 19 wherein the shield is configured to retract the tissue margin when inserted inside the body opening or orifice, and wherein the shield is configured to remain in the locked configuration only when placed into the body opening or orifice and subject to circumferential pressure exerted by the tissue margin onto the shield.

* * * * *